United States Patent
Yoo et al.

(10) Patent No.: US 11,752,334 B2
(45) Date of Patent: *Sep. 12, 2023

(54) METHOD FOR TREATING A PATIENT HAVING A PELVIC FLOOR DYSFUNCTION

(71) Applicant: EBT MEDICAL, INC., Toronto (CA)

(72) Inventors: Paul B. Yoo, Toronto (CA); Michael Sasha John, Larchmont, NY (US)

(73) Assignee: EBT Medical, Inc., Toronto (CA)

(*) Notice: Subject to any disclaimer, the term of this patent is extended or adjusted under 35 U.S.C. 154(b) by 123 days.

This patent is subject to a terminal disclaimer.

(21) Appl. No.: 17/301,334

(22) Filed: Mar. 31, 2021

(65) Prior Publication Data

US 2021/0213283 A1 Jul. 15, 2021

Related U.S. Application Data

(63) Continuation of application No. 16/946,458, filed on Jun. 23, 2020, now Pat. No. 11,446,489, which is a continuation of application No. 15/855,117, filed on Dec. 27, 2017, now Pat. No. 10,722,709, which is a continuation of application No. 15/439,415, filed on Feb. 22, 2017, now Pat. No. 9,884,187, which is a continuation of application No. 15/160,468, filed on May 20, 2016, now Pat. No. 9,610,442, said application No. 15/855,117 is a continuation-in-part of application No. 14/553,427, filed on Nov. 25, 2014, now Pat. No. 10,549,087.

(60) Provisional application No. 62/171,549, filed on Jun. 5, 2015, provisional application No. 62/165,037, filed on May 21, 2015, provisional application No. 62/024,912, filed on Jul. 15, 2014, provisional (Continued)

(51) Int. Cl.
| | |
|---|---|
| A61N 1/36 | (2006.01) |
| A61N 1/04 | (2006.01) |
| A61N 1/05 | (2006.01) |
| A61N 2/00 | (2006.01) |
| A61N 2/02 | (2006.01) |

(52) U.S. Cl.
CPC ....... *A61N 1/36007* (2013.01); *A61N 1/0456* (2013.01); *A61N 1/0502* (2013.01); *A61N 1/0553* (2013.01); *A61N 1/0556* (2013.01); *A61N 1/3606* (2013.01); *A61N 1/36017* (2013.01); *A61N 1/36107* (2013.01); *A61N 2/006* (2013.01); *A61N 2/02* (2013.01)

(58) Field of Classification Search
CPC .. A61N 1/0472; A61N 1/0456; A61N 1/0556; A61N 1/36017
See application file for complete search history.

(56) References Cited

U.S. PATENT DOCUMENTS

2010/0152808 A1* 6/2010 Boggs, II ............. A61N 1/0456
607/46

* cited by examiner

Primary Examiner — Brian T Gedeon
(74) Attorney, Agent, or Firm — Rosenberg, Klein & Lee

(57) ABSTRACT

A method to treat a patient having a pelvic floor dysfunction by establishing a neurostimulator having a processor and a signal generator to generate a stimulation signal. The processor is set to one or more parameters effective in the treating of the patient's pelvic dysfunction when the stimulation signal is applied to a saphenous nerve of the patient. The neurostimulator is configured to provide the stimulation signal to a stimulator in accordance with a stimulation protocol. At least one stimulator is positioned next to a portion of the saphenous nerve of at least one lower limb of a patient. The processor is operationally activated to provide the stimulation signal to the stimulator for treatment of the patient.

39 Claims, 56 Drawing Sheets

Related U.S. Application Data application No. 61/944,744, filed on Feb. 26, 2014, provisional application No. 61/909,679, filed on Nov. 27, 2013.

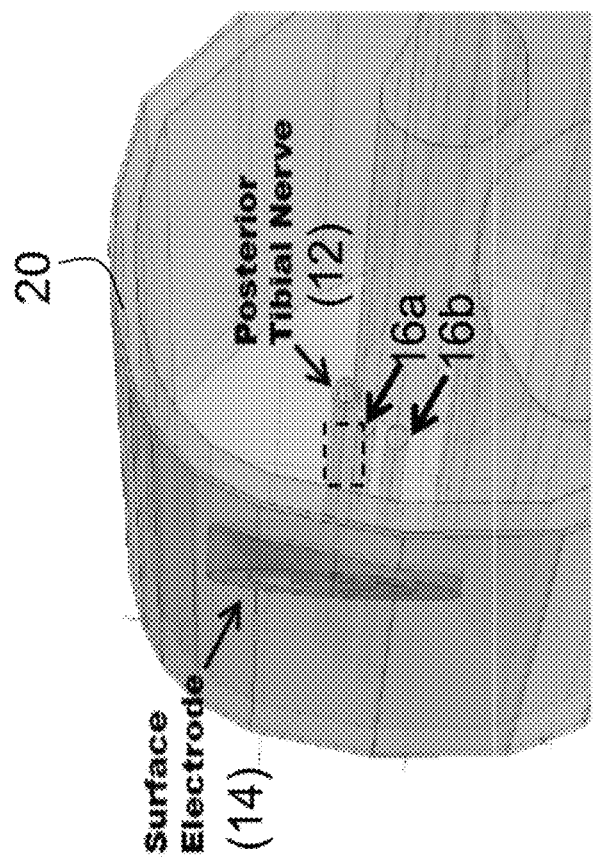
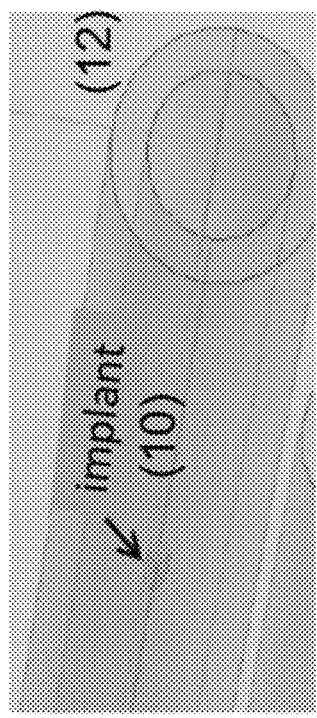
Fig. 1a
Fig. 1b

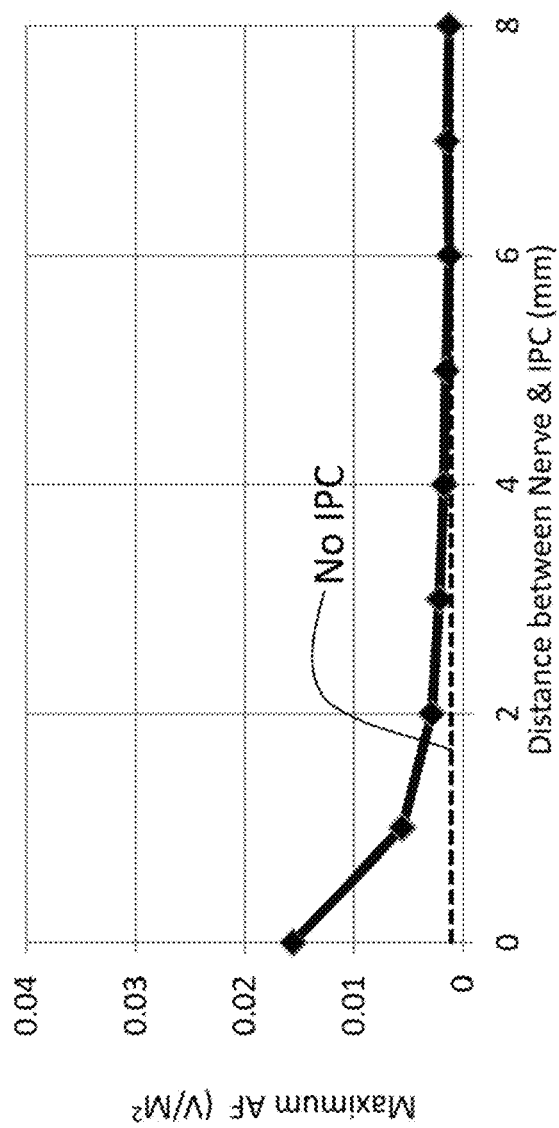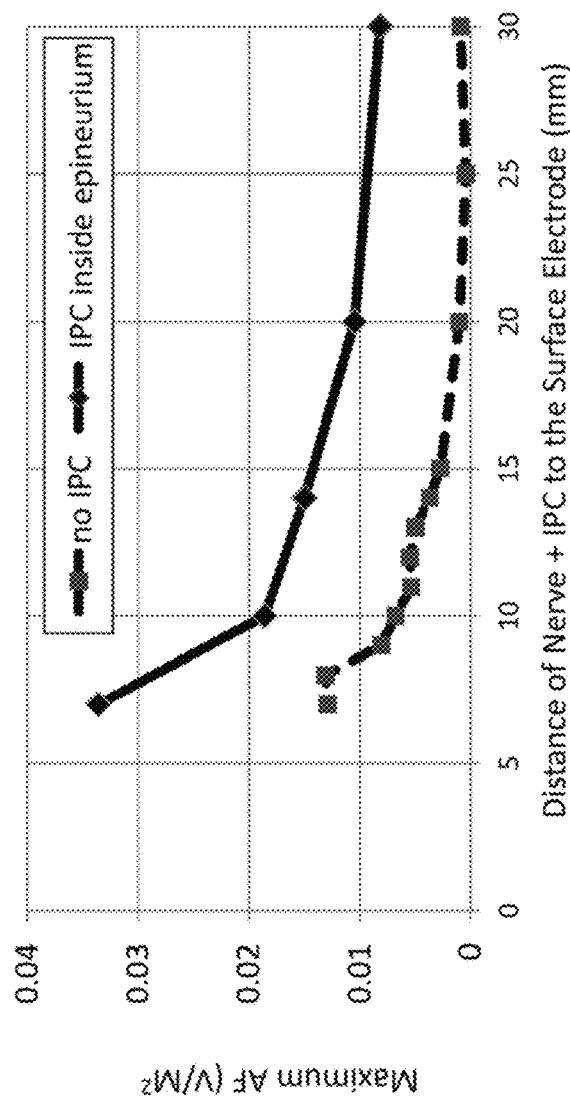

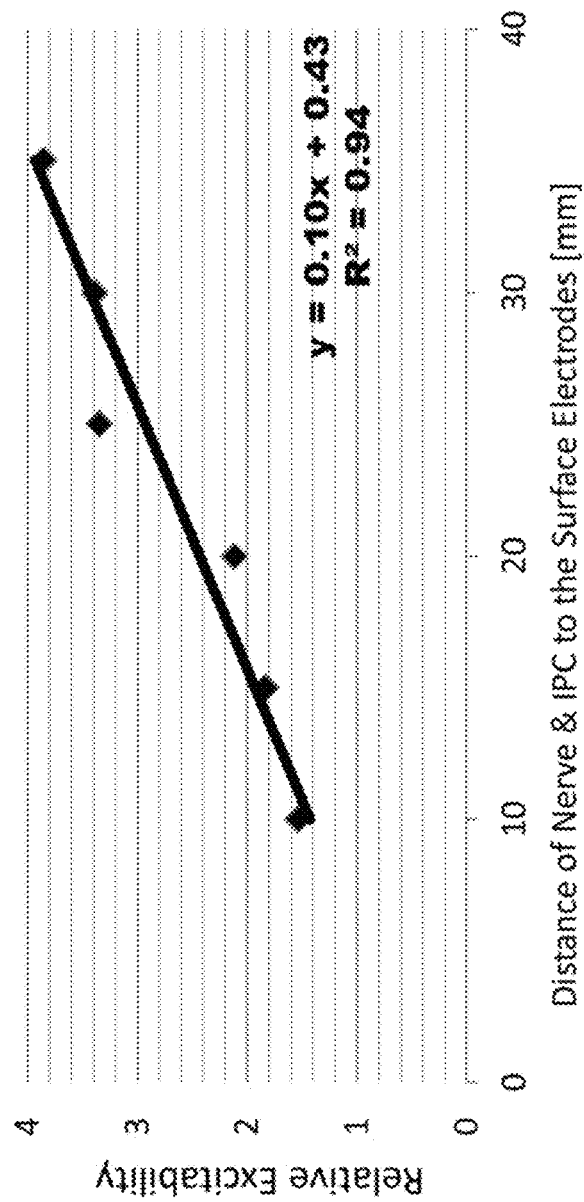
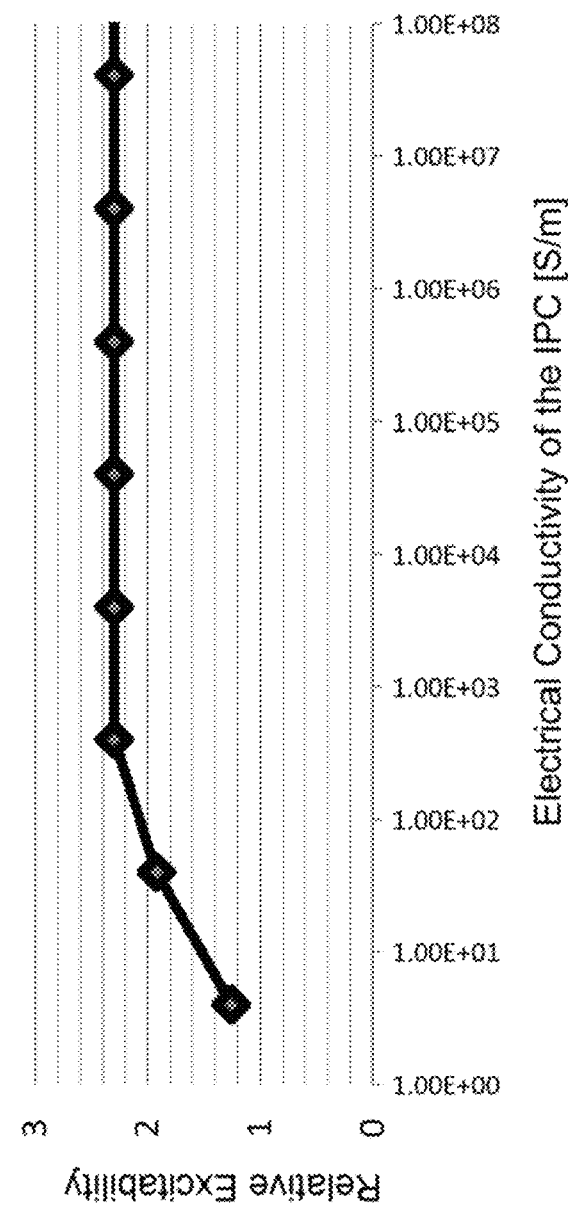

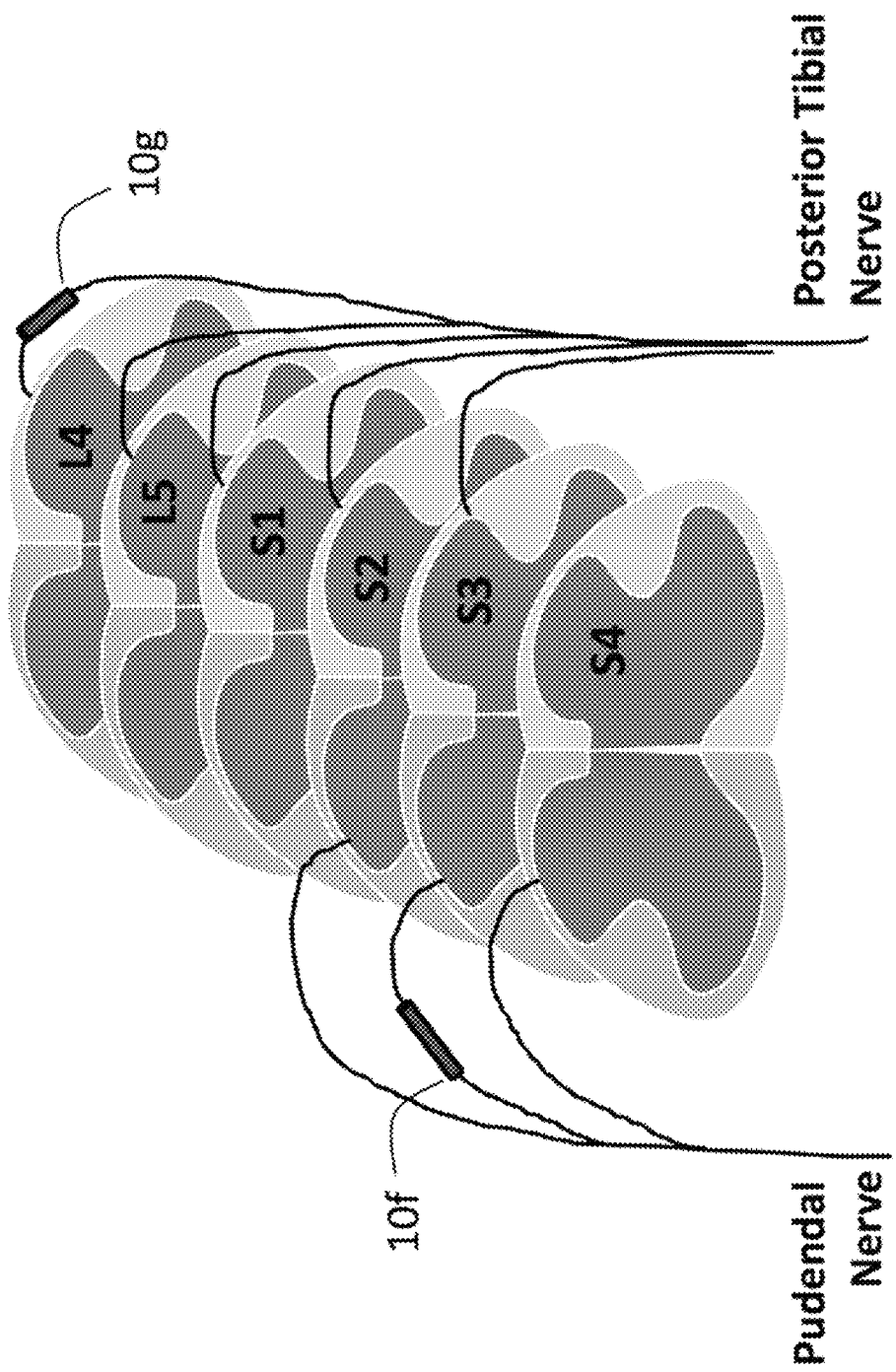

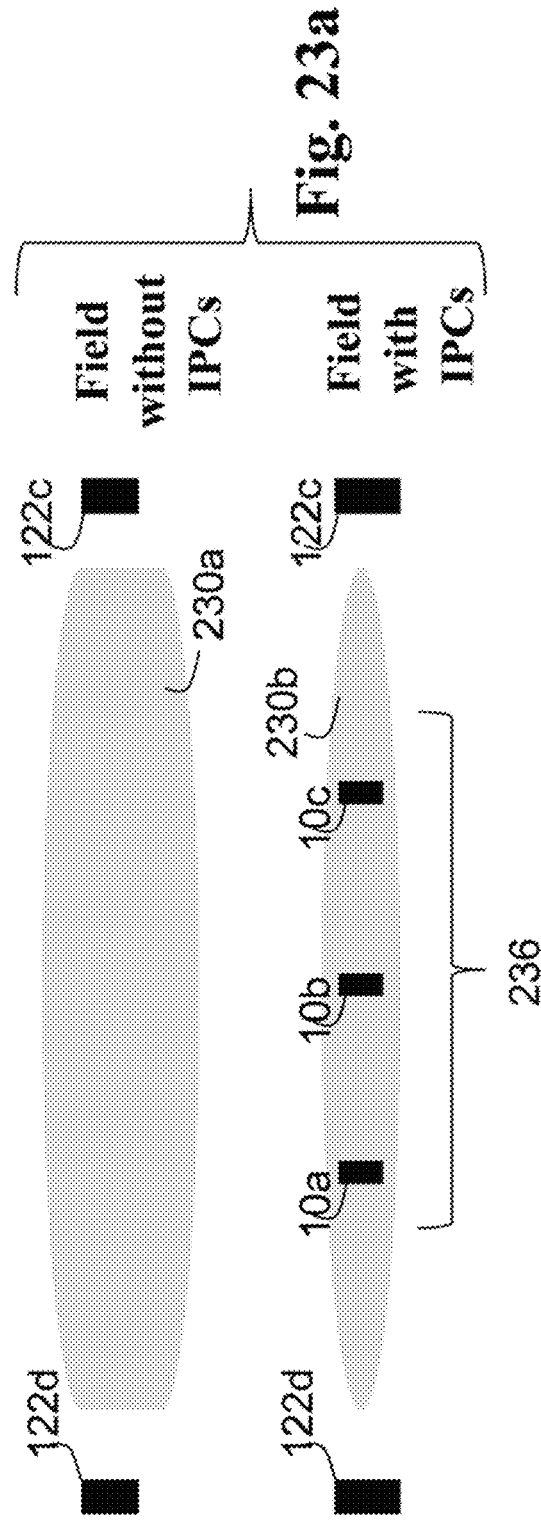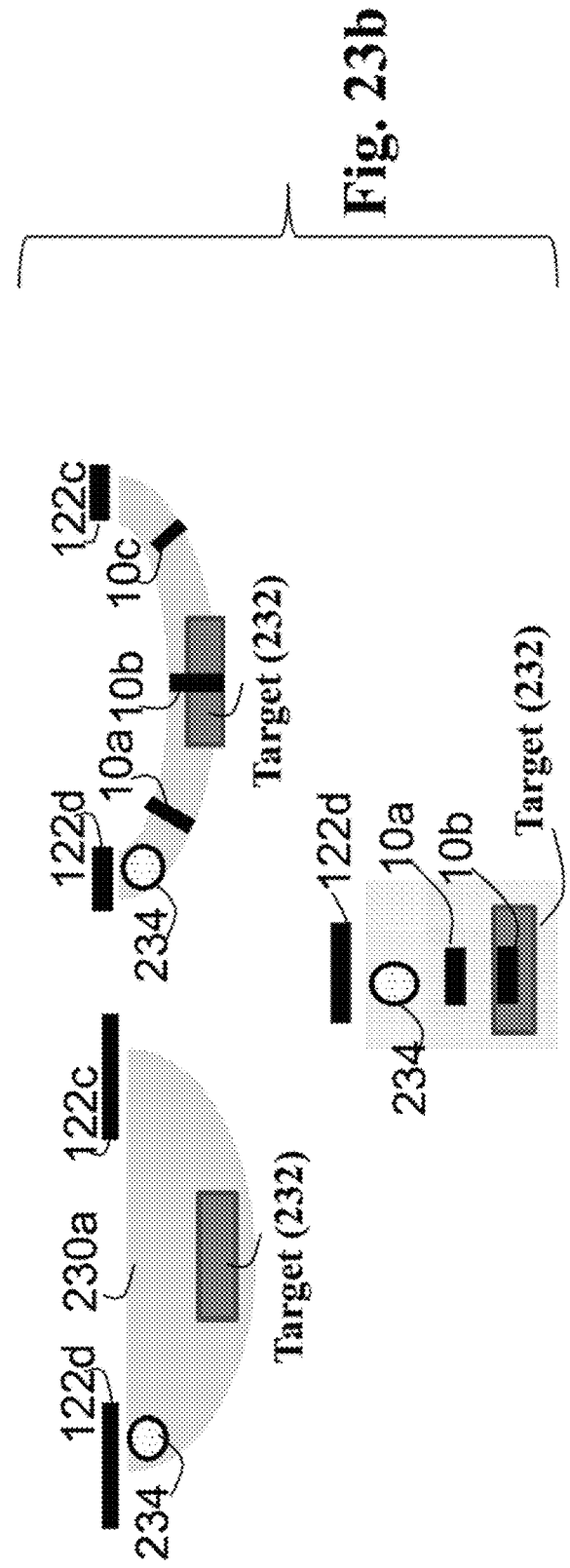

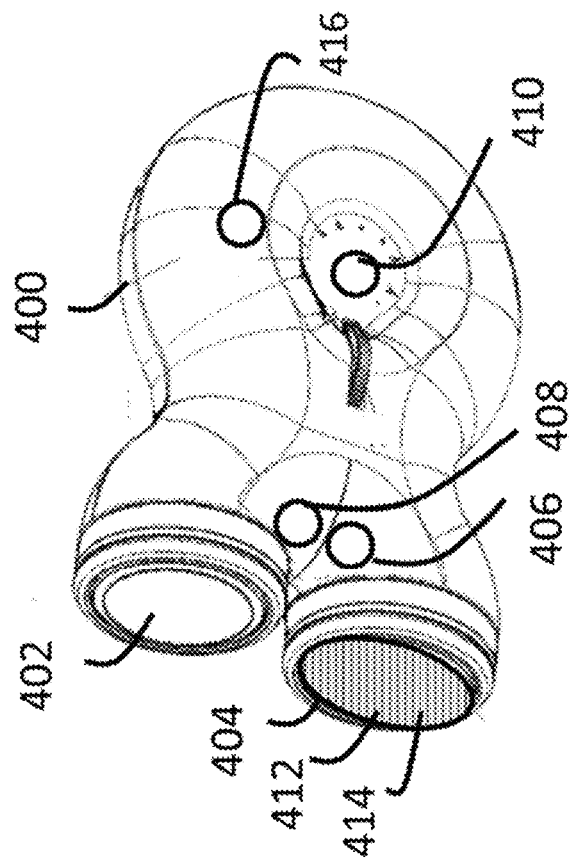
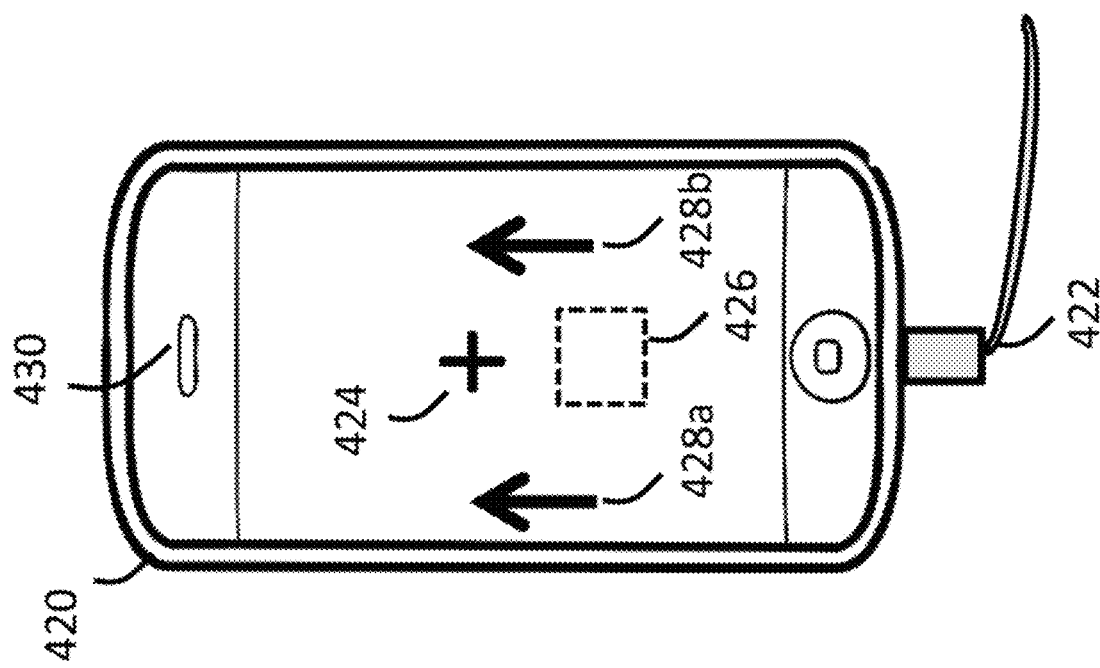
Fig. 24b
Fig. 24a

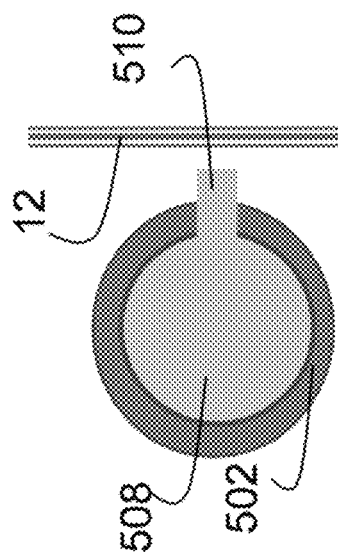
Fig. 28b
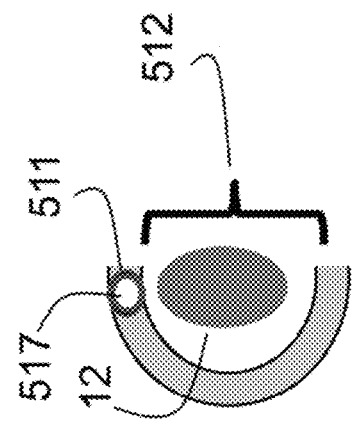
Fig. 28e
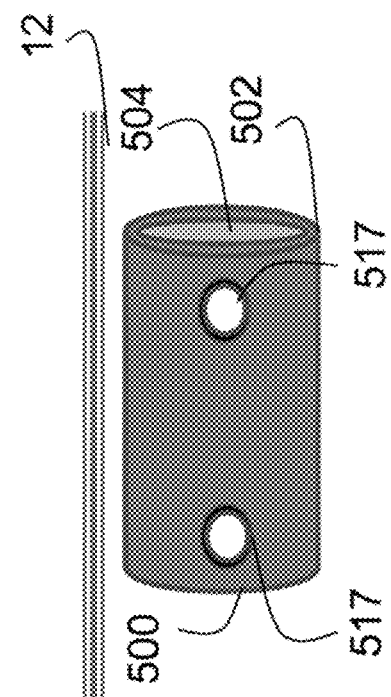
Fig. 28a
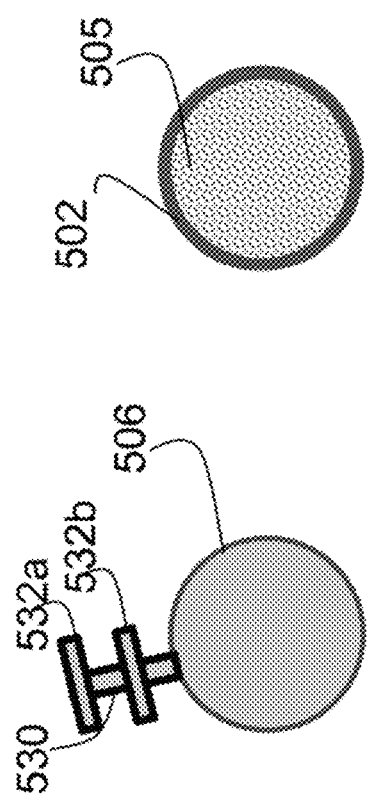
Fig. 28d
Fig. 28c

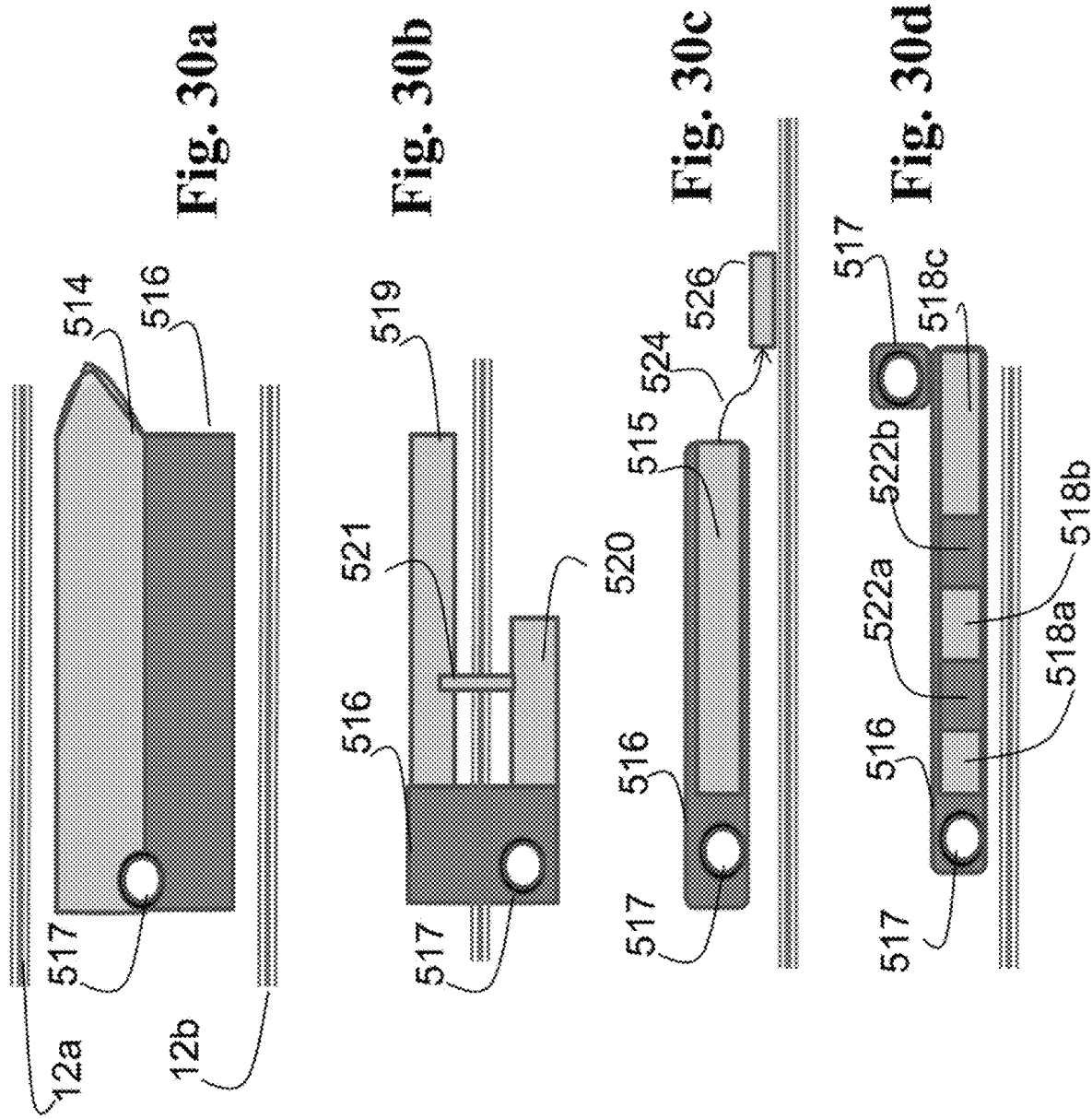

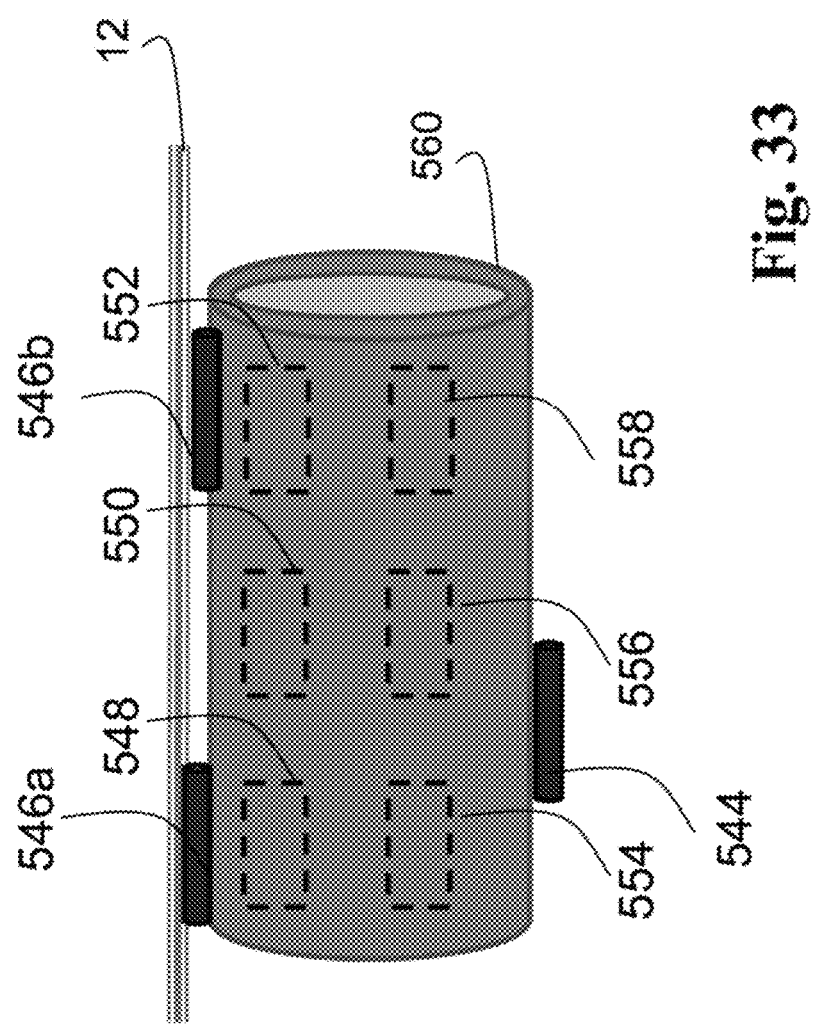

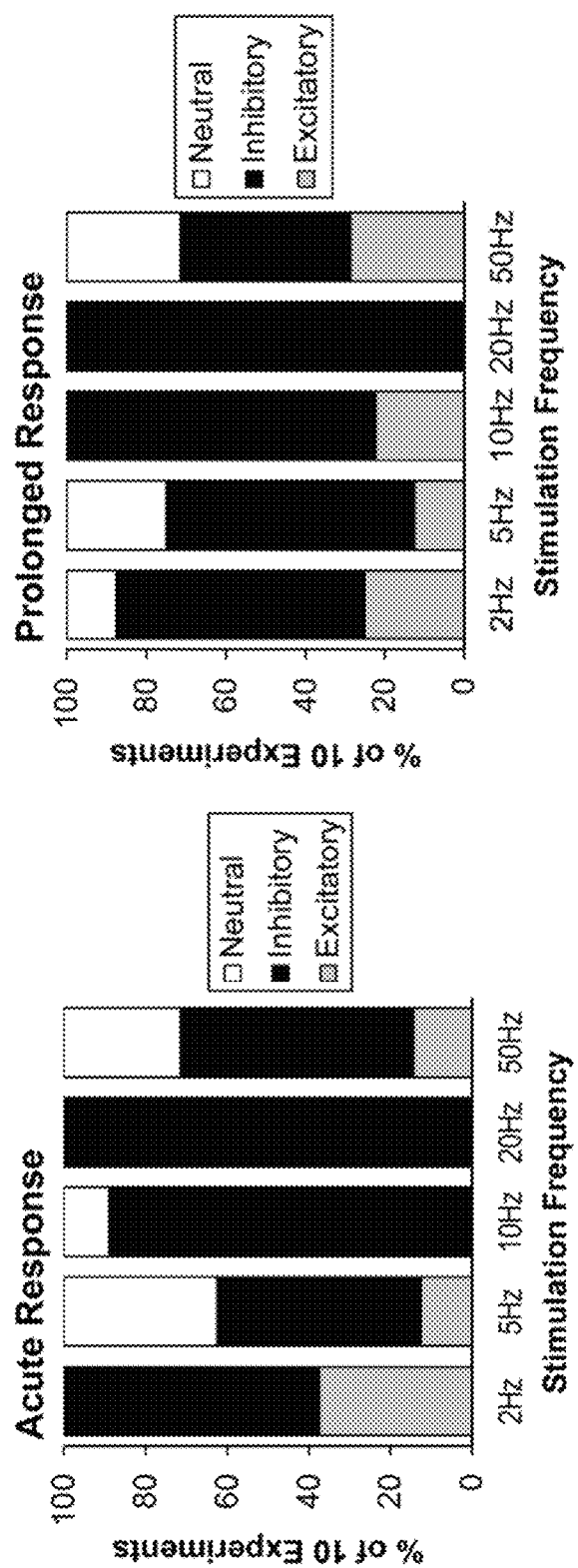

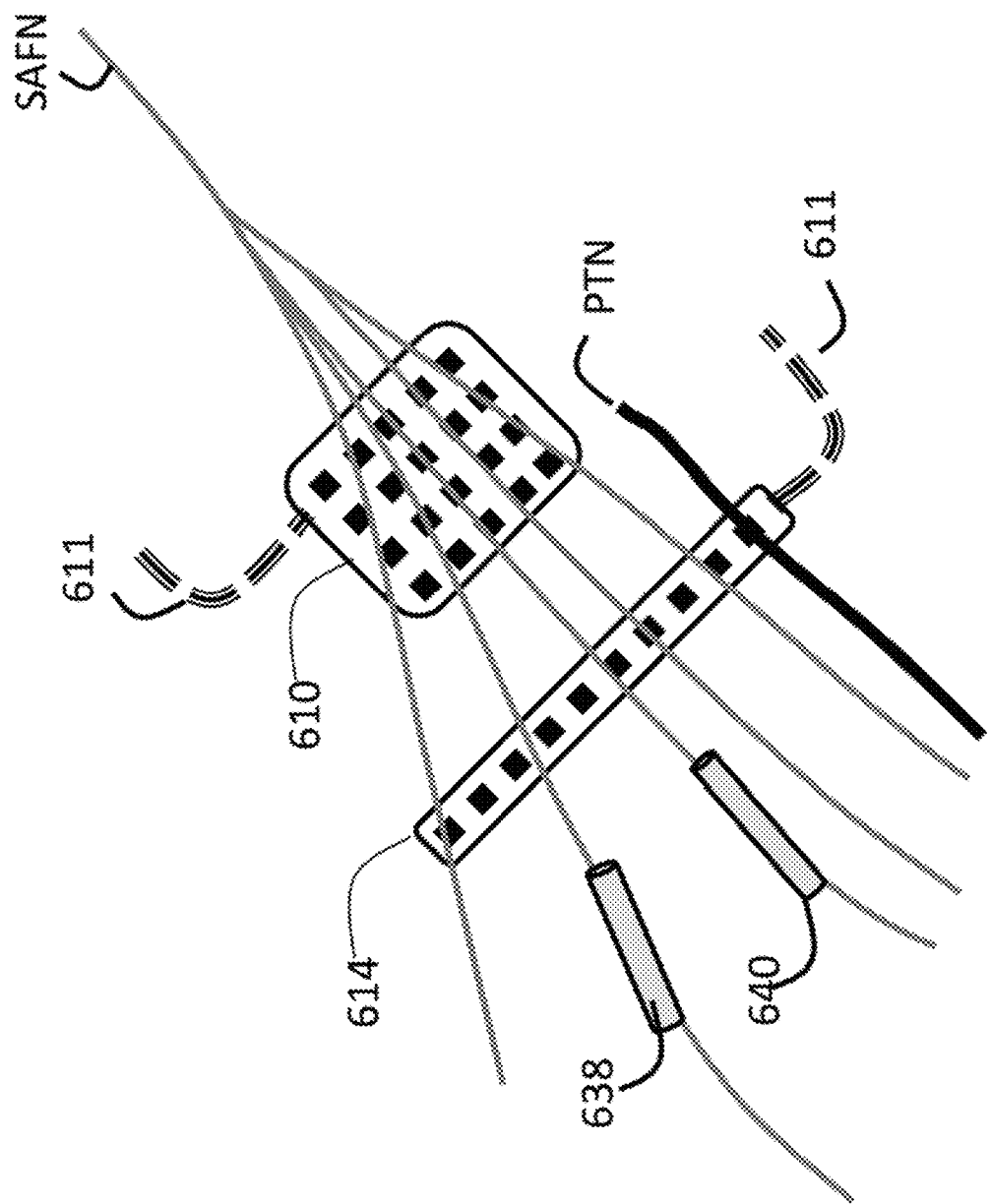

METHOD FOR TREATING A PATIENT HAVING A PELVIC FLOOR DYSFUNCTION

REFERENCE TO RELATED APPLICATIONS

This Patent Application is a Continuation of patent application Ser. No. 16/946,458 filed on 23 Jun. 2020, currently pending, which is a Continuation of patent application Ser. No. 15/855,117 filed on 27 Dec. 2017, (issued as U.S. Pat. No. 10,722,709), which is a Continuation Application of patent application Ser. No. 15/439,415 filed on 22 Feb. 2017, (issued as U.S. Pat. No. 9,884,187), which was filed as a Continuation of application Ser. No. 15/160,468 filed on 20 May 2016 (issued as U.S. Pat. No. 9,610,442), which is based upon U.S. Provisional Patent Application Ser. No. 62/171,549 filed 5 Jun. 2015 and U.S. Provisional Application Ser. No. 62/165,037 filed 21 May 2015.

Patent application Ser. No. 15/855,117 filed on 27 Dec. 2017, (issued as U.S. Pat. No. 10,722,709) is additionally a Continuation-In-Part of application Ser. No. 14/553,427 filed on 28 May 2016, (issued as U.S. Pat. No. 10,549,087), which is based upon Provisional Patent Application Ser. No. 61/909,679, filed on 27 Nov. 2013, Provisional Application Ser. No. 61/944,744, filed on 26 Feb. 2014, and, Provisional Patent Application Ser. No. 62/024,912, filed on 15 Jul. 2014.

INCORPORATION BY REFERENCE

This Patent application hereby incorporates by reference, U.S. patent application Ser. No. 16/946,458, U.S. patent application Ser. No. 15/855,117, U.S. patent application Ser. No. 15/439,415, U.S. patent application Ser. No. 14/553,427, U.S. patent applications Ser. Nos. 15/160,468, 61/909,679, 61/944,744, 62/024,912, 62/165,037, and 62/171,549 which are hereby incorporated by reference in their entireties for all purposes.

FIELD

The subject concept relates to the field of modulating biological tissue.

BACKGROUND

Nerve stimulation (neurostimulation) technology includes applications such as electrical neuromodulation, functional electrical stimulation, and therapeutic electrical stimulation. Nerve stimulation is an effective clinical tool used to treat various chronic medical disorders and conditions. Examples include (1) deep brain stimulation (DBS) for treating Parkinson's disease and essential tremor, (2) spinal cord stimulation for treating pain and urinary dysfunction, and (3) peripheral nerve stimulation for treating overactive bladder, pelvic floor disorders and dysfunctions, pain, obstructive sleep apnea, headache, migraine, epilepsy, depression, hypertension, cardiac disorders, and stroke. Peripheral nerves may include, for example, the vagus nerve, occipital nerve, cranial nerves, spinal nerves, pudendal nerves, cutaneous nerves, and the sciatic and femoral nerves.

Therapeutic efficacy of neurostimulation technology is attributed to selective activation of targeted tissue or neural circuitry, using a stimulation signal that is appropriate for a selected target. This is normally achieved by low recruitment of non-targeted tissue or neural circuit(s). Unintended activation of non-targeted nervous tissue, by a broad or incorrectly localized stimulation field, may deter therapeutic benefit. Unintended modulation of biological system(s) may also be due to, for example, inhibitory rather than, or in addition to, excitatory effects, or other unwanted activity or physiological responses. Unintended modulation may produce side-effects and outcomes that are contrary to the intended response.

The state-of-the-art method, for addressing the issue of selective nerve activation, is to minimize the distance between a stimulating electrode and the nerve targets, and in certain cases isolate the electrode with insulating material. This usually requires precise implantation of an electrode, connecting wires, and a pulse generator (e.g., for brain or spinal cord stimulation). This solution may involve highly-invasive surgery that may be associated with significant risk and discomfort. Disadvantages may include neural or vascular damage, revision surgeries, periodic replacement of pulse generator, surgical complications, and potentially life-threatening infections.

The peripheral nervous system provides a neural substrate that is relatively conducive for selective nerve stimulation of individual nerve branches. However, long-term viability of permanently implanted neurostimulation systems can become complicated by issues related to repeated mechanical movement of lead wires connected to the pulse generator (e.g., lead fracture and/or component migration). Although transcutaneous electrical stimulation can provide a more simple and non-invasive approach, selective nerve activation is not readily achieved.

In many instances, the ability to selectively activate a specific neural target by implanted nerve stimulation systems is also far from ideal when systems with multiple components must be implanted. The current-state-of-the-art methods aimed at improving stimulation selectivity involve the design and implementation of various types of neural interfaces: multi-polar (or multi-contact) deep brain stimulation DBS leads, multi-polar paddle-type electrodes for spinal cord or subcutaneous stimulation, microelectrode arrays (e.g., Utah Array or Michigan Probe, or Huntington Medical Research Institute electrodes), and multi-contact nerve cuff electrodes (e.g., Cyberonics Inc., Case Western Reserve University). A main objective of these electrode designs is to maximize the number of electrode contacts such that an 'optimally-positioned' stimulation location, or an 'optimal combination of one or more electrode contacts', can be used to achieve effective therapeutic outcomes. Improved nerve stimulation selectivity can increase the efficacy of treatment in some instances, such as unintended stimulation of adjacent nerves.

Advances in minimally-invasive nerve stimulation have been realized clinically. Wireless implantable electrode probes have been developed for achieving less invasive methods of selective nerve stimulation. The BION (Alfred Mann Foundation, Boston Scientific) is a glass or ceramic covered electrode that can be percutaneously injected into a region of interest. It can be self-powered or passively charged by radio frequency (RF) pulses. Long-term use may be complicated by migration of the BION from its original implant location. This migration may cause both reduced therapeutic effects and increased stimulation-evoked side effects due to activation of other (non-target) tissue. Nerve stimulation systems (e.g., MicroTransponder Inc. SAINT™ System) which are smaller, less expensive, and less technically complicated than the BION may be advantageous in treatment of some disorders. Micron Devices has developed an implantable neurostimulators, similar to the BION, which uses wireless power in the RF and/or microwave frequency rage and non-inductive antennas which receive electromagnetic energy radiated from a source located outside of the patient's body to produce nerve stimulation. Energous technology is developing wireless technology that utilizes multiple antennae to provide improved transmission and harvesting of wireless energy and is developing within the implantable device space. These technologies may allow smaller form factors.

Another example of nerve stimulation technology is the floating light-activated micro-electrode (FLAME). FLAME uses an analogous design approach to the BION however, instead of RF pulses, the implanted electrode converts near infrared light into electrical pulses. Clinical use of FLAME technology is currently limited, primarily due to poor penetration of light into biological tissue and other technical hurdles.

Transcutaneous magnetic stimulators (TMS), termed "transcranial magnetic stimulators" when used for brain stimulation, are used to treat disorders such as migraine (e.g. Neuralieve Inc.) by using an external magnetic stimulation device to stimulate central or peripheral tissue targets. The fields induced inside the tissue by one or more pulses (pulsed electromagnetic stimulation) may be less localized than desired.

Transcutaneous electrical nerve stimulation (TENS) is another non-invasive approach to activating nervous tissue. Companies such as Cefaly have designed TENS systems to work specifically on nerve cells affected by pain. The TENS system developed by Cefaly works by introducing electric impulses to act on the nerves that transmit migraine pain such as a bifurcation of nerves known as the trigeminal nerve. In addition to pain, TENS systems have been used to apply electrical fields to the brain in order to modulate sleep, anxiety, depression, pain, attention, memory, and other types of cognitive/sensory processing. Tens systems are also being developed to enhance performance of athletes. The current system and method may be used with such a TENS system in order to focus on an area, or population, of nerves that are electrically activated.

Electrocore Inc. has developed both non-invasive electrical (e.g., TENS) and implantable magnetically driven stimulators that electrically stimulate nerves such as the vagus nerve. For vagus nerve stimulation (VNS) therapy, a handheld device is placed on the surface of the skin just above the vagus nerve, which is palpated by the pulsating carotid artery. The clinical efficacy of this approach is currently undergoing validation. Given the anatomical characteristics of the vagus nerve (e.g., distance from the skin surface, embedded within a neurovascular bundle), there may be challenges associated with TENS based VNS. Factors such as overweight patients with subcutaneous tissue (e.g., fat deposits) may prove challenging since this increases the distance between the stimulating electrode and the vagal target.

Uroplasty has developed both cutaneous and percutaneous stimulation systems for the treatment of urological disorders. The main therapy currently implemented involves posterior tibial nerve stimulation, which relies on percutaneous injection of a needle electrode near the patient's ankle.

Both Electrocore Inc and Uroplasty are currently engaged in developing implantable stimulation systems for activating nervous tissue, where the implanted stimulator is wirelessly powered by magnetic induction. This approach obviates the need for using an implantable battery, percutaneous or sub-cutaneous leads connecting to a power source, and it may also decrease the complexity of the implanted circuitry. This system has not yet completed clinically trials, and so the associated disadvantages are currently unknown.

Modulation of biological tissue, such as nervous tissue, presents the opportunity to treat a myriad of biological and physiological conditions and disorders. Modulation can include interacting with, and controlling, a patient's natural processes. Modulation of tissue can include nerve modulation such as inhibition (e.g. blockage), activation, modification, up-regulation, down-regulation, or other type of therapeutic alteration of activity. The resulting biological response may be electrical and/or chemical in nature and may occur within the central or peripheral nervous systems, or the autonomic or somatic nervous systems. By modulating the activity of the nervous system, for example, through activation or blocking of nerves, many functional outcomes may be achieved. Motor neurons may be stimulated to cause muscle contractions. Sensory neurons may be blocked, to relieve pain, or stimulated, to provide a biofeedback signal to a subject. In other examples, modulation of the autonomic nervous system may be used to adjust various involuntary physiological parameters, such as heart rate and blood pressure.

SUMMARY

A transcutaneous tissue stimulation system and method is provided which includes an electrical generator positioned external to a patient. A stimulator is electrically coupled to the electrical generator and is positioned on the surface of the patient's skin. An implanted, electrically conductive member is positioned on, or contiguous to, a target nerve tissue for stimulation of the target nerve tissue to modify the electrical field signals generated by the electrical generator and provided by the stimulator for the purpose of modulating signals from the nerve tissue to the brain, to the central or peripheral nervous system, or other target, of the patient.

Stimulation systems and methods are described for providing advantages related to increasing therapeutic efficacy of nerve stimulation, improving the comfort of a patient relative to other therapeutic solutions, decreasing the cost of treatment, and/or providing for a simple treatment and/or implantation procedure.

An objective of the current system is to provide systems and methods which provide selective nerve stimulation, and stimulate specific nerve branches or selected portions of a nerve or nerve fascicle.

Another objective of the current system is to provide one or more small implanted components to provide selective nerve stimulation and thereby offer improved long-term clinical therapy. This system and method aims to avoid activation of non-targeted nervous tissue, which can both limit the overall therapeutic effects and exacerbate stimulation-evoked side effects.

Another objective of the current system and method is to provide for a nerve stimulation system having external components and an implanted passive element which is configured to allow therapy to achieve the same, or improved therapeutic benefit as that which would otherwise be achieved when using only transcutaneous nerve stimulation without an implanted passive element.

Another objective is to provide systems and methods for providing stimulation of tissue using complementary or "paired" configurations of external stimulation elements and subcutaneously implanted passive elements.

Another objective is to provide systems and methods for providing a selective increase in neural excitability, where a single neural target (located among one or more other nerves) is independently activated or multiple nerves are activated independently using one or more implanted elements and applying different stimulation parameters such as stimulator location, electrode contacts which are active, amplitude, frequency, duty cycle, and waveform.

Another objective is to provide systems and methods for achieving effective therapeutic nerve activation with relatively lower stimulation amplitude and/or shorter pulse width than what is achievable using prior art methods (e.g., TENS).

Another objective is to provide systems and methods for reduced activation of non-targeted nervous tissue (i.e., minimize stimulation spillover).

Another objective is to provide systems & methods for decreasing nerve stimulation-evoked side effects.

Another objective is to provide systems and methods for providing improved transcutaneous electrical nerve stimulation, intra-vascular stimulation of nervous tissue, and augmented selective activation of peripheral and central nervous system tissue.

Another objective is to provide systems and methods for providing improved TENS for certain fibers during VNS (e.g., small myelinated B-fibers and/or unmyelinated C-fibers), while avoiding, for example, A-Type fibers.

Another objective is to provide systems and methods for providing improved modulation of tissue targets that may include glandular tissue, fatty or lipid tissue, bone tissue, muscle tissue, and nerve tissue.

Another objective is to provide systems and methods for improving a number of clinical conditions and their related treatments including, for example: a) Overactive Bladder treatment (or any disorder or condition related to bladder activity or voiding) by posterior tibial nerve or sacral nerve stimulation; b) Chronic pain and treatment by stimulation of the lower back or lower extremities; c) treatment related to migraine and headache; d) Obstructive sleep apnea and treatment related to hypoglossal, vagal, or superior larygeal nerve stimulation; e) various conditions such as epilepsy, headache, and depression which may be treated by vagus nerve stimulation; and f) various other conditions that may be treated by improving selective targeting of specific tissue.

Another objective is to provide systems and methods for providing stimulation of tissue using improved configurations, materials, orientations, embodiments, and spacing of external stimulation elements, cutaneous stimulation elements, and implanted passive elements which are not physically connected to the stimulation sources.

Another objective is to provide systems and methods for providing stimulation of a first tissue target that is approximately cutaneous and also providing for stimulation of a second target that is a nerve that is relatively distal from the skin surface.

Another objective is to provide systems and methods for augmenting other therapies in order to increase the number of patients that benefit, augment the magnitude of therapeutic benefits, and/or decrease the frequency of repeated therapeutic interventions that may be significantly more invasive.

Another object of the subject system and method is to allow magnetically-induced electric fields, or sound or light stimulation, to achieve more specific modulation of target tissue or neural circuits.

Another object of the system and method is to permit a functional focusing and/or shaping of a TMS field so that selective activation is promoted.

Another object of the invention is to selectively stimulate nerve targets using stimulation signals that are specific to those targets (e.g. having a target specific frequency that is selected based upon assessment of the patient), and adjusting or switching the nerve targets or the stimulation signals to become or remain effective, and well selected, based upon the understanding that the full posterior tibial nerve and its branches, as well as other nerves disclosed herein may provide unique acute and prolonged post-stimulation responses related to bladder activity and related treatments.

A further object of the invention is to selectively stimulate nerve targets, including nerve branches or combinations thereof, using stimulation signals that are effective and specific to those targets for the treatment of a pelvic floor disorder.

A further object of the invention is to selectively stimulate novel nerve targets in novel manners including the saphenous nerve, and associated L2, L3, and L4 spinal nerve roots and moreover improving therapy by, for example, using stimulation signals that are defined for those targets and which have been shown to provide therapy of a patient, either alone or in combination with other currently known targets, for the treatment of a pelvic floor disorder, and in order to modulate, increase, or decrease bladder activity and also to provide symptom relief.

These and other objectives and advantages of the invention will now be disclosed in the figures, detailed description, and claims of the invention.

In the illustrated embodiments, any steps shown in the figures may occur in a different order, may be repeated, may lead to different steps of the method shown within each figure, or may lead to steps shown in other figures. Steps and components shown may be included or excluded from a particular embodiment, and this may occur conditionally, or according to the system or treatment protocol implemented by a therapy program. The therapy program may be implemented partially or fully by one or more processors of a medical system which may include an external, or a partially or fully implantable neurostimulator. The therapy program can be adjusted according to control by, or therapy plan implemented by, a patient, doctor, remote medical service, or caregiver.

BRIEF DESCRIPTION OF THE FIGURES

FIGS. 1a-1b show a schematic diagram of one embodiment of an enhanced transcutaneous nerve stimulation (eTNS) system implemented in a lower limb, where the system, or finite element model thereof, includes a surface electrode, and a passive element (implantable passive component or "IPC") that is placed in close proximity to the posterior tibial nerve, and FIG. 1b is a close-up of the area enclosed by the dashed box of FIG. 1a.

FIG. 2a is a graph showing results from a computer simulation that depicts the relationship between the activating function (AF: measure of neural excitability) and the distance between the IPC and the target nerve, where the distance between the surface electrode and the nerve is kept constant (a higher AF indicates a lower nerve activation threshold).

FIG. 2b is a graph showing computer simulation results that depict the effects of the IPC on the AF, and the distance between the surface electrode and the target nerve was increased (depth from skin surface=7 mm to 30 mm).

FIG. 3a is a graph showing modeled results of relative "neural excitability" as a function of nerve depth from the skin surface (the relative excitability was calculated as the ratio of the AF between the "IPC present" condition and an "IPC absent" condition).

FIG. 3b is a graph showing modeled results of the effects of the electrical conductivity of the IPC on the relative neural excitability (AF).

FIG. 11 schematically depicts the selected spinal nerve roots that converge to form the pudendal (S2-S4) and posterior tibial (L4-S3) nerves. Two surgically placed objects (e.g., nerve cuffs) are indicated as IPCs (10f and 10g) on the S3 and L4 roots, respectively.

FIG. 23a is a schematic diagram of an embodiment of the subject system in which a plurality of IPCs provides for the shaping of an electrical field.

FIG. 23b is a schematic diagram of an alternative embodiment of the subject system in which a plurality of IPCs provides for the shaping of an electrical field.

FIG. 24a is a schematic diagram of an embodiment of a controller for a portable TNS system.

FIG. 24b is a perspective schematic view of a portable TNS system.

FIGS. 28a-e show schematic views of further embodiments of IPCs.

FIGS. 30a-d show schematic views of additional embodiments of IPCs.

FIG. 33 is a schematic view of an embodiment of an implantable active component.

FIGS. 36a and 36b show summaries of the percentage of experiments that resulted in inhibitory, neutral, or excitatory bladder responses (acute and prolonged), across stimulation frequencies between 2 Hz and 50 Hz, applied at 25 µA

FIG. 50a is a diagram of a multi-contact planar and lead-type electrode array for selectively activating one or more nerve branches such as branches of the saphenous nerve and posterior tibial nerve.

DETAILED DESCRIPTION OF THE PREFERRED EMBODIMENTS

Figure 1C:
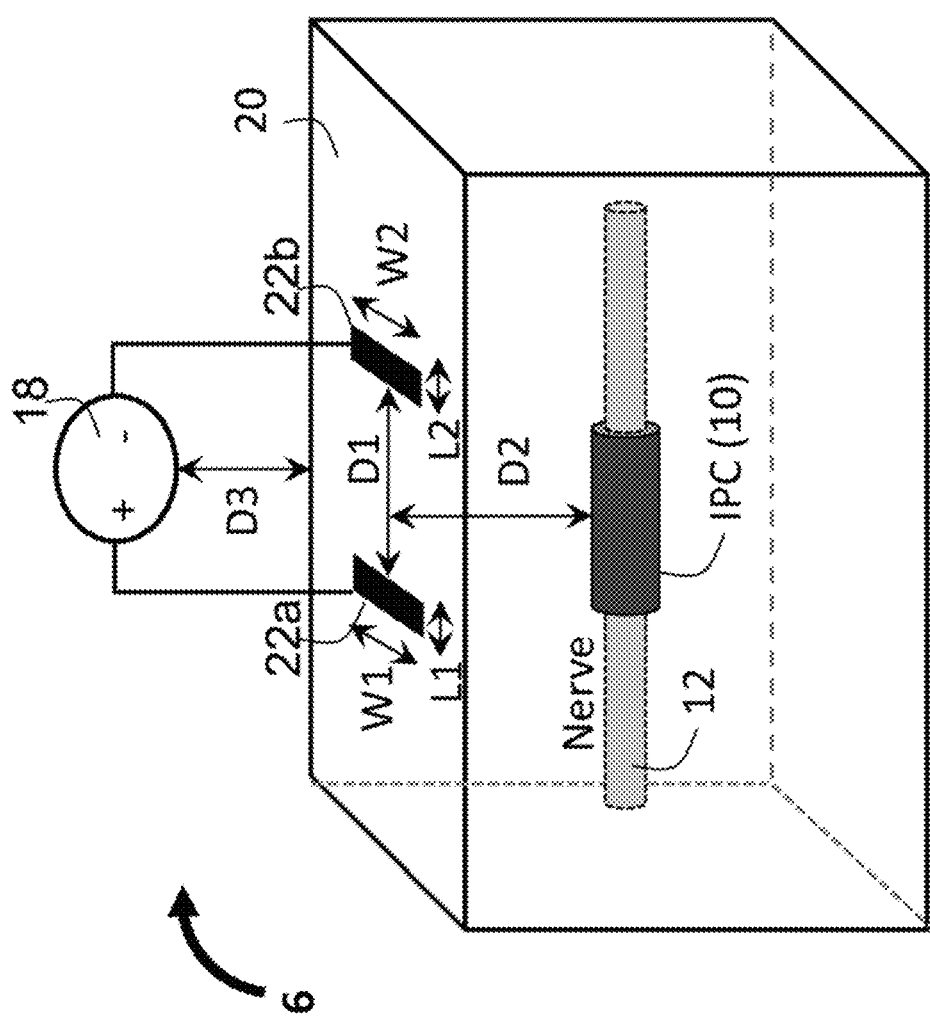
FIG. 1c shows a schematic diagram representing another embodiment of the enhanced nerve stimulation system, or finite element model thereof, and includes a pair of stimulating surface electrodes, with lengths (L1,L2) and widths (W1,W2), placed on the surface of the skin of a patient, with an inter-electrode distance (D1), as well as an implant (IPC) located at a given depth distance (D2) from the skin surface.

Reference will now be made in detail to exemplary embodiments of the present disclosure, examples of which are illustrated in the accompanying drawings. Wherever possible, the same reference numbers will be used throughout the drawings to refer to the same or like components. When titles are provided to the different sections of the disclosure these are merely to highlight certain themes in the application and are not meant to constrain or limit the invention concept in any manner.

Embodiments of the present disclosure relate generally to systems and methods for modulating tissue through the delivery of energy. Tissue modulation/stimulation, which includes nerve or neural modulation, can cause for example, inhibition (e.g. blockage), excitation, modification, regulation, and/or therapeutic alteration of activity and patterns of activity. These changes can occur in the central, peripheral, or autonomic nervous systems. Tissue modulation may include providing energy to the tissue to create a voltage change, and in the case of a nerve can be sufficient for the nerve to activate, or propagate an electrical signal (action potential(s)). Nerve modulation/stimulation may also take the form of nerve inhibition, which may include providing energy to the nerve sufficient to prevent the nerve from propagating electrical signals or "nerve block". Nerve inhibition may be performed using approximately continuous or ongoing application of energy, and may also be performed through the application of enough energy to inhibit the function of the nerve for some time after the application. Other forms of neural modulation may modify the function of a nerve, causing for example a heightened or lessened degree of sensitivity. As referred to herein, modulation of a nerve may include modulation of an entire nerve and/or modulation of a portion of a nerve. For example, modulation of a motor neuron may be performed and may only lead to changes in those portions of the neuron that are proximal to, or distal to, the location to which an energy field is applied.

FIGS. 1a and 1b show one embodiment of the invention which is a novel system and method for improving the selective modulation of targeted biological tissue such as various components of the nervous system. FIG. 1a shows a cutaneous surface electrode 14 located near a tissue target 12, such as the posterior tibial nerve. A selective increase in neural excitability (i.e., reduced stimulation threshold) of the tissue target 12 is achieved by placing a biologically-compatible 'implant' 10 in sufficiently close proximity to the targeted neural tissue 12, as shown in FIG. 1b (close-up of the target 12 of FIG. 1a, which shows the implant 10 embedded within the epineurium). Under certain circumstances, presence of this implant 10 can also increase the amount of electrical charge or energy needed to activate non-target nerves 16a, 16b located in the vicinity of the target, thereby supporting increased stimulation selectivity or specificity (note: anatomically, 16a and 16b are posterior tibial vein and artery blood vessels, however in this example we are treating these as non-target nerves for purposes of illustration). In most embodiments, the implant 10 (or implantable passive component "IPC") is at least partially electrically conductive, and has at least one conductive portion which may be a conductive surface. The conductive portion is preferably a highly conductive material for promoting electrical nerve activation. The IPC is not physically connected to any electrical power source but rather is positioned to modify the electrical field, energy, or power that affects the targeted (nervous) tissue 12. The IPC may be physically secured directly to nerve tissue or surrounding connective tissue, for example, by a suture. The IPC may have a connector portion to assist with its implantation and securing. In one embodiment, the IPC serves to modify the field generated by a cutaneously located stimulator 14 such as an electrode that receives stimulation signals from an external nerve stimulator (also termed neurostimulator or pulse generator) 18.

In another embodiment of the invention which can be used, for example, in order to test, adjust, and select therapy parameters, the system components and target tissue may be simulated using a software model comprised of computer code which can be implemented by a processor in a computer, for example, a finite element model of the human lower leg. An analogous finite element model of the human lower limb can approximate this scenario by setting the virtual surface electrode at a constant current (e.g., −1 mA, cathode) and the proximal cut surface of the virtual leg as the return (anode). However, in the real world, the return electrode can be placed anywhere on the patient, or alternatively cutaneous (surface) stimulation can be delivered by a pair of electrodes (bipolar configuration). The electrode 14 may be bipolar having both anode and cathode portions (e.g., concentric ring electrodes), with non-conductive material between, or it may be monopolar with the return electrode located at a distal location. FIG. 1a shows an electrode configuration, where the electrode 14 is placed at the level of skin 20 near the IPC 10.

FIG. 1c shows an alternative embodiment of the enhanced nerve stimulation system having at least two surface electrodes 22a, 22b that are placed on the skin surface 20 in a bipolar configuration where one electrode serves as anode (+) and the other as cathode (−). Although, in this example, stimulator lengths L1 and L2 and stimulator widths W1/W2 are set to 5 mm and 2 mm, respectively, the widths and lengths of the two electrodes may be different, and the electrode stimulators may also be of different shapes (rather than both being rectangular). The IPC 10 may be implemented as a semi-annular or annular cuff-type electrode which is embodied as a hollow cylindrical cuff that partially or completely wraps around a nerve 12, and is in close contact with the outer surface of the nerve. The interelectrode ("IE") distance is indicated by the D1 double-headed arrow located between the two stimulators 22a, 22b, while depth (distance between the surface stimulators and the IPC) is represented by the D2 double-headed arrow. An electrical source 18 is connected to a pair of cutaneous electrodes that are affixed to a patient's skin 20 near at least one IPC 10. The electrodes may include at least one anode electrode 22a and at least one cathode electrode 22b so that current flows through the tissue between the at least two electrodes and also provides electrical stimulation to target tissue such as nerve 12, and is influenced by at least one IPC, positioned within the patient. As will be shown, certain characteristics of the therapy system (and the corresponding parameters of the model) can influence the ability of the external stimulators 22a, 22b to stimulate the nerve 12. For example, a) the widths W1,W2 and lengths L1,L2 of the surface electrode stimulators 22a, 22b, b) the distance D1 between the two stimulators relative to the length of the IPC, c) the distance D2 between at least one stimulator and the IPC, d) the alignment between the edge of at least one stimulator and at least one edge or "end" of the IPC, e) the distance between the IPC and the nerve, and f) the conductivity of the IPC, can all contribute to enhancing the electrical modulation of nervous tissue 12. Other factors such as the thickness, shape, and orientation of the IPC relative to at least one stimulator, may also alter the excitability of the targeted nerve. The system shown in FIG. 1c, illustrates both how it may be implemented physically, when used to modulate nerve activity of a patient, as well as how it may be simulated as a computer model which is calculated by a processor in order to test/assess, adjust, and select therapy parameters. In this embodiment, the IPC was modeled as a hollow cylindrical shell placed around and including contact with the outer surface of the nerve.

An embodiment of a method for clinically implementing the stimulation system may involve an assessment process which may be termed IPC assessment process, when an IPC is used. The initial step of the process can include creating a computer or physical model (or mixture of the two) which simulates, for example, at least one stimulator, the patient and patient tissue, at least one of a target and non-target tissue, and either no IPC or at least one IPC. When two simulations are compared, one in which the IPC is present and one in which the IPC is absent, then the two modeled results may be compared in order to assess the effect of the IPC. In the next step, the model can be adjusted to simulate how a change in each modeled parameter can affect the stimulated tissue, and accordingly suitable stimulation protocols and parameters may be derived for subsequent use in a patient. In a following step, the model and simulated results are then used to customize an improved stimulation system for use with an individual patient. The model parameters can be adjusted based upon patient measurements. For example, patient measurement may include structural and anatomical measurements obtained by physically measuring characteristics of the patient, such as by obtaining sensed data including imaging data related to light/laser, ultrasound, MRI, x-ray or other imaging modality. Patient measurements may also include functional measurements of impedance, bloodflow (e.g. infrared spectroscopy measurements), EMG, data related to muscle (e.g. bladder) contraction, data related to bladder capacity, and the like. The IPC assessment process, such as that just disclosed, can be realized in steps 34 and/or 48 of FIG. 17, and/or this process may be done within, before, or outside of, the other steps shown in the figure. Patient measurement data can also be used to adjust stimulation protocol parameters and system components (e.g. IPC shape), used during therapy, according to individual patients. This can be done to improve therapy and may occur during a step of initial therapy assessment, for example, as in step 250 of FIG. 22c. Patient measurements may be used intermittently (e.g., every 6 months to one year of maintenance PTN stimulation) to confirm proper stimulation settings are maintained or require modifications.

A number of advantages of one aspect of the invention can be demonstrated by computational models. The simulations support the idea of selectively enhancing neural excitability by manipulating the extracellular potential gradient that is generated along the targeted nervous tissue by electrical stimuli. This voltage gradient may be characterized according to a model that is widely referenced in the literature to predict the relative neural excitability (Rattay, F. (1989). "Analysis of models for extracellular fiber stimulation." IEEE Trans Biomed Eng 36(7): 676-682). This is referred to as the 'activating function' (AF) and is defined as the second spatial derivative of the extracellular potential along an axon. In one computer model implemented as computer code to be processed by a computer with a processor according to the invention, the model allows a user to alter modelled parameters such as the length, position, shape, thickness, and conductivity of at least one IPC, distance from the IPC to a nerve, parameters for characterizing a nerve and surrounding biological tissue including, for example, electrical conductivity, distance of the IPC from at least one stimulator, the shape of the stimulator, additional stimulators that may be used, the 3 dimensional distances between the stimulators, and modes of stimulation such as monopolor or bipolar and whether a simulated signal generator utilizes a stimulator as cathode or anode in the provision of simulated stimulation signals. The output of the model can include results such as the activating function of a nerve.

The simulated data that will be shown herein were obtained using a limited set of stimulation protocols (e.g., a single steady-state pulse). Although the system may often operate linearly, in order to enable stimulator-IPC pairs to operate well when using a larger set of stimulation protocols, the system configuration and stimulator+IPC pairings may have to be adjusted (especially for very high frequency stimuli, such as, for example above 1 kHZ). The modelling can be repeated for a range of alternative stimulation signals (e.g., frequencies, pulse shapes, polarities, and durations) and the system configuration can be adjusted to accommodate these. Alternatively, only stimulation signals empirically determined to be successful for a given system configuration can be used during the provision of stimulation treatment. Additionally, look-up tables may be derived for different stimulation signals and system configurations, so that the system components can subsequently be easily selected or adjusted appropriately for a particular therapy. The data of the lookup tables may be used to determine the characteristics of IPCs and stimulators according to the stimulation signals/parameters, and geometries of system components. The adjustment/assessment of the system configuration can occur in step 48 of FIG. 17, or step 250. The influence of non-conductive portions of the IPC on nerve activation can be modeled as well.

The computationally derived simulation data shown in FIGS. 2a-8, 9b, and 9c were obtained by implementing a 3-dimensional finite element model that consisted of a surface electrode(s), a peripheral nerve (endoneurium, perineurium, and epineurium layers), an IPC (cuff-type hollow cylinder or solid rod), biological tissue (dermis, fat, muscle and bone), and a large saline bath. Electrical stimuli were applied in either a monopolar or bipolar fashion. Monopolar stimulation (modeled as per FIG. 1a) was achieved by setting the surface electrode at the skin interface as the cathode and the surface of the other anatomical objects (e.g., distal cut-end of leg) as the anode. For bipolar stimulation (modeled as per FIG. 1c), one electrode was set as the cathode and the other as the anode. All electrical conductivity values were obtained from the literature (Yoo and Durand, Selective Recording of the Canine Hypoglossal Nerve Using a Multi-contact Flat Interface Nerve Electrode, IEEE Trans Biomed Eng, 2004). The resulting extracellular potential (within the endoneurium region) obtained from the finite element model was used to compute the AF of individual nerve fibers. In MATLAB this was calculated as the second spatial difference of extracellular potential.

In the absence of an IPC, the electrical stimulation signals provided by the surface electrodes would normally stimulate the neural target tissue 12, and any non-targeted nerves within close proximity to the surface stimulator. It is an advantage of the current invention to provide the IPC to increase neural excitation of targeted nerve(s), and thereby effectively modulate one or multiple neural circuits that produce therapeutic effects. Although the exact mechanisms for the novel phenomenon which is the basis of this aspect of the system and method are not completely understood it may be helpful to conceptualize the system as follows. In one embodiment, the IPC may act to modify the extracellular electric potential generated by the surface electrodes, in order to focus the electrical field (i.e., act as a "lightning rod"), and thereby "enhance" the second spatial derivative of this field along a given target nerve. This enhancement can be seen in relation to changes in the nerve's activating function (AF). The AF is commonly used to quantify the excitation of nervous tissue. In this manner the present invention may serve to provide several advantages such as focusing the field toward an intended tissue target and away from adjacent tissue in order to produce improved therapy with less stimulation-evoked side effects. Another advantage is that the system and method permits the electrical therapy to use less power, at one or more stimulators, in order to supply the therapy and obtain a given effect that is either not normally attainable without more power, or which may not be attainable at all in the absence of the IPC. Using less power at the stimulation site can also provide other advantages such as greater patient comfort.

Figure 17:
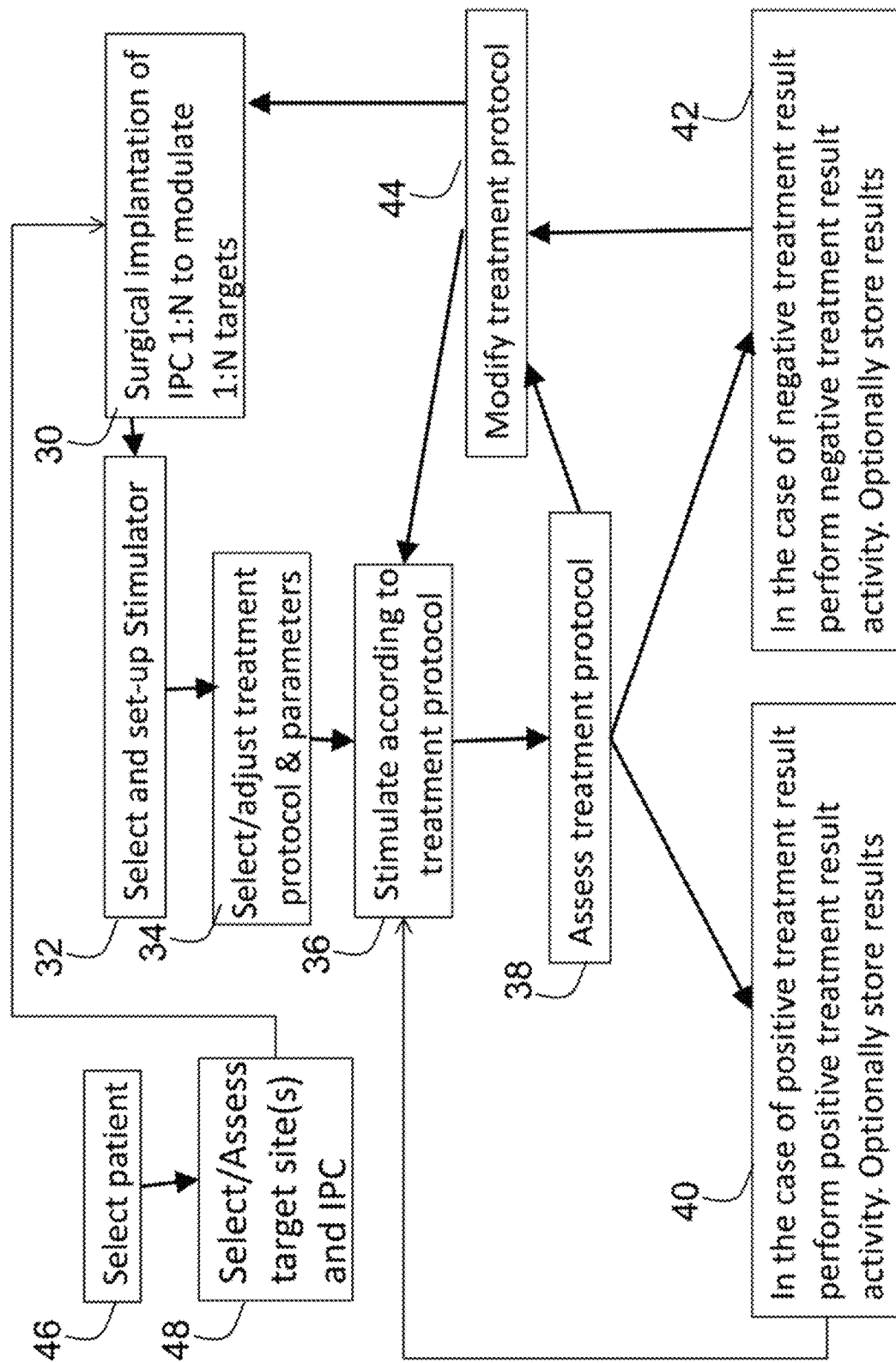
FIG. 17 is a logic flow block diagram showing a method for providing treatment to a patient.
Figure 22A:
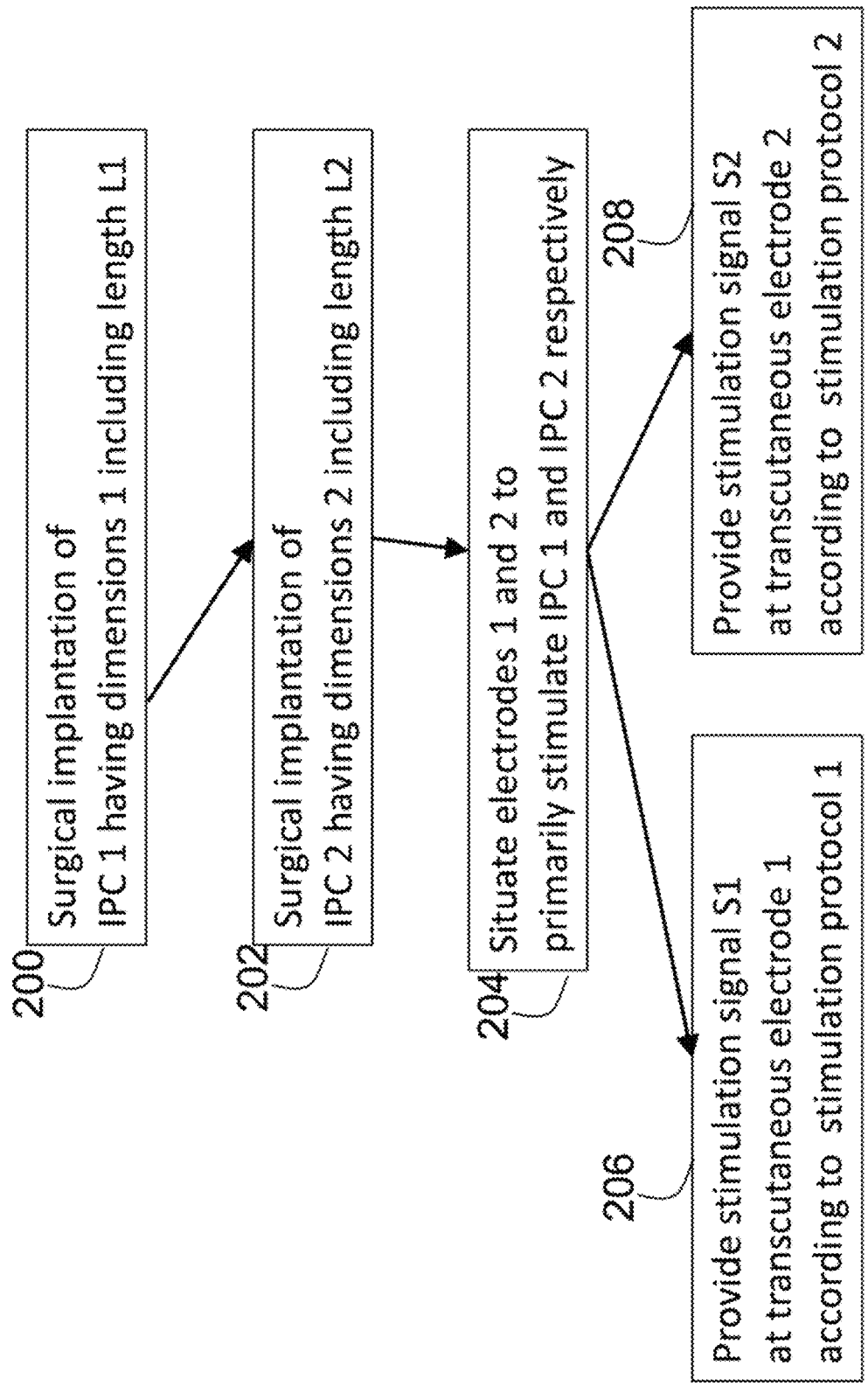
FIG. 22a is a logic block flow diagram for a method of using the eTNS system to stimulate using more than one IPC.
Figure 22B:
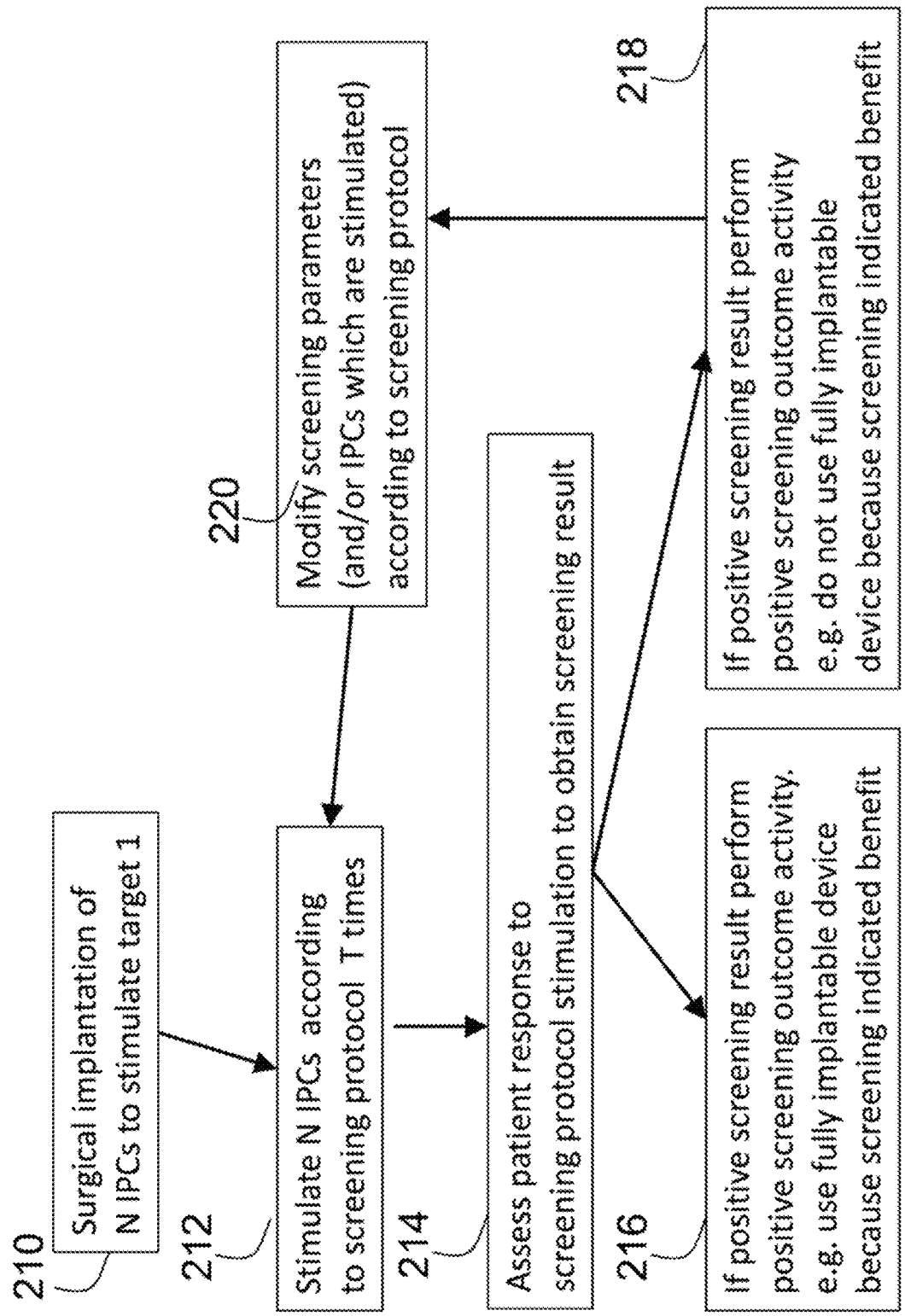
FIG. 22b is a logic block flow diagram for a method of using the eTNS system as a medical screening test.
Figure 22C:
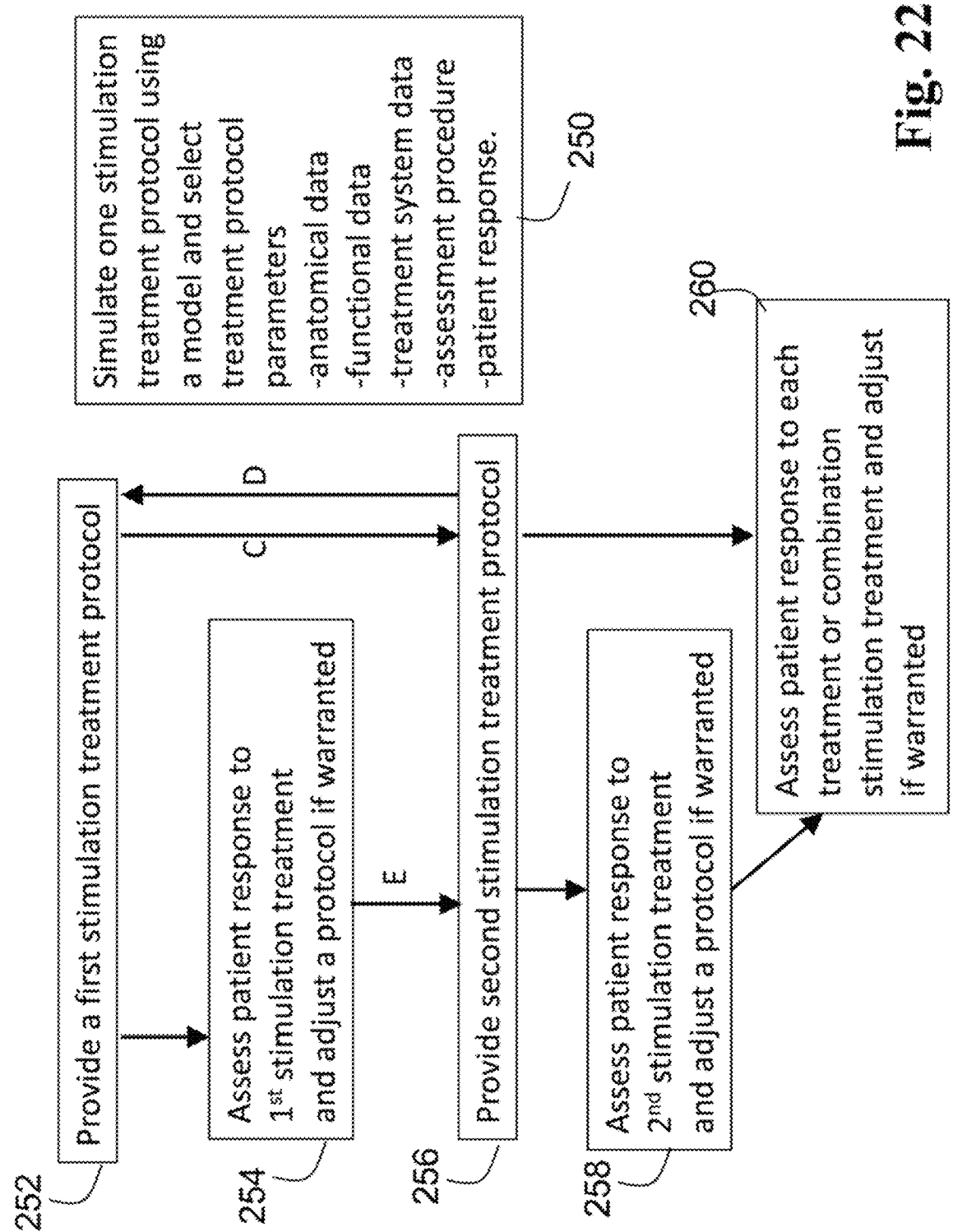
FIG. 22c is a logic block flow diagram for a method of providing a first stimulation treatment and second stimulation treatment for providing therapy.

Further advantages may be obtained if the IPC physical characteristics are configured for improved performance, such as may occur, in various embodiments, as part of step 48 of FIG. 17, or step 250 of FIG. 22c. For example, as will be shown, the IPC can provide larger improvements in performance when it is of an appropriate size, shape, material, and electrical property (e.g., higher conductivity than surrounding tissue). When configured according to certain considerations (e.g., size and location of at least one stimulator), the presence of the IPC 10 can reduce the net activation threshold of the targeted neural tissue. The "modification" of a stimulation field, according to the current invention, may include functionally modulating (e.g., redirecting, blocking, focusing, relaying, shaping, and/or otherwise having an effect on) the stimulation field so that the energy that reaches the targeted tissue enhances the effects of the applied stimulus to a greater degree than what may be achieved in the absence of the IPC.

One embodiment of the invention comprises implanting an IPC as shown in block 30 of FIG. 17 (e.g., metal nerve cuff surgically placed partially or fully around a specific nerve branch) that will be used in conjunction with various transcutaneous, percutaneous (e.g., needle electrode), implanted, or other electrical stimulation devices, such as in step 36. These may include conventional transcutaneous electrical nerve stimulation (TENS) devices, implanted multi-contact lead electrodes (e.g., Medtronic Interstim device), intravascular nerve stimulation systems, implantable spinal and neurostimulators, and deep brain stimulation systems. Various physical parameters of the IPC (e.g., shape, length, width, thickness, density, curvature, material(s), resistivity/conductivity, relative permittivity) may also be used to shape, enhance and/or otherwise modify fields, and the parameter may be set or adjusted in block 34 in relation to at least one stimulator (i.e. "stimulator-IPC pairing"). In embodiments, the fields may be produced by electrical stimulators, sound stimulators, or magnetic stimulators, such as those used in transcranial magnetic stimulation (TMS). When used with magnetic stimulation devices, the IPC may be shaped, positioned, and oriented, relative to the 1 or more coils that generate one or more stimulation fields. When the IPC is used with TMS stimulators, the method and system may be referred to as enhanced TMS (eTMS). When realized as part of an eTMS embodiment, the IPC may be constructed using material with lower electrical conductivity than that used for eTENS. In an embodiment, the electrical source 18 of FIG. 1c may be replaced by a magnetic source which utilizes magnetic coils as stimulators 22a, 22b, (and which may be separated from the IPC by distances represented by parameters termed D2+D3) to provide a magnetic field such as a time-varying magnetic field. When the setup of FIG. 1c is realized as a model, with the electrical source 18 replaced by at least one magnetic source generator, additional model parameters can be related to the strength, orientation, distance (e.g., D2/D3), 3-dimensional location, and shape of one or more magnetic coils. Use of a magnetic stimulator with at least one coil 152 (which can be realized for example by stimulation device 400' of FIG. 24c, or 50 of FIG. 18a) is shown in relation to providing vagal stimulation of a patient, by stimulating Implant #3 142c, in FIG. 21.

The following are non-limiting definitions for several terms that will be used in this disclosure which are provided to facilitate comprehension of the invention. In parts of the disclosure the terms may be used slightly differently as should be evident in those parts.

Targets. Targets for enhanced excitation may include any anatomical component of the human nervous system. The activation of targets may be used to modulate neural circuits or reflexes to achieve a desired clinical or therapeutic effect. These may include one or multiple nerves of the peripheral nervous system or a sympathetic nerve chain and/or all of the associated structures and nerves in communication with the sympathetic nerve chain. Certain targets may be very advantageously targeted by the current invention, such as targets that move or rotate or targets which are small. For example, it may be easier to stimulate an IPC which has been implanted in a portion of the eyeball which is coupled to a stimulator that sits outside of the eyeball, than to attempt to chronically implant an electrode that is capable of transmitting power along a path that requires the electrode to remain fixed and unbroken over a period of time. Another example is a target which may be within the vestibular system, or a facial or cranial nerve that is prone to movement which would make the use of a relatively larger, fixed electrode difficult. Another target may be in the foot, or near an ankle, where using a small IPC with an external stimulator will not be prone to the same damage or risk of electrode migration of an electrode which is tethered to a stimulator and which experiences shearing and pulling forces. As will be disclosed, targets for targeted stimulation using IPCs can also be various types of tissue such as muscle or bone.

Conditions. The medical conditions that can be treated by methods of the present system and method include a host of conditions such as, but not limited to, skeletal, immunological, vascular/hematological, sleep related, metabolic, muscular/connective, neurological, visual, auditory/vestibular, dermatological, endocrinological, olfactory, cardiovascular, reproductive, sexual, urinary, voiding, psychiatric, gastrointestinal, respiratory/pulmonary, inflammatory, infectious (bacterial, viral, fungal, parasitic), traumatic, iatrogenic, pelvic floor conditions and dysfunctions, drug induced and neoplastic medical and surgical conditions. Other conditions for which the technology may be applied are disclosed throughout this specification.

Treatment. As used herein, the term "treating" a medical condition encompasses, for example, therapeutically regulating, preventing, improving, alleviating the symptoms of, reducing the effects of, and/or diagnosing a medical condition. As used herein, the term "medical condition" encompasses any condition, disease, disorder, function, abnormality, or deficit influenced by the nervous system. Further, the methods of the present invention can be used to treat more than one medical condition concurrently. Non-limiting examples of medical conditions that can be treated according to the present invention include genetic, skeletal, renal, dental, immunological, vascular or hematological, muscular or connective tissue, neurological, ocular, visual (treated with or without concurrent visual stimulation), auditory or vestibular, tinnitus (treated with or without concurrent auditory stimulation), dermatological, endocrinological, olfactory, cardiovascular, reproductive, urinary, fecal, psychiatric, gastrointestinal, respiratory/pulmonary, neoplastic, or inflammatory medical conditions. Further, the medical condition can be the result of any etiology including vascular, ischemic, thrombotic, embolic, infectious (including bacterial, viral, parasitic, fungal, abscessal), neoplastic, drug-induced, metabolic, immunological, collagenic, traumatic, surgical/iatrogenic, idiopathic, endocrinological, allergic, degenerative, congenital, or abnormal malformational causes.

Further, treatment may include stimulation. Stimulation may include any type of modulation of physiological or biological related activity. Thus stimulation and modulation may be used interchangeably when the intention is to describe the influence of a generated field upon human tissue. Other conditions for which the technology may be applied for "treatment" are disclosed throughout this specification. Treatment may also include providing benefit to a human by producing a desired effect, such as, stimulation provided to promote weight loss.

Implant Component. The implanted component that is often referred to as an implantable passive component "IPC" may be as simple as a passive conductive element. The IPC may also have securing structure such as flaps that can be mechanically folded over to situate and secure the IPC in place. The IPC may have a least one suture hole for securing the IPC in place. The IPCs may be of many shapes and sizes and may have physical dimensions that are configured based upon the tissue target where it will be used, the distance of the target from the stimulator, and the size of a stimulator, as well as other factors. The IPC may have conductive and non-conductive surfaces and portions, as well as more than one conductive portion, which are not electrically continuous with a different conductive section. When an IPC has circuitry that is driven by electrical or magnetic fields or otherwise has active components such as circuitry then the IPC becomes an implantable active component "IAC", such as a neurostimulator that is externally powered or self-powered by internal power. The IPC may be configured so that permanent implantable pulse generators can be attached to the IPC in the case where the IPC will be used, or subsequently used, as a nerve cuff. In this case the IPC functions as an electrode of an implanted neurostimulator. Allowing an IPC to be connected to an implantable neurostimulator can be advantageous such as may occur if cutaneous stimulation provided in combination with an IPC is found to be inefficient, or becomes inefficient over time and an implantable stimulator will then be used to provide stimulation signals to the IPC without having to implant another electrode. In various embodiments of the invention an IPC, IAC, nerve cuff, or implantable neurostimulator may be used to provide stimulation signals to target tissue. It should be understood that these examples, are non-limiting. For example, in the case of selective nerve branch stimulation an embodiment of the invention may be approximately realized using any of the following: IPC, IAC, self- or externally-powered neurostimulator which works with a multi-contact nerve cuff.

Stimulator. A stimulator is a system component that supplies a stimulation signal to tissue. A stimulator may refer to a tens electrode, an electrode lead having at least one electrical contact, one or more electrode contacts, nerve cuff, a multi-contact electrode, a spinal stimulation lead, a magnetic coil, a sound, vibration, or light transducer, or other component for emitting energy for modulating tissue. The stimulator transmits at least one stimulation signal to tissue that is provided by, for example, an electric, magnetic, or sonic signal generator, a pulse generator, or an implanted a neurostimulator. In a neurostimulation system, it is generally understood that the neurostimulator will supply a stimulation signal to a stimulator which may be realized as at least one electrode.

Stimulator-IPC pairs. At least one stimulator and at least one IPC can be selected or adjusted so that these work well together in the intended manner to provide enhanced, targeted stimulation to a tissue target, compared to that which occurs when an IPC is not used. For example, a stimulator-IPC pair may include a stimulator that has a physical dimension set in relation to the IPC so that the two are well "matched". The physical dimension of an IPC or (at least one) stimulator can include, for example, the shape, size, length, orientation, and thickness of at least one conductive portion. Further, a stimulator-IPC pair may be matched by being configured so that the stimulator and IPC have at least one edge that is aligned, which has been shown, in some instances, to provide for increased enhancement of effects on the target in the stimulation field.

Electrical fields and IPC-stimulator orientations. Various types of signals and fields may include electrical, magnetic, or both (and can also be (ultra-)sound, vibration, or laser/light). In some embodiments, a modulation signal may include a moderate amplitude and moderate duration, while in other embodiments, a modulation signal may include a higher amplitude and a shorter duration. Various amplitudes and/or durations of field-inducing signals which are provided by stimulators such as 88, 90 may result in functional (i.e., super-threshold) modulation signals. Whether a field-inducing signal rises to the level of a modulation signal can depend on many factors (e.g., distance from a particular nerve to be stimulated; whether the nerve is branched; orientation of the induced electric field with respect to the nerve; type of tissue present between the electrode stimulators and the nerve; size of the IPC; suitability of pairing between the stimulator and IPC, etc.). Whether a field inducing signal constitutes a modulation signal (resulting in an energy field that may cause nerve modulation) or a sub-modulation signal (resulting in an energy field not intended to cause nerve modulation) may be affected by the proper alignment (e.g., x-, y-, and/or z-axis orientation and/or displacement) of at least one edge of the IPC and the stimulator. Both modulation and submodulation fields may be created as part of the invention.

Stimulation/treatment/therapy protocol. Protocols can be implemented under control of a closed or open loop algorithm implemented by processing circuitry of an implantable neurostimulator, under direction of a physician, as adjusted or selected by a patient during therapy, or otherwise. Many of the protocols that are described herein for implantable neurostimulators are understood to equally well accomplished by a doctor in a clinic or a patient at home, with appropriate modification, without departing from the spirit of the disclosed invention. Any protocol that is disclosed as being carried out by an implantable device with electrodes may also typically be considered a candidate for being accomplished by a partially or fully external stimulation system, and vice versa. It is generally understood, that a step of a method of stimulation disclosed herein can be embodied within a stimulation protocol accomplished by, for example, a fully implantable neurostimulation system. A therapy/treatment protocol may include not only a stimulation protocol, but also a sensing protocol and may also include rules and algorithms for how to process sensed data and how to change stimulation parameters based upon the evaluation results of sensed data. The therapy protocol may also include the provision of concurrently supplied drug therapy under control of a device or by the patient.

FIG. 2a shows a graph of the results of a modeled AF of a single axon located within the posterior tibial nerve (PTN) in response to a simulated current pulse (−1 mA) applied by a surface electrode stimulator. A computational finite element model was used to assess enhancing the excitability of the PTN. The model consisted of a 3-dimensionally reconstructed human lower limb with a surface electrode placed over the PTN. The anode was the proximal cut surface of the lower leg (farthest from the surface electrode). As indicated in FIG. 1a, the IPC 10 is simulated as a highly conductive material placed in close proximity to the nerve and was modeled as a rod with diameter=0.2 mm and length=5 mm. The graph shows the simulated effects of varying the distance between the IPC 10 and the target nerve 12 on the calculated AF. In all simulations, the maximum AF value was used to determine the excitability of the targeted nerve. The AF was calculated for a series of simulations, where the distance between the implant and the PTN was decreased from 8 mm (outside the epineurium) to 0 mm (direct contact with nerve bundle, perineurium). The results of FIG. 2a indicate that the IPC—for the given length, diameter, shape, and conductivity—begins to enhance neural excitability at a distance of approximately 3 mm from the nerve. This enhancement continues to increase to almost 8-fold when the implant is embedded within the connective tissue layer surrounding the nerve itself (the "epineurium"). The graph suggests that, using this setup, a steep benefit is gained as the IPC-to-nerve distance is reduced below 2 mm. Modifications to the modelled or real world system configuration (e.g., size and location of the stimulator, IPC or nerve) may change the shape of the graph. However, in a typical embodiment of the IPC, the conductive component will likely be implanted to reside along the nerve which it stimulates such that its entire length is adjacent to the nerve. In an embodiment the IPC is implanted to reside approximately parallel to the target nerve and is secured at two or more sites, such as both at its proximal and distal end, in order to deter migration and rotation.

FIG. 2b shows the simulated results reflecting changes in the AF as the distance between the IPC and nerve combination ("Implant+Nerve") and at least one of the stimulating electrodes is increased. The effects of the implant on neural excitability were quantified by comparing the maximum AF between the control case (labeled as "no IPC" in the figure) to the case where an IPC was placed in close proximity to the nerve (i.e., inside the epineurium). The implant caused a 184% increase in AF for a nerve located 7 mm from the skin surface (i.e., site of stimulating electrode). Compared to the nerve without an IPC (labeled as 'no IPC', dashed line), the AF is consistently greater with the IPC placed close to the nerve (labeled as "IPC inside epineurium", solid line). Further, at a stimulator-to-IPC distance of 30 mm the AF achieved by the IPC is similar to the AF achieved at a stimulator-to-nerve distance of under 10 mm, when no IPC is used. Benefit may be also obtained at greater distances beyond those shown in the graph (and other graphs disclosed herein, which are not meant to be limiting).

Repeated computer simulations at stimulator-to-nerve distances of up to 3 cm (as per FIG. 2b) showed the AF drops precipitously over the initial 15 mm and asymptotes at about 25 mm. This trend is the same for both cases (with and without the IPC), but clearly shows the IPC enhances neural excitability at all nerve depths.

FIG. 3a shows modeled results of the "relative excitability" of the target nerve, calculated as the ratio of the AF of an "IPC present (rod)" condition compared to an "IPC absent (no rod)" condition (see FIG. 2b). The positive slope indicates that the enhanced neural excitability effect due to the IPC is relatively greater for nerves located further away from the surface electrode stimulator. FIG. 3a simulation results suggest that stimulation amplitude required for transcutaneous nerve activation can be significantly reduced using an IPC. FIG. 3a data suggest that the stimulation amplitude at the surface may be reduced to approximately 25-50% of the original stimulation intensity, since the relative excitability (RE) moves from about 1.8× to about 4×.

FIG. 3b shows the effects of electrical conductivity of the IPC (rod-type implant) on the RE (relative excitability) of the target nerve Enhancement of neural excitability (quantified as the relative excitability) is maximally achieved when the electrical conductivity of the IPC equals or exceeds 4E+2 S/m (or approximately 1.00E+3 on the graph). This lower boundary corresponds to an electrical conductivity that is approximately 5 orders of magnitude greater than that of the nerve (e.g., epineurium). These results suggest that most highly-conductive metals would serve as appropriate IPC materials for enhancing TENS, with platinum or gold serving as good candidates. Of course various conductive alloys, and semi-conducting material which may be suitably doped, may be used to create at least portions of the IPC.

Figure 4A:
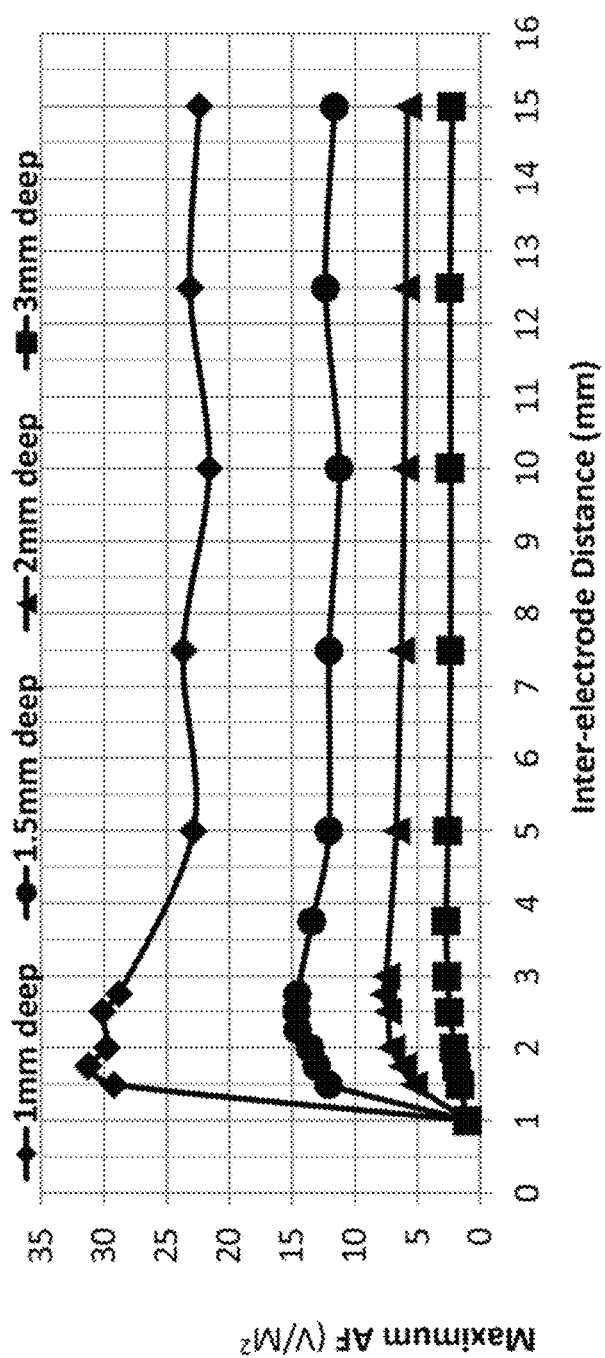
FIG. 4a is a graphical representation showing data from computer simulations (according to setup shown in FIG. 1c) that calculated the AF generated by conventional TENS (no IPC) as a function of both the depth of the nerve (D2, depth distance to nerve from cutaneous stimulation electrode) and the distance between the anode and cathode surface electrodes (D1, inter-electrode distance is the x-axis).

FIG. 4a shows the effects of nerve depth (from skin surface) on the inter-electrode distance between two surface electrode stimulators (bipolar stimulation, see FIG. 1c). The effect was quantified by the maximum AF calculated from computer simulations of the rat PTN that simply included surface stimulators and did not also incorporate the subcutaneous placement of an IPC. These results are relevant to transcutaneous stimulation embodiments of the invention having bipolar surface electrodes. The finite element model, having a monopolar setup which is illustrated in FIG. 1a, and which was used to generate results presented in FIG. 2a, 2b and FIG. 3a, 3b, was modified to approximate transcutaneous electrical stimulation of the PTN in a rat. This modification simply involved scaling all components of the model to that of rodents: nerve radius (0.38 mm), nerve depth (1.5 mm), skin thickness (0.46 mm), pair of surface electrodes (2 mm×1 mm) comprising the anodic and cathodic electrodes. The results of this computer model indicate that optimal nerve activation (maximum AF) is achieved when the inter-electrode (stimulator) distance approximates the depth of the nerve from the skin surface (1 to 3 mm). The maximum AF at an inter-stimulator distance of 1 mm showed low neural excitation for all nerve depths. This suggests the electrical current is effectively shorted between the cathodic and anodic electrodes. When an IPC is used, the results may change due to the physical dimensions of the IPC and stimulators, both in absolute and/or relative terms.

These results indicate that deeper nerves are more easily activated by bipolar electrode pairs when greater separation is used. In one embodiment of the system 6, shown in FIG. 1c, the inter-stimulator distance D1 should be varied proportionately to the distance between a surface stimulator and the nerve D2. The effects relating to spacing of the surface electrodes, in relation to depth of stimulated tissue target, may be applicable whether an IPC is used or not. In general, if the electrodes are placed closer together the area of highest current density will be relatively superficial, while further spaced electrodes will cause the current density to be higher in deeper tissue. Electrode stimulator size will also change the current density, with larger electrodes decreasing current density relative to smaller electrodes. Accordingly, placing a smaller electrode closer to the nerve or IPC with a larger electrode (dispersive electrode) remote from (further away) the tissue target should cause the current density to be higher near the smaller electrode (near the tissue target). Cutaneously applied electrode size and position characteristics will therefore alter the characteristics of the current density and path. When an IPC is used, this relationship must also be considered in relation to the specifications of the IPC. If the IPC and stimulators are "paired" with respect to selected characteristics, in order to increase the effectiveness of stimulation, then these pairing should be considered with respect to factors such as depth of the IPC/nerve, and may be part of step 250. Stimulation of a deeper nerve may require a larger spacing of the surface stimulators, which may, in turn, require an increased length of IPC. These, as well as other considerations may be used in the adjustments to the current invention stimulation systems and methods of providing therapy to a patient.

Figure 4B:
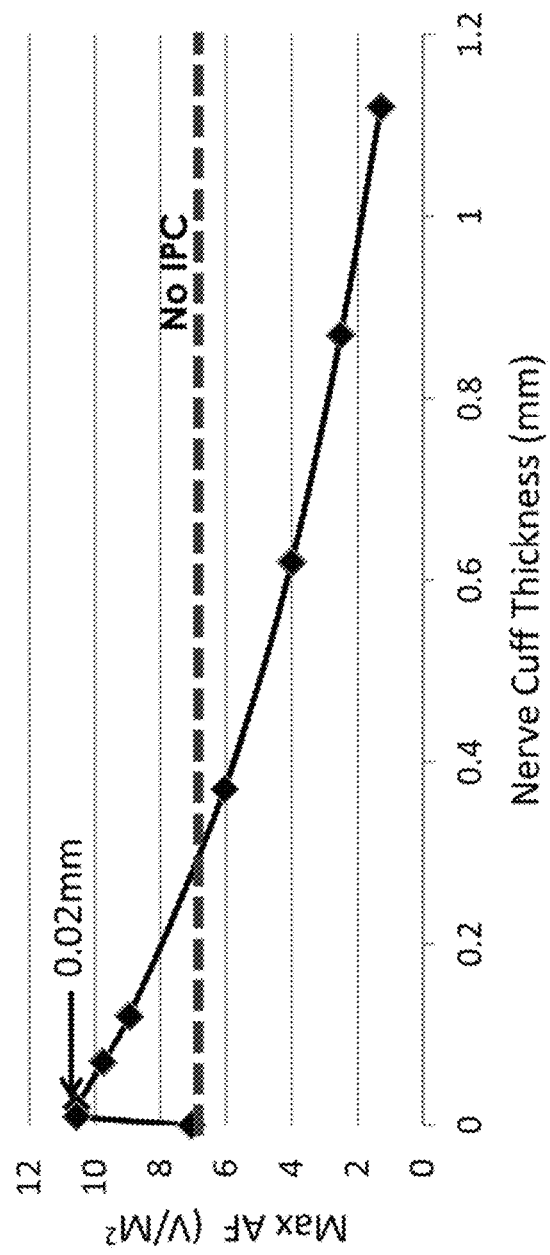
FIG. 4b is a graphical representation showing data from computer simulations that depict the effects of IPC thickness (i.e., thickness of cylindrical wall of nerve cuff) on enhancing neural excitability ("Max AF") and shows that, compared to the case of 'no IPC', an IPC thickness of less than 0.3 mm increases AF, while a thickness above 0.3 mm was found to reduce neural excitability.

FIG. 4b shows a graph of computationally generated simulation results exploring the effect of IPC thickness. These IPC physical characteristic results are relevant to, and can be used to guide, the adjustment the IPC shape characteristics. Instead of the IPC modeled as a solid cylindrical rod placed within the epineurium (FIG. 1b), the IPC was modeled as a simple cylindrical cuff wrapped around the nerve (FIG. 1c). This practical and simple design is currently used for many implantable nerve cuff electrodes. With the cuff length set at 5 mm, the thickness of the cylinder was varied from zero (reflecting no IPC) up to 1.2 mm. The results of this study suggest that neural excitability is maximally enhanced by thinner IPCs (e.g., 20 μm thickness), at least in the case of implants with a length of 5 mm and a relatively shallow nerve depth of 2 mm. Various manners of modifying the IPC physical characteristics may also serve to increase excitability, aside from adjusting the shape characteristic to create a thin IPC. For example, the physical characteristics can be selected so that the IPC created of a mesh, or using material with different electrical conductivity, may also be simulated to assess performance and/or selected for use to provide improved excitability. In one embodiment, using a material such as mesh that decreases the mass of the implant, increases flexibility and adaptability of the IPC, and increases patient comfort, or has other advantages may improve the performance of the system and decrease the likelihood of adverse events. Further, it should be noted that, for the simulation signals and parameters investigated in the study, an IPC thickness of less than 0.3 mm increased AF, while a thickness above 0.3 mm was found to reduce neural excitability. When using a bipolar stimulation configuration, a therapy system may rely upon different IPC thickness to "selectively" activate targeted nerve(s). Since increasing thicknesses of the IPC above a certain dimension (e.g., IPC thickness=0.3 mm) was found to increase the activation threshold, in one embodiment, an IPC of increased thickness above that threshold thickness can be used to suppress activation of adjacent non-target nerves at this particular nerve depth. In combination with this, a thinner IPC, configured to increase the excitability of a nerve, can be used on the target nerve.

Figure 4C:
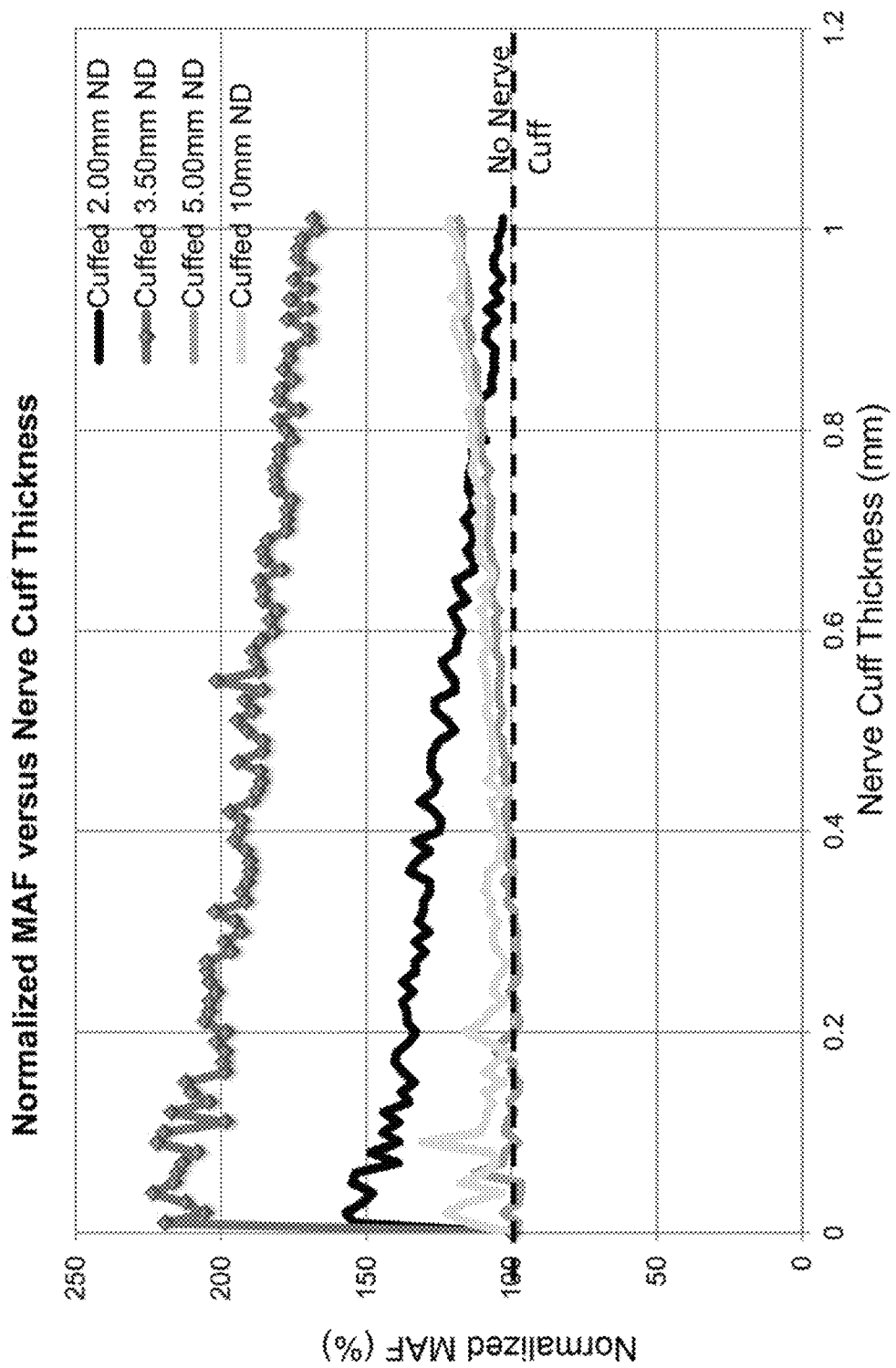
FIG. 4c is a graphical representation showing data from computer simulations showing the normalized Max AF as a function of both the thickness of the nerve cuff (IPC) and the depth distance of the nerve from skin surface (ND).

FIG. 4c is a graphical representation showing data from computer simulations involving a monopolar stimulator used to activate a peripheral nerve placed at varying depths. In this embodiment, the normalized MAF (maximum activating function) increased as the thickness of the IPC (cuff-type implant) was decreased, at nerve depths (ND) of 2 mm and 3.5 mm. The enhanced effects of reducing IPC thickness at these relatively shallow nerve depths corroborate our simulations that used bipolar stimulators (FIG. 4b). However, at deeper nerve depths (5 mm and 10 mm) the normalized MAF increased as the IPC thickness was increased. This enhancement in neural excitability indicates that greater overall electrical conductivity of the IPC may play an important role for nerves located relatively farther from the skin surface. As a result, this suggests that eTENS activation of nerves at relatively greater nerve depths may be further enhanced such as by using different IPC material (e.g., higher electrical conductivity), and larger dimensions (e.g., thickness or length, see FIG. 8).

Figure 5A:
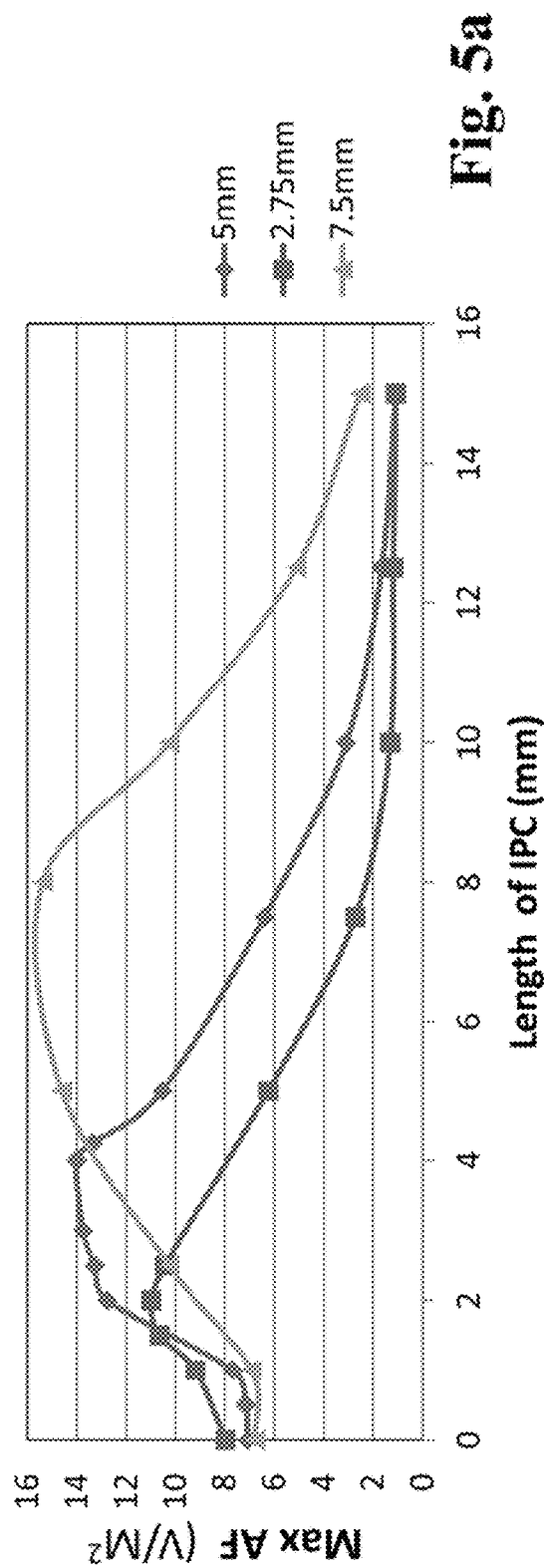
FIG. 5a is a graph of data from computer simulations, (finite element model of FIG. 1a scaled to dimensions of a rat), that depict the relationship between the length of the IPC (cuff-type) and the distance between the bipolar stimulating surface electrodes (similar to the setup shown in FIG. 1c).

FIG. 5a shows a graph of simulated results of the combinations of inter-electrode distance and IPC length for achieving effective peripheral nerve activation (i.e., lowest activation threshold). In a model of rat PTN stimulation (e.g., as per the set-up of FIG. 1b) the peak of each trace corresponds to an IPC length that is very similar in physical dimensions to the inter-electrode distance. The data suggest that enhancement of neural excitation is improved when the inter-electrode distance approximates, or is a little less than, the length of the IPC, for the range of IPC lengths shown and for the stimulation waveform and protocol used. Changes in the AF were studied in response to varying the length of the implant, from 0 mm (no implant) up to 15 mm. These simulations were repeated for different inter-electrode distances: 2.75 mm, 5 mm, and 7.5 mm. For each given inter-electrode distance and bipolar configuration, the maximum AF was achieved when the implant length approximated this distance (e.g., 8 mm implant length for an inter-electrode distance of 7.5 mm). Accordingly, in a system for providing eTENS therapy 6 the IPC length can be set in proportion to the distance between at least 2 stimulators, such as being equal to, or slightly less than, or having other relationship to the distance between the two electrodes.

In FIG. 5a, the zero mm data points are equivalent to not using any IPC ("no IPC"). Accordingly, any system and method which utilizes an IPC that increase the AF above the no-IPC condition can provide enhanced nerve excitability. Further, any AF which is below the no-IPC condition, for example, IPC lengths of about 12 to 15 mm when the inter-electrode distance is any of those tested in the figure, will serve to decrease the excitability of that nerve. Accordingly, providing IPCs that cause decrements in excitability to non-target nerves may provide a strategy for further increasing the selective activation of a targeted nerve. Even when not discussed explicitly, in all other figures of this application, when the AF drops below the no-IPC condition, the results could be understood to be relevant to providing greater selectivity of target nerve stimulation when the IPC is used with non-target nerves.

Additional computer simulations were also conducted using a single monopolar surface electrode that was aligned to the center of the IPC 10. The width (W) remained the same, but the length was varied. The anodic (return) electrode was modeled as being placed far away from the active cathode. The results of this study showed that maximum AF (i.e., lowest stimulation threshold) was achieved when the length (L) of the single electrode was larger than the IPC. In other words, when the mono-polar electrode was sized to fit exactly in between the pair of electrodes in FIG. 1c the optimum activation was not found. While the results of FIG. 5a, suggest that optimum nerve stimulation is achieved when the opposing edges of the IPC align (approximately) with those of the surface electrodes, this may be true for bipolar but not monopolar stimulation. It is likely that in one embodiment of a clinical system, the edges of the IPC and at least one electrode should be approximately aligned (e.g., spatial and angular alignment), while alignment of two parallel edges may only improve bipolar stimulation. Initial data has suggested that in the case of monopolar stimulation, increased activation is obtained when the monopolar electrode is longer than the IPC (data not shown). Accordingly, in one embodiment of the system which uses a monopolar electrode, at least the length or width of the stimulator should be made to be larger than then IPC, and further only one edge of the IPC should be aligned with an edge of the stimulator electrode.

Figure 5B:
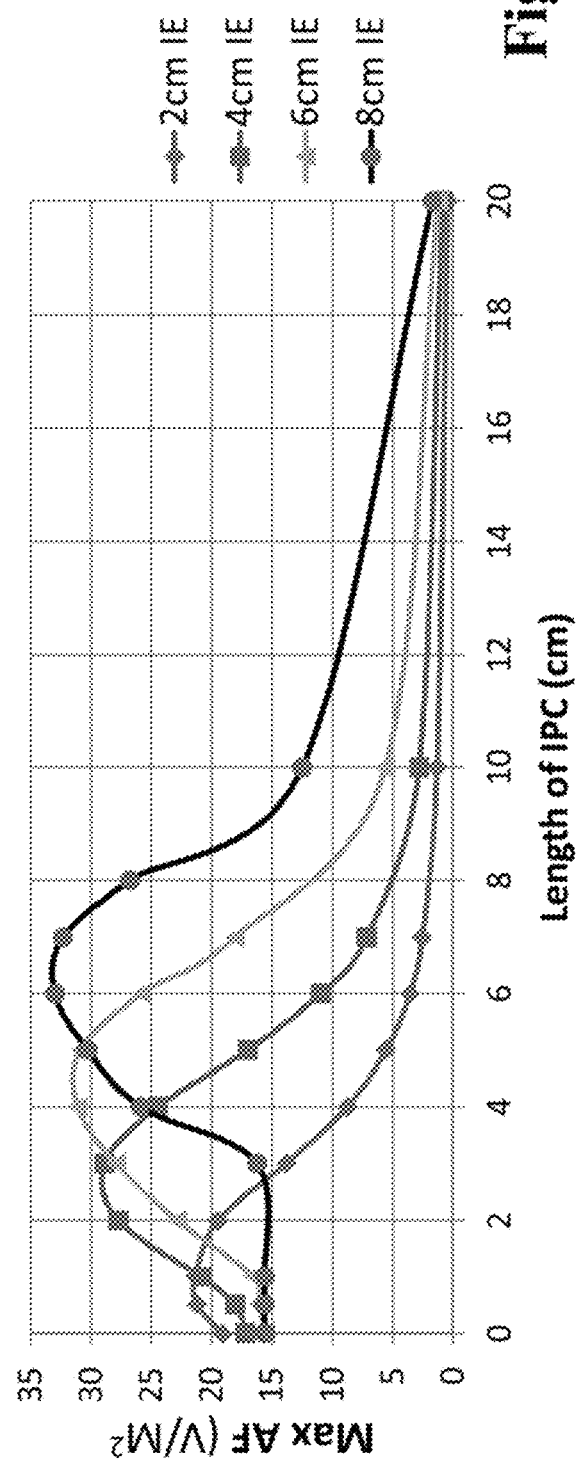
FIG. 5b is a graph of data from computer simulations (finite element model of FIG. 1a scaled to dimensions of a human) of enhanced transcutaneous nerve stimulation (eTENS) that are in agreement with findings from an experimental rat model (i.e., results of FIG. 5a).

FIG. 5b shows a graph of computer simulations using the original human PTN model (inter-electrode distance range: 2 cm to 8 cm) that confirm the results of the rat PTN model translate to larger physical dimensions.

Figures 6A, 6B:
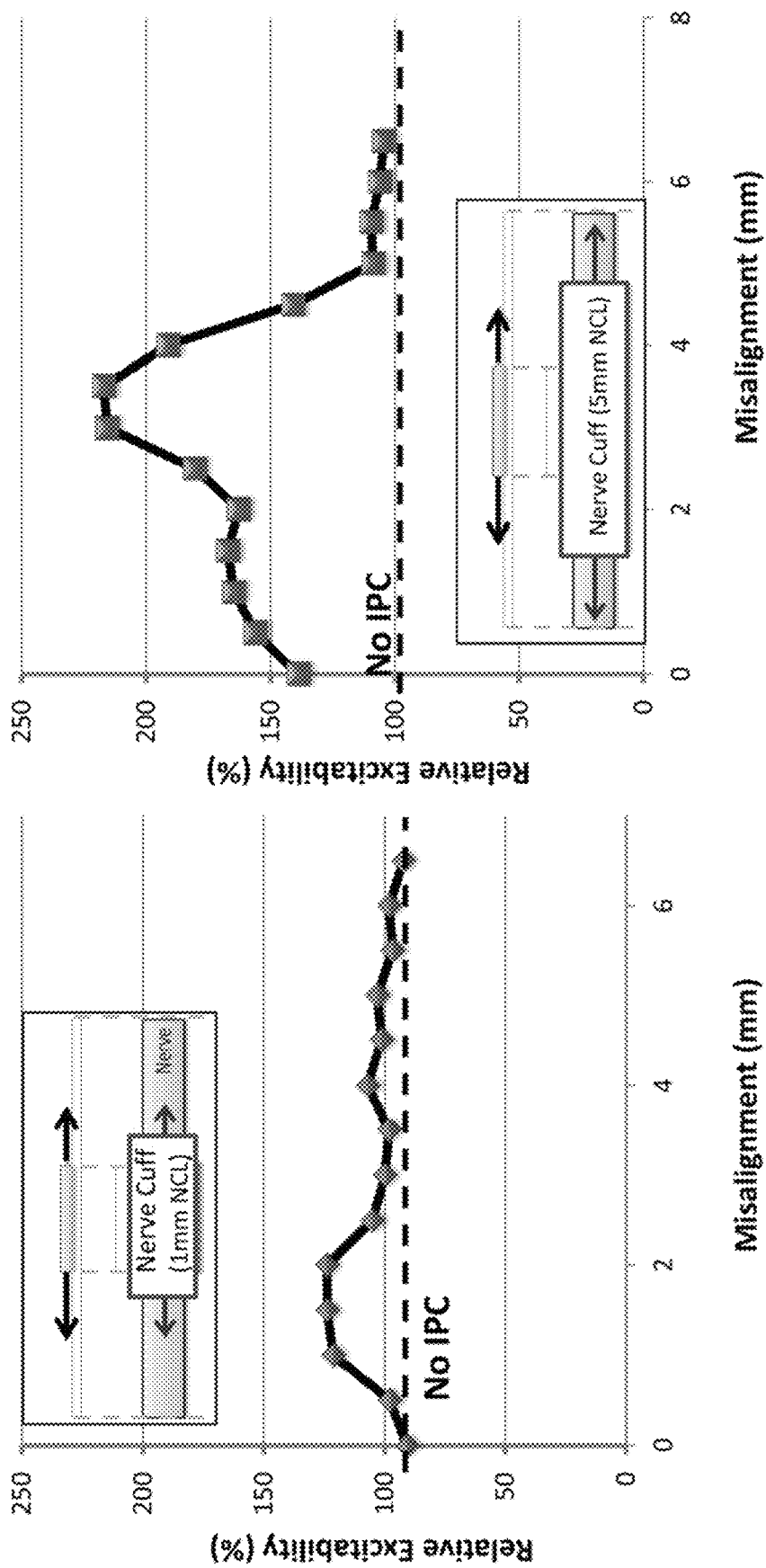
FIG. 6a is a graph of data from a computer model of eTENS (scaled to dimensions of a rat) involving monopolar surface stimulation in which the surface electrode (area=1 mm×1 mm) and IPC (nerve cuff length, NCL=1 mm) are of similar dimensions, and initially aligned as depicted in the inset diagram (misalignment=0 mm) and in which the relative excitability (% AF normalized to TENS with no IPC) is calculated as the IPC is shifted along the nerve (surface electrode is stationary) such that the misalignment increases from 0 mm to 6.5 mm.
FIG. 6b is a graph of data from a computer model of eTENS (scaled to dimensions of a rat) involving monopolar surface stimulation, in which the dimensions of the surface electrode (area=1 mm×1 mm) are smaller than the IPC (nerve cuff length, NCL=5 mm), and in which the IPC is shifted along the nerve (surface electrode is stationary), such that the misalignment increases from 0 mm to 6.5 mm

FIG. 6a shows a data from a computer model that simulated eTENS using a monopolar surface electrode. When both edges of the electrode (length of 1 mm along the nerve) and the IPC (nerve cuff length of 1 mm) are aligned (misalignment=0 mm), the AF is actually below that of TENS without any IPC. However, as the IPC is moved along the nerve, the AF becomes approximately 1.25 times greater than that for conventional TENS. In this example (nerve depth=2 mm), the 'enhancing effect' of the IPC persists even with an inter-edge gap (distance between the right edge of electrode and the left edge of IPC) of up to 1 mm (i.e., misalignment=2 mm). Beyond this misalignment, the IPC has negligible effect on neural excitability. Accordingly, in one embodiment of the system which uses a monopolar electrode, the alignment of the IPC and stimulator should be adjusted, as per step 48 in FIG. 17, so that the inter-edge gap provides improved AF. The nerve depth in this example was only 2 mm and different relative excitability function results may be obtained when simulated for other nerve depths which can then be used to adjust the clinical embodiments of the systems and methods of the current invention.

FIG. 6b shows data from a computer model that is similar to FIG. 6a, but with a longer IPC (nerve cuff length=5 mm). These results show that if the IPC is longer than the surface electrode and that the electrode overlaps with the nerve cuff (misalignment up to 2.5 mm), the AF of the target nerve is enhanced by 1.4 to 1.8 times that of conventional TENS. Maximum enhancement is achieved (increased AF by 2.2 times) when the inter-edge gap (between the electrode and IPC edges) is between 0.0 mm and 1.0 mm (which occurs when the misalignment is about 3 mm). At inter-edge gaps greater than 2.5 mm (misalignment above 5 mm), the IPC does not affect neural excitability. It should fairly easy to implement the current invention during treatment with inter-edge gaps that produce at least 25% increase in excitability compared to when no IPC is used. Although the effects of IPC alignment at deeper nerve locations are not explored here, initial results indicate the alignment effect may be less pronounced for nerves further from the skin surface (similar to what is seen with nerve cuff thickness, FIG. 4c).

Figure 7:
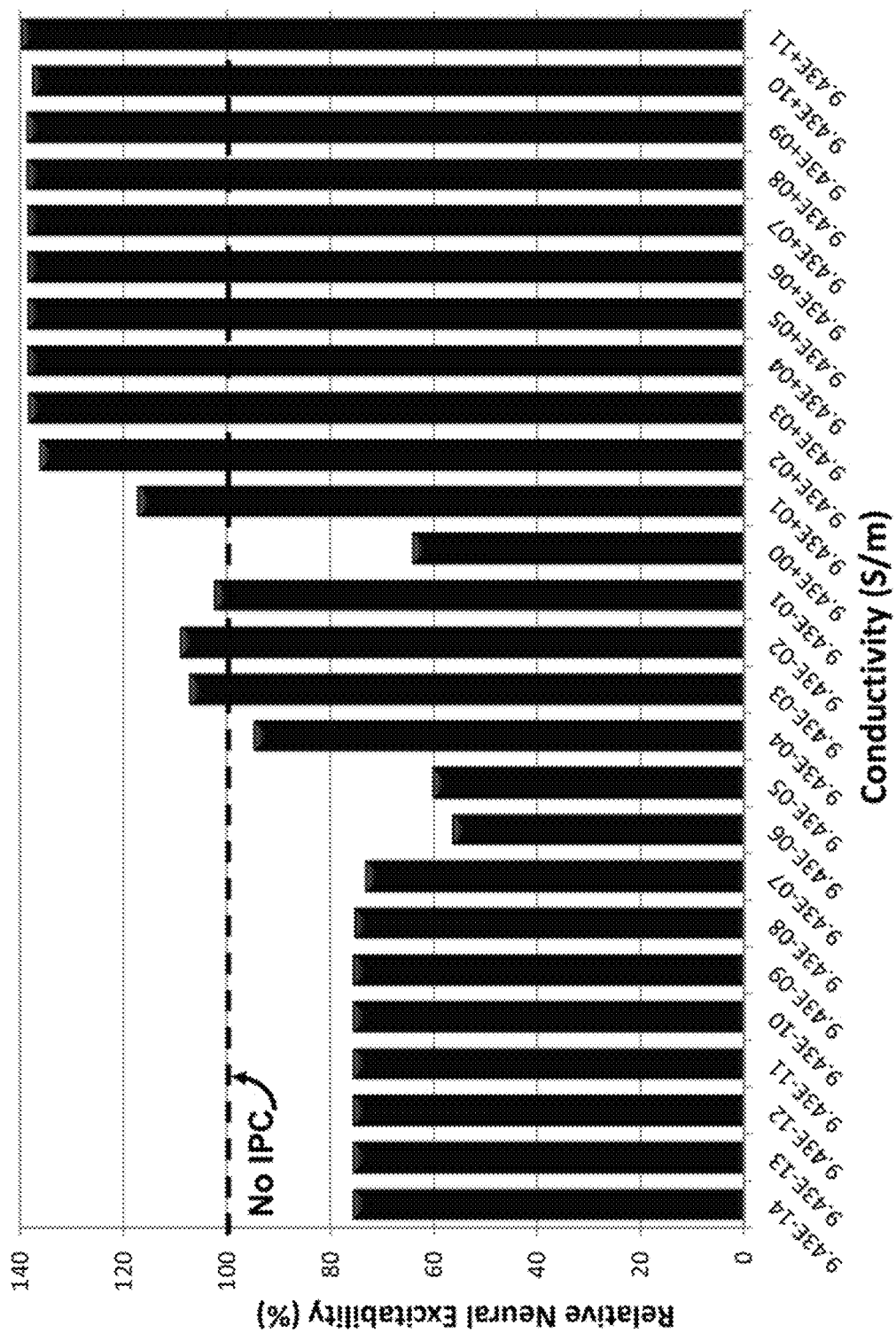
FIG. 7 is a graph of data relating to the effects of the electrical conductivity of the IPC (monopolar stimulation model in FIG. 6a) on the "relative neural excitability (%)", as the conductivity values were increased from 9.43e-14 to 9.43e+11.

FIG. 7 shows a graph of computationally generated results exploring the effects of the electrical conductivity of the IPC on the relative neural excitability using monopolar stimulation (nerve depth=2 mm, IPC thickness 0.02 mm). For conductivity values above 9.43E+2, there is observed enhanced neural excitation (as shown in FIG. 3b). However, at electrical conductivity values between 9.43E-4 and 9.43E-1 there is observed negligible effects of the IPC (no change in relative excitability); whereas at conductivity values below 9.43E-5 there is observed reduced excitation of the nerve on which the IPC is implanted. These findings suggest a novel system and method of increasing the selective activation of a targeted nerve in which a highly conductive IPC is implanted on the target nerve. Additionally, a poorly conductive IPC may be placed on or near one or more non-target nerves to deter unwanted activation. As with the other characteristics of the system, the proper conductive characteristics for one or more IPCs can be selected or adjusted based upon simulated modelling or based upon system configuration including, for example, the number and position of IPC and stimulators which will be used during treatment.

Figure 8:
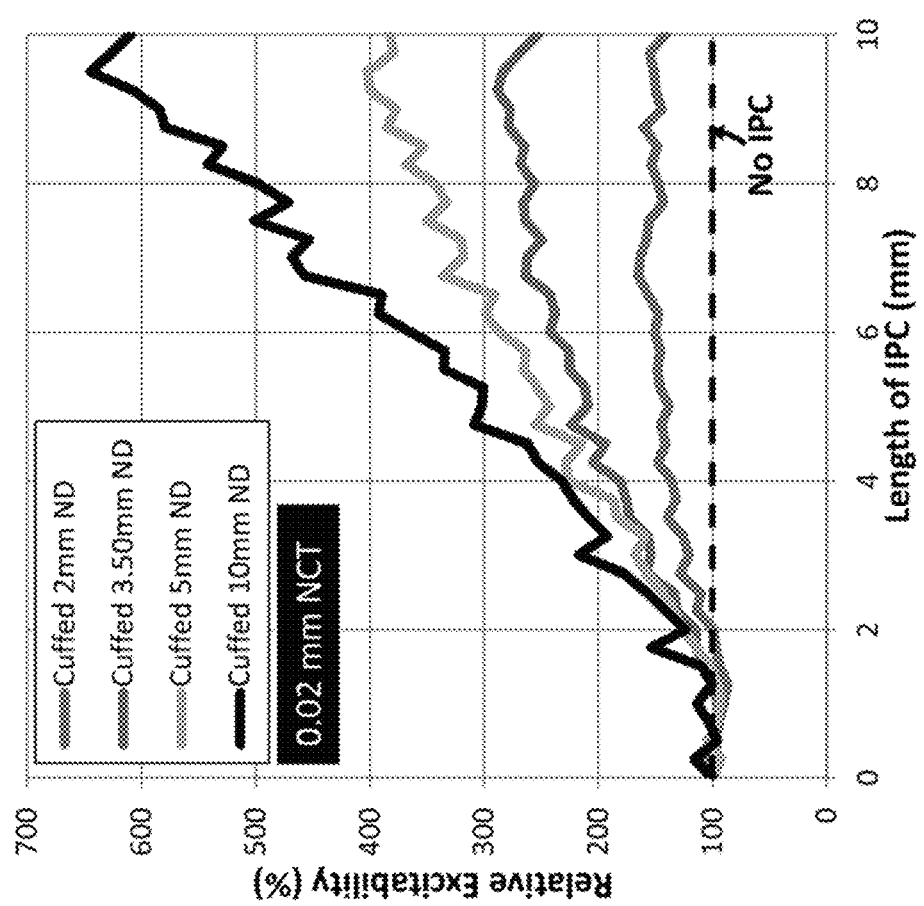
FIG. 8 is a graph of data from a computer model of eTENS (monopolar stimulation model in FIG. 6a), where the effects of IPC length on relative excitability were simulated for an IPC with 0.02 mm nerve cuff thickness (NCT, refer to FIG. 4b), and where the length of the IPC ('cuffed around the nerve') was increased from 0 mm (no-IPC baseline condition) to 10 mm for 4 different cases of nerve depth (ND) from the skin surface.

FIG. 8 shows the relationship between the length of the IPC and the depth of the nerve (ND). In this computational model, the IPC was a nerve cuff with 0.02 mm thickness and the IPC+nerve was positioned at 4 different nerve depths: ND=2 mm, 3.5 mm, 5 mm, and 10 mm from the skin surface. For this example of monopolar stimulation, the data indicates that increasing the length of the IPC can markedly increase neural excitability. This 'enhancement effect' is more pronounced for nerves located further away from the skin surface. For shallow nerve depths (2 mm), the effects of increasing the IPC length are diminished beyond 4 mm, with the neural excitability increase showing a plateau at approximately 1.5× of conventional TENS (no IPC). In contrast, at deeper locations (10 mm ND), the AF continues to increase up to IPC lengths of 9.5 mm, where the neural excitability reaches a 6.5 multiple of conventional TENS. In an embodiment of the system and method of providing eTENS stimulation, the length of the IPC can be adjusted, as per step 48 in FIG. 17, in order to derive the desired increase in neural excitability. Additionally, in some embodiments, for deeper nerves, longer IPCs should be selected to provide improved enhancement of neural excitability. Further for deeper nerve targets, increasing the thickness of the IPC may provide for increased excitability of the target nerve (FIG. 4*b* shows increased MaxAF at lower thickness, compared to higher thicknesses, because that nerve target was relatively superficial).

Figure 9A:
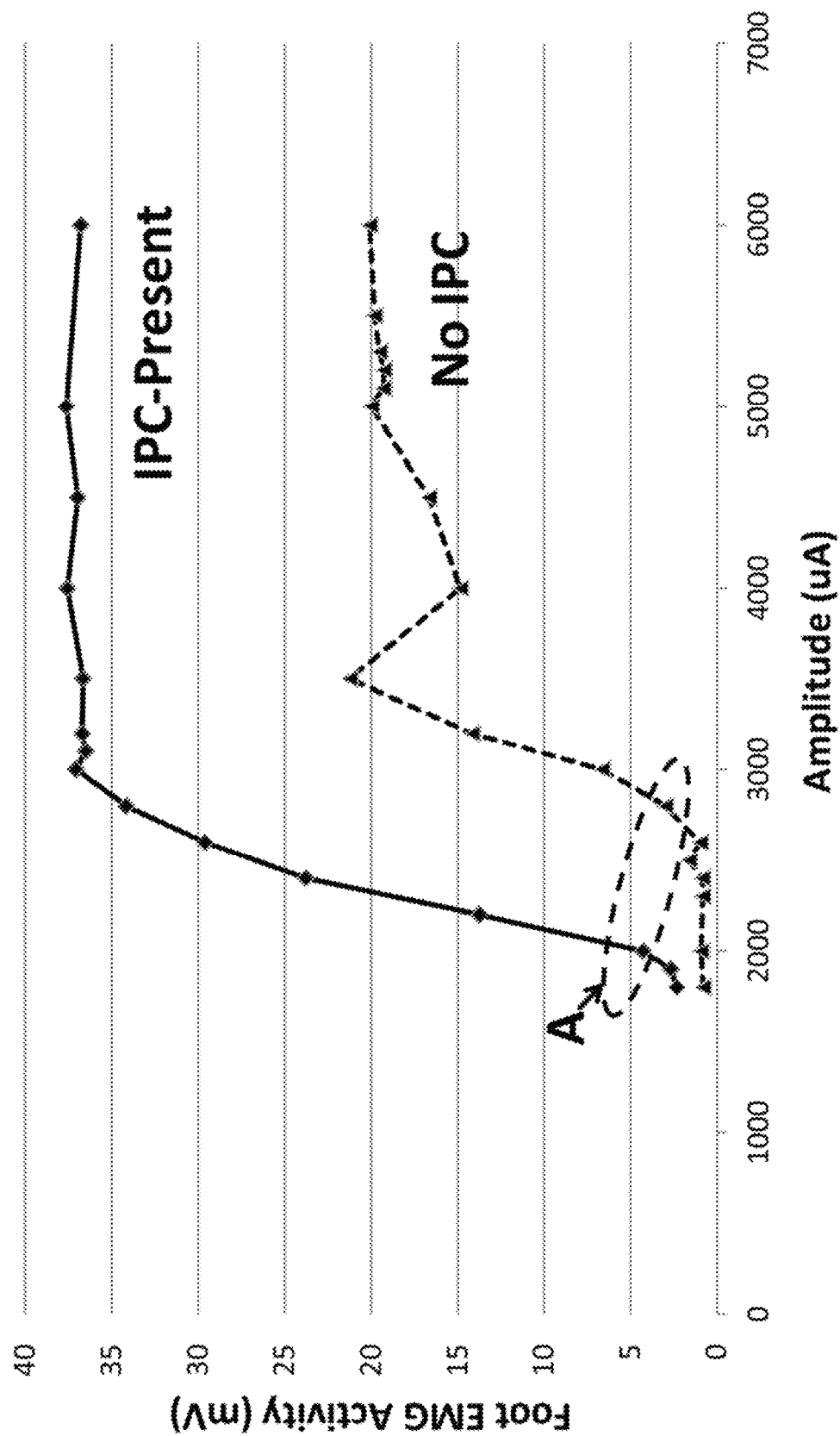
FIG. 9a is a graph of data from an experiment conducted in an anesthetized rat, where a surface electrode (5 mm×5 mm) was placed on the posterior-medial surface of the hind limb to stimulate the posterior tibial nerve and a pair of insulated stainless steel wires was inserted into the ipsilateral foot to measure muscle activation (EMG). The return "anodic" electrode was a needle inserted percutaneously through the abdominal fat pad, ipsilateral to the stimulated leg.
Figure 9C:
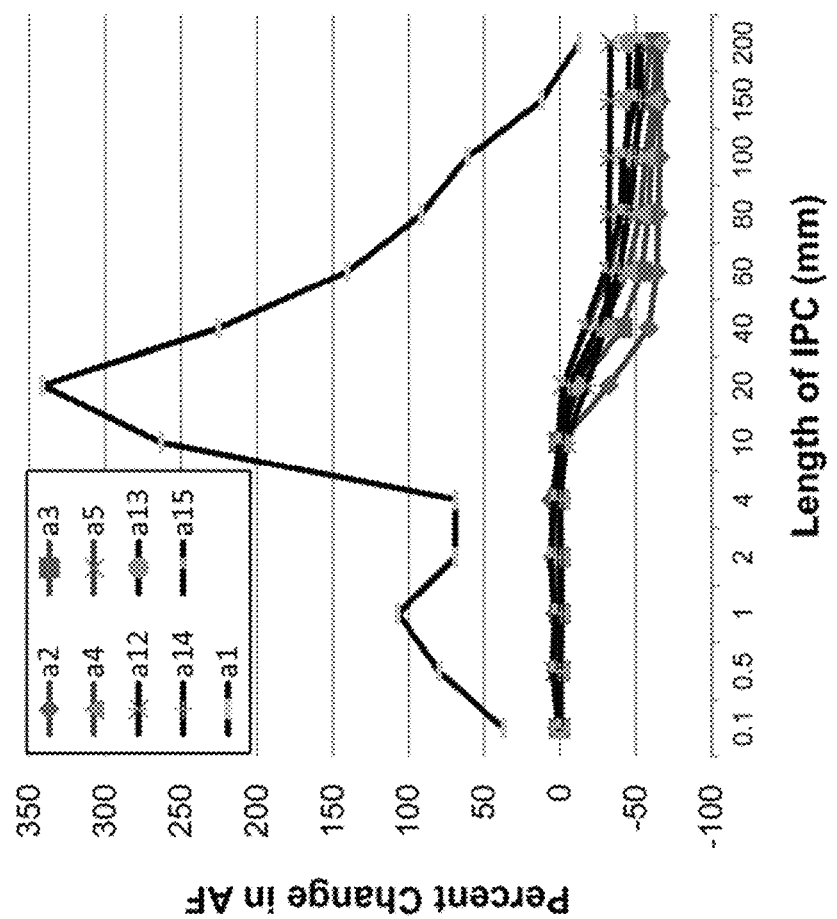
FIG. 9c is a graph of data derived from the computer simulation of FIG. 9b, where the target nerve (a1) shows increased AF which peaks when the IPC length is between 10 and 40 mm, while the non-target nerves show reduced AF, supporting both increased sensitivity and specificity, respectively, to the stimulation electrode.
Figure 9B:
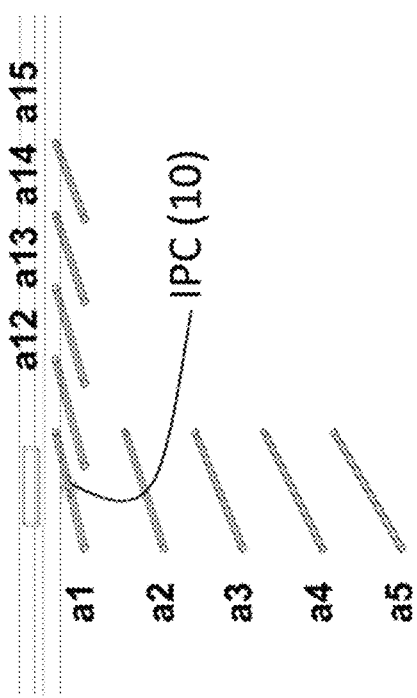
FIG. 9b shows the experimental set-up of a computer simulation, where a surface electrode (10 mm×10 mm) was positioned over an array of peripheral nerves (diameter=1 mm, length=100 mm) and the target nerve (a1) was positioned directly below the stimulating electrode at a depth of 3 mm from the skin surface. Additional nerves were positioned in both vertical (a2 to a5) and lateral (a12 to a15) fashion with respect to a1. The distance between each nerve was 10 mm.

FIGS. 9*a,b,c* show the effects of an IPC on the recruitment properties of transcutaneous nerve stimulation. These results were obtained from rat experiments (FIG. 9*a*) and computer simulations (FIG. 9*b*,9*c*). FIG. 9*a* shows data supporting IPC enhanced excitability that was obtained from in vivo studies in anesthetized rats. A monopolar surface (cathodic) stimulating electrode (5 mm×10 mm) was placed over the PTN of the left leg immediately rostral to the calcaneous (ankle bone). The return electrode (anode) was connected to a needle inserted through the abdominal fat pad, ipsilateral to the active cathode electrode. A pair of de-sheathed stainless steel wires were inserted into the foot, ipsilateral to the cathodic electrode and connected to a low-noise amplifier. This electrode was used to record the electromyogram (EMG) evoked by transcutaneous PTN stimulation. Results from one experiment are shown in FIG. 9*a*, which illustrates that the presence of the IPC 10 around the PTN (immediately rostral to the ankle) lowers the nerve stimulation threshold by 30% of that seen when no IPC was used. The figure characterizes the recruitment of foot EMG activity that was elicited by transcutaneous PTNS, with (solid line) and without an IPC (dashed line) placed around the nerve. The implant was implemented experimentally as an aluminum cuff. The data indicate that the IPC 10 of the current invention can effectively (1) lower the stimulation threshold (labeled "A" in the figure) for activating the PTN (2000 uA vs. 2800 uA) and (2) produce larger EMG activity (37 mV vs. 21 mV), as may occur through recruitment of more PTN fibers, or improved coherent activation, by transcutaneous stimulation. In addition to the threshold occurring at a lower amplitude of stimulation, the maximum foot EMG activity in the no IPC condition never reaches the maximum attained in the IPC condition. EMG serves as a proxy index to suggest the IPC improves coherent synchronous activation or recruitment of a larger total number of fibers, in response to nerve stimulation.

FIG. 9*b* shows a diagram of the computer model, which was used to investigate the effects of the IPC (implanted on target nerve "a1") on the neural excitability of non-target nerves (a2-a5 and a12-a15). FIG. 9*c* compares the computationally derived activating function (i.e., nerve excitability) of multiple nerves, where one (a1) has been instrumented with an IPC. As the length of IPC was increased from 0.1 mm to 4 mm, the excitability of the target nerve showed a 50% to 100% increase in the AF; while there was little change in the excitability of non-targeted nerves. Further, at IPC lengths of 10 mm to 60 mm, the excitation properties of the targeted (a1) and non-targeted nerves begin to diverge more dramatically. The percent change in AF for target a1 reaches a peak at 20 mm (342% increase), while the remaining nerves exhibit a 40% to 60% decrease in excitability beyond this IPC length. This data support an embodiment of the system and method of providing eTENS stimulation, wherein the IPC is provided for a target nerve to increase the sensitivity to stimulation, and within certain ranges the IPC can also increase stimulation specificity by decreasing the effect of the electrical field on non-target nerves.

While the experimental data (FIG. 9*a*) confirms enhanced neural excitation achieved by an IPC placed around the target nerve, the computer model results (FIG. 9*b*) show that the IPC can concomitantly reduce the excitability of surrounding (non-targeted) nerves. Accordingly, a single highly-conductive IPC may minimize any stimulation-evoked side-effects normally caused by unwanted activation of adjacent nervous tissue. While the mechanism for enhanced selectivity, at a given stimulation level, is not yet fully understood, it may be that the IPC provides a lower resistance path for the electrical field and thereby decreases dispersion of the field around the area of the IPC. As such, as will be disclosed later, embodiments using 1 or more IPCs may be used to shape, bias, deform, focus, or guide an electrical path (or magnetic field) through tissue. It may be that when used in humans to stimulate different targets, the guidelines for producing improved pairing can be different. For example, with longer IPCs than were tested here, the alignment of the stimulator edge may be found to improve pairing when aligned with the middle rather than the edge of an IPC. Both modeled and empirical results can be used to improve stimulation systems using one or more IPCs. Additionally, with IPCs tested using lengths at least 1 cm, recent unpublished data from the laboratory of Dr. Yoo has indicated that longer IPCs are better and accordingly, in an embodiment an IPC should be at least 1 cm long. In a further embodiment, it may be that the IPC can be may be even longer if the nerve target is accessible across that length in order to provide improved enhancement of stimulation.

Treatment of Incontinence and Related Disorders

A central use for the systems and methods of the present invention relate to treatment of chronic lower urinary tract dysfunction, such as overactive bladder and detrusor underactivity related to urinary retention. For simplicity the term overactive bladder (OAB) may be used to refer to various types of voiding disorders and urological dysfunctions (e.g. pelvic floor disorders), without intending to be limiting. The following example embodiments of the invention for the treatment of disorders are provided in the context that the embodiments and principles can be generalized to tissue modulation treatment of other disorders to provide various benefits.

Figure 10B:
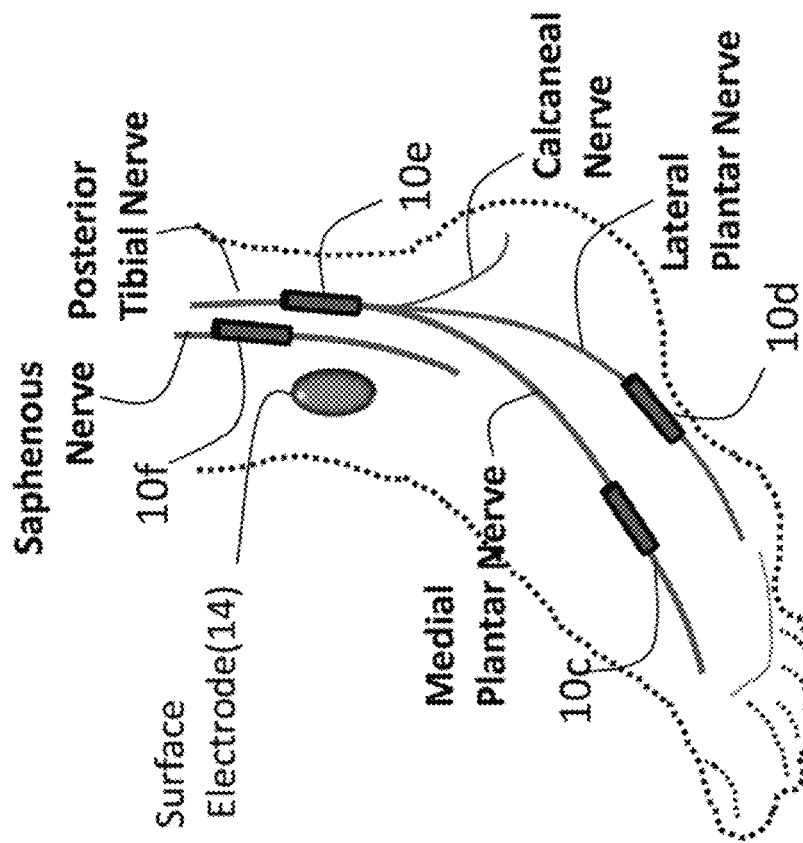
FIG. 10b schematically depicts the posterior tibial nerve (PTN) and saphenous nerve descending the posterior-medial aspect of the human leg. The PTN divides into the medial plantar nerve (MPN) branch, lateral plantar nerve (LPN) branch, and calcaneal nerves; whereas the saphenous nerve innervates the skin and underlying tissue layers along the medial-posterior surface of the lower leg/ankle/foot area. Suitable candidate implant locations for nerve cuffs (which can serve as the IPC of the current invention or which may operate as electrodes in conjunction with an implanted neurostimulator) are shown proximate to individual nerves.
Figure 10A:
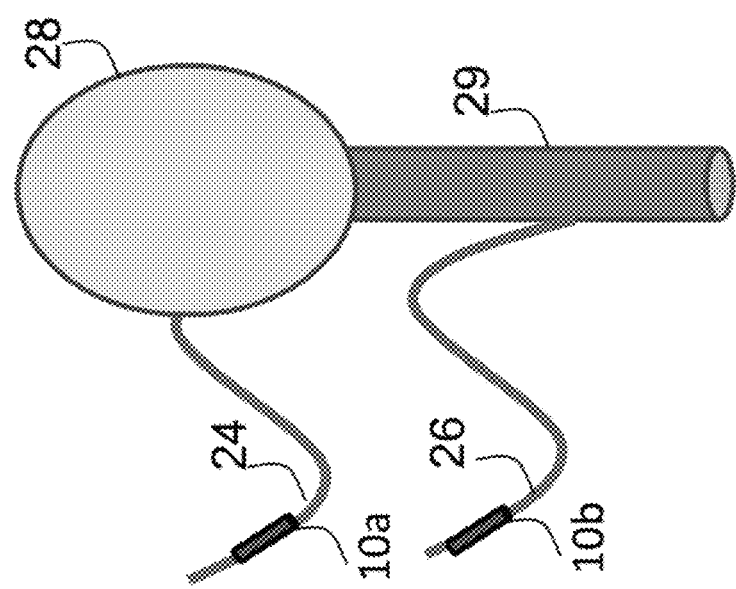
FIG. 10a is a schematic system view containing relevant neuroanatomical landmarks for electrical neuromodulation of the urinary bladder, with the urinary bladder and urethra innervated by the pelvic and pudendal nerves, respectively.

FIG. 10*a* and FIG. 10*b* show various embodiments of enhanced nerve stimulation systems, where selective activation of targeted nerves can be achieved by placing an IPC 10 in close proximity to, in direct contact with, embedded within, or wrapped around, these nerve bundles. Depending on a specific therapeutic protocol, one or more IPCs can be used for enhanced transcutaneous nerve stimulation at one or more sites. In embodiments, the target nerves can include, for example, the pudendal nerve, pelvic nerve, posterior tibial nerve, medial plantar nerve, lateral plantar nerve, calcaneal nerve, saphenous nerve, sacral nerve root and lumbar nerve root.

In FIG. 10*a* the urinary bladder 28 and urethra 29 are shown diagrammatically on the left side of the figure as innervated primarily by nerve targets such as the pelvic 24 and pudendal 26 nerves, the electrical activation of which can be enhanced by IPCs 10*a* and 10*b*, respectively. One embodiment of a system and method of selective pelvic or pudendal nerve stimulation may be achieved by providing therapy according to a therapy protocol to deliver electrical pulses using a stimulator that is at least one of an intravesicle or intraurethral electrode, or by using at least one electrode array. The stimulator would stimulate nerve targets for which IPC's have previously been implanted (e.g., pudendal nerve). This setup may allow for advantages such as permitting a stimulation electrode to migrate slightly while the IPC remains well situated with respect to the nerve target. The stimulator may be permanently implanted or temporarily inserted in similar manner as urethral catheterization (e.g., as in cases of spina-bifida, neurogenic bowel or bladder dysfunction) and can receive stimulation signals from a neurostimulator having a pulse generator. Selective activation of a neural target which includes at least one subset of nerves within the pudendal nerve (e.g., dorsal genital nerve, nerve to urethral sphincter, and nerve to external anal sphincter) may also be achieved by strategically implanting an IPC and stimulating an implanted electrode paired to the IPC using a pulse generator. The pulse generator may be external to the patient and provides a stimulation signal using wired or wireless connectivity. Therapeutic stimulation can also be provided using TENS or TMS to provide stimulation signal to an IPC from various locations such as on the posterior surface (above the gluteus maximus muscle). Potential clinical indications for the paired-use of an IPC and stimulation electrode can include, for example, urinary retention, urinary incontinence, fecal incontinence, stress incontinence, and urinary and pelvic pain.

FIG. 10b shows example nerves innervating the lower leg and foot. The posterior tibial nerve (PTN) descends down the posterior-medial aspect of the calf before dividing into the medial plantar nerve (MPN), lateral planter nerve (LPN), and calcaneal nerves. The saphenous nerve (SAFN) is a cutaneous sensory nerve that branches off the femoral nerve in the upper thigh. The nerve travels down the medial-anterior aspect of the leg, provides a sensory branch to the knee and continues down the leg to provide sensory innervation of the medial-posterior aspect of the lower leg. Suitable implant locations for nerve cuffs, which are connected to implanted neurostimulators or which serve as the IPCs (10c-f) of the current invention are shown proximate to individual nerves (a cuff is not shown on the calcaneal nerve to avoid cluttering of the figure). Selective stimulation of the MPN or LPN can also be realized by implanting IPCs adjacent to a junction where the PTN splits into the MPN and LPN. At least one stimulator 14 can be placed on the skin next to any of the IPCs in order to provide eTENS therapy. In the figure the stimulator appears just above the ankle, and is shown in an anterior portion of the ankle, rather than posterior, to avoid cluttering of the figure. Various anatomical landmarks may be used to assist in providing stimulation of SAFN and its branches by correctly positioning, for example, a percutaneous needle electrode, a TENS electrode, an implanted stimulator, IPC neurostimulator. As will further be reviewed as discussion of FIG. 50e, in an example clinical embodiment, the stimulator is placed about 1 cm to 3 cm cephalad and about 1 cm anterior to the medial to provide stimulation of the anterior branch of the distal portion of the SAFN. In another embodiment the stimulator may be implanted between the medial malleolus and the anterior tibial tendon, just lateral to the saphenous vein. Alternatively, a location cephalad (e.g., 3 or 5 cm) and more posterior to the medial malleolus and superficial to the PTN can be used to target the posterior branch of the distal portion of the SAFN. In surgical procedures, the SAFN may be pharmacologically blocked near the ankle to provide anesthesia at the foot, which suggests the location and access to this most distal part of the SAFN is both relatively superficial and predictable. Access to either anterior or posterior branches of the distal portion of the SAFN are located superficial to the PTN, which is commonly 1.5 cm to 2 cm from the skin surface in the ankle area, and in an embodiment positioning a stimulator 0.5 to 1.5 cm below the skin may provide a suitable target location. In some individuals, division of the distal portion of the SAFN into anterior and posterior branches at locations greater than 3 cm cephalad to the medial malleolus, and thus access to these branches may vary from patient to patient. Additional locations for stimulation include the distal portion of the SAFN which can terminate in multiple locations: the integument proximal to the tip of the medial malleolus, the anterior aspect of the medial malleolus near the posterior edge of the greater saphenous vein, near the posterior aspect of the medial malleolus, and cutaneous areas near to hallux. Accordingly, the SAFN may be stimulated using a needle, IPC, or stimulator at a location targeted at or adjacent to the medial malleolus. Further, multiple smaller SAFN branches may be stimulated near the skin that they innervate. When the SAFN is stimulated percutaneously or cutaneously, the return electrode can be realized, for example, as a disposable electrode attached the instep of the foot, or the medial aspect the calcaneous on the same leg on which the SAFN is stimulated, or a site medial aspect of the knee. Ultrasound guidance could improve success rates for correctly and easily locating the SAFN. In an embodiment, correct placement of a stimulation device targeting the SAFN can be further confirmed by the patient's report of 'cutaneous tingling or paresthesia', which will be different from that evoked by PTN stimulation often perceived as sensation radiating down the foot or foot muscle activation). In an embodiment, selective electrical activation of the PTN or SAFN may be occur successfully when accompanied by a perceived cutaneous sensation and reported by patients. In contrast, PTN stimulation will typically evoke sensations radiating along the foot, while SAFN activation will generate cutaneous sensations on the medial surface of the lower leg. Other locations for the IPCs can also be selected such as positioning an IPC at the level of, or below, a patient's knee in order to enhance stimulation of a nerve such as the saphenous nerve. A number of sites and methods for stimulating various lower limb nerves (which are suitable targets for some embodiments of the invention), and recording responses to the stimulation to measure neural response, are described in Chap 6, p. 125-145, of Electrodiagnosis in Diseases of Nerve and Muscle: Principles and Practice (2013), $4^{th}$ Jun Kimura (ed), Oxford University Press, which is incorporated by reference herein.

The current clinical model of PTN stimulation for the treatment of bladder disorders is that by providing stimulation of the PTN "trunk", stimulation is provided to the multiple nerve branches (e.g., LPN and MPN) that converge and pass through this nerve trunk. Stimulation, such as percutaneous stimulation, of the PTN is viewed as an efficient manner of providing nerve stimulation in the treatment of OAB since one stimulation target can serve to stimulate multiple relevant nerve pathways. The experimental results which are shown in FIGS. 13-15 were derived using a novel animal model that relies upon a continuous bladder-fill paradigm (repeated filling and voiding) that may provide more realistic results than other models of bladder function. This model, results, and nerve branch stimulation paradigms of the experiments that were done, collectively provide a new understanding of peripheral and PTN stimulation and OAB treatment and show, for the first time, that selective stimulation of nerve branches can provide clinical benefit over full PTN trunk stimulation. For example, for a particular frequency the stimulation of the MPN and LPN both show larger inhibitory changes, than stimulating the entire PTN nerve trunk, in bladder contraction activity relative to a pre-stimulation baseline level. Selective PTN nerve branch stimulation may lead to greater therapeutic effects and fewer non-responsive patients. These findings, and the insight provided therefrom support the design of new systems and methods of treatment, and serve as an advantage of the current invention.

The novelty of the experimental findings presented here may be supported in part by the difference between these results and those reported by others (e.g., Su et al, 2013) in which the bladder was maintained at a constant volume, whereas the model used here relies upon continuous filling and voiding of the bladder. This difference supports the idea that if no realistic type of voiding is provided in the animal model, then the effects of the stimulation which are evaluated at various frequencies may have different effects, than those shown here. The "continuous bladder-fill paradigm" used to obtain these data is novel compared to models of the prior art and the continuous filling of the bladder can cause the stimulation protocol to produce different effects than what occurs with models commonly used in the prior art. Accordingly, the stimulation-related results shown in FIGS. 12 and 13-15 may be absent from, in contrast with, and lead to different conclusions about the clinical efficacy of particular stimulation protocols, compared to results that have been found previously by others.

FIG. 11 shows stimulation targets which are spinal nerve roots that converge to form the pudendal (S2-S4) and posterior tibial (L4-S3) nerves. Two surgically placed IPCs (10f-g) are indicated proximate to the S3 and L4 roots. Electrical stimulation may occur outside the spinal cord or may be realized using a system that stimulates neural targets (for example, following a laminectomy or by surgical or percutaneous placement of electrodes) by accessing a target through the foreman (e.g., sacral stimulation). In this example embodiment, the nerves near the IPCs are modulated by stimulators external to the patient such as on the patient's skin (i.e., lower back) superficial the IPC locations. When the IPCs are implanted as part of a therapy for the treatment of pain, then the IPCs can be implanted on, or near, one or more nerve roots (or spinal cord itself) relevant to pain signaling pathways in order to suppress the signals related to the pain. When IPCs are implanted as nerve cuffs that are for use with an implanted neurostimulator, the IPCs can be realized as multi-contact electrodes of one or more leads connected to the neurostimulator 110, or electrode contacts on the housing of the neurostimulator itself.

Figure 12:
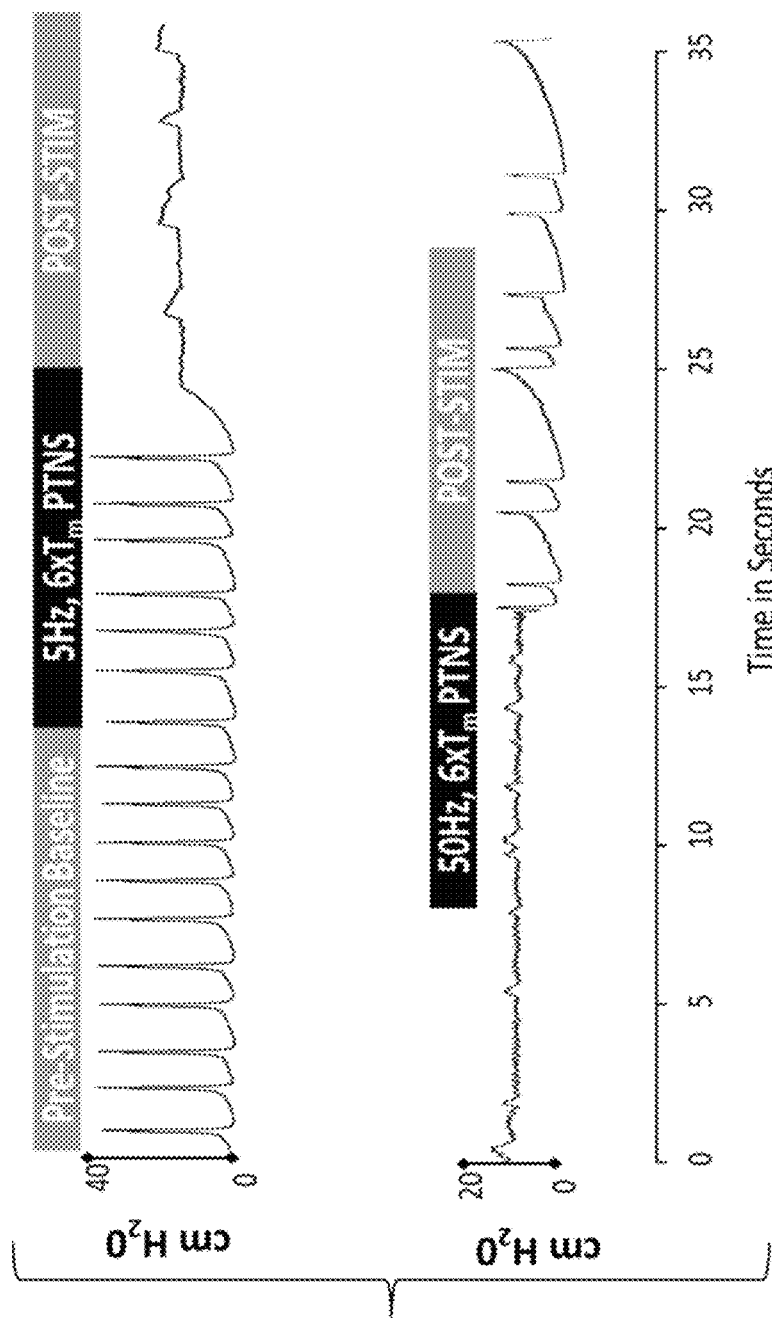
FIG. 12 is a set of graphs of experimental data that characterizes the effects of PTN stimulation on the bladder of urethane-anesthetized rats. At 5 Hz PTN stimulation (top trace) both acute inhibition during stimulation (black bar) and prolonged inhibition following stimulation (gray bar labeled as POST-STIM) were found. At 50 Hz PTN stimulation (bottom trace), only post-stimulation excitation (gray bar labeled as POST-STIM), was found.

FIG. 12 illustrates the results of an experiment in anesthetized rats that indicates that direct electrical stimulation of the PTN can modulate bladder function in a frequency-dependent manner. The experimental setup used to generate this data involved catheterization of the bladder dome in urethane-anesthetized rats. The catheter is connected, in series, to a pressure transducer and a syringe filled with saline. An infusion pump is then used to realize a novel "continuous bladder-fill paradigm", where repeated reflex bladder contractions are elicited (FIG. 12, top trace). The top graph shows a 10-minute train of electrical pulses delivered to the PTN at 5 Hz. In this example of 5 Hz PTNS, a slight but noticeable reduction in the bladder contraction frequency can be visually seen during the 10-minute stimulation trial ("acute" change relative to the pre-stimulation baseline). This is followed by complete inhibition of the bladder that persists beyond the end of the PTNS trial ("prolonged" post-stimulation inhibition). In contrast, the bottom graph shows recovery of bladder activity following a 10-minute trial of PTNS applied at 50 Hz. This particular example shows the abrupt transition from a flaccid (passively leaking) bladder before PTNS to one that generates robust sustained bladder contractions following this high-frequency PTNS. The bladder-excitatory effect remains persistent following the termination of PTNS. While the top trace shows an example of a stimulation protocol that can be used during treatment to decrease bladder activity, the bottom shows how the stimulation protocol can be used to modulate the bladder to increase contractions.

In this model, the PTN was surgically accessed and a bipolar stimulating nerve cuff electrode was implanted directly onto the nerve. The stimulation amplitude was set at 6 times the threshold required to evoke a foot twitch (i.e., the minimum amplitude that works for this experimental set-up, or "6×Tm"). Although not observed in this example, this bladder-excitatory response typically occurred during stimulation and the evoked activity continued after the end of the 10-minute pulse train into the post-stimulation period.

Figures 13A, 13B, 13C:
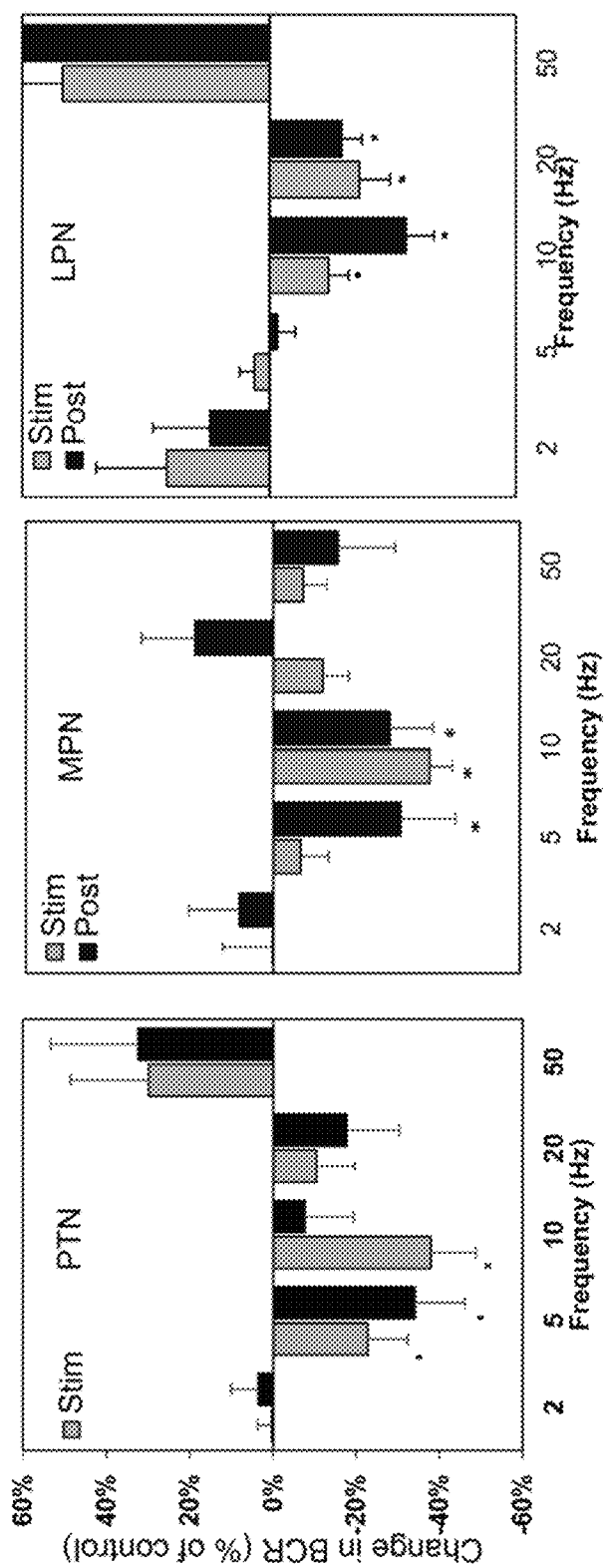
FIGS. 13a, b, c are graphs showing summary data of electrical stimulation of (A) PTN, (B) medial plantar nerve (MPN), and (C) lateral plantar nerve (LPN) in anesthetized rats (e.g. summaries of raw data such as that seen in FIG. 12). Bladder inhibition (defined by % reduction in bladder contraction rate (BRC) with respect to baseline) is observed during stimulation at lower frequencies (e.g., 5 Hz to 20 Hz), whereas bladder excitation is observed at 50 Hz for PTN and LPN stimulation.

FIGS. 13a, 13b, 13c, shows the summary data from a set of 11 experiments that followed the same PTN stimulation protocol and "continuous bladder-fill paradigm" used in FIG. 12. There is a clear frequency-dependent modulation of the urinary bladder in response to electrical stimulation of the PTN trunk that is distinct compared to selective nerve branch stimulation as shown in FIG. 13a for the PTN, FIG. 13b for the medial plantar nerve (MPN), and FIG. 13c for the lateral plantar nerve (LPN). FIGS. 13a-c and FIGS. 14a-f are similar to data shown in Kovacevic M and Yoo P B, Reflex neuromodulation of bladder function elicited by posterior tibial nerve stimulation in anesthetized rats. Am J Physiol Renal Physiol. 2015; 308(4):F320-9, incorporated by reference herein.

It is important to note that each stimulation frequency range can exhibit unique PTNS-evoked responses. FIG. 13a shows PTNS resulted in bladder inhibition at low frequencies, such as 5 Hz to 20 Hz; whereas bladder excitation is observed in response to stimulation at higher frequencies such as 50 Hz. Stimulation at 5 Hz and 20 Hz elicits both acute (labeled "Stim" in figure) and prolonged (labeled "post") inhibition of the bladder; 10 Hz stimulation evoked primarily acute bladder inhibition with weaker prolonged inhibition; and 50 Hz stimulation elicits both acute and prolonged bladder excitation. Although using a stimulation protocol which provides at least one signal modulated within a range of approximately 5-20 Hz as therapy for bladder dysfunction may be utilized, in an alternative embodiment the stimulation protocol can be further tailored. For example, a distinction may be made between acute results seen for modulation of bladder activity which resulted during stimulation with the prolonged results obtained after stimulation. The acute response may be just as relevant as the post-stimulation response in the treatment of OAB. For example, when the duration of the stimulation is increased beyond the 10 minutes used here, and/or is repeated periodically or provided continuously during treatment, then the acute response may dominate the therapy response. Additionally, when a system and method is used to provide acute modulation of a bladder condition (e.g., the detection of an event for which modulation is responsively provided such as patient pushing a button on an external programmer that indicates that bladder urgency symptoms are too severe) then the acute response may be more relevant than the prolonged response in determining therapy parameters of the stimulation protocol. Accordingly, based on these results, in some individuals, PTNS therapy which includes a stimulation protocol that provides at least one signal in either the 5 Hz or 20 Hz range for PTN stimulation may be suitable to treat idiopathic overactive bladder symptoms. A stimulation protocol using a signal in the 10 Hz range for PTN stimulation could be suitable for the treatment of neurogenic bladder symptoms (e.g., spinal cord injury, multiple sclerosis, or diabetes). With respect to higher stimulation frequencies, the data suggest a stimulation protocol using a signal in the 50 Hz range (e.g., 50+/−10 Hz) for PTN stimulation could be suitable for modulating urinary retention (related to detrusor under-activity), or bowel retention (i.e., constipation). While 50 Hz was used, higher frequency ranges such as 100 Hz (or higher) may also result in modulation (e.g., excitation) of bladder activity.

FIG. 13b shows summary data from experiments (same setup as FIG. 12 and FIG. 13a), where the MPN was activated by direct nerve stimulation. In these rat experiments, selective activation of the MPN evoked robust bladder inhibition at 5 Hz (prolonged) and 10 Hz (acute and prolonged). Although 50 Hz stimulation of the MPN failed to elicit a bladder excitatory response as was the case for the PTN, 20 Hz stimulation appears to elicit a prolonged excitatory effect. In one embodiment, a method using an MPN stimulation protocol having at least one frequency selected from the range of 5-20 Hz can be used to treat OAB, while limiting to approximately the 5 to 10 Hz range may be preferred when stimulation is not continuously provided, and 10 Hz may be preferred when stimulation occurs continuously. These data suggest that—in lieu of stimulating the entire PTN—low frequency stimulation of the MPN is well suited for treating OAB symptoms. Additionally, a stimulation protocol using 20 Hz MPN stimulation may help with treating urinary retention. The inconsistency of the excitatory response at 20 Hz suggests that electrical stimulation of the PTN or other PTN branches (e.g., LPN or calcaneal nerve), at least at 20 Hz, may be a better candidate for successful mediation of this bladder excitatory reflex than the MPN. In order to stimulate the MPN, the external stimulators, such as TENS electrodes which provide stimulation alone or in conjunction with IPCs can be situated along the medial-plantar surface of the foot, in regions near the large toe, or other suitable location such as near the junction where the PTN branches into the LPN and MPN or at the respective spinal nerve roots. Percutaneous, optical, (ultra) sound-based, or other types of stimulation may also be provided using appropriately configured stimulators.

FIG. 13c shows summary data from experiments (using same setup as FIGS. 13a, 13b and FIG. 14a,b,c) where the LPN was activated by direct nerve stimulation. In these rat experiments, selective activation of the LPN evoked robust bladder inhibition at 10 Hz and 20 Hz (acute and prolonged), while 50 Hz stimulation (similar to PTN stimulation, FIG. 13a) elicits an acute and prolonged excitatory effect. This data suggests that—in lieu of stimulating the entire PTN or the MPN—low frequency stimulation of the LPN (10 Hz to 20 Hz) is suitable for treating overactive bladder symptoms, while 50 Hz MPN stimulation will help with treating urinary retention. In order to stimulate the LPN, in one embodiment, surface stimulation can be delivered along the lateral-plantar surface of the foot, regions near the smaller toes, or other suitable location such as near the junction where the PTN branches into the LPN and MPN or at the respective spinal nerve roots.

Figures 14A, 14B, 14C:
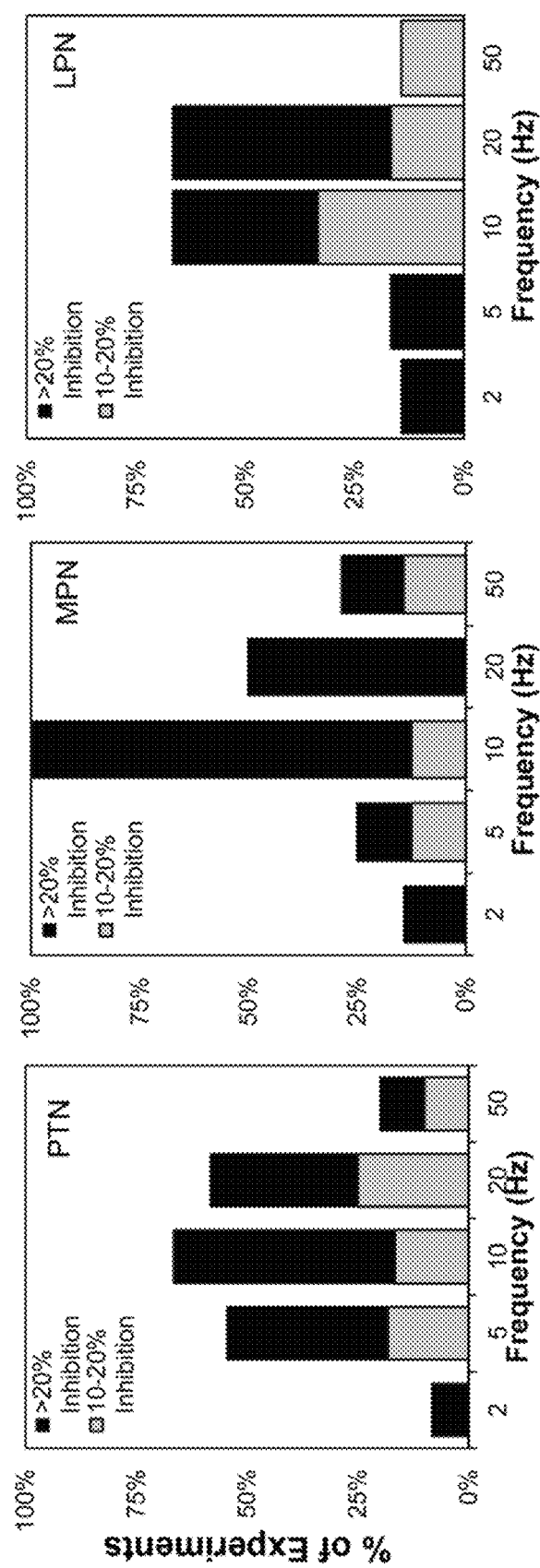
FIGS. 14a, b, c are graphs of summary data of percentage of experiments (total 11 rats) that exhibited an acute reduction in BRC (i.e. acute bladder inhibition) during each 10-minute stimulation trial of the PTN, MPN, and LPN in anesthetized rats.
Figure 15:
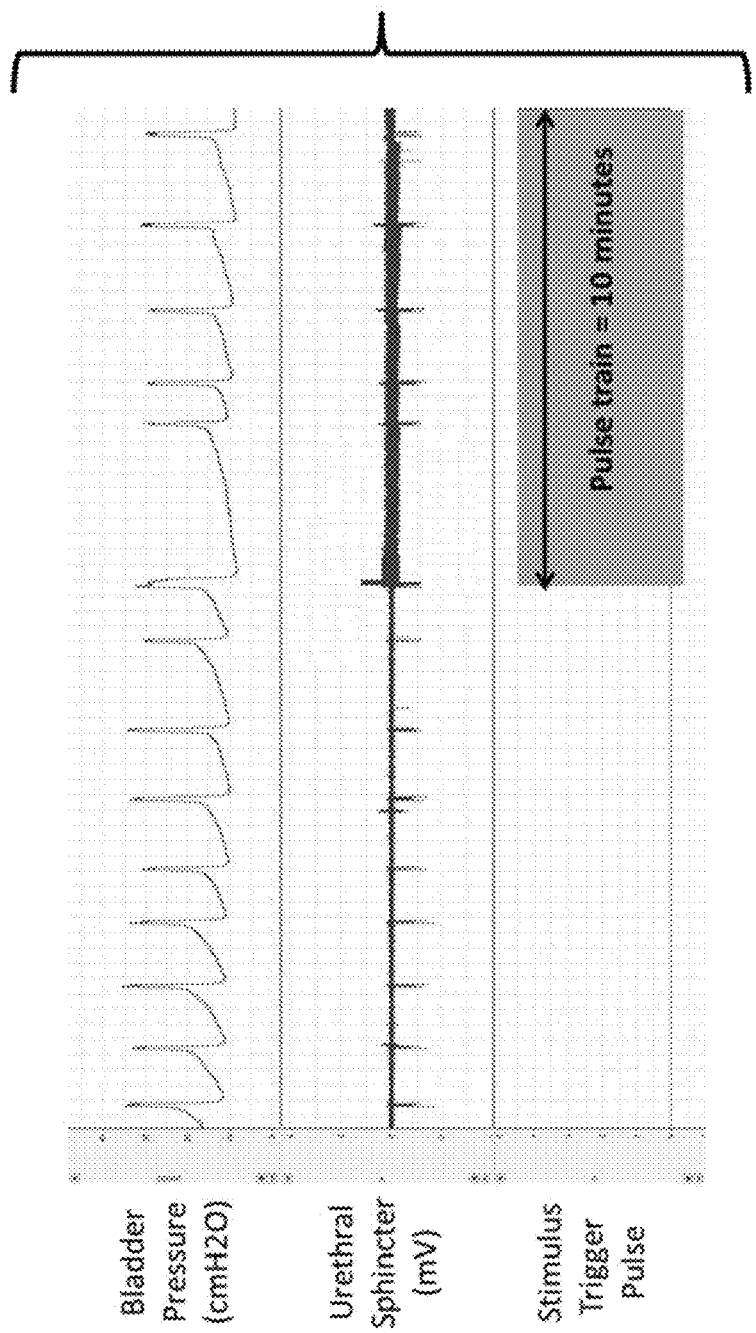
FIG. 15 is a graph of experimental data from an anesthetized rat, where electrical stimulation (0.3 mA, 5 Hz) of the Saphenous nerve (branch was accessed below the knee) resulted in an acute 25% decrease in BCR during stimulation as evidenced by the top trace, while middle trade shows other recorded activity and the lower trace shows the duration of the pulse train.

FIGS. 14a-to-14c show the summary data (from 11 rat experiments) of the positive response rate of acute bladder inhibition (defined as a minimum of 10% decrease in bladder contraction rate (BCR)) that resulted during nerve stimulation. This is expressed as the percentage of experiments that evoked changes in response to stimulation of the PTN, MPN, and LPN. Overall, the frequencies at which nerve stimulation resulted in statistically significant reductions in BCR FIGS. 13a,b,c yielded response rates in the range of 50% to 67%. Interestingly, 10 Hz MPN stimulation yielded an acute bladder-inhibitory response in every experiment, which suggests that this stimulation parameter setting could be used to maximize the patient response rate for treating OAB, and especially for providing stimulation acutely to the MPN to relieve acute bladder symptoms such as urgency or incontinence. In an embodiment, percutaneous stimulation can be provided to the MPN by inserting the needle below the medial malleolus after the junction of the PTN into the LPN/MPN. In a further embodiment, this MPN stimulation can be provided if percutaneous stimulation of the PTN is not effective. In a further embodiment, therapy can first be provided, for example, at 20 Hz at the conventional site for PTN stimulation and then for example at 10 Hz at the MPN for non-responders. Alternatively, therapy can include providing stimulation at both these sites during a single treatment session in order improve rates of patient response.

Figures 14D, 14E, 14F:
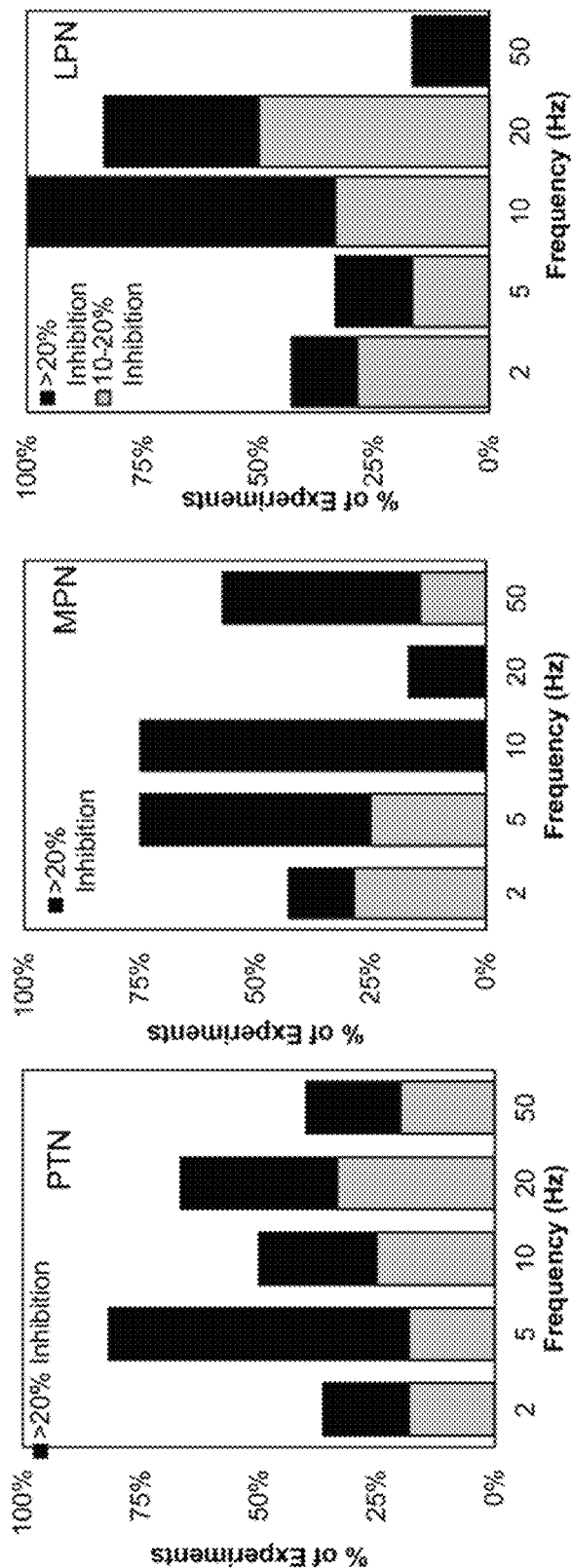
FIGS. 14d, e, f are graphs of summary data of percentage of experiments (total 11 rats) that exhibited a prolonged reduction in BRC (i.e. prolonged bladder inhibition) following each 10-minute stimulation trial of the PTN, MPN, and LPN in anesthetized rats.

FIGS. 14d-to-14f show the summary data (from 11 rat experiments) of the positive response rate of prolonged bladder inhibition (defined as a minimum of 10% decrease in BCR) that resulted following each nerve stimulation trial. This was expressed as the percentage of experiments that evoked changes in response to stimulation of the PTN, MPN, or LPN. Overall, the frequencies at which nerve stimulation resulted in statistically significant reductions in BRC (FIGS. 13d,e,f) yielded response rates in the range of 75% to 82%. Interestingly, 10 Hz LPN stimulation yielded a prolonged bladder-inhibitory response in every experiment, which suggests that this stimulation parameter value could be used when stimulating the LPN to maximize the prolonged patient response rate of percutaneous or other therapy used for treating OAB, especially chronic overactive bladder symptoms.

FIG. 15 shows sample data that demonstrates the effects of saphenous nerve stimulation on ongoing bladder function. This study was performed in an anesthetized rat that utilized our "continuous bladder-fill paradigm". A 10-minute train of electrical pulses (pulse-width=0.2 ms, frequency=5 Hz, amplitude=0.3 mA) was applied to the saphenous nerve using a nerve cuff electrode. In this single stimulation trial, a noticeable decrease in BRC (approximately 25% decrease) was found that was indicative of reflexive bladder inhibition. This experimental evidence suggests that saphenous nerve stimulation could provide a therapeutic target for treating OAB either as a single nerve target or in combination with other neural substrates (e.g., PTN, MPN, LPN, pudendal nerve), each electrically activated according to effective stimulation parameters. The results also suggest the SAFN target can produce bladder modulation using a stimulation signal that is 25% of the amplitude used for the PTN, MPN, and LPN sites, indicating a more sensitive bladder reflex that may be especially effective in providing therapy, and further may be successful for patients who did not respond to other targets such as the PTN.

The experimental results which are shown in FIGS. 12-15 provide novel understanding of peripheral nerve stimulation for treatment of OAB. As shown in FIG. 13a,b,c, selective nerve stimulation can provide therapeutic advantages over full PTN trunk stimulation because, for example, at certain frequencies the MPN and LPN both show larger post-stimulus decrements in BCR relative to the pre-stimulus levels. Clinically, in humans, therapy using selective nerve stimulation may also lead to larger clinical effects of therapeutic stimulation, enable greater time between maintenance treatments, and may lead to a decreased number of non-responders. Moreover, combining the data of FIG. 13a,b,c with the data of FIG. 14a,b,c, further suggests that selective MPN and LPN stimulation therapy can lead, not only to larger physiological responses but can also benefit a greater proportion of patients, when compared to PTN trunk stimulation. Although the overall acute response to 10 Hz was about −40% BRC for both PTN and MPN, selective MPN stimulation showed a 100% response rate among all 11 experiments while PTN was below 75%, suggesting that the MPN may provide successful therapy, or acute therapy, to a greater number of patients than PTNS. Similarly, combining the data of FIG. 13$d,e,f$ with the data of FIG. 14$d,e,f$, indicates that group mean level of the overall post-stimulation (i.e., prolonged) response to 10 Hz was about −30% BRC for both MPN and LPN during the post-stimulation period. However, when compared to MPN stimulation, selective LPN stimulation not only showed a similar response rate for "greater than 20% reductions" in the BRC, but it also showed a minimum 10% reduction in BRC in all remaining experiments (i.e., overall 100% response rate). This suggests the LPN may be a superior target for more prevalently providing at least a minimum level of therapy in long-term treatment of OAB (e.g., where stimulation may not occur chronically).

A number of additional conclusions can be drawn from combining the novel data of FIGS. 13$a,b,c,d,e,f$ and 14$a,b,c,d,e,f$. For example, the data suggest that treatment protocols using PTN stimulation may provide inferior therapeutic efficacy than selective LPN or/and MPN branch stimulation as reflected in a lower total proportion of responders and a smaller physiological effect (e.g., prolonged at 10 Hz). Secondly, a system and method of OAB treatment which uses a stimulation protocol that combines selective stimulation of at least two of PTN, LPN, and MPN targets may produce improved (size and prevalence of) results than using a stimulation protocol at a single site and such a protocol is an embodiment of the invention. Thirdly, a system and method of OAB treatment which uses a stimulation protocol that combines stimulation of at least two frequencies (e.g. alternating), applied to at least one of PTN, LPN, and MPN targets may produce improved therapy, than using stimulation protocols that utilize a single site and single stimulation frequency and such a protocol is an embodiment of the invention. Additionally, treatment which uses a stimulation protocol of the PTN trunk having a frequency such as 20 Hz, may simultaneously modulate a nerve branch (e.g., MPN) in manner that contributes signals that increase rather than decrease in BRC (e.g., see FIG. 13$b$) and decrease the net change in BRC. In contrast, selective nerve stimulation of only one of the nerve branches may produce the desired decreased in BRC, without this type of unintended side-effect. These findings, as well as other insights based on these data, serve, in part, as the innovative, novel, and unobvious basis for a number of methods and systems of the current invention. In relation to these results, it is interesting to note that a common Uroplasty treatment of the PTN uses a percutaneous stimulation protocol having a signal with current level of 0.5 to 9.0 mA which is modulated at 20 Hz. The data of FIG. 13$a$ suggests that 5 Hz, and possibly 10 Hz when stimulation occurs in an ongoing manner, may provide a larger effect of PTN stimulation in the treatment of OAB.

Assessing the data of FIG. 13$a$-$c$ suggests that PTN bladder activity response is not the simple summation of LPN and MPN responses (e.g., 10 Hz post stimulation response at PTN is smaller than that found for either individual branch). This suggests that selective nerve branch stimulation may be better than (and/or provide different results than) stimulating the full trunk, in at least some patients. Further selective MPN or LPN stimulation may provide unique therapeutic outcomes. It follows that a patient that does not respond well to modulation of a particular target may respond better to a different frequency or target nerve fascicle. Nerve stimulation protocols implemented in a clinic using external stimulation devices, or those implemented by implantable neurostimulators, can first stimulate different nerves selectively with of an individual during an assessment period and can then use stimulation protocols with site and frequency parameters that are successful during treatment provision.

In an embodiment for electrically stimulating the SAFN for treating medical symptoms and disorders may involve the use of eTENS, where an IPC 10$f$ is implanted on the nerve (FIG. 10$b$) near the medial malleolus and is electrically coupled with a surface electrode stimulator 14. Other possible locations for surgically implanting an IPC or neurostimulator may include subcutaneous locations at the level of (1) near the knee, (2) upper thigh, (3) pelvic area, and (4) spinal nerves (L2 to L4). The stimulation parameters (amplitude, frequency, duty cycle, etc) applied by surface electrodes at these areas may be similar to those used clinically for percutaneous PTN therapy.

Stimulating the SAFN at the level near the knee may hold advantages over stimulating near the ankle for both implantable and percutaneous treatment. For example, some patients may have edema near the ankle which will not extend to, or be as severe near, the knee. Further, in some subjects the distal portion of the SAFN may simply be difficult to localize or access near the medial malleolus. Compared to the ankle, the size and number of axons within the SAFN branch is significantly larger near the knee and may allow for both easier stimulation and greater therapeutic effects. With respect to implantable embodiment, the ankle region may be found to be subject to larger movement than the tissue near the knee leading to larger risks of migration and the patient may not find implanted device near the ankle to be comfortable. Accordingly, due to considerations of patient comfort, clinical efficacy, ease of identifying and targeting the nerve, treating the SAFN near the knee may hold advantages.

At and below the level of the knee a neurostimulator or a lead of the neurostimulator can be positioned to either stimulate the main SAFN nerve branches such as the infrapatellar branches, the SAFN branch which courses superficially down the anteromedial lower leg, or the cutaneous branches that derive from the main nerve and supply the skin of the anterior thigh and anteromedial leg. While the main SAFN nerve branch just below the knee is visible, its many smaller branches terminate across the skin surface. In one embodiment the SAFN nerve is detected using imaging data or by moving to a candidate location, stimulating cutaneously or percutaneously, and determining whether or not the subject feels sensations in their lower leg, or both. The SAFN may then be stimulated to provide treatment. In an embodiment using an implantable system component such as an IPC, neurostimulator with leads, or microneurostimulator with contacts on its housing, a main branch of the SAFN can be surgically accessed and the relevant system component(s) implanted. Alternatively, multiple smaller SAFN branches may be stimulated near the skin that they innervate. In an embodiment, an electrode with multiple contacts such as seen in FIG. 50$a$ is implanted under the skin and used to stimulate many SAFN branches that innervate the skin. Because these may not be visible even using magnification or sonogram techniques candidate stimulations may be assessed using patient feedback. Prior to implantation the patient may undergo an assessment procedure in which correct activation of the SAFN is first assessed by a percutaneous electrode stimulating at one or more candidate sites. A grid may be drawn on the patient's leg and squares of the grid used as landmarks. Candidate sites and depths which produced appropriate responses (e.g., cutaneous sensation radiating towards to the ankle) can be recorded. In the next step the surgeon then implants one or more electrodes or IPCs at one or more selected SAFN stimulation sites. After an interval during which the patient recovers, one or more stimulation protocols can then be assessed. For example, when an electrode with multiple contacts is used different combinations of electrodes may be assessed in order to determine which electrodes meet a criterion such as causing cutaneous sensation. One electrode contact is then selected to provide stimulation treatment and a second electrode contact also be selected or a portion of an implanted neurostimulator can serve as the second electrode. During treatment the stimulation may then be provided and the amplitude increased until sensations are felt by the patient lower in the leg. The amplitude used during subsequent treatment may be adjusted to be more than, equal to, or less then the amplitude that produced sensation depending factors such as patient comfort and prior response to therapy such as a change in baseline with respect to a measure such as daily urinary frequency and/or urinary incontinence episodes following treatment. This procedure may also be used for assessment and implantation to provide treatment in the medial malleolus region.

The appropriate placement of a neurostimulator and its electrodes can be done using various localization methods in addition to or instead of those just described when larger SAFN nerve branches, rather than then cutaneous terminals, is the nerve target. In an embodiment, determining where a stimulator should be implanted is to use fluoroscopy, x-ray, and/or ultrasound sonography. A stimulator can be implanted using standard surgical techniques or can be assisted by tools such as customized catheters designed to deliver a small neurostimulator to target region. Determination of placement can also be assisted by MRI data or a 3D model of the relevant area of a patient, and implantation can be guided by stereotactic frame-based methods, or simply visually by the surgeon if the implantation occurs surgically rather than percutaneously via a guiding cathether or enlarged needle.

In an embodiment SAFN stimulation can be provided transcutaneously using a first surface TENS electrode placed near the knee and a return electrode placed, for example, at 3 finger widths below the medial condyle of the tibia. A relatively large TENS electrode which is at least 4 cm×8 cm may be used to minimize any discomfort and/or increase the number of SAFN fibers terminating onto the skin surface (medial aspect of lower leg). The stimulation amplitude is then increased to an assessment threshold, for example, up to 40 mA, until sensation is felt at the location of the surface electrodes and down the lower leg. If this does not occur then the TENS electrode is moved to another location and the operation is repeated. When sensation in the leg is obtained then the treatment stimulation can occur for an interval such as 30-60 minutes. In an embodiment, SAFN is provided as an at home supplemental treatment by a patient every day, or less frequently, in combination with clinic treatments done percutaneously in order to produce an advantage such as allowing for less frequent maintenance visits or improved therapeutic response. Additionally, using a TENS set-up similar to that just disclosed recent data from the laboratory of Dr. Yoo has suggested that 14 out of 15 subjects were able to detect a cutaneous sensation of tingling indicating that the SAFN was stimulated successfully by an external stimulator prior a level of stimulation that would cause pain to the subject. Further, in the 1 subject that did not detect this sensation, moving the tens electrode and trying again may have produced positive results. These results support that TENS-based stimulation of the SAFN between the knee and the ankle, and preferably closer to the knee, using an amplitude of approximately between 10 mA and 50 mA. Additional therapeutic benefit may be obtained by providing this bilaterally.

Candidate locations for implanting IPCs, implantable electrodes, and/or pulse generator device may include subcutaneous locations at the level of (1) the ankle, (2) the knee or below the knee, (3) upper thigh, (4) pelvic area, and (5) spinal nerves (L2 to L4). The electrode stimulators may be, for example, a single- or multi-contact (1) lead-type electrode, (2) cuff-type electrode, (3) helical or spiral type nerve electrode, (4) injectable cylinder or pellet-type electrode, or (5) wire-type electrode. The electrode stimulators may receive stimulation signals from an implanted pulse generator, external electrical source, TMS source, sound source, or light source (e.g., laser) or other modality of providing energy.

Figure 16:
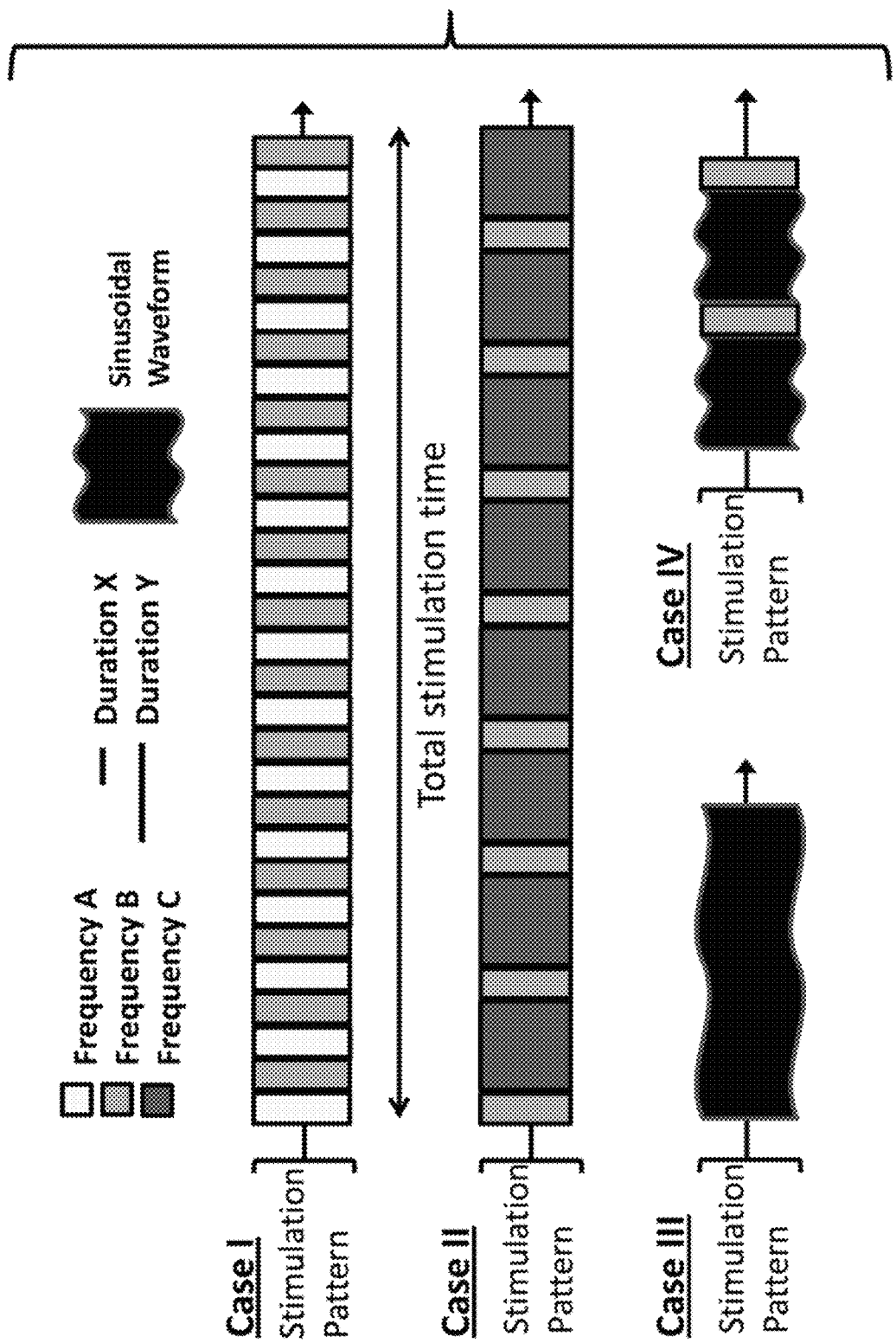
FIG. 16 shows alternative exemplary embodiments of different electrical nerve stimulation patterns that can be used with the present invention to improve various neuromodulation therapies.

In an embodiment a neuromodulation system for modulating a nerve target to modulate bladder activity comprises: a) an implantable active component having a receiver comprising a secondary coil, circuitry to convert magnetic energy into electrical energy, optionally power storage, pulse generation circuitry, safety circuitry, and at least one stimulator having at least one electrode contact capable of stimulating at least one spinal root nerve target of a patient selected from the group of L2, L3 and L4; b) an external neurostimulator comprising a power source, circuitry to emit magnetic signals, at least two predetermined programs to control said magnetic signals, and a primary coil that serves as a stimulator; c) the primary coil of the external neurostimulator and the secondary coil of said implantable active component being capable of forming a connection by inductive coupling, whereby said external stimulator is capable of controlling the stimulation of said at least one spinal nerve root targets which is provided by the implantable component using a stimulation frequency and amplitude that has been shown in the patient to cause decreased bladder activity. The external stimulator can be realized as part of an external device (EXD) which is configured with a processor for receiving patient input and controlling stimulation therapy, and the input can allow the patient to manually start, stop, and adjust therapy provided by the implanted active component. The EXD can be further provided with a protocol selection mechanism having at least two predetermined stimulation protocols that may be selectively operated, the first using a signal that is related to long term post-stimulation modulation of bladder activity which occurs after the stimulation has stopped and the second using a signal that produces relatively acute modulation of bladder activity during stimulation FIG. 16 shows sample embodiments of stimulation protocols for applying electrical pulses to target nervous tissue. An advantage of these protocols is supported by experimental data (e.g., FIG. 13-FIG. 14), which demonstrated reflex bladder inhibition can vary as a function of stimulation frequency. In one embodiment, a method may utilize more than one stimulation frequency, which has previously met some treatment criterion that is associated with successful patient outcome (e.g. prior success in that patient or a similar patient population), in order to provide the advantage of increasing the rate of successful patient response. A 'hybrid-frequency' stimulation method of activating nervous tissue is presented in cases I and II, where electrical pulses of the stimulation signal can be, for example, square, sinusoidal, or rectangular in waveform shape and can be applied in monophasic or biphasic fashion. In one embodiment, the stimulation protocol for OAB treatment requires alternating two frequencies at a target site, such as providing PTN stimulation at 5 and 10 Hz, MPN stimulation at 5 and 10 Hz, and/or the LPN stimulation at 10 and 20 Hz. Two or more sites may be stimulated at a particular time or preferably the sites can be alternated. One example stimulation protocol can include three different stimulation signals modulated at different rates (A=5 Hz, B=10 Hz and C=20 Hz) and 2 different pulse train durations (e.g., X=1 minute, and Y=6 minutes). The two stimulation signals (e.g. A and B), can both occur for a duration of X (e.g., case I), or the two (or more) stimulation signals (e.g., B and C) can occur in an alternating manner with a duration of X and the other can occur with a duration Y (e.g., case II), which are different. For example, a clinically useful stimulation protocol may be used if a patient can tolerate the first stimulation pattern (B) better than the second stimulation pattern (C) in which Y can be made longer than X. Further to increase patient comfort a pause-duration, during which no stimulation occurs, can be inserted into one or more time intervals of any stimulation sequence. In addition to comfort, another issue is effectiveness. For example, the first stimulation signal (defined by the first stimulation signal set of parameters) may need to be provided for a longer interval than then the signal provided by the second protocol before a desired effect occurs. Other values of the stimulation signal such as pulse width, rise time, waveshape, current and voltage level, in addition to total duration, may be adjusted due to factors such as subjective tolerance, stimulation site, nerve target, acute response to treatment, response to treatment over time, or due to patient data such as patient bladder diary records or quality of life surveys, patient input data related to controlling or adjusting stimulation provided by an implanted device, or data sensed from sensors which are assessed by a doctor or by an algorithm implemented by the treatment system.

In another exemplary method of improving PTN or MPN stimulation (case I), the stimulation protocol is comprised of an interleaved pattern of stimulation in which 1-minute trains of 5 Hz and 10 Hz stimulation signal pulses are delivered throughout a single clinical treatment session. The total stimulation time during a treatment session may be in the range of 30-60 minutes. In a second embodiment (case II), the stimulation protocol occurs by stimulating the LPN with a protocol that has stimulation parameters that define a stimulation signal pattern with interleaved pulse trains of 10 Hz for 1 minute, and 20 Hz for 6 minutes. These two example stimulation protocols may facilitate better patient response than using a single stimulation signal to increase therapy benefit.

These stimulation paradigms may be delivered using TENS or TMS, with or without an IPC, percutaneous nerve stimulation, ultrasound and laser-based stimulation signals, and by a fully or partially external or implanted neurostimulator. In an embodiment the implanted component may consist of a multi-contact nerve cuff electrode, multi-contact lead-type array, or a multi-contact paddle-type electrode configuration.

The use of alternating stimulation protocols between two stimulation parameter sets that are designed to provide benefit can be applied to the clinical treatment of other disorders as well. For example, the treatment may include vagus nerve stimulation, deep brain stimulation, spinal cord stimulation, etc. The two or more alternating stimulation parameters can be adjusted for each individual patient in order to provide improved treatment. The adjustment may be done using stimulation parameters which were derived using a calibration or testing/assessment procedure that occurs before (after, or during) the treatment is provided, and which may also be carried out before each treatment session occurs.

In another embodiment (case III), electrical stimulation may be a sinusoidal waveform that is applied to one or more cutaneous surfaces that best activate a target such as (1) the PTN, (2) MPN, (3) LPN, (4) calcaneal nerve, and/or (5) SAFN. These areas may include the medial aspect of the lower leg, medial-posterior aspect of the lower leg, posterior surface of the foot, medial aspect of the glaborous surface of the foot, and the lateral aspect of the glaborous surface of the foot. The frequency of the sinusoidal signal may be tuned to, for example, 2000 Hz, 250 Hz, and 5 Hz. According to Koga et al (Koga et al, Molecular Pain, 2005), these frequencies can preferentially selected to activate $A\beta$, $A\delta$, and unmyelinated C-fibers, respectively. This suggests an alternative embodiment using TENS/eTENS to deliver therapy for OAB in which, for example, a 2 kHz signal may be used to preferentially stimulate fibers to mediate a bladder inhibitory response, especially in the case of the superficial SAFN target.

Stimulation protocols may also use stimulation signals such as interferential stimulation signals which may be provided by two or more stimulators to target nerves that are located near the skin surface. In an embodiment the stimulation protocol is adopted under control of a processor to the geometry of the stimulators to provide summation at a target nerve such as the SAFN. Further, the frequency or other characteristics of the stimulation signals may vary over time such as occurs with a chirp-frequency modulated stimulus.

In another embodiment (case IV), both pulse-type and sinusoidal waveforms may be combined to selectively target multiple nerve targets. With a single surface stimulator 14 placed on the medial-posterior surface of the lower leg (e.g., between the medial malleolus and the ankle for PTN and anterior to the malleolus for SAFN) and an IPC implanted on the PTN 10e, a stimulating pattern of alternating sinusoidal and pulse-type waveforms is applied. The sinusoidal waveform may be applied at a frequency of 250 Hz to target $A\delta$-type fibers/receptors within the SAFN, whereas electrical pulses are applied at 5 Hz to target the PTN. The durations of each waveform (sinusoidal and pulse-type) applied to each target may be the same or different, such as, 5 minutes and 1 minute, both 1 minute, or 1 minute and 5 minutes, respectively.

FIG. 17 shows an embodiment of the invention for the treatment of overactive bladder or urinary retention (i.e., detrusor under-activity) that comprises a treatment method which uses an eTENS system including the combination of an IPC 10e placed on the PTN trunk and a surface electrode 14 placed superficial to the IPC 10e. eTENS stimulation of a patient with an IPC placed on the PTN may be selected if an assessment 48 shows that this might provide suitable therapy. The assessment 48 may include using percutaneous stimulation of the PTN to determine if this is effective in treating a patient and/or produces a desired outcome, and may occur over several weeks or months of treatment sessions. If stimulation of the PTN nerve trunk is deemed unsuitable as an outcome of the assessment (e.g., uncomfortable PTNS-evoked sensation or non-satisfactory treatment response by the patient), then an alternative stimulation protocol can be assessed by repeating step 48. For example, stimulation of at least one of the SAFN, MPN or LPN can be assessed, and an IPC can be implanted proximate to either the SAFN, MPN or LPN if any of these provide sufficient therapeutic benefit. FIGS. 12-14f show data supporting that a stimulation protocol which uses the PTN may produce better or worse therapeutic results than stimulation of the LPN or MPN, and further, these nerve branch targets may be successful in patients who did not respond to PTN trunk stimulation. The assessment of the SAFN, LPN or MPN can occur using a percutaneous or TENS stimulation protocol (with or without at least one IPC) or may use light, sound, pressure, or other modality to stimulate the nerves during assessment 48. Assessment may also include evaluation of acute responses while the stimulation occurs, or post-stimulation responses which may occur minutes, hours, days or weeks after stimulation. Assessment may entail evaluation of a measure (e.g. bladder activity) in absolute terms or relative to a different period such as a subject's pre-treatment baseline, or in comparison to age and sex matched population normative data. Assessment protocols can include use of bladder diaries, assessment of bladder contraction, and other patient data. Assessment can include filling a patient's bladder (e.g., using a transurethral catheter) and then asking the patient to rate a measure while stimulation is provided. For example, a visual analog scale can be used in which the patient rates bladder comfort from 1 (most comfortable) to 10 (least comfortable) or a longer term bladder diary may be assessed. The assessment protocols can also be used during the assessment of the treatment protocol as per step 38. During assessment 38, 48 or treatment 36, the placement of at least one surface stimulator 14 for the stimulation of selected SAFN or PTN nerve branches could involve the plantar surface of the foot (and/or other suitable location such as toes, lateral or dorsal foot surfaces). Assessment may also include algorithmic (e.g., under control of a processor in a neurostimulator) or manual evaluation of any data sensed by any external or internal sensor as described herein.

Due to the results of this assessment 38, 48 (or without such assessment), improved therapeutic efficacy may be provided using a stimulation protocol which includes the co-activation (either at the same time or different times) of targets selected from the group including the MPN, LPN, PTN, and pudendal nerve (e.g., dorsal genital) fibers, as is supported by the novel data shown in this specification. In a related embodiment, an additional stimulation may occur without an IPC, or with an IPC located in close proximity to the dorsal (clitoral or penile) nerve or the corresponding spinal roots (e.g., S3). Another therapeutic target involves electrical activation of the saphenous nerve. This can be stimulated directly by percutaneous stimulation, TENS, or as part of a system in which an IPC 14 is be implanted on a main SAFN nerve branch or just under the skin surface and coupled to a TENS electrode 14 or receives stimulation signals from an implantable neurostimulator. Supporting physiological data for this reflex pathway is provided in FIG. 15. In further embodiments, specific combinations of the PTN, PTN branches and/or the SAFN may be implemented by surgically placing individual IPCs on each neural target and selectively activating each nerve using target-specific stimulation parameters. In some of these therapeutic embodiments, at least one implantable pulse generating device, may be used alone or in combination with the methods and systems of enhanced electrical stimulation (i.e., eTENS) which may improve the therapy of the pulse generator.

In a further embodiment, the models of FIGS. 1a and 1c, are used to select characteristics such as the physical dimensions of, and approximate 3 dimensional locations of, at least one stimulator and IPC as well as stimulation protocols, during the assessment 48. An example of such a method is shown in FIG. 17 in which at least one stimulator is selected and set up for use with an IPC 32 and then used to provide stimulation to modulate tissue of the patient 8. The stimulation occurs according to the stimulation protocol selected in step 34. The stimulation protocol may define the stimulation parameters that are used to create at least one stimulation signal that is applied to the nerve target in order to modulate bladder activity. Parameters of the stimulation protocol which is defined, adjusted, or selected in step 34 may include any characteristic related to the stimulation signal. The characteristic may be selected from the group of: voltage, current, duration of stimulation, frequency, duty cycle, bursting pattern, burst or non-burst pulse trains, shape of the stimulation pulses or waveforms, pulse width, pulse shape, pulse amplitude, polarity, and other parameters related to various waveform types that have been disclosed. The term stimulation frequency may also be understood to be repetition rate. The stimulation frequencies may also denote an "average rate" at which electrical pulses are delivered to the nerve. In addition to applying pulses with a constant inter-pulse interval (e.g., 20 Hz=50 ms inter-pulse interval), electrical pulses may be applied in bursts or varying duty cycles that will approximate the stated "stimulation frequencies". Various other parameters can be set for the stimulation signal and these may be adjusted in any step that discloses adjusting a stimulation frequency. Additionally, a stimulation protocol can be used in which more than one frequency of stimulation is provided either simultaneously, sequentially, or at different times (e.g. FIG. 16). The stimulation protocol may also be provided according to times of day, pre-programmed times, according to the preferences of the patient or doctor, responsively according to patient symptoms, sensed patient data, or otherwise. In a preferred embodiment the stimulation is intended to produce a desired effect which is to decrease bladder activity or otherwise treat a condition related to OAB. In one embodiment a stimulation protocol can cause stimulation to occur initially in a chronic, or frequent manner (e.g. 1 hour on, 1 hour off), until a patient receives sufficient therapeutic benefit. In step 34, the protocol can then be adjusted, for example according to a treatment schedule, in order to reduce the therapy by decreasing the duration for which stimulation occurs (e.g., 1 hour on, 2 hours off), or decreasing amplitude of the waveforms from a first level to a second lower level, in order to decrease side effects or energy usage of a neurostimulator system (e.g., to increase battery life).

In another embodiment of the invention, at least one selected stimulator 14 is used to provide a stimulation waveform to a nerve target such as the PTN or LPN in order to augment bladder activity in a patient desiring treatment of a condition related to detrusor underactivity (e.g., urinary retention). In a preferred embodiment the stimulation is intended to produce a desired effect which is to increase bladder pressure in a sustained manner. This may be selected to be a frequency that has been shown to produce this effect in that patient, or is a likely candidate, such as high frequency stimulation in the approximately 50 Hz or higher range (e.g., 40 to 200 Hz). The system and method can be achieved percutaneously, using a cutaneous electrode either with or without also implanting an IPC in order on enhance therapy, or otherwise. If an IPC is to be used with the patient 8, this can occur in step 30. The stimulator may be selected in step 32, as part of a fully external, implanted or partially implanted system. Step 32 can include implantation of a fully implantable stimulator and stimulation device. In step 32, the system may also be realized by selecting a stimulator which is at least one coil that provides magnetic stimulation either directly to the nerve, or by way of an IPC. In another embodiment, an implanted stimulation device can convert a magnetic or RF field provided by an external stimulator into an electrical field. In step 30, an IPC may be selected according to the stimulator that will be used. Stimulation can be provided for treatment, induction of treatment, treatment maintenance, in combination with other therapy (e.g., drug), or as part of a screening test procedure. At least a portion of the steps in FIG. 17 may be used to carry out an induction, maintenance, or screening protocol rather than an ongoing treatment protocol that is performed in isolation. For example, the treatment protocol can be done as a maintenance protocol in conjunction with periodic percutaneous treatment (as per one embodiment of FIG. 22b).

Different portions of the population will respond to particular stimulation parameters (e.g., stimulation frequency) better than others. The correct stimulation frequency for a patient may be derived, for example, using a method which starts with a first protocol (a candidate protocol selected in step 34), as shown in FIG. 17. The selected first protocol 34 can use an initial frequency such as 5 Hz. In the next step of the method that frequency is used to stimulate according to a treatment protocol 36. The results can then be evaluated 38 for a selected time interval. The step of assessing the treatment protocol 38 can include comparing or processing data from before, during, and/or after the stimulation occurs and can include a single assessment period or multiple which can span across, for example, minutes, hours, weeks or months. The assessment of the processed data can be done by a doctor, patient, or a device of the system such as a physician programmer 70. The assessment may be both objective, such as accomplished using an algorithm to process by a processor and evaluate sensed data, or may utilize subjective parameters provided by the patient. Data collected for treatment assessment in step 38 may include storage of sensed data in a device memory, requesting that a patient input data into a system device such as a computer (having a processor, and conventional computer circuitry and capacity), smartphone, or keep a diary/log, or by any other manner of collecting data. The next step can include N iterations of adjusting the stimulation protocol parameters 44, stimulating again 36, and performing N evaluations of treatment in order to obtain treatment test results. The treatment test results can be calculated upon the assessment data which is collected during the assessment. For example, the results of the stimulation using at least 2 treatment protocols (as adjusted in step 44) are compared. In the case where at least one treatment protocol produced a positive treatment result (a result that meets a treatment criterion), then a positive treatment result activity can occur 40. The adjusting of stimulation protocol parameters can include iteratively selecting different stimulation signals so that the assessment relates to different candidate stimulation frequencies, and/or candidate stimulation targets such as PTN, LPN, MPN, and SAFN (including the terminal branches that innervate the skin).

One positive treatment result activity is that the stimulation protocol that produced the best improvement in the patient's condition can be selected for subsequent treatment 34 and applied 36 during subsequent treatments. Subsequent treatments may only include steps 32 to 36, or periodically the treatment protocol can be again assessed 38 to ensure that treatment is remaining effective. In the case of negative treatment result, then a negative treatment result activity can occur 42. Such an activity is to modify treatment protocol 44 and repeat stimulation 36. Alternatively, a negative treatment result can include for example, IPC explanting and/or implantation of an IPC in another location or implanting an IPC with different characteristics, repositioning of an IPC, implantation of another IPC in order to attempt to improve the outcome by adding an additional stimulation site, or other surgical or treatment adjustment. A patient's demographics (age and gender), symptoms, and other patient data may also influence the success of certain stimulation protocol parameters (e.g., stimulation frequency range) in producing a therapeutic effect and may be used by the system and method in order to select at least one candidate protocol 34. Stimulation parameters used for treatment, or the test protocol used to determine at least one clinically effective stimulation parameter, can be selected and adjusted 34 according to patient data, patient demographics, symptoms, or other patient or disease characteristics. The method of FIG. 17 can be applied to AOB treatment, or any other condition or disorder for which treatment may be sought (e.g., vagus nerve stimulation for treatment of headache).

The setting 34 and subsequent maintenance or adjustment of modulation parameters can occur similarly to the methods used in many wired neurostimulation embodiments and according to the related methods disclosed herein and in the prior art cited herein. For example, in some embodiments, the processor 58 of a device used in the neurostimulation system may employ an iterative process in order to select modulation signal parameters that result in a desired response which is measured or observed in a patient. Upon determining that a modulation signal should be generated, the processor 58 may cause generation of an initial modulation control signal based on a set of predetermined parameter values of the treatment regimen. If feedback from a feedback circuit in the sensing or processing module indicates that a calculated measure reflects that a nerve has been suitably modulated (e.g., if an increase in a degree of coupling is observed using a correlation measure between measured activity and the stimulation signal, or a change between a non-stimulus condition to stimulus condition exceeds a threshold level criteria related to positive outcome 40), then processor 58 operates in a similar manner or operates according to a successful outcome operation. If, on the other hand, an evaluation 38 of the "feedback signal" suggests that the intended nerve modulation did not occur 42 as a result of the provided modulation signal or that modulation of the nerve occurred but only partially provided the desired result (e.g., movement of a patients tongue only partially away from the patient's airway while still allowing for unwanted blockage in a method which is used to treat apnea or aspiration), then processor 58 may change one or more parameter values 44 associated with the modulation control signal (e.g., the amplitude, pulse duration, etc.). The steps of this method can occur in an open or closed loop (e.g., under the guidance of a control law using sensed data as input) manner, or a mixture of the two and can also utilize one or more control laws.

In the case where tissue modulation did not produce a desired outcome, the processor 58 may modify the protocol 44, such as adjust one or more parameters of the modulation signal periodically or otherwise until the "feedback signal" or calculated measure indicates that successful modulation has occurred. Further, in the case where tissue modulation occurred, but this did not produce the desired result, the processor 58 may attempt at least one other stimulation paradigm that has been defined in the treatment regimen in order to attempt to provide a different outcome. If a different outcome does not occur, then a device of a neurostimulation system operating to perform the treatment regimen may be configured to provide an alert warning signal a patient or physician to this result or at least store this result in its memory. In one embodiment this alert may indicate that a patient should move an external stimulator to a different location to establish the suitability of the pairing between a stimulator and IPC. This can serve to ensure that there is a sufficient degree of coupling between internal and external system components. Based on a newly determined degree of coupling, the processor 58 or patient can select new parameters for the stimulation signal that is subsequently used.

In one mode of operation, which is an assessment routine (e.g., steps 36, 38, 44 and/or 48), the processor 58 may be configured to sweep over a range of parameter values until desired nerve modulation is achieved. For example, the stimulus amplitude of the modulation signal may be ramped up to a point which is higher than that which would be used during longer term stimulation therapy. This may allow a patient, or a sensor which senses data from a patient, to easily measure an effect that indicates therapeutic efficacy, such as indicating that stimulation of a target nerve is capable of producing a desired change in a patient, or indicating that the external and internal components of a neurostimulation system are correctly aligned. After the assessment routine has confirmed a successful system configuration, such as correct stimulator and IPC alignment, the patient can then initiate therapy using a normal, reduced, level of the modulation signal. Alternatively, if the result does not indicate that a target level of modulation occurred, then the system may be reconfigured, for example, a stimulator of an external device may be moved and the assessment repeated. Assessment routines may occur over extended periods such as multiple days and can utilize temporary system components such as temporary leads or IPCs.

The stimulation provided to the nerve targets shown in FIGS. 10 and 11, or other targets stimulated during treatment, may occur using a system configured for using cutaneous electrodes to provide transcutaneous electrical pulses to a nerve or to nerve+IPC surgically placed on, around, or near the intended nerve target(s). Stimulation may also be provided by systems and methods designed to deliver electrical pulses using one or more of, for example, percutaneous electrode stimulators, cutaneous electrodes, implanted electrodes, implanted stimulation devices powered by magnetic or RF means, implanted electrodes powered by electrical means, and implanted electrodes powered by an implantable pulse generator. Further, the nerves may be modulated by electrical, magnetic and/or chemical means (e.g., as part of step 40). Drugs may be provided by injection, orally, or otherwise, prior to, during, or after, electrical nerve modulation during treatment as part of the treatment. Nerve activity may also be modulated by surgical, pressure, optical (e.g., laser stimulation), (ultra-)sound, genetic, or other means of influencing nerve activity during therapy. The stimulation can be provided chronically, acutely, periodically, or responsively by a doctor, patient, or device having sensing capability. For example, stimulation could be provided for 15 minutes each day, or may be provided in response to bladder pressure which is sensed by a sensor implanted or eternal to the patient. Stimulation can be provided that is responsive to patient's needs. For example, a patient may use an external device to communicate with an implantable device and cause it to operate to provide stimulation for a given duration starting 40 minutes after eating lunch, or in response to a button press, for example in order to cause urination to occur (due to the provision of nerve modulation that produces bladder excitation) while the patient is in the lavatory.

Therapy for overactive bladder and related disorders can be provided responsively 36 to user input such as a button press on the EXD 72 which is communicated to the processor of a neurostimulator, or may be detected by an implanted stimulator in response to sensed data from a patient, in response to sensed pressure, flow, motion, position or other data, or in response to time data such as clock time or a time interval such as time since last voiding. OAB may be particularly problematic when the patient is sleeping and so therapy can be delivered during that time. Providing therapy to a sleeping patient may allow the patient to experience fewer side effects, such as unwanted tingling. The therapy protocol may trigger a stimulation protocol to begin in response to a patient input (provided when the patient is going to sleep) and may dictate that stimulation should start 1 hour after sleep onset and last for a duration such as 3 hours. The occurrence of sleep may also be detected in response to evaluation of time data (e.g. 12 a.m.), sensed data, motion data, etc indicating, for example, that the patient is laying down and not active.

Treatment of Incontinence Related Disorders Using Pudendal Nerve Co-Activation

Some studies in anesthetized rats have only demonstrated reflexive bladder inhibition during PTN stimulation while failing to show excitatory effects (e.g., Su et al., Am J Physiol Ren Physiol 2012, Su et al., NAU 2013). These prior studies found that only 10 Hz PTNS was effective at inhibiting the bladder in rats. A difference between the experimental setups of this prior art and that used to derive the results disclosed herein is the provision of continuous urodynamic bladder filling ("Continuous bladder-fill"). The prior art studies used an isovolumetric bladder model in which there is no fluid flow through the urethra during bladder contractions. In contrast, the continuous fill model used to generate the data of FIGS. 13-15, and elsewhere, shows that these unexpected bladder reflexes (both inhibitory and excitatory) are produced, or unmasked, when both the PTN and pudendal nerve (urethral) afferents are simultaneously activated. A method of using this model to derive candidate stimulation parameters for treatment using simultaneous stimulation of two nerves is an aspect of the current invention.

Although the influence of PTN (Su et al., Am J Physiol Ren Physiol, 2012; Su et al., NAU 2013) and pudendal nerve (Peng et al., Am J Physiol Reg Int and Comp Physiol, 2008) afferents on bladder function has been shown individually, the combined effects of activating both pathways has not previously been demonstrated since the prior models do not provide for combined activation. The combined activation is likely more than just the sum of the multiple reflex pathways because the effects of stimulation, as well as stimulation at particular frequencies, using only 1 nerve may be different than the case where other nerves are also activated. The novel model disclosed here, combined with the lack of success of other prior art models to yield similar data, allowed the discovery of this relationship which serves as the basis for some embodiments of the disclosed invention. The simultaneous stimulation has been shown to produce clinically effective stimulation in a model where the bladder is modulated by a first stimulation site (e.g, pudendal, sacral, and/or pelvic nerve) when this occurs with co-activation of stimulation of a second site (e.g., PTN or MPN or LPN). Further, by removing the modulation of the bladder by the first site, the stimulation at the second site can become much less effective producing, or at least demonstrating bladder modulation in response to stimulation. These findings support the novel approach of modulating bladder function by co-activating SAFN, PTN, LPN, and/or MPN as well as the pudendal nerve afferents in a patient suffering from a urological disorder. Accordingly, in one embodiment of the method shown in FIG. 17, at least one of the steps 30-36 can be adopted so that both the pudendal (or sacral or pelvic) nerve and at least one of the PTN, a PTN nerve branch, or SAFN (or branch) are both stimulated. A stimulation protocol of at least one neurostimulator which is configured to provide stimulation signals to stimulators configured to stimulate these two targets, may be configured to provide co-activation, for example, at the same time or in an interspersed manner. Further, the combinations include stimulation of the nerve root spinal sites related to the PTN, SAFN, or their branches may serve as surrogate.

In one embodiment, shown in FIG. 10a-b electrodes or IPCs are implanted around, or in close proximity to, target sites on nerves in the region of the foot as well as on or near 1) the pudendal nerve, either the urethral sensory or the dorsal genital nerve, 2) the PTN, and 3) the SAFN. In an embodiment, up to three independent stimulation sources may be used to deliver electrical stimulation to these target nerves. Further, in embodiments at least three IPCs 10 or leads may be surgically placed on or around spinal nerve roots that best represent the sensory afferents of the pudendal, PTN, LPN, MPN and SAFN as illustrated in FIG. 10a-b and 11. In one aspect of this latter embodiment, surface electrodes could be applied on the lower back, and more specifically may correspond approximately to the locations of the sacral and lumbar nerves. Stimulation can be provided by external stimulators and IPCs 10 and/or at least one neurostimulator having at least one implanted component. Transcutaneous pulses can be delivered by two or more electrodes or a surface array of multiple-contact electrodes (e.g., two or more electrodes can be placed on the patient's back using the system of FIG. 18a), in which specific contact(s) of an electrode grid array can be used to selectively activate targeted spinal roots with the use of IPCs.

In addition to stimulating the entire pudendal nerve at a particular stimulation site, the coactive stimulation provided by the stimulation protocol may be applied to the any of the particular branch of the pudendal nerve (e.g., dorsal genital nerve or urethral sensory nerves), or to the pelvic nerve branches (e.g., bladder neck sensory nerve). Further, the co-active stimulation parameters for the nerve branches may be the same, or different, as those used for the full pudendal nerve. The timing of electrical stimulation of both pathways (e.g., PTN and pudendal) may be applied in a synchronous or asynchronous manner.

Therapeutic electrical stimulation for OAB can be applied in varying doses according to the stimulation protocol (e.g., duration=5 minutes to 1 hour) and intervals (e.g., daily, twice-daily, or weekly) that both maximize therapeutic efficacy and/or patient comfort. For the treatment of urinary retention, electrical stimulation may be applied up to a pre-voiding time such as 30-minutes before and during the "anticipated time" to empty the bladder. Further, a sensor, such as an implanted sensor for measuring patient data related to bladder volume could facilitate stimulation timing. A stimulation system having at least one implanted component and having sensing module 55 for obtaining and evaluating sensed data in order to provide feedback or closed loop control of therapy by a stimulation module 54 would be one suitable candidate system. A sensor 634 may be used to provide sensed data to an implantable neurostimulator which could process the data and then, if merited, communicate this data to an external patient device which, in turn, could provide visual, auditory, or other signal to a patient signaling that voiding is warranted. A patient can operate a external device to cause the implantable neurostimulator to stop/start neurostimulation to modulate activity such as to provide therapeutic bladder inhibition.

Based on the results of FIGS. 13-15, a further embodiment of treatment for bladder disorders may involve a stimulation protocol involving stimulation 626 of at least one PTN and/or SAFN branch and concomitant activation of the pudendal nerve (dorsal genital or urethral sensory). The ability to activate these excitatory and inhibitory bladder reflexes by selective PTN branch stimulation suggests that systems using combination stimulation of neural pathways can be utilized for improving therapy for bladder disorders.

Based on the results of FIGS. 13-15, a further alternative embodiment of treatment for OAB involves providing a first stimulation signal, for example, in the 5 Hz range for the PTN, MPN, and/or SAFN and providing a second stimulation signal to provide simultaneous pudendal nerve stimulation. The second stimulation signal can be in a range from, for example, 5 Hz to 20 Hz, or 2 Hz to 50 Hz. The second stimulation signal can alternatively, or additionally, be used to stimulate a nerve target which is the sacral nerve and/or pelvic nerve (e.g., via S3).

Based on the results of FIGS. 13-15, a further embodiment of a system and method for treatment of OAB may involve providing a stimulation signal, for example, 10 Hz stimulation of at least a first nerve target including the PTN or SAPH branch. A second stimulation signal can also be used to provide co-activation of the pudendal, sacral, and/or pelvic nerve stimulation. The second stimulation signal can occur, for example, at 1 Hz to 100 Hz, and preferably between 2 Hz to 50 Hz.

A further embodiment of OAB treatment involves providing a first stimulation signal of approximately 20 Hz to at least a first nerve target which is the PTN, LPN or SAFN. A second stimulation signal can provide approximately simultaneous co-activation of the pudendal nerve using, for example, at approximately 2 Hz to 25 Hz.

A further embodiment of treatment for OAB involves providing a first stimulation signal of for example, approximately 50 Hz to a first nerve target which is the PTN or LPN. A second stimulation signal can provide co-activation of a second nerve target which is the pudendal nerve stimulation, for example, at approximately 2 Hz to 50 Hz. This embodiment can be used to increase the bladder activity of a patient.

In another embodiment, a first nerve target (e.g., the PTN or MPN) is provided with stimulation that occurs periodically while simulation of a second nerve target (e.g., S3) is chronically provided such as by an implanted neurostimulator in order to provide better treatment than the latter alone due to different mechanisms of the two targets. Various stimulation protocols may be designed so that stimulation at the first and second nerve targets occurs at different or overlapping times. However, as has been disclosed, approximately simultaneous co-activation by stimulation of the second site may augment the influence that stimulation at the first site has in modulating bladder activity. In embodiments, the stimulation parameters for the first site and second site, can include stimulation parameters for the second site which are based upon the data of FIGS. 13-15 and selecting those frequencies which were found to provide larger modulation. Alternatively, different stimulation parameters can be used.

Increased Therapeutic Benefits

Based on the results of FIGS. 13-15, novel systems and methods of selectively stimulating the various PTN nerve branches may offer improved therapy. For example, in an embodiment a stimulating electrode that targets the tissue of, or proximate to, the large toe (with a return electrode located on the medial surface of the foot, or elsewhere) can selectively activate the MPN. An electrode can be located to provide stimulation to a target near the three smaller toes to activate the LPN (with a return electrode located on the lateral surface of the foot, or elsewhere). The stimulators may be applied and held in place using conductive electrode cream as is often done with TENS, may be held at appropriate locations by an elastic band, disposable electrode, or sock. In order to increase the responsiveness of the nerves to stimulation, IPCs can be implanted in the foot to activate the target nerve. The IPCs can also be implanted below the medial malleolus after the bifurcation of the PTN to enable selective stimulation of the MPN or LPN.

The limited efficacy of PTN stimulation near the medial malleolus serve to highlight some selective PTN branch stimulation benefits. During PTN stimulation other nerves that converge in the PTN, such as the calcaneal nerve, may be electrically activated and cause great discomfort to a patient. The unwanted activation of such non-targeted nerve fibers can limit the total amplitude of the stimulation signal and thereby limit the sufficient recruitment of targeted fibers needed for suppressing bladder symptoms. Even at larger amplitudes, PTN modulation of bladder activity can be less than that enabled by selective nerve branch stimulation. Su et al (Am J Physiol Ren Physiol 2012) showed an upper limit of stimulation amplitude (4×Tm in rats), beyond which PTNS fails to suppress bladder activity. Selective nerve branch stimulation may enable TENS therapy to occur either at home or in the clinic, rather than requiring percutaneous stimulation to provide sufficient energy to modulate bladder activity.

Electrically stimulating more than one PTN nerve branch, as occurs with PTN trunk stimulation, may cause certain nerve fibers to produce small effects, no effect, uncomfortable/painful side-effects, or effects opposite to that of the intended modulation of bladder activity. For example, electrical stimulation of the entire PTN at 5 Hz produces post-stimulation inhibition which is similar to that seen when stimulating only the MPN (FIGS. 13, 14b) while having little or even an opposite effect via stimulation of the LPN. Selectively activating a specific nerve branch, instead of the entire PTN, may provide advantages such as less side effects, increasing the number of recruited nerve fibers, and greater treatment efficacy.

At higher stimulation frequencies, selective PTN branch stimulation may provide an effective means of generating or increasing bladder contractions and thus improving voiding efficiency. The inability to empty the bladder is characteristic of what is called urinary retention, where among myriad factors the underlying pathology may involve detrusor underactivity. As an example, stimulation of the PTN at 50 Hz produced about a 30% increase in BRC as a % of control (pre-stimulation) while stimulation of LPN produced a 130% increase (the response in FIG. 13C extends far beyond the top of the graph). In contrast, MPN stimulation generally produces a decrease, rather than increase, in bladder activity at this higher stimulation frequency. These data suggest that bladder excitation by stimulation of the whole PTN is partially retarded by co-activation of the MPN (although the PTN response is not the simple net effect of modulation of PTN and LPN). As such, a system and method which uses a stimulator for providing at least one stimulation signal in selective activation of the LPN may improve the treatment of detrusor underactivity compared to PTN. Selective stimulation of individual PTN branches may be accomplished using percutaneous, TENS, eTENS, magnetic and other stimulation methods as are disclosed herein. Further, both assessment and stimulation protocols can stimulate the LPN, MPN, and PTN (as well as other peripheral nerves such as the SAFN) to uniquely produce different amounts of bladder excitation or inhibition. If a particular frequency and/or nerve target combination does not provide the desired modulation or therapeutic effect during either assessment or provision of therapy, then an alternative combination could be attempted since it may provide improved therapy. Stimulation parameters and sites that provide improved modulation can be stored (e.g., as part of step 630) and subsequently used during by the stimulation protocol used during therapy 626.

The data presented in FIGS. 13-15 suggest that selective PTN branch stimulation may provide a means of increasing the 60% to 70% of patients who respond to PTN stimulation therapy, and improving the extent to which unwanted bladder symptoms are suppressed and abnormal bladder activity is treated. Selective PTN branch stimulation can activate one nerve using a selected amplitude and frequency or can be applied to multiple nerve branches, either simultaneously or in an alternating fashion. These experimental results were obtained using pulses applied at 6 times the threshold for motor movement of the foot in anesthetized rats. Although this is significantly higher than what is used in humans (typically the threshold for foot twitch), anesthesia effects may be partially responsible for such high stimulation amplitudes. The benefits of different stimulation sites and signal characteristics used in humans may depend on the maximum amplitude tolerated by individual patients.

Induction and Maintenance Therapy for OAB

FIG. 22c shows an embodiment of the current invention as a method of treating OAB comprising combining a first step of providing a first treatment protocol 252 such as stimulating the PTN percutaneously during a first treatment interval, which may occur inside or outside of a clinic, and the second step of providing a second treatment protocol 256, during at least one second treatment interval, such as an additional therapy that may include at least one of selective PTN branch stimulation including, for example, LPN and MPN stimulation. The therapy provided during the second treatment protocol 256 is realized using either transcutaneous or percutaneous stimulation, and which may use an IPC to improve stimulation. The second treatment protocol 256 can be provided at approximately the same time or within the same treatment session as the primary treatment protocol 252 (e.g., percutaneous stimulation in the clinic). Alternatively, the second treatment protocol 256 can be provided between first treatment protocol treatments of the first therapy 252 in order to improve the therapy (e.g., clinically based percutaneous treatment sessions in a clinic as may occur during therapy induction) or as maintenance therapy. The additional therapy provided by the secondary treatment protocol 256 can be provided using an external device configured to provide different types of stimulation signals (e.g., a TENS device, in the patients home). The provision of secondary therapy 256 can also be provided by stimulation signals and modalities such as RF, light/laser, sound/ultrasound, or other modes of stimulation that use various technologies as are disclosed herein. The provision of secondary therapy 256 can be implemented using an IPC which is used in conjunction with an external stimulator to provide an electrical, ultrasound, or laser stimulation signal other type of enhanced nerve stimulation, as disclosed herein. The secondary therapy 256 can comprise a secondary stimulation protocol that stimulates cutaneously located nerve branches (e.g. SAFN) while the first therapy protocol provides a first therapy that stimulates deeper nerves (e.g. PTN). In addition to providing the first and second stimulation treatments, in an alternative embodiment, the effects of these treatments can be assessed 254, 258 and used to adjust at least one of the treatment protocols. For example, if therapy does not meet at least one therapy criterion then a treatment such as the second treatment can be adjusted by changing the stimulation protocol according to at least one of the following: changing from LPN to MPN stimulation, changing from MPN to LPN stimulation, and changing a characteristic of the stimulation signal that is used. Alternatively, the patient response to the first stimulation protocol can be used to adjust the second stimulation protocol 256 (arrow E). For example, if percutaneous treatment of the PTN is found to produce a large therapeutic response at a particular frequency, then that same frequency can be used in the selective nerve branch stimulation. Alternatively a different frequency range can be assessed and selected for the secondary stimulation protocol. As shown in FIG. 22c (arrows C and D) the primary and secondary treatment protocol may simply be provided in an interleaved fashion. When the secondary treatment protocol 256 is home based, it may be repeated several times before the first (clinic based) protocol 252 is again repeated. In this manner, eTENS home based therapy may be used to extend the durations between which clinic-based percutaneous therapy occur. The secondary treatment protocol can be provided by the patient one or more times each day, one or more times each week, or as infrequently as one or more times each month, depending upon the patient response to treatment. Regardless of whether the secondary treatment protocol is provided in a clinic or at home, this may occur during stimulation sessions of 30 to 90 minutes. The protocols which define the provision of the first and second treatments 252,256 may define, for example, duration of treatment, inter-treatment intervals, and the stimulation signal, target nerves, and method of providing stimulation to a target nerve. These stimulation parameters can be adjusted according to the patient or doctor based upon an assessment of the patient response. The assessment of the patient response to treatment which occurs in steps 254, 258, and 260 can include assessment of patient data, and can be used to adjust the stimulation treatment protocols in various manners. For example, assessment of the patient response can lead to increasing or decreasing the interval between stimulation treatment, changing stimulation parameter such as those related to waveform, current, voltage, stimulation site, and duration of each treatment.

Additional Embodiments for Therapy for OAB

In an embodiment, a method and system for improving nerve stimulation treatment efficacy in a refractory patient, who has been assessed 254 as not responding sufficiently to a first treatment protocol which is PTN treatment, comprises administering a second treatment protocol 256 which is a combination therapy. The therapy can combine stimulation of the PTN with stimulation of one of the LPN or MPN (or LPN can be combined with MPN). The stimulation is at least one of transcutaneous, with or without an IPC, percutaneous, or may be provided by at least one implanted neurostimulator device having a pulse generator. Because the LPN and MPN can provide different efficacy than PTN stimulation, the combination therapy stimulation may produce larger and more consistent results than any of these alone. The therapy may also be applied to a patient who is not refractory. Combination therapy may occur at the same time, at different times (to avoid interaction effects), and may occur unilaterally, or one stimulation signal can be applied to the left side of body while the other is applied to the right (i.e. bilateral stimulation). When this therapy is accomplished by one device 50, the device should be provided with a signal generator configured to provide at least two independent stimulation signals to stimulate two therapy targets of a patient and to implement either monopolar or bipolar therapy at each site. A signal generator module 62 may contain two pulse generators, each of which is configured to provide selected stimulation protocol which is applied to a nerve stimulated by a stimulator of the device 50, according to combination therapy defined in a therapy protocol.

Because combination treatment does not allow assessment of the individual treatments, a system and method of treating a patient with bladder dysfunction can comprise treatment with a first stimulation protocol to the PTN for a first period 252, and then if assessment of response to the stimulation 254 indicates the stimulation is not effective, an alternative second treatment protocol is selected 256 to provide at least one of the LPN or MPN. Alternatively, treatment of the LPN, can be followed by a second protocol stimulating PTN or MPN.

Systems and Methods for Providing Nerve Stimulation

Figure 18A:
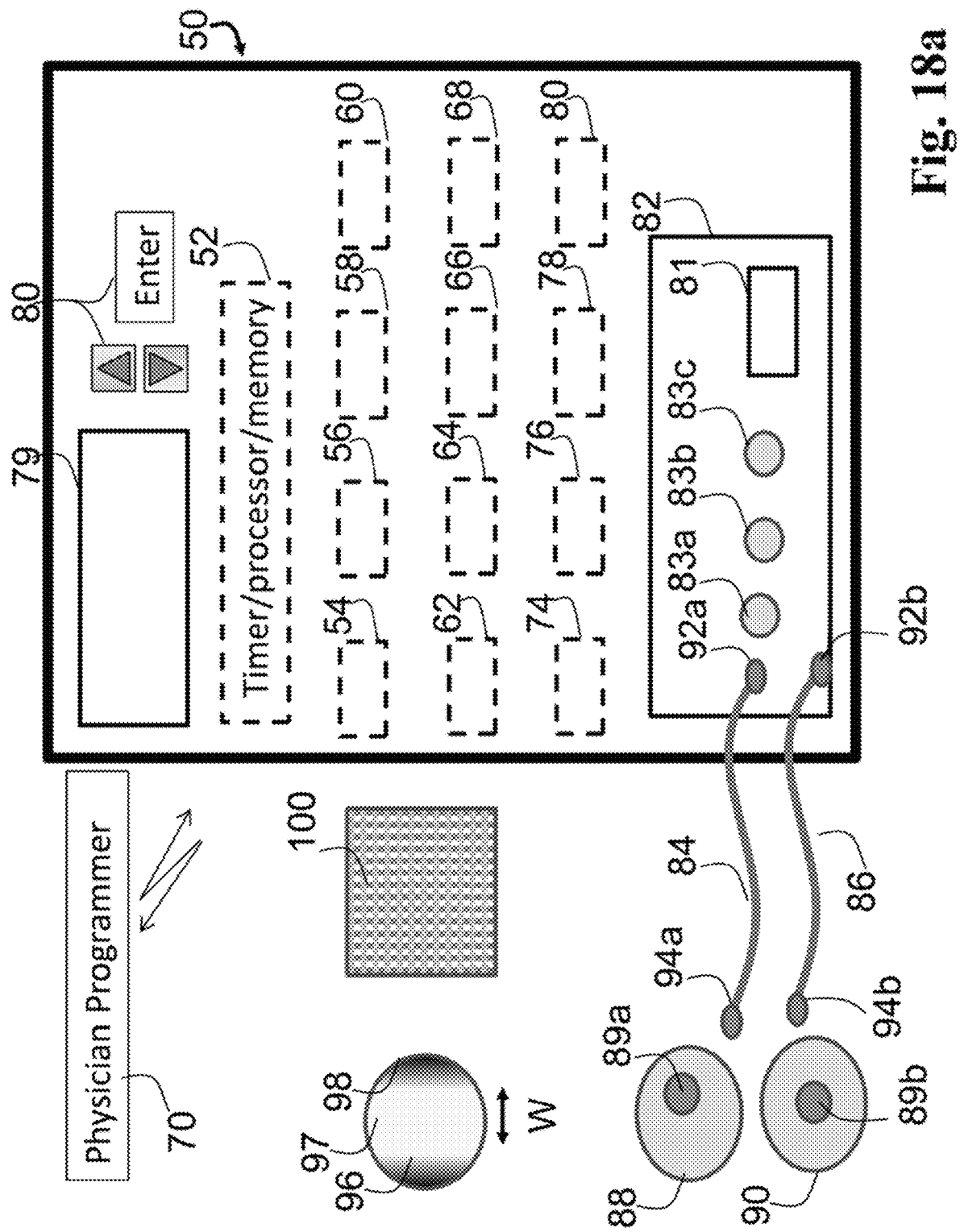
FIG. 18a is a schematic diagram of a tissue stimulation system which may be used to realize the current invention including the provision of tissue stimulation.

FIG. 18a shows a nerve stimulation device 50 that can be used to realize the methods and systems of the current invention. The device 50 is illustrated with a number of modules and components which may be included or adjusted in various embodiments. The device 50 comprises a control module 52 having a processor and control circuitry for controlling the various other modules such as the stimulation module 54 and sensing module 55 according to user input and/or treatment protocols and parameters stored in the protocols and parameters module 66. Treatment protocols can include stimulation protocols, sensing protocols, and evaluation protocols. These protocols may enable the device 50 to responsively adjust its operation in relation to the evaluation of sensed data, detection of events, patient input, time intervals, and other triggers that can cause the selection, provision, and adjustment of therapy. The device 50 can also simply provide stimulation continuously. The control module 52 has a timing module 56 including a real time clock and a timer, a processing module 58 including at least one processor for operating software, and processing information and parameter settings that are stored in memory module 60 and which allow for control of device 50 operation. The stimulation module 54 can control at least one waveform generator/signal processor such as module 62 that contains circuitry for generating pulses or arbitrary waveforms for output including alternating current (AC) and/or direct current (DC) signals to be used by one or more electrical, magnetic, optical, sonic, ultrasonic or other types of stimulators. The sensing module 55 (shown in FIG. 18b), may be realized as part of the AD/DA module 64 when AD/DA circuitry allows for both signal generation and acquisition, and contains circuitry and protocols for conditioning and analyzing sensed data and can also for providing power to, and/or communicating with, sensors. The processing module 58 enables the assessment of sensed data and can provide detection of events that are defined to cause delivery or adjustment of stimulation. This may occur in a closed loop manner, or may cause information (information about the sensed data) or signals (a flashing light) to be presented to a user of the device 50, such as by an external patient device 72 or physician programmer 70, who may then provide or adjust therapy. The processing module can aid in, for example, processing data as part of steps such as 38, 40, 42, and 258. For example, sensed data can be compared to at least one treatment criterion, and if the criterion is passed then stimulation is not changed (or is not provided), and if the treatment criterion is not passed, then stimulation is adjusted or provided, as defined by the treatment protocol. The processing module 58 may be configured to store a historical data record in order to track patient data, and usage and compliance data which may be especially helpful in allowing a doctor or patient to assess compliance when the patient uses the system at home. An AD/DA module 64 allows for conversion of input and output signals as well as amplification, digital signal processing, filtering, conditioning, and also contains safety circuitry to ensure patient safety. The AD/DA module 64 may also contain circuitry for multiplexing signals across different sensors or stimulators. The apparatus 50 also includes a communication module 68 for providing wired and/or wireless communication with other devices (e.g. an IPC which has communication circuitry and/or RFID identification means to communicate with the device 50, a physician programmer 70 or patient external device (EXD) 72. The communication module 68 can communicate with a computer at remote medical facility (which may serve as a second type of physician programmer 70' that allows device communication and programming to occur remotely) either directly, via the EXD 72, Bluetooth, or WiFi connection. The communication module can provide signals to transceivers which provide one way or two way communication of wireless power and/or data signals to implantable components such as neurostimulators. All wired or wireless communication can be realized at least partially using the internet, a local area network, and may also include means for magnetic, radiofrequency (RF), optical, sonic, and/or other modes of data and power communication with other devices. The communication module 68 and/or EXD 72 may include circuitry and routines for establishing WiFi, Bluetooth, cellular, magnetic, magnetic inductance, microwave, RF, electrical, optical, sonic, RFID, or other types of communication using communication/interface ports 82 which may control related devices. The communication module 68 is configured for use with USB connectors and the like. The communication module 68 of the device 50, as well as communication circuitry which may be provided on a stimulator 14 and/or IPC 10 may operate to send or receive signals using near field, far field, induction, magnetic resonant induction components, coils, antennae, and/or rectennae, optical sensors and stimulators, sonic stimulators and sensors, etc. This allows for successful communication of identification, data or power signals between any external and internal components of a particular embodiment of the invention. The apparatus 50 also has a power supply module 74 which can include components such as a battery, AC and DC converters, diodes that function to rectify wireless power signals harnessed by rectennae and circuitry related to the conversion or provision of power which may be related to harvesting or transmission of wireless signals, and can provide a power cord for connecting to a wired power source through at least one of the communication/interface ports 82. In an embodiment, a processor of the simulator that provides simulation related to therapy resides within the physician programmer 70 which may be realized as a laptop computer that can calculate and provide the model result data. These data may be used by a physician, and can be used by control circuitry of a neurostimulation system, to adjust and control the stimulation circuitry in order to provide stimulation to the patient according to a stimulation protocol. In an embodiment the computer module performing the simulation is adjusted based upon imaging data scanned from a patient, such as collected MRI or sonography in order to reflect the physical characteristics of an area of a patient's body within which the stimulation target is located. The activation and control of the stimulation grid array 100 may occur according to results provided by the simulation in order to increase the probability that the IPC will successfully serve to enhance the stimulation of target tissue.

The communication module 68 can work in conjunction with the user interface module 76 which contains hardware and software for presenting information to a user (e.g. patient or physician) and obtaining information/input from the user. Although the device 50 may communicate with a physician or patient programmer 70,72, such as may be realized by a specialized device, smartphone or tablet computer, the device 50 may also have at least one signaling module 78 with related circuitry and control a display 79 for presenting visual data in both text and graphical format, and for presenting alarms which are related to the provision of therapy and contain a speaker for presenting auditory signals. The signaling module 78 can have a Bluetooth enabled sound system that communicates with a speaker, or sound transducer such as a hearing aid by way of the communication module 68. The device 50 can also contain patient interface module 80 with controls such as a keyboard, nobs, switches, etc. to allow a user to provide input, such as through a menu guided system, as well as adjust operation of the device by manually adjusting nobs related to the operation of the device. It is obvious that various modules such as modules 78, 79, and 80 can also be realized within the physician or patient programmer 70,72.

Both the control module 52 and the waveform generator module 62 may be configured with safety hardware and software routines, including calibration routines to calibrate the apparatus 50 and to ensure proper functioning. In some embodiments, the control module 52 allows stimulation programs to be implemented according to protocols stored in the device memory and according parameters that can be adjusted by a user's manual input obtained by the patient interface module 80, but the safety routines may limit the adjustments to be safe.

The device 50 may use at least a first stimulator conduit 84, a second stimulator conduit 86, to communicate signals to a first stimulator 88 and second stimulator 90. In an embodiment, conduits comprise single or multi-stranded electrically conductive, insulated electrode lead wires and stimulators may be electrically conductive cutaneous electrodes. The first conduit 84 has a first end connector 92 that may contain a plug that electrically couples to a first stimulator interface port 83*a* of the interface 82. The first stimulator 88 is preferably secured to the second end connector 94 of the stimulator conduit 84 using a stimulator connector 89*a*. The stimulator connector 89*a* may be an adaptor such as a metallic snap that is configured to connect with the second end connector 94*a*.

The second conduit 86 also has a first end connector 92*b* and a second end connector 94*b*. The first end connector 92*b* of the second conduit 86 electrically couples to a second stimulator interface port 83*b*. The second stimulator 90 can be connected to the first end connector 94*b* of the second conduit 86 using an electrically conductive connector 89*b*. The second stimulator interface port 83*b* may be connected to a TMS device to control the provision of magnetic stimulation as part of the system and method of the current invention.

Additional wire interface port 83*c* is shown that allows for another stimulator to be used. Additionally, rather than stimulators, the interface ports 83 can be connected to sensors. Further, when the stimulators are, for example, cutaneous electrodes, then the electrode can serve as both stimulator and sensor at different moments in time. In other words a stimulation electrode 88 can serve as sensor when the sensing module rather than stimulation module is operational for a specific port during a period when sensing occurs.

The interface ports 83*a-c* may each be configured to connect to conduits having a plurality of wires. S stimulator connectors 89 configured on the stimulators can be configured to receive multiple conduit end connectors. For example, a conduit 84 may be realized as a ribbon cable that terminates in an end connector 94*a* having multiple contacts configured to attach to at least one stimulator end connector 89 and with the other end 92*a* configured to be plugged into an interface port 83 which is configured to operate multiple contacts related to the channels of the conduit 84. Accordingly, in an embodiment rather than having a single conductive surface of one polarity, a stimulator may be realized as at least one bipolar electrode having a first contact 96, and a second contact 98, connected to circuitry of the device by two stimulator connectors 89 (not shown) that are configured to attach to at least one end connector 94*a* of a conduit 84, and which may be separated by non-conductive surface 97. In an embodiment the bipolar electrode components including the contacts 96,98 and the non-conductive surface 97 that has been paired with the IPC length. The contacts 96, 98 may serve as an anode and cathode respectively or may both be anode or cathode with another electrode, located elsewhere, serving to complete the circuit. In a preferred embodiment the non-conductive surface would have a width that was the same width "W" as that of an IPC of the current invention. In an embodiment, the non-conductive surface may be transparent so that a user can see the IPC under the skin or a marking on the surface of the skin in order to aid alignment during affixation of the stimulator to the patient. Further, a stimulator can be configured as an electrode grid or multi-electrode array 100 having multiple contacts arranged in a grid pattern or otherwise, each of which is configured to communicate with a unique contact of a connector 89 and then channel of a conduit 84 so as to be individually operable during stimulation. In an embodiment used on the skin surface, unlike a "Utah" array which typically uses needle electrodes to stimulate nerves in vivo, the contacts may reside on a flexible or rigid substrate and be about 1 cm by 1 cm, with 0.5 cm of non-conductive material distance between—the individual contacts can be routed using individual wires to an interface having multiple contacts which communicates with the device 50. Alternatively the individual contacts of a grid can be activated by signal routing/multiplexer circuitry incorporated in the grid array to route the electrical signals to the appropriate electrode contacts, for example, under control of the processor 52. In an embodiment, individual electrode contacts of the electrode array 100 may be used to electrically stimulate the patient, and improve alignment with an IPC or target nerve, using signal routing and control circuitry in the stimulation module 54 of the device 50 to provide for spatial or temporospatial defined stimulation patterns. The grid array stimulator 100 may contain a signal router in order to cause spatial, or spatial-temporal patterns to be implemented using contacts of the grid array, under the control of the stimulation module 54, or the module itself may contain the multiplexor. The electrode grid 100 may also incorporate optical elements, such as LEDs, which can assist with visualizing a shape of the active grid elements and aligning an active electrode grid area with an area of skin 20 of a patient 8 or with an implanted IPC. The interface ports 83 may also connect in a wired or wireless manner to communicate with and/or power various sensors, such as sensors that are configured to measure bladder activity, bladder pressure, bladder fullness, or other characteristic related to a condition or disorder being treated. Additional sensors and stimulators are not shown in addition to sensor/stimulator electrodes 88,89 to avoid cluttering of the figure. A treatment protocol can be stored in the protocols and parameters module 66 which causes the grid array to provide stimulation using 2 or more unique row activations in a manner that assists with aligning the active element of the grid with an edge of the IPC. For example, the grid array stimulator 100 may have a grid of 10 rows of contacts and 12 columns of contacts. One stimulation protocol can have a first step where a stimulation signal is provided by all the elements of rows 1 and 10, a second step where a stimulation signal is provided by rows 4, and 10, and a third where stimulation is provided by rows 8 and 10. In each step, unique row activation is provided for 1 minute, and within a 30 minute stimulation period, it is likely that a row of the array stimulator and an edge of an implanted IPC will approximately align. In this example, within the 30 minute stimulation period this stimulation protocol at least 10 minutes should be well paired with an eTENS system component. Additionally, rather than using entire rows during an activation, the array stimulator can activate the electrode contact elements 1-4 of row 1, elements 5-8 of row 4, and elements 9-12 of row 8. Rather than horizontal rows, the grid stimulator can also activate other patterns such as a diagonal row in order to provide stimulation arrays that are oriented correctly with respect to the edges of the IPC. Lastly, the grid array can use arbitrary patterns rather than rows and the grid elements do not need to be square.

The width of non-conductive surface 97 can be set to provide improved stimulation by an IPC. For example, the data of FIG. 3A to FIG. 8B, support an embodiment of a method having a Step 1 in which an aspect such as the width or length of the IPC is adjusted/selected in relation its implanted depth (i.e., distance from a cutaneous stimulator to the IPC). In step 2 a physical characteristic of at least one stimulator (e.g., the distance between the edges of the stimulator and a second stimulator, or the location of an edge of the stimulator) can then be set according to at least one physical aspect of the IPC (e.g. IPC length) in order to provide for "pairing' and improved activation of the target nerve. In step 3, treatment is provided to the IPC using at least one suitably paired stimulator.

Figure 18B:
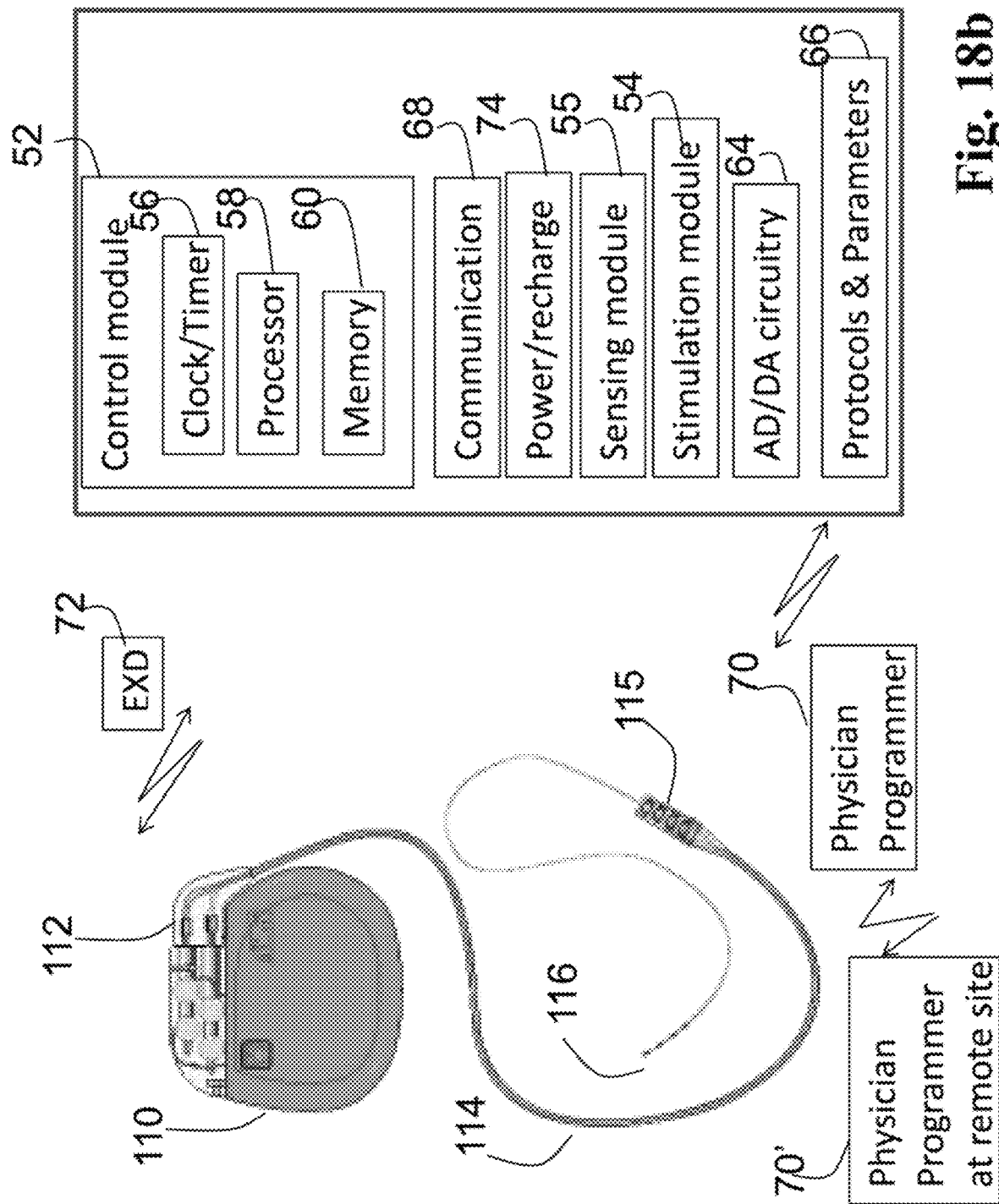
FIG. 18b is a schematic diagram of a tissue stimulation system including an implantable electrical stimulation system which may be used to realize the current invention.

The modules described for the apparatus 50 are for illustration purposes only and the device 50 used by the system of the present invention can be realized with less than or more than the modules and system components shown in FIG. 18*a* or 18B and described in this specification, or can be realized in alternative embodiments. For example, rather than having a protocols and parameters module 66, the information related to stimulation protocols and parameters can be simply stored in the memory module 60. Similarly, rather than having a stimulation module 54 and a waveform generator module 62, equivalent functionality can be realized an AD/DA module 64 which contains these modules and all other necessary hardware, software and/or code required to provide stimulation and sensing. Accordingly, in device 50, disclosed components may be omitted and modules may communicate with, and share, resources of other modules. Any of the modules of the device 50 shown in FIG. 18*a*, can be realized partially or fully in the physician/patient programmer 70, or EXD 72, or neurostimulation system of FIG. 18*b*. The modules may be within the device 50 housing or may exist externally and communicate with wired or wireless manners.

The apparatus 50 may be realized as a portable or desktop instrument that controls accessories. The system can be implemented, at least in part, as customized hardware that plugs into a port of an smart-phone or tablet computer or which communicates with the smartphone or computer so that some of the modules shown in FIG. 18*a* are realized by the smart phone or computer. The device 50 should have accessory ports, such as USB ports, to allow wired communication and connection to other system components and accessories.

The device 50 can use stimulators incorporated within the housing itself rather than being connected to the device 50 by wires. In one example of this type of embodiment the stimulators can be configured as re-usable electrode stimulation plates rather than disposable electrodes. The apparatus 50 may also use percutaneous stimulators including needle electrodes. The apparatus 50 may be realized using electrical stimulators distributed by companies such as Uroplasty and Electrocore and Medtronic for providing various types of stimulation including electrical and magnetic stimulation. In alternative embodiments of the invention, the stimulators can be configured to work with IPCs or implantable active components (IACs) such as those which are magnetically driven. Stimulators used by the device 50 can be coils which induce magnetic fields in and around the implantable components and/or in the tissue itself. In general, it is obvious with respect to providing therapy, that either an IAC, IPC, or conventional neurostimulation system which uses an implantable pulse generator and stimulator electrode, with at least one contact, can all be used relatively interchangeably in order to provide stimulation using the protocols and nerve targets disclosed herein.

The transcutaneous tissue stimulation system can contain a signal generator for generating a stimulation signal. The signal generator can provide a stimulation signal that is appropriate for at least one modality of stimulation such as electrical, magnetic, (ultra)sonic, optical, thermal, or other method of stimulating tissue directly, in combination with an IPC, or IAC. At least a first stimulator, coupled to said signal generator, is also provided and adapted to be positioned adjacent to a patient to provide a signal to modulate target tissue in the patient. In an embodiment at least a first IPC is located adjacent to or contiguous with a target tissue for enhancing the modulation of said target tissue by the signal provided by the stimulator. The stimulator and IPC can be paired so that modulation of tissue is enhanced relative to the modulation that occurs in the absence of the IPC.

In an embodiment where a stimulator provides magnetic or electrical stimulation transcutaneously, the IPC is configured with at least a portion that is electrically conductive. A device that is configured to provide magnetic stimulation to tissue, having a stimulator that is at least one stimulation coil, is disclosed in U.S. Pat. No. 8,052,591 entitled "Trajectory-based deep-brain stereotactic transcranial magnetic stimulation", and in US2013/0317281 entitled "Transcranial magnetic stimulation for improved analgesia", and in U.S. Pat. No. 6,453,204 entitled "Magnetic electrode for delivering energy to the body", and in U.S. Pat. No. 8,676,324 entitled "Electrical and magnetic stimulators used to treat migraine/sinus headache, rhinitis, sinusitis, rhinosinusitis, and comorbid disorders", in US2014/0247438 entitled "Systems and methods for vagal nerve stimulation", and in U.S. Pat. No. 8,435,166 entitled "Method and Apparatus for magnetic induction therapy", all of which are incorporated herein by reference in their entirety for all purposes, and may be realized as part of the system of the current invention. When a magnetic coil is used to provide a magnetic field, the signal generator 62 may serve as an impulse generator capable of powering the magnetic coil stimulator.

In an embodiment where the stimulator provides sonic stimulation, the IPC is configured with at least a portion that is responsive to the sonic stimulation signal. For example, the IPC can be configured with a portion that has physical characteristics (size, density, shape, structure) that allow it to absorb, reflect, or resonate with the sound energy more than human tissue in order to enhance modulation of activity of adjacent nerve tissue. A device that is configured to provide ultrasonic stimulation to tissue is disclosed in US20140194726 entitled "Ultrasound Neuromodulation for Cognitive Enhancement", in WO2014127091 entitled "Transcranial ultrasound systems", in US20110270138 entitled "Ultrasound macro-pulse and micro-pulse shapes for neuromodulation", and in US20110190668 entitled "Ultrasound neuromodulation of the sphenopalatine ganglion", which uses at least one stimulator which is an ultrasound transducer coupled to a signal generator 62, all of which are incorporated herein by reference in their entirety for all purposes, and may be realized as part of the system of the current invention.

In an embodiment where the stimulator provides optical stimulation, the IPC is configured with at least a portion that is responsive to the optical (e.g., laser) stimulation signal. For example, the IPC can have a portion with characteristics (size, shape, structure, reflectance, absorption) that allow it to absorb or reflect the optical energy more than human tissue in order allow the IPC to modulate the activity of adjacent nerve tissue. A device that is configured to provide optical stimulation to tissue is disclosed in U.S. Pat. No. 8,715,327 entitled "Baroreflex modulation using light-based stimulation", which uses stimulators which are light sources such as diodes, incorporated herein by reference in its entirety for all purposes, and may be realized as part of the system of the current invention.

When the IPC is used in conjunction with electric, magnetic, sonic, or light based stimulation, it may be realized as a nerve cuff, a solid rod, a hollow rod, a mesh structure, or other structure that allows the IPC to enhance the modality specific energy that is supplied by at least one transducer that serves as a stimulator of the invention.

The methods and systems for providing enhanced electrical stimulation provided by one or more IPCs, relative to what occurs without at least one IPC, is termed "eTENS". When the stimulator and paired IPC utilize ultrasonic tissue stimulation this is known as termed "eUltrasound", when the stimulation modality is light it is termed "eLaser", and when the modality is a magnetic field applied to tissue targets, which may or not also require transmission of the magnetic field through the cranium, it is known as "eTMS". The use of a passive element to enhance, focus, bias, or otherwise enhance the effect of externally applied stimulation to the modulation of tissue may be extended to other stimulation modalities as well.

A method of providing transcutaneous nerve tissue stimulation can comprise operating a signal generator 62 for generating a stimulation signal and operating at least a first stimulator coupled to said electrical generator 62, and positioning the stimulator adjacent to a patient to provide a signal to modulate a tissue target in the patient, and implanting an IPC adjacent to or contiguous with a target tissue for enhancing the modulation of said target tissue by the signal provided by the stimulator. The stimulation signal provided by an electric, magnetic, optical, or ultrasonic transducer may cause enhanced modulation of tissue relative to modulation in the absence of the IPC.

FIG. 18b shows a stimulation system configured to provide electrical stimulation to a tissue target, such as tissue near an IPC and may be realized by an implanted device 110 such as an implantable neurostimulator such as that used deep brain stimulation or spinal stimulation. The implanted device 110 has all the electronics typically provided in a modern implantable neurostimulator including components to provide for control 52, stimulation 54 which may include charge balancing circuitry to deter problems at the electrode tissue interface, as well as a safety circuitry such as a current limiter, communication 68, timing 56, and power supply 74 which may include both a battery and coil-based and/or antennae-based recharging circuitry for obtaining wireless power. Sensing capacity may also be provided via a sensing module 55 which may contain, for example, accelerometers, angle/position sensors, and which can communicate with sensors disposed on the housing of the device 110. Similar to the stimulation module 54, the sensing module 55 may communicate with a conduit 114, connected to the device header port 112, or an accessory port. The other modules shown on the dotted box on the right side of the figure that may serve an implantable device were already reviewed in FIG. 18a. The implanted device 110 will have ports 112 for securely connecting to an electrical conduit 114 (which may have an intervening connection member 115 to connect various types of implantable electrode conduits and sensors) and for communicating stimulation pulse waveforms along the length of the conduit to at least one stimulator 116 such as stimulation electrode which contains at least one contact, but often multiple contacts, to enable bipolar stimulation to occur. In FIG. 18b there are multiple contacts at the distal tip of the conduit 114. In an embodiment of the invention where at least one IPC is used with the implanted device 110 but is not connected to the device, the IPC would preferably have a length that was set proportionally to the inter-contact distance between two of the contacts of the stimulator 116, and preferentially the IPC length would be the same as the inter-contact distance. Further it would be preferable for the edge of at least one IPC to be aligned with the edge of one of the stimulation contacts. In the case of monopolar stimulation (e.g., tip to can) the electrode contact may be made to be longer than the length of the IPC. In this embodiment, the IPC serves to stimulate a tissue target that is not immediately adjacent to a stimulator lead physically connected to the neurostimulator by way of a conduit.

The implanted neurostimulator device 110 may be any approved device on the market, such as the Restore™ Neurostimulator, which can adjust the stimulation in the treatment of chronic pain based upon factors including a patient's posture (e.g. sitting to lying down, from lying down to standing up). The apparatus may be realized by a device such as the InterStim® System for Sacral Neuromodulation, the Neuropace system for providing responsive neurostimulation to the brain in the treatment of epilepsy, or vagal nerve stimulation systems provided by Cyberonics for the treatment of, for example, epilepsy and depression. In an embodiment, rather than being located in, or near, the torso to provide spinal stimulation, the neurostimulator is located in a lower limb site such as between the ankle and the knee. A microneurostimulator such as the BION can also be used.

Figure 19:
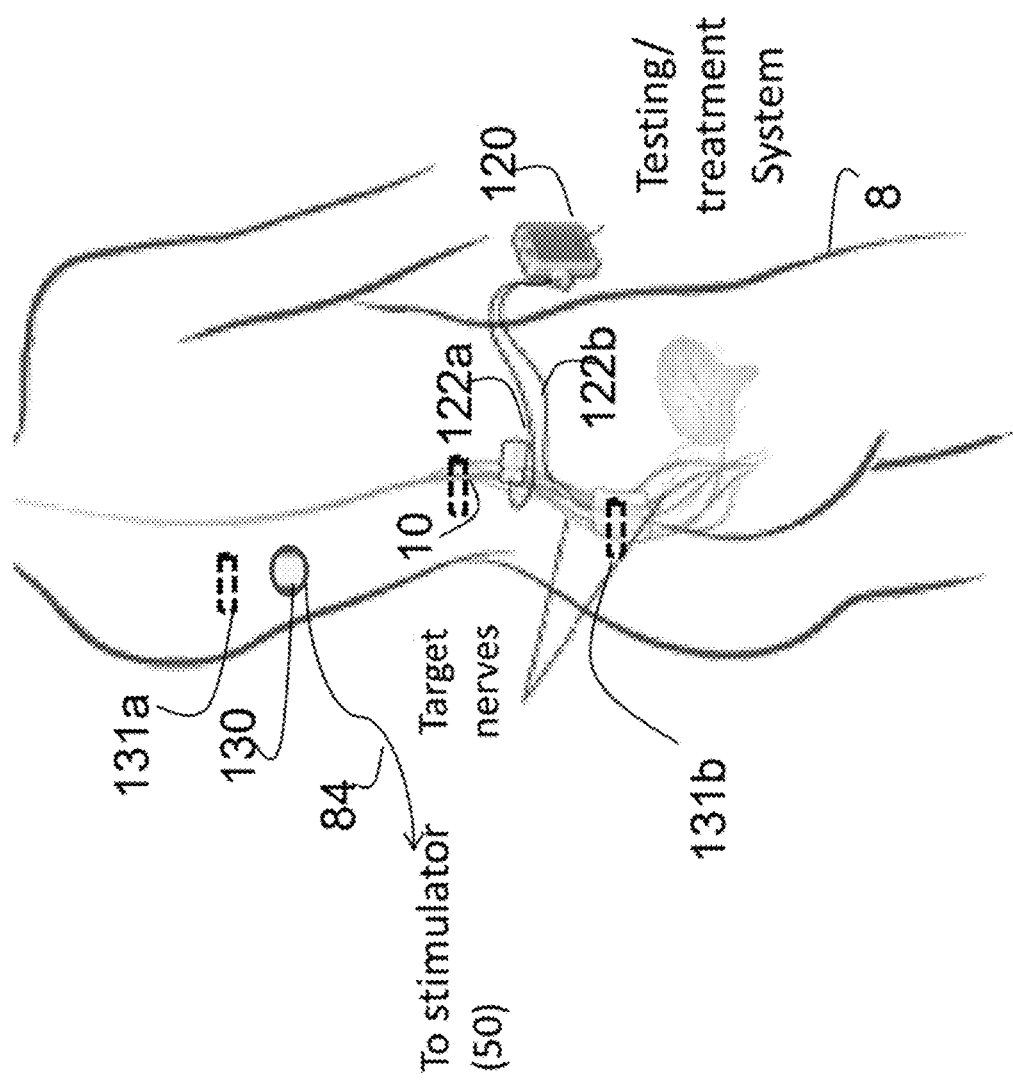
FIG. 19 is a schematic diagram of an alternative nerve stimulation system which may be used with transcutaneous stimulation.

FIG. 19 shows a schematic of an external electrical nerve stimulator 120 which may be used with either cutaneous or percutaneous connections to realize the current invention. For example, the stimulator can provide for percutaneous stimulation to electrodes 122a, 122b to stimulate the nerves (e.g., lumbar or sacral) of a patient (such as may occur during a trial stimulation period to assess patient response to stimulation at one or more candidate sites). An external neurostimulator 50 can also provide stimulation conduits 84 that terminate with cutaneous electrodes 130 placed superficial to one or more IPCs 131a, 131b implanted on or near spinal nerve roots such as the sacral or lumbar nerves. The IPC may be placed near the stimulation electrode contacts 130 and may be of a selected shape, orientation, and distance from the stimulation electrodes, according to the principles and innovative models of the current invention, so that target nerves may be selectively stimulated while minimizing or preventing the activation of nearby nerves which are not targets of the stimulation. Some leads and methods of implanting leads for stimulating targets such as spinal root targets have been disclosed in US APP Nos. 20140343656 (to Wechter), 20140324144 (to Ye), 20140324133 (to Deisseroth), and 20120203308 (to Gerber), PCT/US2014/029683, (to Perryman), and 20140081363 (to Clark), which may be used by the current invention and are all incorporated by reference herein. For example, the type of stimulator, applicator, and supporting structure disclosed in US 20010025192, entitled "Single and multi-polar implantable lead for sacral nerve electrical stimulation" can be used for stimulation of various spinal roots disclosed herein, and is incorporated by reference. It is understood that any embodiment using a nerve cuff that uses an implantable neurostimulator may use a conventional lead rather than a nerve cuff without departing from the invention.

In an embodiment, percutaneous stimulation electrodes 122a, 122b stimulate nerve cuff IPCs 10, 131b located at lumbar and sacral nerve targets, respectively. If either or both sites are found to be useful then a neurostimulator can be implanted and attached to the nerve cuffs to continue therapy. Alternatively, the IPCs may be operated as an eTENS system in conjunction with an external cutaneous stimulator (similar to 130 but not shown to avoid cluttering of the figure) which receives stimulation signals from an external device 50.

Differentially activating one or more subsets of neural pathways with IPC technology can provide the advantages of (1) improving modulation of a selected therapeutic outcome, (2) decreasing at least one stimulation-evoked side effect, (3) providing concomitant, but unique, stimulation related to each of a plurality of IPCs in order to provide for selective modulation of physiological responses associated with specific somatic or autonomic nerves, such as areas along these nerves (4) providing concomitant, but unique, stimulation to inhibit one or more physiological responses associated with somatic or autonomic nerves where IPCs have been implanted, (5) providing a mixture of stimulation which serves to both activate and inhibit different physiological responses (direct or reflexive) associated with either somatic or autonomic nerves or both, and (6) provide for improved selective modulation of specific motor responses and response pathways. In one embodiment, selective nerve activation is achieved by managing the relationship between the physical dimensions (e.g., length) of one or more IPCs to approximate dimensions of one or more corresponding stimulators. This relationship can follow principles derived using, for example, the results of FIG. 4 to FIG. 8.

Figure 20A:
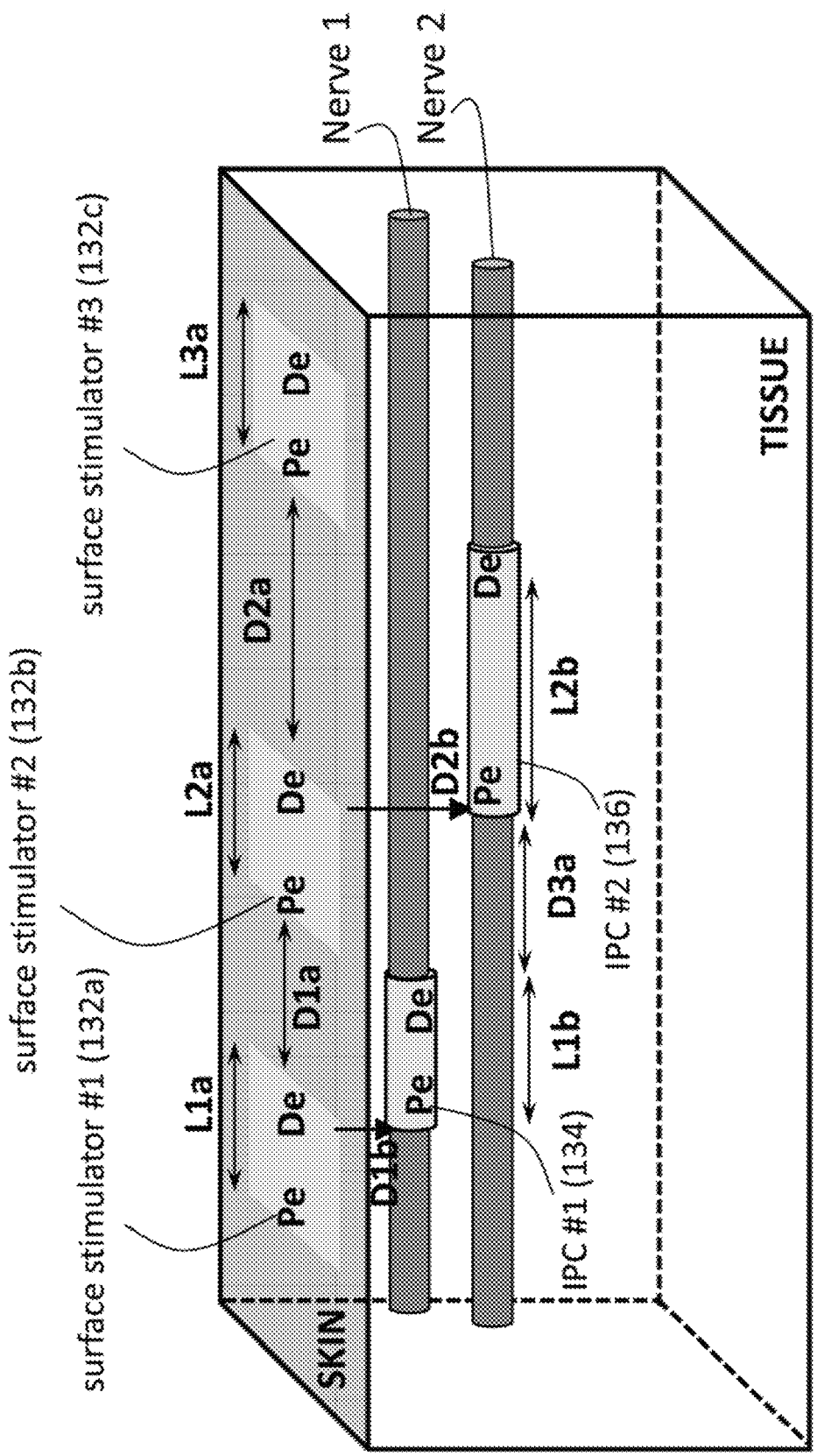
FIG. 20a is a schematic diagram of an embodiment of a system for selective (eTENS-based) activation of multiple nerves using a bipolar stimulation paradigm.

FIG. 20A shows embodiments of a system configured for selective activation of multiple neural targets (labeled Nerve 1 and Nerve 2). The system (or a model simulating the system) can be comprised of two or more IPCs placed in close proximity to, or around, nervous tissue targets to assist in providing selective activation of a single or plurality of nerves or tissue located within the body (e.g., muscle, connective, and fat tissue). In an embodiment this strategy can be implemented using bipolar electrodes, where the IPC lengths (L1b, L2b) are approximated by the distance between the surface stimulating electrodes (D1a, D2a). All electrodes, and IPCs that run along the length of the nerve, may be positioned in relation to proximal end (Pe) and distal end (De) of each system component. The depths of the IPCs from the skin surface (D2a, D2b) may be varied. At least one of the length, thickness, shape, conductivity, and edge position of an IPC can be set ("paired") according to other system characteristics, for example, the distance from the surface, position of stimulator edges, distance between the surface stimulators, or other dimensions of one or more surface stimulators according to the findings of the current invention related to enhancing nerve modulation. The surface stimulators can be connected to sources of energy such as stimulus generators, and may be configured to reside on a single non-conductive support backing structure in order to maintain appropriate inter-stimulator spacing and orientation (e.g. D1a). Although the orientations of the stimulators are shown as all the same and are aligned with the edges of the IPCs, it may be that angling one or more stimulators by an amount, for example +/−30%, may increase the probability that a portion of an edge of a surface stimulator will intersect an edge of an IPC, and this may be found to be a preferred embodiment because it facilitates setting up the system with less accuracy needed with respect to edge position. The system can enable the activation of a single nerve bundle using a given set of stimulation parameters (e.g. particular amplitude, frequency, pulse width, bursting pattern, duration, waveform, and duty cycle), or modulate two or more different neural pathways with the same or different sets of stimulation parameters. Surface stimulators 1, 2 and 3 can be independently operated, or stimulator 2 can be a common return for stimulator 1 and 3. When used to stimulate nerves such as those below the knee, the system configuration can be realized for both legs of a patient to provide bilateral stimulation.

Figure 20B:
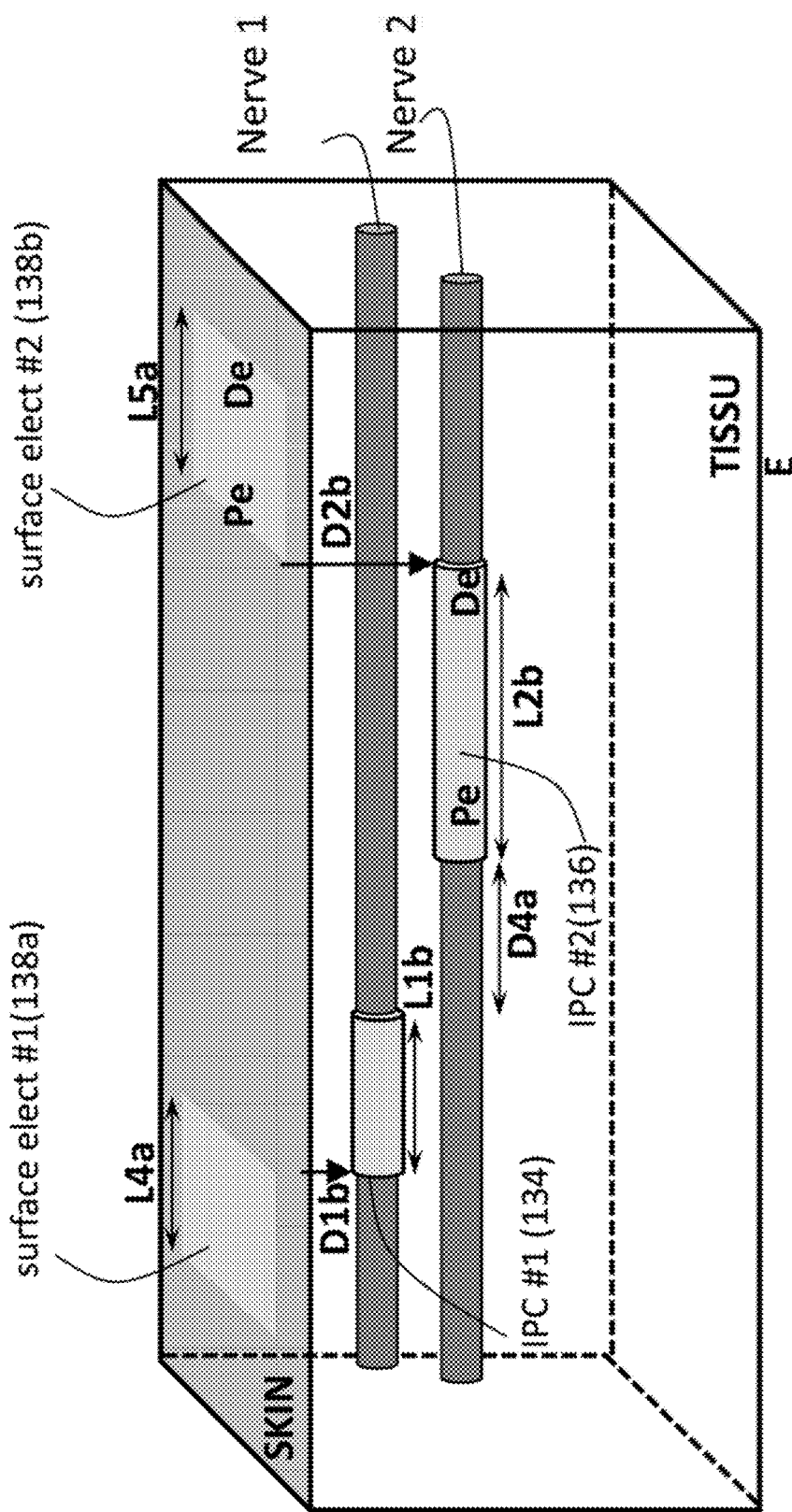
FIG. 20b is a schematic diagram of an embodiment of a system for selective (eTENS-based) activation of multiple nerves using a monopolar stimulation paradigm.

FIG. 20B shows another embodiment of selective nerve activation by enhanced transcutaneous nerve stimulation (eTNS) through the use of monopolar stimulating surface electrodes 138a 138b. The physical dimensions of each IPC 134,136 and the corresponding "paired" electrode (138a and 138b, respectively) are selected to match in order to provide selective eTNS (i.e., improved neural excitability of selected neural targets). In this case, the lengths of the two passive IPCs 134, 136 (realized as nerve cuff form factor placed around nerves 1 and 2) are L1b and L2b, respectively. Selective activation of each individual nerve is achieved by applying electrical pulses (transcutaneously) through surface electrodes 1 and 2, where selective enhancement can be improved by matching the edges of the IPC+stimulator pair. The stimulation delivered through each surface electrode will, in turn, primarily result in the corresponding generation of action potentials in each respective nerve. In an example monopolar embodiment, at least the proximal edge ("Pe") or distal edge ("De") of the IPCs is preferably aligned with an edge of a corresponding surface electrode. Correspondence, in the lengths of the stimulator and IPC "pair" a well as the alignment of the edges of the IPC and surface electrode, can be an important factor for improving selective activation of individual nerves in some monopolar and bipolar embodiments. Although in the figure L4a and L1b appear about the same length, L4a may be larger or smaller than L1b (i.e., stimulator length may be >, =, or <compared to IPC length). A stimulator-IPC pair can be matched to provide enhanced stimulation according to the principles of the current invention. All the physical parameters of the stimulation system can be simulated using the models disclosed in this invention in order to determine improved implementations within individual patients.

Figure 21:
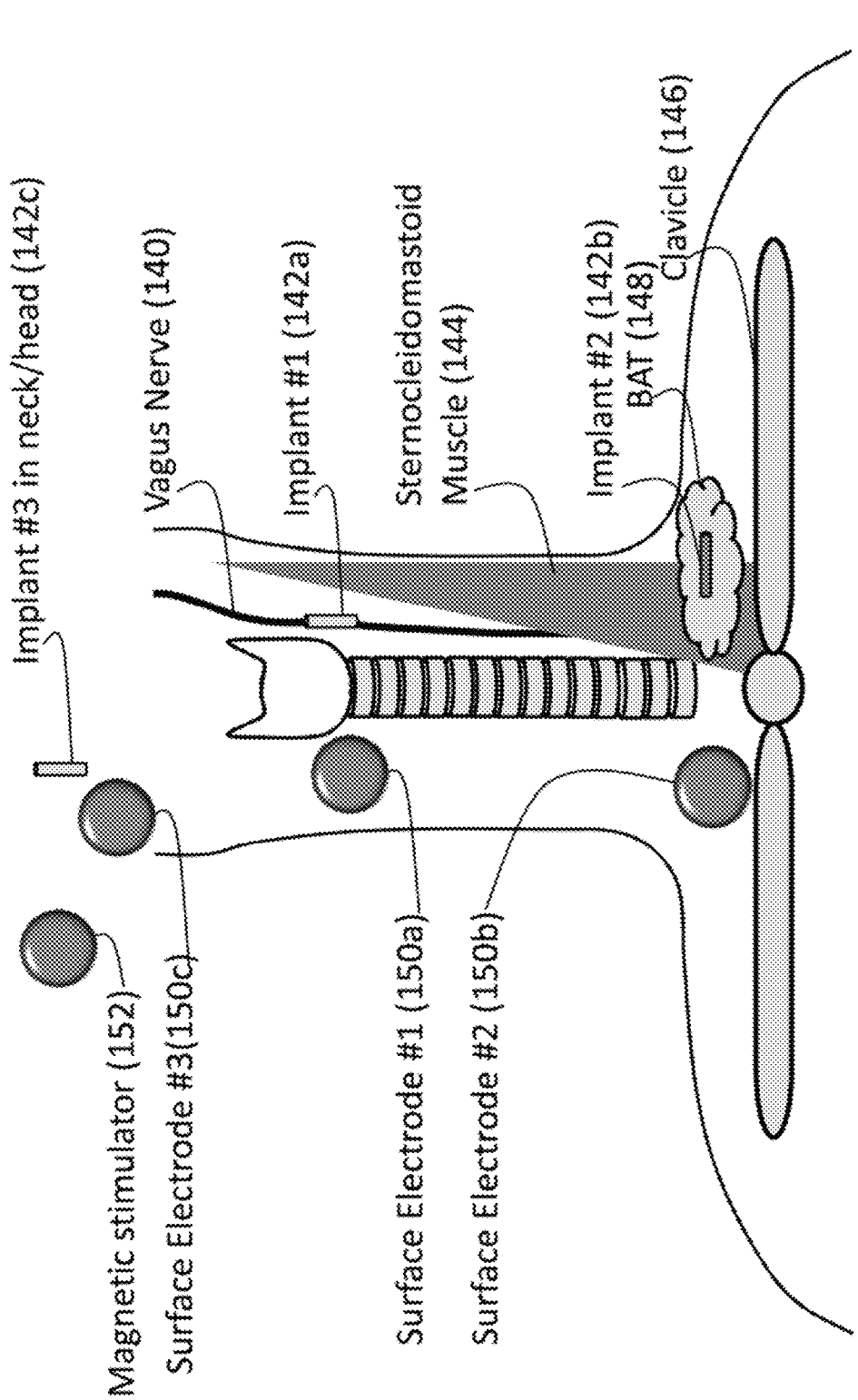
FIG. 21 is a schematic diagram of the enhanced transcutaneous nerve stimulation (eTNS) system for electrically activating nervous tissue at sites in the neck and upper chest.

FIG. 21 shows a schematic of system embodiments for activating nerves of the head, neck and upper chest, such as those of the autonomic nervous system. The system may be implemented for stimulating the vagus nerve 140 for treating epilepsy, migraine, blood pressure, depression, or respiratory disorders using IPC #1 142a. A second IPC 142b is shown implanted to activate sympathetic nerves within brown adipose tissue or "BAT" 148 (e.g., at a supraclavicular location) to treat obesity. Surface electrodes 1 150a and 2 150b are illustrated contralateral to the corresponding implanted IPCs in order to avoid cluttering of the figure, but would typically be located ipsilateral and appropriately aligned with the IPCs according to the inventive principles.

Selective activation of either the vagus nerve 140 (or selected fibers) or nervous tissue within the BAT 148 can be achieved by stimulator electrode 1 150a or electrode 2 150b, respectively, either of which may serve as anode or cathode. In a monopolar configuration the return surface electrode for either electrode 1 or electrode 2 can be placed on an anatomically appropriate location selected to cause minimal unwanted physiological or sensory activity at the return electrode site (e.g., tingling). The return electrode may be placed on the upper shoulder or hip. Electrical stimulation can also occur in a bipolar fashion, where each surface electrode is bipolar (with 2 contacts of opposite polarity) and is preferably placed such that at least one edge of a contact is aligned with one of the two edges of an IPC (see alignment of IPC #2 with stimulator #2 in FIG. 20A).

BAT stimulation may comprise placing a pair of surface electrodes laterally, relative to the IPC, whereas vagus nerve stimulation could comprise the placement of a pair of surface electrodes both rostral and caudal to the IPC. In another embodiment, two IPCs can be surgically positioned bilaterally (e.g., to stimulate left and right cervical vagus nerves). Activation of vagus nerve, or the autonomic nerves located within the BAT, can be achieved in a monopolar fashion where a first surface electrode is placed over the left IPC and a second electrode (i.e., return) is placed over a contralateral IPC. Each surface electrode can serve as an anode or cathode. To assist with spacing, two or more electrodes can be positioned on a non-conductive support backing structure such as a foam pad, and each contact can be connected to an electrical source of the respective polarity.

In an embodiment, the IPC #3 142c may be placed in the upper throat or locations in the head, face, or ears to treat disorder such as obstructive sleep apnea and headache as will be disclosed. In an embodiment, a magnetic stimulator 152 may induce a field in tissue near the IPC which causes an electrical field in the tissue and allows for selective activation of a tissue target.

Active and Distributed Embodiments

Although the systems and methods shown here do not have a pick-up electrode that is routed to a stimulation electrode, the findings reported here may have implications for such as system. In an embodiment the principles of the current invention, can be used to configure and improve a stimulation router system (SRS), such as that described in U.S. Pat. No. 8,332,029 entitled "Implant system and method using implanted passive conductors for routing electrical current" to Glukhovsky, which is assigned to Bioness Inc. For example, the "pick-up electrode" of the SRS may be configured for receiving a field provided by at least one selected stimulator in a manner according to the current invention. For example, the SRS may include a component that has physical dimensions and alignment with at least one external stimulator according to the principles of the current invention.

In an embodiment, an IAC can be realized as an implanted neurostimulator that obtains its power from an external magnetic stimulator and is provided with circuitry to convert the magnetic to electrical energy. Although the magnetic stimulator 152 and IPC #3 142*c* of FIG. 21 uses a passive IPC, an alternative embodiment may use a stimulator 152' that is configured to work with an IAC having active components 142*c*' such as a wireless power receiver 544 and related circuitry for controlling harvesting of magnetic fields to produce electrical stimulation signals. Either system may be operated using methods such as that shown in FIG. 22*b* which, in an embodiment, provides stimulation with an IPC for a selected duration in order to determine if a (typically larger) device should subsequently be chronically implanted in the patient, such as an implantable chronic vagal nerve stimulator. Embodiments of the current invention that are related to screening can be realized using a system akin to the magnetically powered neurostimulator disclosed in US App. 20130310895 entitled "Neurostimulator system apparatus and method" or the magnetically powered neurostimulator disclosed in US App. 20120101326 to Simon et al, entitled "Non-invasive electrical and magnetic nerve stimulators used to treat overactive bladder and urinary incontinence", incorporated herein by reference in their entirety for all purposes.

The generation of electric fields designed to penetrate intervening tissue may be provided by surface stimulators configured to generate an electric field with field lines extending generally in the longitudinal direction of one or more nerves to be modulated. In embodiments, stimulators may be separated along the longitudinal axis of a tissue target such as a nerve to facilitate generation of such an electric field. The electric field may also be configured to extend in a direction substantially parallel to a longitudinal direction of at least some portion of the tissue or nerve to be modulated. For example, a substantially parallel field may include field lines that extend more in a longitudinal direction than a transverse direction compared to a nerve. Orienting the electric field in this way may facilitate electrical current flow through a nerve or tissue, thereby increasing the likelihood of eliciting an action potential to induce modulation. Accordingly, in an embodiment, the orientation of at least one IPC is oriented along the length of a nerve in order to remain effectively paired with at least one stimulator, that is similarly oriented, in order to provide for enhanced stimulation of the nerve.

Tissue Modulation for Screening and Treatment.

In an embodiment an IPC 10 may be configured for implantation in a subject in a location that permits the modulation of target tissue which is a nerve 12 situated such that intervening tissue exists between the IPC 10 and the nerve 12. Intervening tissue may include muscle tissue, connective tissue, organ tissue, or any other type of biological tissue. The location of IPC 10 does not require contact with nerve 12 for achieving effective neuromodulation. However, placement of the IPC 10 located directly adjacent to nerve 12 is preferred for effective neuromodulation, such that little intervening tissue exists. During an implantation procedure locations and amounts of stimulation can be tested for the IPC 10, in order to assess suitability of various stimulation protocols, implant sites, response to stimulation, or effectiveness of therapy. Candidate locations for the stimulator may also be assessed. The IPC and stimulator "pair" can be sequentially tested and adjusted until a set-up is found that provides sufficient stimulation of a tissue target to meet a selected or therapeutic criterion. Additionally different sizes, shapes, and numbers of IPCs and stimulators may be assessed during the implantation procedure.

A stimulator 14 can be configured for use at a location external to a patient 8, either directly contacting, or close to the skin 20 of the patient. A stimulator providing a magnetic field to tissue near an IPC, or to the IPC itself, does not need to reside directly upon the skin. Alternatively, the stimulator 14 may be configured to be affixed to the skin 20 of the patient via adhesive, or an elastic band, sock or other securing mechanism that serves to hold stimulator 14 in place. The stimulator 14 should be placed so that it is paired with the IPC by being suitably positioned, oriented, angled, and/or configured with physical dimensions so that the IPC effectively provides enhanced modulation. The dimensions of at least one IPC and at least one stimulator may be adjusted or selected according to the distance that will exist between these two system components during stimulation of a patient.

Screening.

As a screening method eTNS has advantages over using percutaneous stimulation (PNS). Once the IPC is implanted, its effect can remain very constant with respect to increasing the activating function of a particular portion of nerve proximate to the IPC. In the case of PNS, the needle must be inserted and correctly positioned within the subcutaneous space at the beginning of each stimulation session. Additionally, eTNS can allow a screening period to occur at home because the patient is not required to undergo repeated piercing of the skin. Accordingly, the eTNS allows screening/treatment procedures which may involve more frequent nerve stimulation. Treatment may occur multiple times during the day or daily over several months. This is difficult when clinical visits are needed. Further, if a stimulator is affixed to a person's skin in order to stimulate during normal daily-life activities (perhaps for several hours each day) then eTNS provides significant advantage over PNS since it can occur for long periods of time without inconveniencing the patient. Since implantation of an expensive, chronically implanted neurostimulator is more invasive, the quick and easy implantation of an IPC may be desirable by patients and doctors as a first step in determining a proper therapy course. Even more so when the IPC is embodied as a simple, inexpensive, conductive cuff eTNS also offers advantage over approaches that require a temporary percutaneous leadwire since the IPC approach has less risk for infection. The IPC used during screening can be configured as a nerve stimulator electrode having a connector (e.g. IS-1 adaptor) that can be connected to an implanted device if the screening results determine that a fully implantable, chronic stimulator is warranted.

In an embodiment, at least two different IPCs can be used for screening or treatment therapy. FIG. 22A illustrates a method of implanting a first 200 and a second 202 IPC of lengths L1 and L2, and then situating at least a first and second stimulator 204 so that it is possible to stimulate a first IPC and second IPC, respectively. After the components are paired, treatment can be provided by at least one of the two paired stimulator-IPC pairs 206,208.

FIG. 22b illustrates a method of using eTNS as a method of screening treatment candidate patients who might benefit from various types and modes of neuromodulation therapy (e.g., fully implanted systems). In an embodiment, a method comprises the step of implanting, within the patient, at least one conductive implant proximal to an anatomical target of the patient 210. The target is selected as a candidate therapy target which will be assessed during the steps of the method. The next step 212 is to provide at least one stimulation signal to the patient from a stimulator located outside of the patient according to a screening protocol. There is also step of assessing the patient response to the provision of the stimulation signal provided in accordance with the screening protocol to produce a screening result 214. The screening result can be calculated from a comparison of data before and after stimulation, or may include an assessment of data from before, during, and/or after the stimulation takes place. The screening result can be calculated on data from a single stimulation session or from multiple stimulation sessions, across weeks or months, during which either the same or different stimulation parameters were used. In the screening method, if the screening result is positive then at least one positive screening outcome activity is performed 216. Alternatively, if the screening result is negative then performing at least one negative screening outcome activity 218 is performed. Positive results may be obtained when screening results are compared to at least one screening criterion and the data successfully pass the at least one screening criterion. Negative results may be obtained when screening results fail at least one screening criterion. A screening criterion may be for example, the reduction or increase of a selected type of activity or condition, such as a specified reduction in the number or severity of bladder leaks, episodes of urinary urgency, or headaches are experienced by a patient over a given time period. Examples of positive and negative screening outcomes are now provided.

The method may include, for example, a positive screening outcome activity 216 which includes implanting a fully implantable stimulation system in the case where the patient met at least one screening criterion. The positive screening outcome indicates that a fully implantable system is indicated. Since the patient positively responding to eTNS is interpreted to support that the patient is a good candidate for a more invasive stimulation system.

An alternative positive screening outcome activity 216 is to not implant a more invasive stimulation system. Since a patient met at least one screening criterion the patient any not require a fully implantable, or more invasive, stimulation system. Accordingly, depending upon the aim of the screening test, a positive result may indicate either that a fully implantable system is warranted or that a transcutaneous or eTNS system is sufficient.

In an embodiment, the determination of a clinically appropriate intervention may include a series of screening tests. Initially, a standard type of nerve stimulation is used and based upon the results of that first testing, an eTNS may then be assessed. Based upon the eTNS testing, either the standard, eTNS, or fully implanted system may be selected. If a patient does not respond to either TNS or eTNS, then no system may be implanted. Further, if both conventional and eTNS stimulation fails to meet at least one screening criterion then a different mode of therapy may be warranted—such as implanting a brain stimulation system if eTNS vagal stimulation did work. This can benefit a patient since they skip being let down by being refractory to an implanted vagal stimulation system.

A method may include, for example, a negative screening outcome activity 218 of implanting a fully implantable stimulation system if a patient failed a screening protocol. In this case, screening is negative because the patient failed to meet at least one screening criterion. This outcome may result in providing the patient with a different therapy, may indicate drug therapy should be simultaneously provided, may indicate an IPC location should be changed and the screening protocol redone, may indicate the stimulation protocol parameters should be adjusted a second screening test is done, or may indicate other alternative treatment paths are merited.

In an embodiment, a negative screening outcome activity 218 includes classifying the patient as a non-responder and seeking another type of treatment. Alternatively, a negative screening outcome activity includes changing the stimulation protocol and providing a second screening regimen. The change in the stimulation protocol 220 may include a change in stimulation site where the implant is located. If more than one IPC was implanted changing the stimulation protocol may simply include changing the location of the external stimulator in order to stimulate a different IPC. The change in the stimulation protocol may include a change in stimulation signal including for example, at least one stimulation parameter such as stimulation amplitude, frequency, inter-stimulus interval, duration, and number of treatment stimulations provided within a day, week, or monthly period.

Screening test results may be interpreted in the larger clinical context of a patient. Information such as history of response to pharmaceuticals, the patient's age, symptoms, preferences, and issues related to comfort may all play a role in determining how the results of the screening test are used to adjust subsequent treatment. If several screening criteria are used in a screening test then these may be evaluated together. For example, a first screening criterion may be use a smaller threshold than a second screening criterion. A patient may pass a first screening criterion, indicating that the patient is responsive to, for example, vagal nerve stimulation with an IPC, but may fail to pass a second screening criterion suggesting that an implanted system rather than an eTNS system is merited, or that an eTNS rather than TNS system is required. The external stimulator used in the screening may be an electric, magnetic, sonic, or other stimulator external to the patient.

A screening test may be useful as a measure which serves as an inclusion criterion in a clinical trial. For example, only patients who respond to eTNS therapy may be considered candidates for a permanently, and fully implanted nerve stimulator. In this manner, a clinical study for a permanent nerve stimulator will not include patients failing to respond to eTNS and thereby the trial may be able to show a larger treatment effect.

In one embodiment, a method of screening patient for eTNS, can comprise the steps of providing at least one stimulation signal 212 to the patient from a stimulator located outside of the patient according to a screening regimen, assessing the patient response 214 to the provision of the stimulation signal provided in accordance with the screening regimen to produce a screening result; and assessing the screening result 214 as positive or negative. In the case where the screening result is positive 216 then the method includes performing at least one positive screening outcome activity, while if the screening result is negative then the method includes performing at least one negative screening outcome activity 218. In the case of a at least one of a positive or negative outcome activity, the method includes implanting, within the patient, at least one IPC proximal to an anatomical target of the patient, the target being selected as a candidate therapy target and configuring the stimulator to provide stimulation to the implant. In an embodiment a patent has a brain disorder and the stimulator can be a transcranial magnetic stimulator. The IPC can be implanted within tissue that is at most 2 inches from the surface of the cortex (or 2 inches from the scalp). An IPC can also be implanted on, or within, a cortical target in order to enhance either TENS (e.g., tDCS or tACS) or electrical convulsive therapy (ECT) in the treatment of disorders such as depression.

Regardless of the screening test, test results can be computed upon a patient's subjective assessment of symptoms or upon evaluation of measured data such as sensed physiological data including electrical brain activity, cardiac activity, blood pressure, a measure of the eye such as pupil dilation, heart rate, or other features which may be used to assess the patient. When the test results are computed upon measured data, sensing 55 and processing 58 modules of a device 50 may provide for the data collection and assessment.

Implantable Component Designs.

A number of illustrative IPC designs are shown in FIG. 28 to FIG. 31 of this application. The IPC may be constructed in alternative shape and structures in different orientations than those shown here for illustration. Some IAC designs, such as that seen in FIG. 33 can be powered by a device that uses magnetic or RF means to power the IAC of the stimulation system, as is disclosed in US 20130085545, entitled "Electrode Configuration for Implantable Modulator" and US 20130079843 entitled 'Apparatus and methods for feedback-based nerve modulation", both to Mashiach, incorporated herein by reference in their entirety for all purposes.

Although, unlike various embodiments of the IPC of the current invention, the Mashiach technology relies upon conversion of electromagnetic signals for all of the embodiments of his invention, some of the principles for the electrode design disclosed by Mashiach are relevant to embodiments of the systems and methods of the current invention both for implementations that use electromagnetic signals and for those that simply use electrical signals provided from an external stimulator in the eTENS embodiments.

As shown in FIGS. 28a-e, The IPC 10 may include one or more structural elements to facilitate implantation, orientation, and securing of the IPC 10 into the tissue of a patient 8. The securing element(s) 517 may include, for example, suture holes, elongated arms, flaps, surgical mesh, biological glue, hooks or spikes of flexible carrier which serve to anchor the IPC to tissue. The anchor elements can facilitate alignment of the IPC 10 in a desired orientation within the patient. In an embodiment, IPC 506 may include a deformable elongated arm 530 having a two wing anchor such as a first extension 532a and a second extension 532b for increased stability. The anchor elements 532a and 532b aid in securing and orienting IPC 506 with respect to a target and stimulator. The elongated arm 530 enables the IPC to be secured slightly distally to soft or hard tissue targets (e.g., nerve, bone, or muscle, etc.) beneath a patient's skin. The IPC 10 may be formed as, or may be adjusted prior to surgery to assume, various shapes such as approximately an elliptical, circular, annular, cylindrical, or rectangular shape, or a shape that is determined based upon a particular target in patient. In embodiments, the shape, size, orientation, rigidity and other characteristics of the IPC can be selected or adjusted to facilitate orientation of the IPC with respect to a particular tissue target to be modulated, the shape of a stimulator, alignment of a stimulator, imaging data or measurements of a patient, or the distance between a stimulator and IPC. When embodied as a fully or partially cylindrical nerve cuff, the two opposing edges of the cylinder may be perpendicular to the IPC length, or at least one may be angled. Further, a beveled, pointed, or rounded, rather than flat, edge may be realized.

FIG. 33 shows an implantable active component (IAC). An IAC may be realized as a microneurostimulator embodied as a small rod form factor that can be implanted in a patient, but in a simple embodiment may be an IPC having at least one active component such as RFID circuitry, rather than being a completely passive IPC. In a more comprehensive embodiment, an IAC has components such as a wireless power receiver module which may contain an antenna, rectenna and/or coil 544 disposed along or outside of the housing of the IAC, electrode contacts 546a,546b that may be realized on the IAC housing or at the distal end of a lead, and modules having circuitry related to providing wireless power harvesting and conversion (wireless power module 548), communication 550, safety and power regulation 552, an identification information module 554 including an RFID chip, memory 556 for storing protocols and information, and control 558. The module circuitry may be mounted on, attached to, or integrated into the IAC, and/or conduits that communicate to the housing such as multi-contact electrode leads, and/or contained within the IAC housing 560, when housing is provided. The modules may be configured for operation and data/power communication in collaboration with an external neurostimulator device 50 in order to realize a treatment protocol and to be controlled by the external device. Sensing modules may also be included in order to provide sensing of sensed signals from a patient 6. Various circuitry and connectors may be used to connect circuitry to the IAC electrode contacts 546. To protect various IAC components from the environment within a patient's body, at least a portion of the IAC and or some of its components may include a rigid or non-rigid housing, a protective coating, and/or a non-conductive support member. In some embodiments, the protective coating/outer layer may be made from a flexible material to enable bending of components such as the electrode leads. In embodiments, the protective coating and/or housing may include for example, an alloy, silicone, silicone rubber, and silicone with polytetrafluoroethylene polyimides, phenyltrimethoxysilane (PTMS), polymethyl methacrylate (PMMA), Parylene C, liquid polyimide, polyurethane, laminated polyimide, polyimide, Kapton, black epoxy, polyether ketone (PEEK), Liquid Crystal Polymer (LCP), or any other suitable biocompatible coating such as selected from the group consisting of lubricious PVP, antimicrobial and anti-inflammatory coatings. In embodiments, the protective coating may include a plurality of layers, including different materials or combinations of materials in different layers.

The IACs and IPCs may have circuitry and include electrodes made of conductive materials, such as gold, platinum, titanium, platinum-iridium, galliumnitride, titanium-nitride, iridium-oxide, or any other biocompatible conductive material or combination of materials such as hydrogel. The IAC/IPC, including its housing, may be fabricated with a thickness and flexibility suitable for implantation under a patient's skin without a large risk of skin erosion. In an embodiment, the IAC/IPC 10 may have a maximum thickness of less than about 4 mm or less than about 2 mm, and the conductive components of the IPC may have a thickness of only 0.02 mm, as supported by the data of FIG. 7. Although the IAC of FIG. 33 is realized as a cylindrical form, which may approximate the cylindrical shape, size, and design of a BION or be realized as a neurostimulator such as those disclosed by Stimwave Technologies SCS neurostimulator (e.g., US Patent App No. 20140031837, "Implantable Lead"), or Micron Devices neurostimulator (e.g., PCT/US2014/029683 entitled Devices and methods for treating urological disorders), the IAC components can be formed into a nerve cuff that wraps partially or fully around a target nerve, or which is designed to cooperate with a nerve cuff or electrode lead to provide electrical stimulation to at least one electrode contact. Percutaneous injection of an IAC or IPC, in very close proximity to a target nerve is possible, but may be prone to potential migration issues over time. However, in some uses, such as stimulation that will be provided only for days or weeks, migration may not be a large concern. An IPC which is simply injected, or has a connection through skin, could be used as a temporary stimulator during initial screening of patients, similar to that used for the Interstim System at the level of the spine (and included in step 210).

Alignment Strategies.

Some advantages of the current invention rely on an IPC being correctly aligned with at least 1 external stimulator. FIG. 24a shows a controller device embodied as a smartphone 420 for controlling a stimulator device 400 shown in FIG. 24b that may be used by the current invention and which is approximated by the GammaCore tissue stimulator. The device 400 can have all the components disclosed in, for example, US App 20130066392 entitled "Non-invasive magnetic or electrical nerve stimulation to treat or prevent dementia", incorporated herein by reference in its entirety. Alternatively, the stimulator device can be implemented in a more distributed configuration and incorporate modules of the device 50 shown in FIG. 18. In an embodiment, two stimulators 402, 404 are provided on the stimulator device 400 which can each be comprised of conductive plates and serve as anode or cathode which may be dynamically assigned using control circuitry of the device 400. Additionally, either stimulator 402,404, may be realized as an electrode grid array 100. In alterative embodiments, the surface of the plate stimulators 402, 404 may be divided into separate regions which may be electrically active or inactive (e.g. insulated, or floating). For example, stimulator plate 404 is shown as comprising a number of horizontal contact surfaces 412 each row of which may be individually activated and which may be separated by non-conductive surfaces such as ridges. Only a portion of the horizontal contacts 412 may be activated to determine the functional shape of the stimulator. Further, the horizontal surfaces 412 can be adjustably activated (by the patient, by the stimulation protocol, by the controller device 420 or otherwise) so that these line up well with at least one implanted IPC 10. Additionally, the horizontal surfaces 412 can serve as at least one bipolar electrode having an adjustable inter-stimulator distance. The stimulator 404 may be rotated (under manual or motor control, when motorized adjustment means is provided within the housing of the device 400) for example, to align the stimulator contacts 412 and the edge of at least 1 IPC. Stimulation protocol parameters (provided by the control device 420 or device 400, of a stimulation program may direct stimulation signals to different contacts 412 at different times during therapy delivery in order to increase the likelihood that during an interval of stimulation the contacts 412 are well aligned with an edge of an implanted IPC.

The controller device 420 can allow a user to control the stimulation and to align a stimulator and IPC. In an embodiment, a digital camera 406 is provided which can capture still frame and video data and the digital data can then be displayed to a user assist in positioning the device 400 correctly. For example, the device 400 can use its communication module 68 to communicate with a tablet, smartphone controller device 420 configured to operate software related to positioning the device 400 during the provision of therapy. Communication can be wireless using a protocol such as Bluetooth or Wi-Fi. Alternatively, communication signals can be sent and received using a physical cable 422 that connects the smartphone controller 420 to the device 400, using at least one accessory port 416 on the device 400 and communicates, for example, using a USB communication protocol. During operation, the device 400 sends the video data to the smartphone which displays images so that the user can see and adjust what area of skin is being stimulated.

In an embodiment a surgical scar or a permanent or temporary tattooed symbol such as the "+" symbol may serve as a location marker 424 for an IPC. In FIG. 24a the "+" symbol displayed by the screen of the smartphone, although the stimulator is not shown being pointed at a patient to avoid cluttering of the figure. There may be 2 markers such as tattoos in order to more accurately align not only the edge, but the axis of the IPC with a stimulator of the device 400. In an embodiment the location marker 424 is electroconductive tattoos and allows for at least one sensor on the device 400 to issue a signal when a stimulator or sensor of the device 400 is in contact with the tattoo. In this embodiment the device 400 is designed to establish a closed electrical circuit wen correctly aligned with the tattoo that is detected by the device 400. For example, an impedance circuit could detect the impedance between the two stimulators, which would be significantly lower when these each are in contact with an electrically conductive tattoo. Alternatively, the tattoo itself could be designed to work with one or more stimulators and can serve as an extension of the stimulator that is aligned with an edge of an IPC. In embodiment, the neurostimulator device 400 projects on the patients skin a box that serves as a visual alignment signal 426. The signal may indicate, for example, where the stimulation field would be located relative to the target "+". Visual graphic signals can be superimposed onto the screen of the smartphone 420 such as navigation arrows 428a and 428b which can indicate to a user how to position the device 400 so as to achieve correct alignment before delivering stimulation. In other words, the users would attempt to make sure the + symbol location marker 424 resides within the box 426 before, and during, stimulation. Further, rather than having a "+" symbol, the device 400 can also provide a location guidance module 408 which may comprise circuitry and routines for assisting in aligning the system components and may also contain an NIRS sensor and/or laser to assist with alignment (e.g., by detecting the proximity of an artery to the stimulator). In an embodiment the "+" location marker 424 may be generated by the controller 420 or device 400 which can optically, or otherwise, detect the position and/or orientation of the IPC 10 and this may be used to guide alignment. A speaker 430 on the controller device 420 may provide auditory guidance cues such as "Please move the stimulator slightly up" or a series of beeps that change in frequency as the edges of the both a stimulator and IPC become well aligned.

In an embodiment, a processor of the stimulator 400 can analyze the visual image data collected by digital camera 406 in order select and activate certain regions of the stimulator plates 402, 404 due to results of calculating upon the data. The regions activated on the stimulators are thereby adjusted to improve alignment of stimulator and IPC components related to the stimulation of a target tissue. In an embodiment, the device 400 communicate with a tablet or smartphone controller device 420 configured to operate to allow a user to modify the stimulation parameters or protocols. Although the device 400 may be provided with controls situated on its housing in to adjust the stimulation, elderly or handicapped patients may not easily accomplish accurate manual control of the stimulation. Using a smartphone or other type of controller 420 disposed external to the housing of the device 400, and connected in a wired (via accessory port 416) or wireless manner may provide greater control and a more user friendly experience that may increase patient compliance.

In an embodiment, a device similar to the GammaCore can have an accessory port 416 that is multifunctional. The at least one accessory port can permit connection to at least one additional system component such as an electrode or other system components or external devices. A stimulator or sensor, such as a disposable electrode, can be attached to a conduit that plugs into the accessory port 416. The device 400, can then stimulate from at least one stimulator 402, 404 in combination with a third electrode located more distally. This may be useful, for example, if the device 400 is configured for both stimulation and sensing which occurs before, during, or after the stimulation. The third electrode allows measurement of dipole (of the third electrode referenced to either 402 or 404) which is larger than that possible using 402 referenced to 404, since these may be on the same side of the dipole. In the recording of cardiac or EEG data, this additional electrode can provide for improved measurement and functionality. This may allow the device 400 to stimulate the vagus nerve and also record cardiac activity using two or more electrodes which connected to the accessory port 416 and placed on the subject to robustly measure ECG activity. The third electrode advantage can be useful for stimulation as well in the case where 2 fixed stimulators are not preferable. Another benefit is that at least one of the two rigid stimulators 402,404 can be used to stimulate the temple of a subject, while the third electrode may be situated at the back of the head in order to cause the stimulation signal to travel from the fixed stimulators to the electrode (i.e. from the front to the back of the head or vice versa). This may ensure a greater transmission of the signal into the patient's brain or cranial nerves than may occur using the two fixed stimulators located proximal to each other. At least one distally located electrode may also be used to provide stimulation to the contralateral vagus nerve, or to provide neurostimulation such as tDCS, either alone or in combination with vagal nerve stimulation.

In an embodiment, the port 416 could be used to record signals from a surface electrode, which could provide a feedback signal (e.g., a measure such as foot EMG) which can be used for assessing a therapy response or aligning the stimulator with the IPC implanted near the PTN. In another embodiment, the EMG electrode can be placed over the larynx to measure vagus nerve activation during eTNS. In an embodiment the device 400 is configured with least one fixed stimulator 402, 404, and at least a port communicating via conduit with a least one electrode located at least three inches away from the fixed stimulator 402, 404.

Figure 24D:
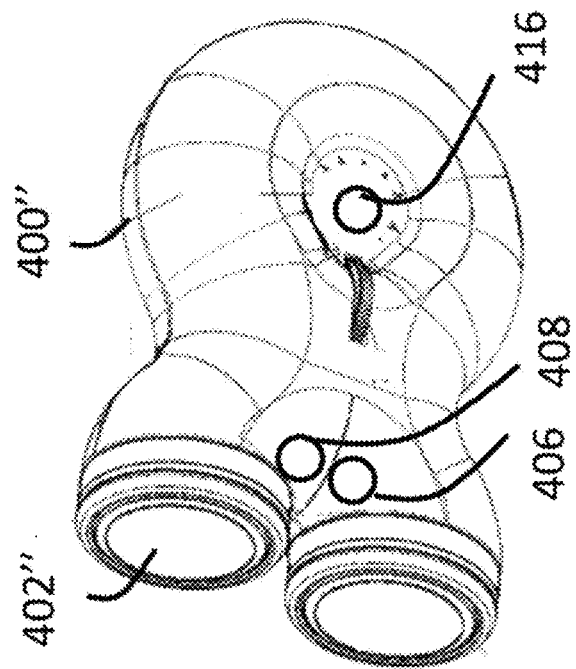
FIG. 24d is a perspective schematic view of a stimulator for providing tissue stimulation using two stimulators.
Figure 24C:
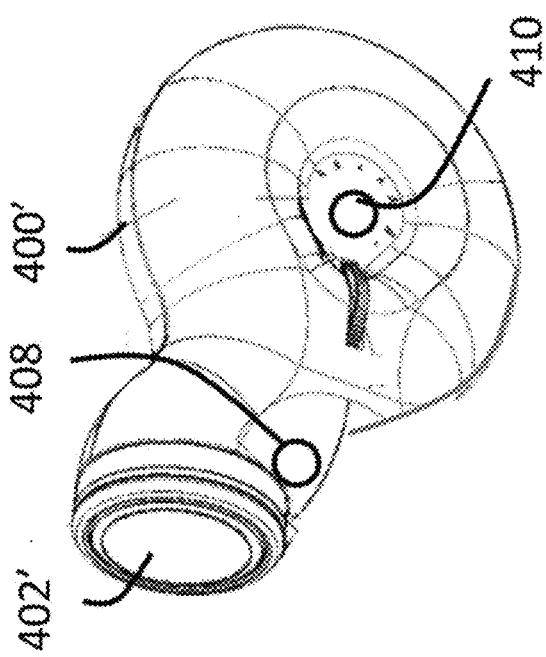
FIG. 24c is a perspective schematic view of a stimulator for providing tissue stimulation using at least one stimulator.

FIG. 24c shows an alternative embodiment in which a portable device 400' has been configured with a stimulator 402' to provide at least one of laser-, ultrasonic-, electric- or magnetic-based stimulation. Although the stimulator is shown as fixed plate in the figure, the stimulator may be adjustable with respect to the device 400' housing. For example, within the housing there may exist movable magnetic coils which may be angled. The coils may be replaceable and adjustable (e.g., a hemholtz coil may be replaced with a figure eight coil). The accessory port 410 is multi-function and may allow for connection and communication to other system components that may provide for various stimulators to be controlled by the device 400'. Although shown as a portable embodiment, the device 400' may be realized as an office based instrument such as device 50. For example, an ultrasound or magnetic stimulator may be much larger than the embodiment shown.

FIG. 24d shows an alternative embodiment in which a portable device 400" has been configured to provide stimulation with a modality specific (e.g., light, ultrasonic, electric or magnetic) stimulator 402". The device 400" may be configured with at least one adjustable stimulator, such that the angel, active elements, or other characteristics of a stimulator may be adjusted in relation to a particular target+IPC combination so that they are well paired. A method for providing transdermal stimulation therapy to a subject comprises positioning a device 400" with stimulator 402" over at least one of the top or bottom surface of a patient's foot or area near the medial malleolus and near an IPC located near a tissue target, and providing a stimulation signal through skin to stimulate the target nerve. In embodiments of the method, the device is placed on the patient's skin to stimulate one of: an IPC located near the big toe of a subject and the tissue target is the MPN; an IPC located near the three smallest toes of a subject and the tissue target is the LPN; at least one IPC located below the medial malleolus and the target is the MPN and/or LPN; an IPC located cephalad and anterior to the medial malleolus and the target is the SAFN; an IPC located posterior to the medial malleolus and the target is the PTN. The IPCs can be implanted in one or both lower limbs of a patient.

Figure 25:
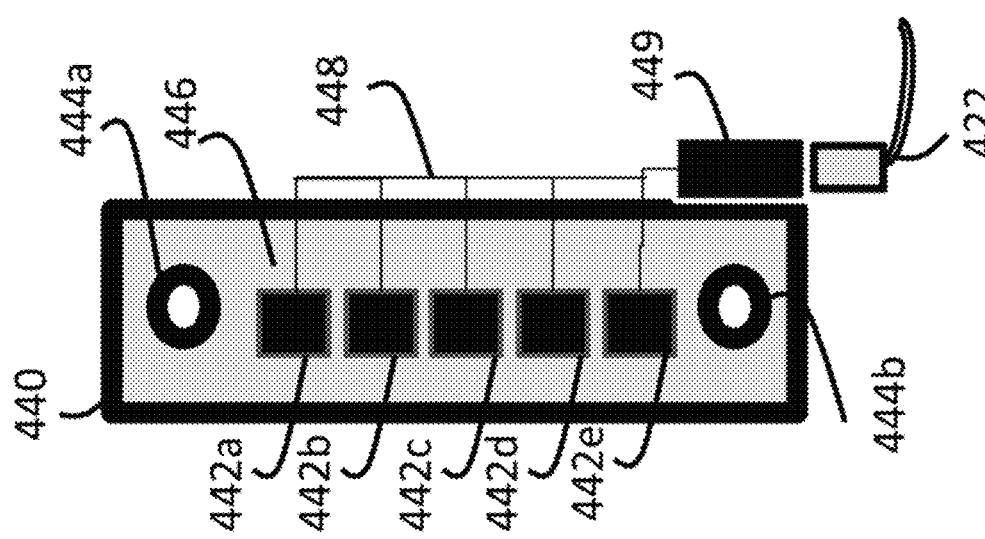
FIG. 25 is a schematic view of a multi-contact array stimulator.

FIG. 25 shows an embodiment having a cutaneous, multi-contact array stimulator 440 that may be used, with the device 400 shown in FIG. 24b, for example, during vagal or tibial nerve stimulation. The array stimulator 440 has a series of electrode contacts 442a-e, all of which may be independently activated. If only contacts 442a and 442b are used to provide a stimulation signal then this would produce a smaller functional stimulation terminal than if 442a-e were used. Subsets of contacts 442a-e can be used to pair the stimulator with an IPC of smaller or large length, by allowing a patient or doctor to control which contacts are used during the provision of therapy or by having these defined or determined as part of a stimulation protocol. The stimulating array 440 may also consist of one or more alignment loops 444a, 444b to aid in providing improved alignment with a subcutaneously located IPC. For example, a patient may have permanent or temporary tattoos placed according to the location of the IPC, such that the holes (444a, 444b) should be aligned with markers on the patient during therapy. The figure shows the top side of the stimulating array 440, having a backing substrate 446 on which the contacts 442 reside which can be fabricated using a flexible and electrically non-conducting material such as silicone elastomer, plastic, or nylon. The bottom side will simply have the surface contacts 442a-e. An adhesive surface or paste can assist in attachment to a subject's skin. The array stimulator may be configured as a single-use disposable multi-electrode. Electrical connections 448 run from each contact 442a-e to a port 449, which connects to a plug on cable 422 so that the stimulator 440 can be controlled and powered from a second accessory port 416 of device 400. The subset of the electrode contracts 442a-442e which are used can be controlled by the device 400, either via manual adjustment, by selecting a particular stimulation protocol, or using a visual interface such as a schematic that is presented on the smartphone device controller 420. For example, a user may activate one or more of the electrode contacts by tapping a corresponding virtual electrode shown on a schematic displayed by the smartphone.

In an embodiment a physical landmark, such as at least one bead (e.g., a biocompatible pellet), may be affixed to the skin or implanted under the skin in order to assist with the correct placement of the device 400 or a stimulator 402, 404. The landmark may provide tactile, visual, or other indication which assists in correctly positioning the external stimulators with respect to at least one implanted IPC.

Controlling and Shaping the eTNS Field

Figure 26C:
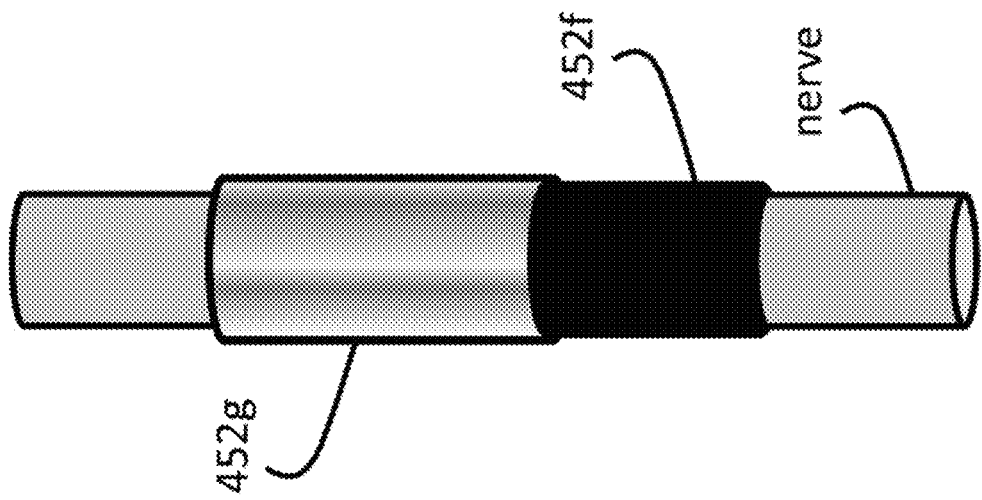
FIG. 26c is a schematic view of an embodiment of an IPC, where an insulating material is applied to the external surface of the conducting material.
Figure 26B:
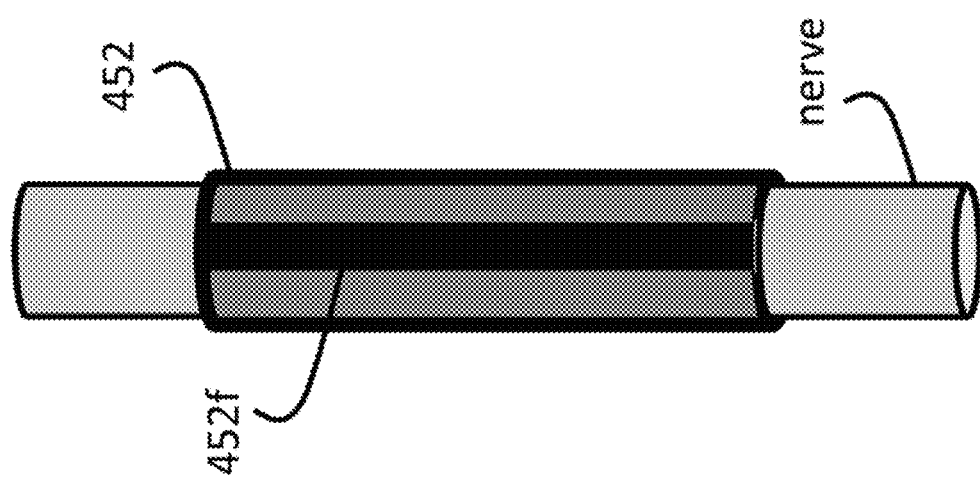
FIG. 26b is a schematic view of an embodiment of an IPC, in which the conductive material is limited to a single conductive strip.
Figure 26A:
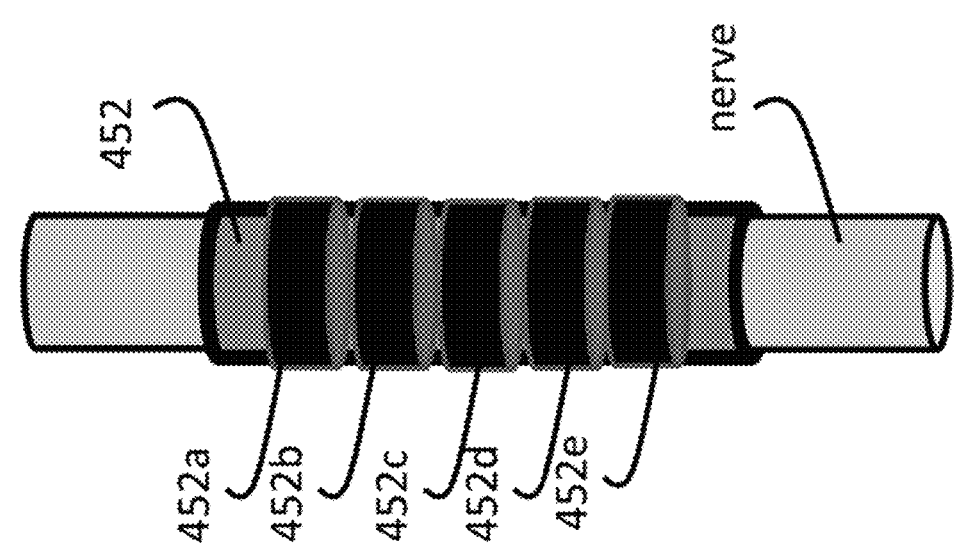
FIG. 26a is a schematic view of an embodiment of a multi-contact stimulator array and a multi-contact IPC array.

In an embodiment the stimulator array 440 may be coupled to an IPC that consists of multiple, electrically-conducting elements that are equally-spaced, or not, with inter-contact 442a to 442e distances along its length as seen in FIG. 26a. By aligning the one of the ends of electrode contacts 442a to 442e with a corresponding edge of the contacts 454a to 454e of the IPC array 452 improved modulation of neural activity may be achieved. The IPC array 452 may also provide advantages even when a single TENS stimulation electrode is used. In an embodiment, the IPC may be 3 cm long and may comprise multiple, such as two, 1.2 cm conductive portions 452a, 452b separated by a non-conductive portion. This design may increase the likelihood that a surface stimulator will be correctly positioned and by increasing the probability that one of its edges approximately aligns with at least one edge of a conductive portion of the IPC array 452. This may allow the external stimulator electrode to be positioned in a less strict manner while still providing stimulation enhancement. In an embodiment, a set of two or more conductive contacts separated by non-conductive substrate are electrically connected (e.g. a conductive element that runs along the length of the IPC) so that an electrical field that reaches any single contact is transmitted along to other contacts of the array. Improved modulation may also be provided by, for example, independently modifying the activating function (e.g., enhanced neural excitation) at one or more locations along a single or multiple nerve(s). Although shown wrapped entirely around a neve, the IPC array can be realized in a cylindrical embodiment that resides adjacent to the nerve, or as a half-cuff wrapped partially around the nerve, or otherwise such as a lead-type multi-contact electrode array. When the inter-electrode spacing is sufficient, or the stimulation signals are provided at different times, each passive contact 452a to 452e can be used to activate fibers at a different stimulation frequency. In this manner, one or more contacts may be used to promote the generation of unidirectional nerve action potentials, or to selectively activate only smaller diameter fibers. The latter two methods can be achieved by various means such as using high frequency stimulation, DC current, or quasitrapezoidal pulses (e.g., Fang Z P and Mortimer J T, IEEE Trans BME 1991; Kilgore K M and Bhadra N, Med Eng Biol Comp., 2004).

In an embodiment, the IPC may be configured to selectively activate a subset of fibers or particular nerve fascicle located within a compound nerve trunk. Examples of such nerves may include the vagus nerve, sciatic nerve, pudendal nerve, posterior tibial nerve, and femoral nerve. This type of spatially selective electrical activation of such subsets of nerve fibers is achieved by designing a hollow cylindrical IPC such as in FIG. 26b that consists of a low- or non-conductive substrate material 452 (or a conductive material covered in a non-conductive coating), and a strip of high-conductive material 452f along the length of the IPC. This embodiment will selectively enhance the excitability of nerve fibers in close proximity to the strip 452f, while adjacent fibers located closer to the less-, or non-, conductive material 452 will exhibit a decreased or no change in excitability. With prior knowledge of multiple targets (e.g., fascicles within a nerve trunk), multiple conductive strips 452f may be strategically placed along one or more IPCs. The conductive strips may also vary in width (around the nerve circumference) and thickness. Again, although the nerve cuff is illustrated in a closed position as a cylinder, it is understood that in a common embodiment the cuff is wrapped partially or fully around the nerve during implantation, and the closed cylinder is merely shown in a simplified manner for purposes of illustration.

In an embodiment, neural enhanced activation may be increased by applying a non-conductive coating to at least a portion of the external IPC surface. The extent to which the non-conductive layer covers the surface may be partial (e.g., one quarter of a cylindrical IPC) or complete (entire surface). This effect may be increased by also applying this insulating layer to the inner surface of the IPC. In this embodiment, the area that must remain electrically exposed to the surrounding environment only includes approximately the circumferential edges at both ends of the IPC. This method and system of enhancing neural excitability works in conjunction with the preferred design of external (e.g., transcutaneous) stimulating electrodes (FIG. 20a and FIG. 20b). In FIG. 26c when portions 452g and 452f are repeated in a serial manner along the nerve, the IPC may be understood as an alternative embodiment of the IPC shown in FIG. 26a.

Figure 27:
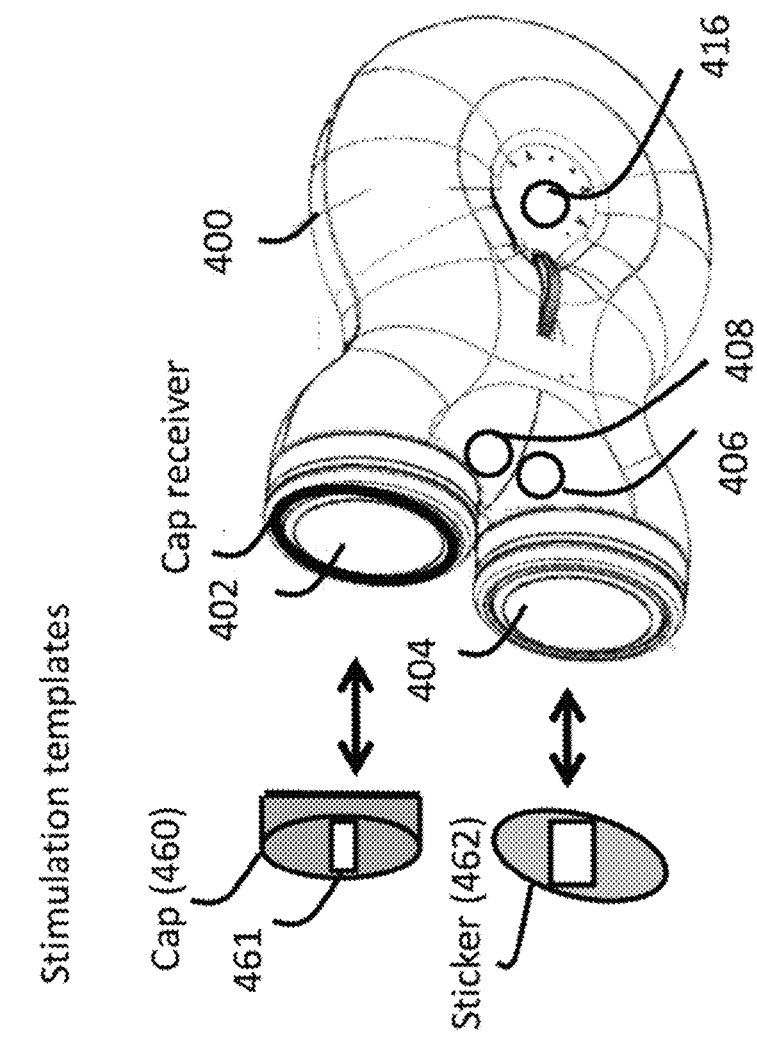
FIG. 27 is a schematic view of a further embodiment of a portable TNS system and stimulation templates.

An alternative embodiment for shaping the field provided by a stimulator is to provide stimulation templates such as shown in FIG. 27. A stimulation template provides the advantage of improved nerve modulation by assisting to align an edge of the stimulator and IPC. Even without an IPC, a shaped field may provide improved therapy compared to using a larger field of a whole surface of the stimulator 402,404. Templates can constrain the stimulator field to allow, for example, shaping of the field applied to tissue. The template may be shaped according to data that is obtained in various manners such as visually by measurement, during the implantation operation, by using imaging data, by using data related to a physical dimension of the IPC, or by using subject feedback during a testing routine that determines the desired area on the surface of the patient's skin where stimulation should be provided or avoided (e.g. to avoid certain side effects). As illustrated, a cap template 460 can be used to shape the field provided at the cutaneous location by having a silhouette 461 or "cut out" that only permits part of the stimulator 402 surface to stimulate a subject's skin. The cap template 460 may be attached to the device 400 by means of a cap receiver component configured within the device housing. In an alternative embodiment, a sticker stimulation template 462 may be used with the stimulator surface 404, having an adhesive on one side such that it can be temporarily affixed to the stimulator surface 404. Rather than using adhesive, the sticker or cap template may be made out of magnetic material so that it can be temporarily affixed and removed from the stimulation surface 404. In a further embodiment a sticker or other template may be affixed to the patient's skin rather than to the stimulation surface.

Regardless of template type, in an embodiment, the stimulation templates should have a depth sufficient to allow gel to be applied so that the silhouette 461 retains the gel while the non-conductive surface of the template remains dry. The silhouette 461 may be further configured with a slight ridge in order to assist in retaining the gel within the shape of the silhouette 461. Instead of being a "cut out" the cap can be ridged such that only a ridged protrudes from the cap surface and engages the skin of the subject. Further, the gel may be similar to the conductive gel often used during ECG recording, or may firmer, such as a conductive paste also used for making EEG recordings. The paste should be sufficiently firm to retain the desired shape of the stimulator. Conductive mediums such as hydrogel, can also be manufactured to fit within the silhouette 461 to provide a shaped field. Instead of a silhouette defining a space, the template may have one or more conductive ridges that protrude to the skin in order to make contact in a more localized manner than the entire surface 402.

IPC Component Designs.

IPCs of the disclosed invention may have many shapes and forms. FIGS. 28-30 illustrate embodiments with the understanding that alternative shapes, dimensions, designs and sizes are possible and may have additional features not shown here.

FIG. 28a shows an IPC 500 which is a rod having an outer sheath 502 that may be comprised of an electrically non-conductive material or conductive material and inner portion 504 that is conductive. An advantage of an embodiment with a non-conductive layer may be that electrical current provided by a stimulator would travel through the conductive portion and the conductive edges may serve as 2 distinct points. This may enhance activation of the adjacent nerve tissue 12 near each edge of the IPC. Alternatively, the IPC 500 may be realized without coating 502 as completely conductive. FIG. 28b shows an alternative embodiment in which the non-conductive outer sheath 502 is partial and only insulates a majority of the conductive portion 508. In this embodiment, a conductive lip 510 extends outside of the sheath and stimulates the nerve 12 which is shown oriented perpendicularly to the IPC. In an embodiment this may be a preferred orientation/configuration when the purpose of the stimulation is to provide a nerve block in a portion of the nerve 12. However, positioning the IPC lengthwise along the nerve is the common configuration for implantation as seen in FIG. 28a. Although not shown, all IPCs illustrated are understood to be configured with anchor elements such as the suture holes, wings, or the like. FIG. 28c shows an IPC embodied as a conductive rod 506 (going into and out of the page, as is the case for FIGS. 28d, 28e, and 29a). IPC 506 may include an anchor element comprised of an elongated arm 530 having a first extension 532a and, optionally, a second extension 532b that may aid in positioning and aligning IPC 506 to a target. FIG. 28d shows an IPC configured as an annular rod of conductive mesh 505 with a non-conductive external support surface 502 that serves to decrease the surface area/density of the IPC. This may serve to increase coupling with a paired stimulator. FIG. 28e shows an embodiment where the IPC is a hollow conductive cylinder 511 which is wrapped partially around a nerve 12, as may be seen with conventional nerve cuff designs. The cylinder has an opening 512 which may change in size during deformation of the IPC as may occur during implantation under the guidance of a surgeon. Because different IPC lengths can be needed depending upon the system configuration, sets of IPCs can comprise IPCs with lengths and or widths that span a range, for example, lengths from 1 cm to 4 cm, in steps of 0.5 or 1 cm along this range. Larger numbers of more common IPC sizes can be provided in IPC kits, for example, as might be stored in stock by a clinic implanting the IPCs as part of tibial nerve stimulation treatment. IPCs designs may also allow these to be cut (e.g., in the case of a rod) or folded over/bent (in the case of a thin, foil-like surface design) to adjust IPC length. IPCs can be customized, prior to or during implant surgery. These modifications may be assisted by use of a biocompatible epoxy or sealant, for example, to protect against a sharp edge created during this modification.

IPCs will typically be realized as a set of pre-determined lengths for the general population of OAB patients. In an embodiment related to PTN stimulation in humans, the nerve depth may be approximately 0.8 to 2.5 cm deep. A common IPC design may have a length of about 1.5 cm, 350 um thickness, and 3 mm inner diameter. One to 4 lengths could likely address the anatomical diversity across the patient population. Imaging data may help to select or adjust IPCs design used for a patient. When using IPCs for selective stimulation of PTN nerve branches, PTN shape and size may be related to the location of the target. More than 1 target can be used during therapy. For SAFN nerve branches, tend to run superficially, it is likely that one or two sizes of IPC should suffice.

In addition to embodiments shown, it should be understood that an IPC can be realized as a conductive rod, cylinder, sheet, or wide thread (e.g. 2-4 mm) such as conductive flexible wire suture secured to tissue near a target nerve, a mesh, a biocompatible conductive gel that is able to maintain its shape (such as a conductive gel, a flexible, organic, composition of conductive polymers patterned onto slices of hydrogel that may be surgically implanted near the target nerve or into a receptacle having a pocket for accepting the gel), a plurality of conductive particles (which may be injected into the target nerve, tissue around target nerve), suitable micro- or nano-based materials that allow both biocompatibility and suitable conductivity, as well as different types of conductive nerve cuff electrodes.

Figures 29A, 29B:
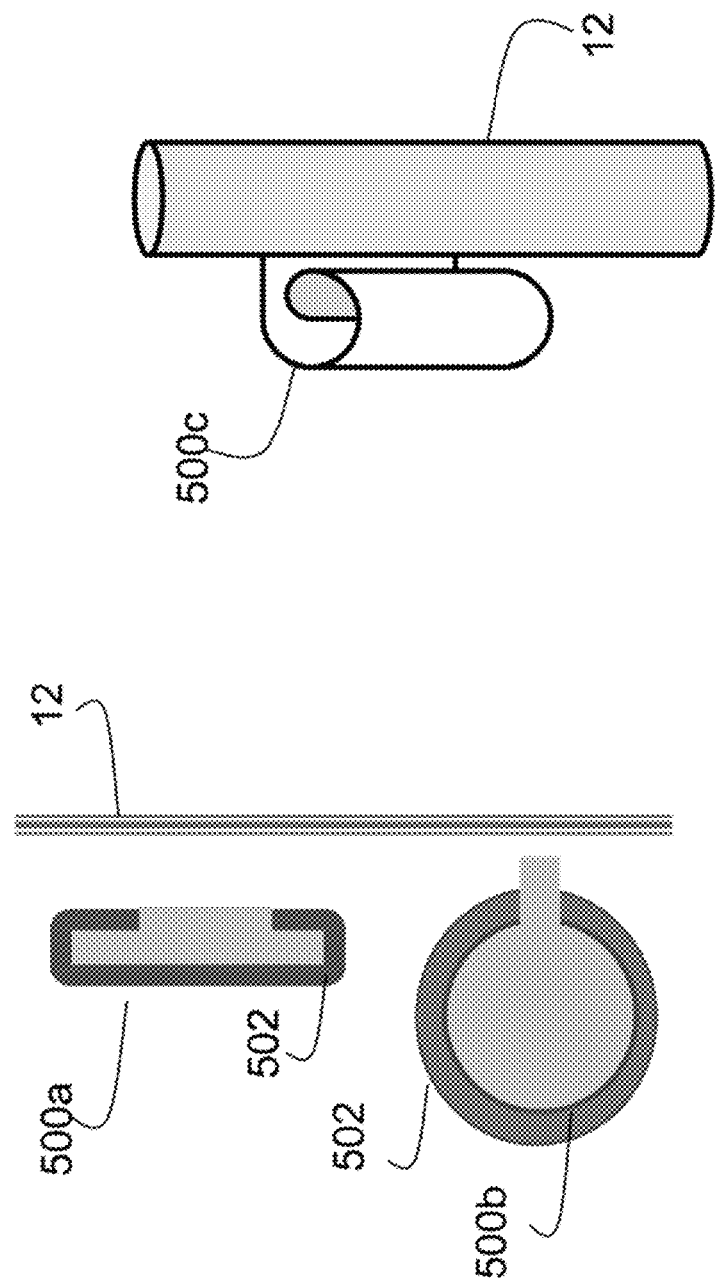
FIGS. 29a,b show schematic views of still further embodiments of IPCs.

FIG. 29a shows two IPCs at locations relative to a nerve target 12 arbitrarily located perpendicularly to the IPC lengths. The first IPC 500a has a first length that is different than 500b in order to allow different external stimulators to differentially stimulate the 2 portions of the target during stimulation. FIG. 29b shows an IPC 500c fabricated such that it coils itself into a hollow cylinder at rest, and selected in size so the inner diameter is equal to or a little larger than the diameter of the nerve 12. This self-sizing property provided an intimate interface between the IPC and the nerve, and also prevents nerve compression by the IPC following implant (e.g., due to swelling).

FIG. 30a shows an embodiment of an implanted IPC with both a conductive portion 514 aligned near a target nerve 12a and a non-conductive portion 516, that can be realized by a coating that deters electrical enhancing of stimulation field, near a non-target nerve 12b and the stimulator is located outsize of the page (i.e. the figure is a size view). Alternatively, a non-conductive portion can also be realized by a coating that only resides on the underside of the IPC (and the stimulator is located at the top of the page). In the case where the IPC is situated between two nerves where one is the target 12a, and the other is non-target adjacent nerve 12b, then the partial shielding may prevent, or deter, the non-target nerve from being effected by the eTENS. Accordingly a stimulator situated at the top of the page, or positioned at the angle of the viewer looking into the page, would preferably provide stimulation to nerve target 12a, while the non-conductive portion 516 would insulate the field from the non-target tissue area 12b. The non-conductive portion may also be longer than the conductive portion. At least one securing element 517 such as a suture hole may be provided on the IPC to allow the IPC to be affixed to tissue in the area of nerve. The terminal end of conductive component 514 has been rounded in order to increase the chance of edge alignment with a surface stimulator, wherein alignment constitutes a portion of the two edges overlapping.

FIG. 30b shows an embodiment of an IPC with at least a first portion 519 and second portion 520 of different lengths which are conductive. This design may increase the chance of enhanced stimulation of a target nerve by increasing the chance that the stimulator will be approximately aligned with at least one edge of the conductive portions 519, 520 of the IPC. Conductive element 521 may serve to electrically connect the two portions 519, 520 that are adjacent the nerve provide additional enhancement relative to when the element is not provided.

In an embodiment, a stimulus router system (SRS, developed at the University of Alberta) is another example of an implanted device that achieves a minimally-invasive means of electrically activating the peripheral nervous system. The SRS consists of a metal disk 515 (termed the 'pick-up terminal') that is physically connected via lead wires 524 routed to an implanted nerve electrode 526. The pick-up terminal is surgically placed just under the skin surface and 'captures and re-routes' electrical pulses applied by an external cutaneously applied electrode. Thus, the nerve electrode is powered by means of a transcutaneous coupling mechanism. The system is currently undergoing clinical feasibility testing. This system is essentially identical to conventional nerve stimulation systems, except for the absence of an implanted pulse generator. Instead of an implanted electrical source, this approach utilizes an external stimulation device and at least one subcutaneous pick-up terminal, which solves the power/control issue at the cost of other potential issues related to long-term use of the SRS. Further, the effectiveness of the SRS system may be compromised by non-optimal design of its surface electrode+pick-up terminal coupling mechanism. The methods and systems of the current invention may possibly be used to improve the SRS system if the pick-up electrode is configured according to the principles disclosed here with respect to pairing of lengths, distances, and edges.

FIG. 30c shows an embodiment of an IPC in which a first conductive component 515 is attached by a flexible conductive element 524 to an electrode 526 located away from the first conductive component. In one case the first conductive component 515 serves as a "pick-up" electrode which can then relay electrical energy to a more distal location. If the first conductive element 515 or electrode 526 is located directly under the skin then this embodiment may approximate an SRS system. However, as the pick-up electrode 515 moves away from the skin then the principles and guidelines of the disclosed invention related to eTENS can be used to pair the IPC with the stimulator in more efficient manner. For example, aligning the edges of a stimulator with the conductive component 515 or electrode 526, or modifying the shape of a stimulator and a paired conductive component 515 and according to the distance between the two system components, as well as other factors, has been disclosed. By following the principles of the invention the distance between the stimulator and SRS conductive component 515 may be made greater than previously understood while still providing sufficient stimulation of target tissue to achieve therapy.

FIG. 30d shows an embodiment of the IPC in which there are several portions with a particular attribute 518a, 518b, 518c (e.g. the attribute may be electrically conductive) which are interspersed by portions without that attribute 522a, 522b (i.e. non-electrically conductive). This design can be used either to stimulate different portions of a nerve or to increase the probability that at least one stimulator edge will align with an edge of a conductive portion in order to increase coupling according to the principles of the current invention. Instead of conductive and non-conductive portions the particular attribute may be sonically resonant to energy provided by, for example, an ultrasonic transducer (the resonant portions can absorb more energy when they are driven at a frequency that matches a natural frequency, or harmonic, of vibration of the stimulator energy). In an embodiment, since acoustic resonance is a form of mechanical resonance, then any stimulator source that produces energy of a frequency that matches the natural frequency of the IPC portion with that particular attribute 518a, 518b, 518c may be used. In an embodiment, the resonant portion of the IPC may be a solid or hollow rod that resonates at a frequency or harmonic of a stimulation signal provided by the stimulator. In an embodiment, a portion with a particular attribute 518a, 518b, 518c is configured to either reflect or absorb light to enhance stimulation of adjacent tissue when an external stimulator provides light or laser energy. For example, the portions may be reflective and may be angled such that light energy sent from a transmitter is reflected by the portions onto a specific area of tissue to be stimulated. Additionally, a tube or nerve cuff created from, or having at least a portion comprised of, a non-conductive material may be used to insulate non-target nerves from electrical fields while a conductive IPC is used to increase target nerve responsiveness to stimulation. In an embodiment, IPC can be configured with non-conductive anchor portions (e.g., "shield-flaps") deployed during implantation to shield non-target tissue from stimulation. The non-conductive substrate 516, that surrounds the other components of the IPC may be formed with an outer ring that lends additional rigidity to the IPC in order to cause it to hold its shape if it is bent, or to resist bending, and may be deployed circumferentially or may also exist along a portion of a side, top, or bottom, of the IPC.

Figure 31:
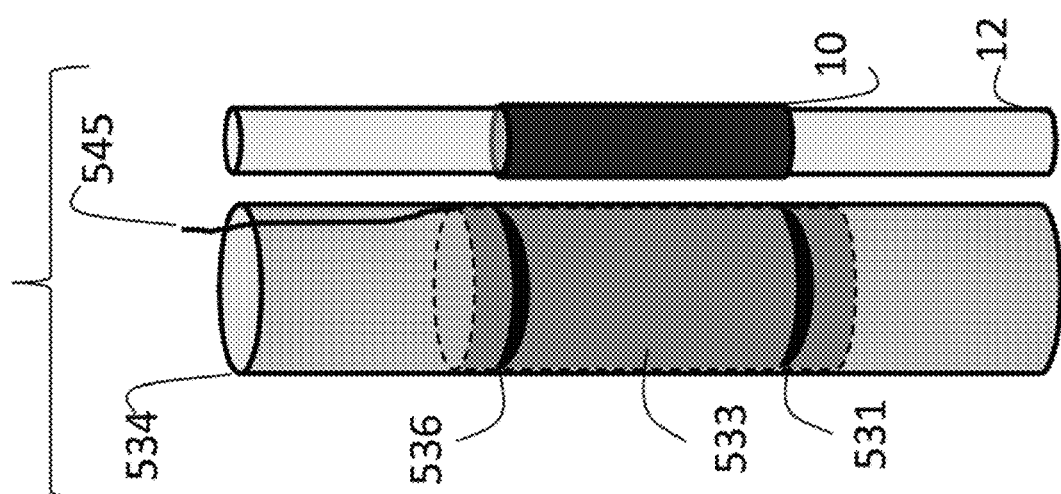
FIG. 31 is a schematic view of an embodiment of an IPC, which is used to achieve enhanced nerve activation by trans-vascular electrical stimulation.

FIG. 31 shows a trans-vascular embodiment of the eTENS system, where an IPC 10 is implanted around a peripheral nerve 12 (e.g., vagus nerve or renal nerve). A nerve stimulation electrode 533 is inserted into and guided through a blood vessel 534 such that it is in close proximity and in proper alignment with the IPC 10. Electrical stimuli can be delivered from active electrode contacts 531 and/or 536. The electrode 533 may be a lead-type electrode or may be fabricated similar to a vascular stent for deployment into the vessel. In addition, the electrode 533 may be powered directly via a lead wire 545, or it may have associated circuitry and be powered wirelessly (e.g., RF signal). This embodiment will enable selective electrical activation of a target nerve 12.

Figure 32:
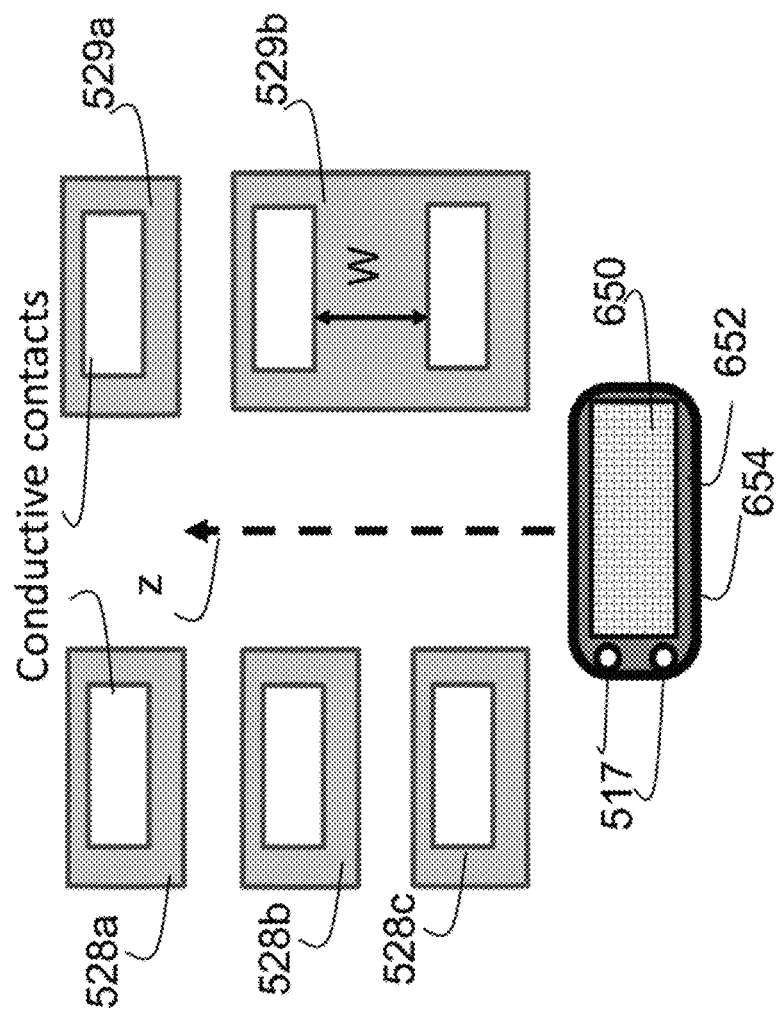
FIG. 32 is a schematic view of two arrays of surface stimulators and an IPC.

FIG. 32 shows two arrays of surface stimulators 528a-c and 529a-b. The stimulators are located on a patient's back and at least one stimulator is paired with an implanted IPC located proximate to a spinal nerve. By activating disposable or re-usable stimulators 528*a* and 529*a* the stimulation signal can be modulated by at least IPC located within the patient. Various spatial patterns of stimulation can be provided by a device 50, that may be connected to the stimulators and that can be controlled to stimulate combinations of the stimulators in order to provide stimulation to a nerve adjacent to the IPC. In an embodiment, by activating selected pairs of stimulators of the array, such as 528*a* and 529*a* and then 528*a* and the upper conductive element of stimulator 529*b*, the stimulation signals can follow different paths when providing stimulation to at least one IPC in a patient. This increase the chance of improved alignment between edges of at least one stimulator and an end of the IPC. There are two conductive elements of stimulator 529*b*, which reside within single non-conductive support backing structure, and are separated by distance "w", which may be related to the length or width of an IPC. In the embodiment of FIG. 32, each of the stimulators can be connected to a device 50/400 which is able to independently activate the stimulators in order to provide spatial or spatial temporal patterns of stimulation according to a therapy protocol stored in the device, or which can be controlled by the patient using manual controls to selectively activate each stimulator. In the figure an IPC is shown which is implanted in a patient at the end of the arrow at point "z". The IPC could be implanted near a spinal nerve root that is to be stimulated, and the IPC contains a conductive mesh 650, surrounded by a non-conductive supporting structure 652 having a relatively more rigid ridge 654 which aids in maintaining the shape of the of IPC.

Clinical Applications

The current invention can be applied in numerous therapies that utilize any form of tissue stimulation.

The enhanced transcutaneous nerve stimulation methods and systems of the current invention can be used for neuromodulation therapy. One embodiment involves electrical stimulation of peripheral nerves that are located in relative close proximity to the skin surface. Some examples of suitable anatomical targets include the occipital nerve, vagus nerve, recurrent laryngeal nerve, sacral spinal nerves, pudendal nerve, posterior tibial nerve, and thoracic/lumbar nerves (lower back). One or more nerve targets can be used to treat acute/chronic pain, lower urinary/fecal dysfunction, epilepsy, depression, dysphasia, and other disorders as is well known. In some of these therapeutic embodiments, an implantable device may be used to provide or supplement the therapeutic effects provided by electrical stimulation therapy. For example, OAB therapy can be achieved by an implanted system that stimulates the sacral nerve, and an enhanced nerve stimulation system that stimulates the PTN.

The enhanced nerve stimulation system may also be used to treat patients who are refractory to drug therapy or conventional transcutaneous stimulation therapy. It may also be used in combination with drug therapy to enhance the therapy or in order to improve the responsiveness of refractory patients.

Embodiments of the present disclosure may be for use with patients having specific conditions which are modulated by electrical stimulation. Embodiments may be used with any patient who desires nerve modulation of the brain or body. In addition to use in patients with obstructive sleep apnea, migraine, headaches, hypotension, hypertension, addiction, eating disorders, etc., embodiments may be used to provide treatment in many other areas. Application can include, but not be limited to: brain stimulation (e.g., treatment of Parkinson's, and depression); stomach muscle stimulation (e.g., gastric pacing); treatment of obesity; back pain; incontinence; overactive bladder; menstrual pain, and/or any other condition that may be affected by tissue modulation.

Embodiments of the disclosed invention can be used in rehabilitation therapies, such as functional electrical stimulation (e.g., chronic spinal cord injury or stroke), that are used to restore lost or impaired function. Examples include rehabilitative strategies involving electrical modulation of upper and lower extremity function, trunk stability, and swallowing. For example, in dysphagia, the IPCs of the current invention could be used to prevent aspiration by enabling an external stimulator to stimulate muscle(s) in a selective and targeted manner.

The disclosed invention can also be used for improving conventional brain stimulation and deep brain stimulation (DBS) therapy. One embodiment involves therapy that is enhanced by surgically implanting one or more IPCs on target tissue in physical proximity to an implanted DBS electrode. The IPC is implanted in a target location to enable suitable electrical activation of a target area that is deemed difficult to selectively activate by the originally implanted DBS electrode. The invention decreases the effect of any sub-optimal placement of, or migration of, a DBS electrode. The IPC may be less likely to migrate because it is not connected to a pulse generator. The IPC may be used with a DBS stimulator which is operated in any fashion (e.g., bipolar mode or unipolar mode). In the case of bipolar mode, the length of the IPC is preferably the same as the distance between the active DBS contacts. In the case of monopolar stimulation, the dimensions of the IPC (e.g. length and thickness) may be defined as a function of the distance between the DBS electrode and the IPC. This novel system and method can compensate for poor electrode placement that may alternatively require higher stimulation amplitudes and/or longer pulse widths. An advantage is less frequent battery replacement and also deterring habituation. Reduced stimulation amplitude can also decrease stimulation-evoked side-effects and stimulation of non-target tissue.

Modulation of Drug Delivery

The methods and systems of the current invention can be used in addition to, or as an alternative to, other prior art drug delivery systems such as for transporting drug carriers across the skin barrier and can be used with micro-needle or subcutaneous drug infusion to guide drugs to a tissue target along an intended pathway.

Accordingly, in an embodiment a patient may be selected who is experiencing a condition, symptom, or state for which the patient wishes to receive treatment. An appropriate drug regimen (e.g. dosage, area of administration, etc) is selected for delivery of drug to a tissue target. At least one IPC is surgically situated in a target area so that target tissue, related to modulation of the condition, is adjacent the IPC. A drug is introduced to the patient by various methods including injection of nanoparticles. At least one stimulator may be positioned external to the patient to provide stimulation to tissue adjacent to at least one IPC. The stimulation may be provided according to a stimulation regimen which provides the therapy. Results are assessed and therapy adjusted if needed.

In an embodiment shown in FIG. 23*a* two stimulators 122*c,d* are placed such that tissue resides between the stimulators. The unshaped electrical field 230*a* which arises will be wider than the stimulators and may be shaped by the heterogeneous and nonlinear impedances of intervening tissue, including skin tissue. By implanting at least one IPC 10a, the electrical pathway between the two stimulators may be shaped (e.g. narrowed). When multiple IPCs are used 10a,b,c then these may serve to form a conductive pathway 236, having a shaped electrical field 230b which is biased more along the pathway and may be more narrow than the unshaped field. In an embodiment one stimulator may be external subcutaneous, percutaneous, or implanted, and the $2^{nd}$ stimulator (can be the same or other type). FIG. 23b shows a second embodiment using IPCs and compares an unshaped field (top left side of figure) and a shaped field (top right side of figure). As shown a drug 234 introduced into the tissue of the patient, may follow a broader field than a patient who also has at least one IPC 10 implanted (in the figure there are 3). When stimulation is provided the drug, in the IPC condition, is guided in its diffusion along the shaped electrical field to the target 232 to provided more directed drug delivery. The bottom portion of the figure shows a monopolar stimulator 122d and two IPCs configure to guide a drug 234 to a target 232, the return electrode is located distally. In an embodiment, the drug may be contained in nano-particles having polarity.

FURTHER DESCRIPTION OF THE INVENTION

With respect to treatment provided by IPC selective nerve stimulation, a patient can be selected with a medical condition selected from the group of, for example, pain, movement disorders, epilepsy, cerebrovascular diseases, autoimmune diseases, sleep disorders, autonomic disorders, pain, abnormal metabolic states, disorders of the muscular system, cardiovascular disorders, pulmonary disorders, inflammatory disorders, and neuropsychiatric disorders. However, as is evident, a main therapeutic focus is treatment of urinary bladder and voiding disorders.

The current invention teaches a system and method that can be used to provide long-term treatment of lower urinary dysfunction related to overactive bladder (OAB), urinary retention (UR), and detrusor underactivity (DU). Various symptoms that can be treated related to, for example, urinary urgency such as failure to be able to postpone the need to urinate; frequency of urination such as the need to urinate at least eight times per day; urge incontinence such as leakage of urine when one has the urge to urinate. A primary biological substrate targeted for modulating urinary function is the saphenous nerve, which is a cutaneous branch of the femoral nerve innervating the lower limb. We will first describe specific characteristics of bladder reflexes that have not been reported previously by others and that will instruct the methods by which OAB therapy can be implemented. Subsequently, we will disclose multiple embodiments of neuromodulation systems that can allow clinicians to provide effective long-term therapeutic outcomes.

The treatment of "overactive bladder" (OAB) can also refer to treatment of conditions of urinary incontinence, high urinary frequency and urinary retention conditions, constipation, urinary problems, and/or various voiding disorders brought on by nerve damage. Other disorders which may be treated are incontinence, urinary pain, erectile dysfunction, idiopathic constipation (as may be achieved by lessening time spent on bowel movements and straining effort, increasing frequency of defecation), interstitial cystitis, high or low frequency of voiding or associated symptoms, symptoms of bladder/pelvic pressure/pain (and may be accomplished in combination with prudential nerve stimulation), urinary urge incontinence and/or detrusor hyperreflexia. Urinary regularity may also lead to increased sexual desire. Overactive bladder treatment may also be used to refer to stimulation which modulates contraction within targets such as the pelvic floor or "pelvic diaphragm". Over time therapy may cause contractions that restore the strength of the organs and muscles within this system that may be a goal of the therapy. Stimulation induced modulation of pelvic floor, sphincter or other targets can alleviate or eliminate many symptoms of urinary/faecal disorders. OAB treatment may include treatment of pelvic floor disorders, such as, bowel disorder including fecal incontinence and the like, and instead of bladder activity the modulation seeks to modulate bowel activity or muscle or tissue related to control of fecal movement, voiding, and containment FIGS. 13a-c show that across the sample population the PTN, and nerve branches MPN, LPN can yield different responses contributing to the differences seen in the average response data. The PTN, MPN, and LPN show unique, frequency-dependent changes in acute bladder activity relative to baseline. FIGS. 14a-c and 14 d-f, show that this effect extends to the prolonged responses as well. Further, for acute response the MPN seems to be the best target while for prolonged response the LPN is best. This suggests that the best target for quelling symptoms related to symptom urgency at the time of stimulation may be different than the target for treatment during the night which should follow through the following day even if stimulation is not provided.

Further, an embodiment of the invention relies upon a newly discovered bladder-inhibitory reflex pathway that produces results that are unique from those obtained with, for example, posterior tibial nerve stimulation, dorsal genital nerve stimulation, pudendal nerve stimulation, and sacral spinal nerve stimulation. This can involve electrical stimulation of the saphenous nerve (SAFN) at a site located within the lower leg. In contrast to prior art, this involves modulation of sensory nerves that are anatomically derived from the femoral nerve and distributed mainly proximally within the lumbar spinal cord (L2-L4 nerve roots). Prior to the results provided herein it was not known, or anticipated, that SAFN stimulation would elicit such a response. Indeed, it is common practice to stimulate the PTN percutaneously, while ignoring the SAFN, although the latter serve as an easier target in some patients and situations. The novel data disclosed here also support that lumbar sacral neuromodulation (between L2 and L4), at or near the associated foramen, may robustly modulate bladder function in manner that may be sensitive to characteristics of the stimulation signal including frequency and amplitude, and which may be more robust then the currently relied upon S2-S4 sacral sites, with S3 being the most common.

The bladder-reflexes evoked by SAFN stimulation were demonstrated using the same anesthetized rat bladder model that was used to obtain the data of FIGS. 13 and 14, and was reviewed in our recently published study for PTN stimulation (Kovacevic and Yoo, 2015). A stimulating bipolar nerve cuff electrode was implanted around the SAFN, which was surgically isolated just below the level of the knee. The bladder was surgically instrumented with a PESO catheter and infused continuously (rate=0.08-0.12 ml/min) with saline. Changes in both acute (during 10-minutes of SAFN stimulation) and prolonged (10-minutes following SAFN stimulation) bladder responses were compared with a baseline condition (10-minute duration, prior to SAFN stimulation).

FIGS. 34-38 show data obtained using monophasic stimulation pulses applied at an amplitude of 25 μA, 200 μs pulse width, and at stimulation frequencies between 2 Hz and 50 Hz. The different stimulation frequency trials were applied in a randomized order.

Figure 34:
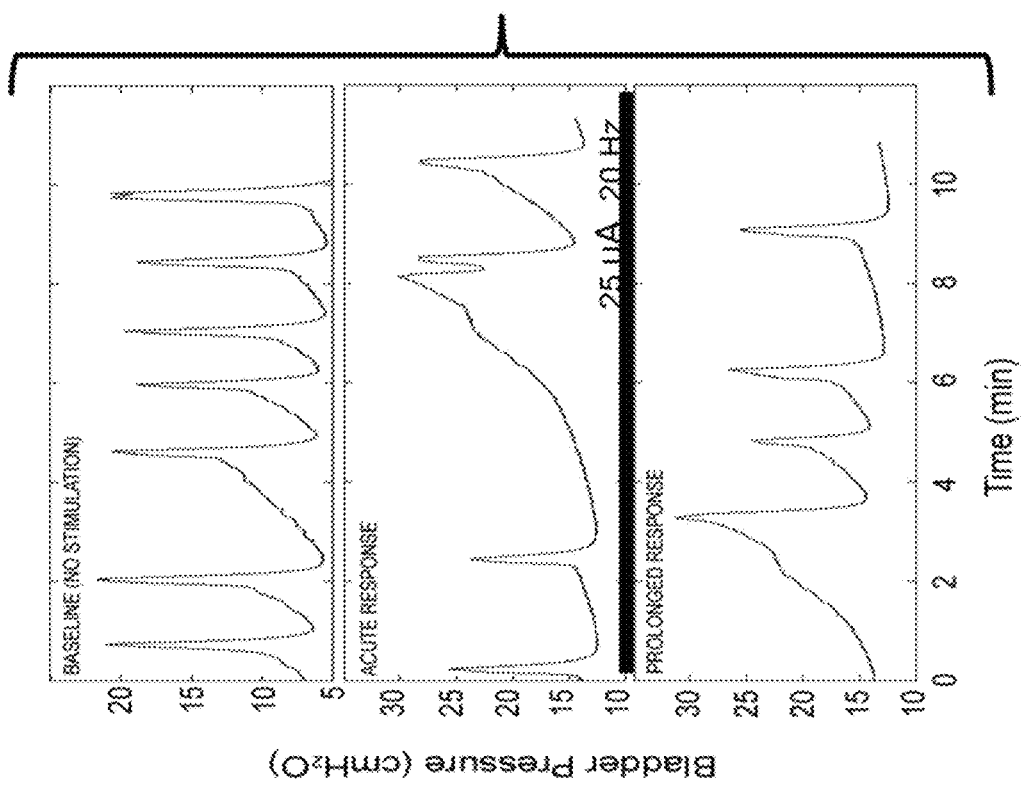
FIG. 34 shows graphs of experimental data for changes in bladder pressure evoked by saphenous nerve (SAFN) stimulation in an anesthetized rat. Compared to baseline, both acute and prolonged bladder inhibition are achieved by stimulation at 25 µA and 20 Hz.

FIG. 34 shows an example typical of bladder inhibition evoked in response to 10-minutes of SAFN stimulation. Compared to baseline (top trace), there is a marked decrease in bladder contraction rate both during and after SAFN stimulation (25 µA and 20 Hz). The acute phase during stimulation (middle trace), shows a particularly extended bladder fill that begins at 2.5 min and ends at approximately 8 min. The inhibitory influence of SAFN stimulation persists after stimulation ends and runs into the prolonged period (bottom trace), where extended inter-contraction intervals, compared to baseline, continue to be observed.

Figure 35:
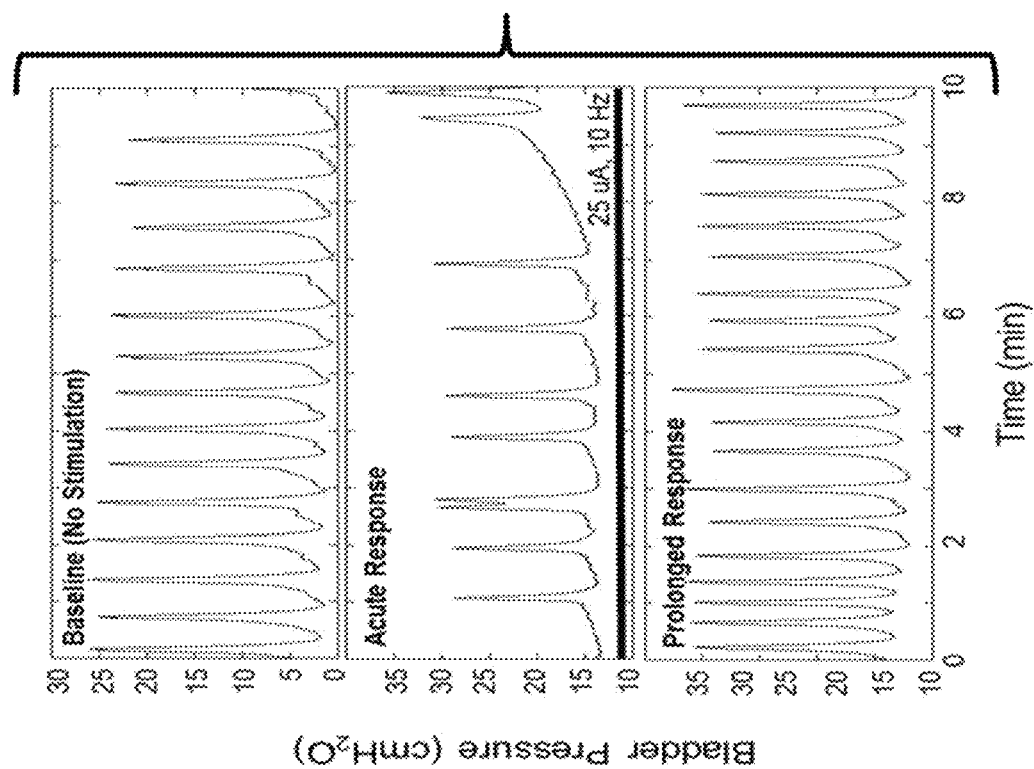
FIG. 35 shows experimental data of acute bladder inhibition (during SAFN at 25 µA and 10 Hz), followed immediately by bladder excitation during the prolonged response phase (10 minutes after stimulus pulse train).

FIG. 35 shows an example of SAFN stimulation resulting in reflex bladder excitation. Following a 10-minute stimulation trial, during which bladder contractions are acutely inhibited, the bladder exhibits an increase in bladder activity (decreased inter-contraction intervals, compared to baseline) indicative of excitation.

Summary data obtained from experimental study are shown in FIG. 36a,b as the distribution of three types of bladder responses that were observed in response to SAFN stimulation: inhibitory (>10% decrease in BCR), excitatory (>10% increase in BCR), and neutral (<10% change in BCR). SAFN stimulation applied at 25 µA and 20 Hz resulted in both acute and prolonged bladder inhibition in all 10 experiments (i.e., 100% response rate). SAFN stimulation at 10 Hz also exhibited only inhibition in the acute condition, and predominantly bladder-inhibitory responses in prolonged time periods. Although the response rates of acute bladder-inhibitory responses were notably lower at frequencies above and below the range of 10-20 Hz, it is noted that the prolonged bladder-inhibitory responses between 2 Hz and 10 Hz were relatively consistent (63% to 78% response rates).

While the data indicate that MPN and LPN stimulation at 10 Hz can, respectively, achieve acute and prolonged bladder inhibition in 100% of rats (FIGS. 14b,14f), a single neural target/stimulation protocol (SAFN stimulation at 20 Hz) achieved 100% response both for acute and prolonged bladder inhibition. Further, the SAFN stimulation achieved these inhibitory responses at approximately 20% of the stimulation amplitude required for MPN/LPN stimulation. This indicates that the SAFN would be a good, or at least sensitive, candidate for a stimulation protocol. The reduced signal amplitude has benefits of reducing power requirements of an implanted device and the potential for less side-effects, such as pain, from unintentional stimulation of non-target tissue.

In addition to inhibition, bladder-excitatory responses occurred at stimulation frequencies above and below the 10-20 Hz range in the acute response, and also at 10 Hz in the prolonged response. While the excitatory bladder reflex was observed in 13% to 29% of experiments (for 5 to 50 Hz stimulation rates), 2 Hz stimulation showed an incidence of 38% in the acute response. The 2 Hz bladder-excitatory reflex suggests a potential treatment for voiding disorders, such as UR and/or DU, whereby a stimulation protocol of a neurostimulation system uses this frequency range (e.g., +/−1 Hz) for at least a SAFN target to produce bladder excitation. This reflex was also observed in response to 2 Hz stimulation of the LPN. Post-stimulation excitation was also evoked by electrical stimulation of the PTN, MPN in FIGS. 13a-13c. Additionally, a stimulation protocol of a neuro stimulation system may use higher frequency stimulation in the 50 Hz range, or higher, for at least one of the PTN, LPN, or SAFN to produce an excitatory bladder response. Stimuli in the 2 Hz range and 50 Hz range could be used for the LPN and SAFN, and the site and stimulation signal parameters that elicit the largest acute and/or prolonged excitatory response can be selected for subsequent therapy in treatment of UR/DU. In addition to these peripheral targets, one or more of their corresponding spinal nerve roots may be selected to be therapy targets that are activated by a stimulation protocol of a spinal stimulation system during treatment.

Figure 37:
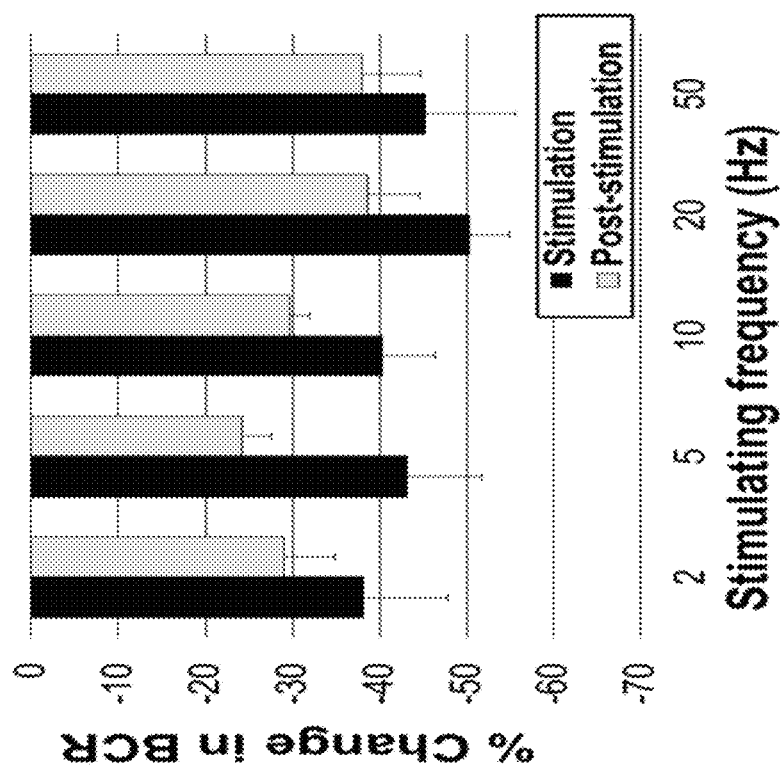
FIG. 37 shows a summary of percentage change in bladder contraction rates (BCR) for all SAFN stimulation (25 µA) trials that were identified as inhibitory (>10% decrease in BCR).

FIG. 37 shows summary of the mean percent decrease in BCR (both acute and prolonged bladder inhibition) averaged over 10 experiments as a function of stimulation frequency rate and does not include (in the mean calculation) any response which increased BCR. Despite the different "inhibitory" response rates to SAFN stimulation shown in FIGS. 36a,b it was found that the magnitudes of the inhibitory responses (for stimulations that evoked decrements in BCR) are robust at all frequencies. This finding suggests that there are other effective stimulation parameters available to patients who may not tolerate or respond to 20 Hz SAFN stimulation. As suggested by the prolonged response rates in FIG. 36b, it may be that 43% to 78% of a human population will also respond well (>10% reduction in BRC) to frequencies other than 20 Hz.

Figure 38:
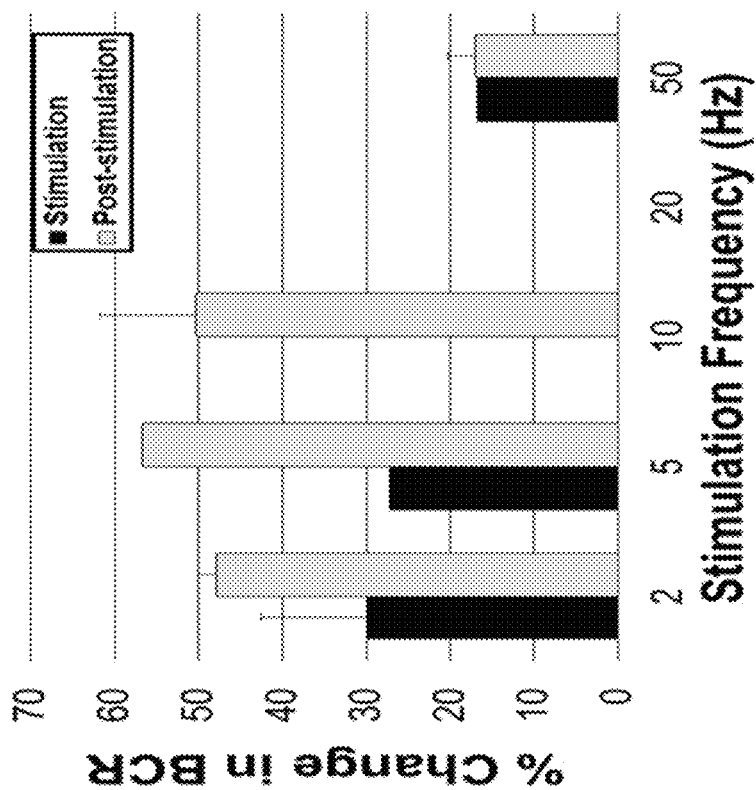
FIG. 38 shows a summary of mean percentage change in BCR for all SAFN stimulation (25 µA) trials that were identified as excitatory (>10% increase in BCR).

A similar examination of the bladder-excitatory responses of FIG. 38 shows that the magnitude of increased bladder activity (increase in bladder contraction rate) is also robust in a small portion of patients, particularly at lower stimulation frequencies (2 Hz and 5 Hz). The observation of an acute excitatory response (e.g., 2 Hz at 25 µA) evoked by SAFN stimulation suggests the clinical use of this stimulation signal/target for providing, at least to some individuals, a rapid (on-demand, or in response to a detected event) method of initiating and/or sustaining a bladder void, such that a sufficiently low residual bladder volume is achieved (e.g., less than 50 ml). In an embodiment, this bladder-excitatory reflex can be induced by stimulation provided by a stimulation protocol to reduce the time needed for a patient with UR or DU to complete the process of bladder emptying (e.g., <1-2 min duration). For example, nerve targets and stimulation signals are selected in stimulation protocols to provide rehabilitation therapy aimed to re-establish normal activity in the bladder system over time. In another example, by achieving more efficient bladder emptying the patient can reduce the duration, amplitude, or provision of inhibitory stimulation subsequently needed for the next urinary cycle.

The data in FIGS. 36a,b indicate that there are some rats (and possibly human patients) that respond differently (are less responsive) to frequencies outside of the 10-20 Hz range, compared to frequencies within that range. If 20 Hz should not be used in a particular patient at the SAFN site, for whatever reason, then as further supported by the data of FIG. 37, stimulation may be able to achieve the same therapeutic outcomes as those who respond at 10-20 Hz. Accordingly, these frequencies can be defined as a fallback stimulation protocol for some patients who do not respond to 10-20 Hz.

Figure 39:
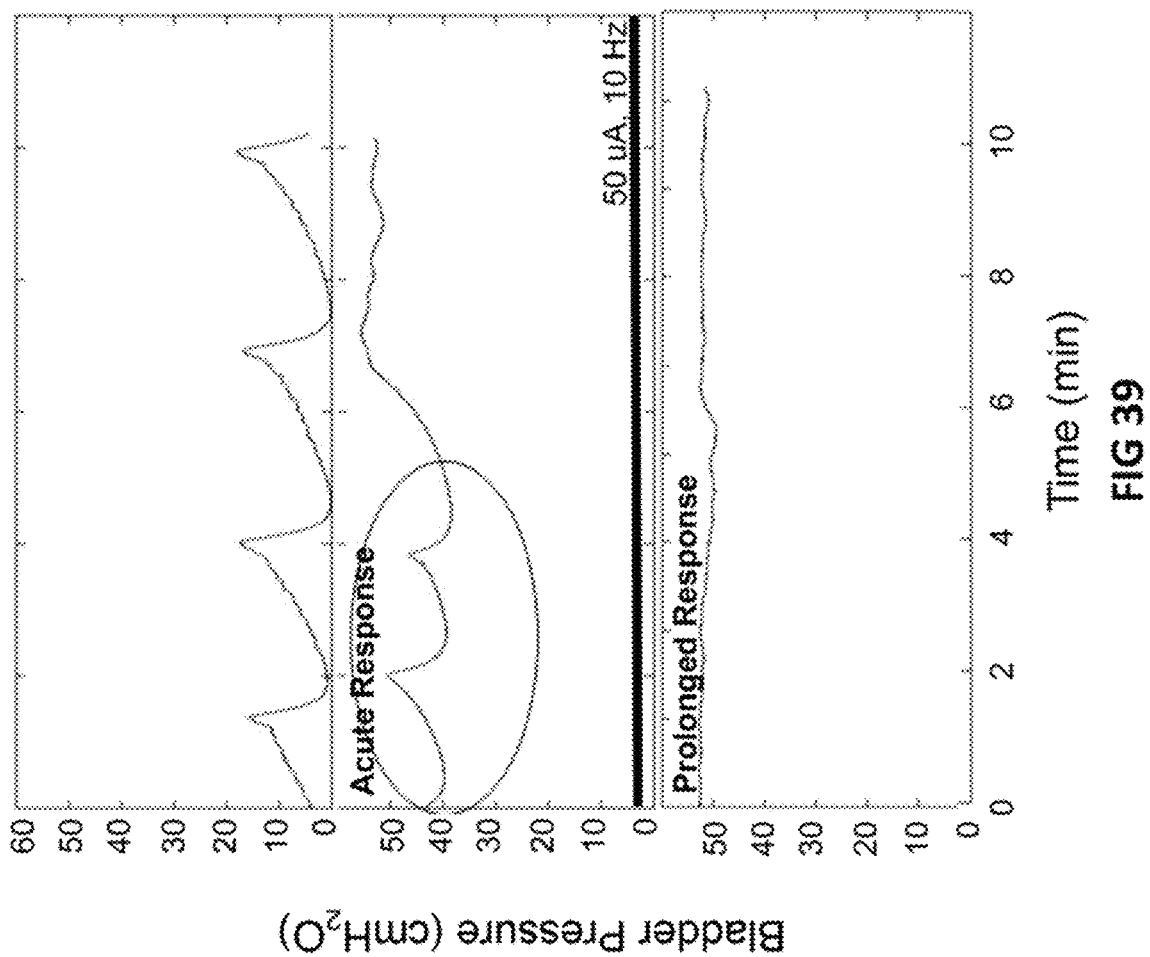
FIG. 39 shows experimental data for both acute and prolonged bladder inhibition evoked by SAFN stimulation applied at 50 µA and 10 Hz, with pre-stimulation bladder activity circled in the middle panel.

Although SAFN stimulation achieved robust bladder inhibition at very low stimulation amplitudes (25 µA, near the sensory threshold), the effect of increasing the stimulation amplitude was also investigated at 10 Hz. FIG. 39, shows very strong bladder inhibition both during and following SAFN stimulation (amplitude=50 µA). In this example, any ongoing bladder activity during SAFN stimulation (circled activity in middle trace) disappears after approximately 5 minutes of stimulation. Beyond this time point, the bladder fills with very high compliance as shown by continuous elevated baseline bladder pressure, while the saline infused into the bladder passively leaks through the urethral meatus as random drops. As shown in FIG. 39 (bottom panel), this state of bladder atonicity (i.e., underactivity) persists well beyond the 10 minute duration of SAFN stimulation.

Figure 40:
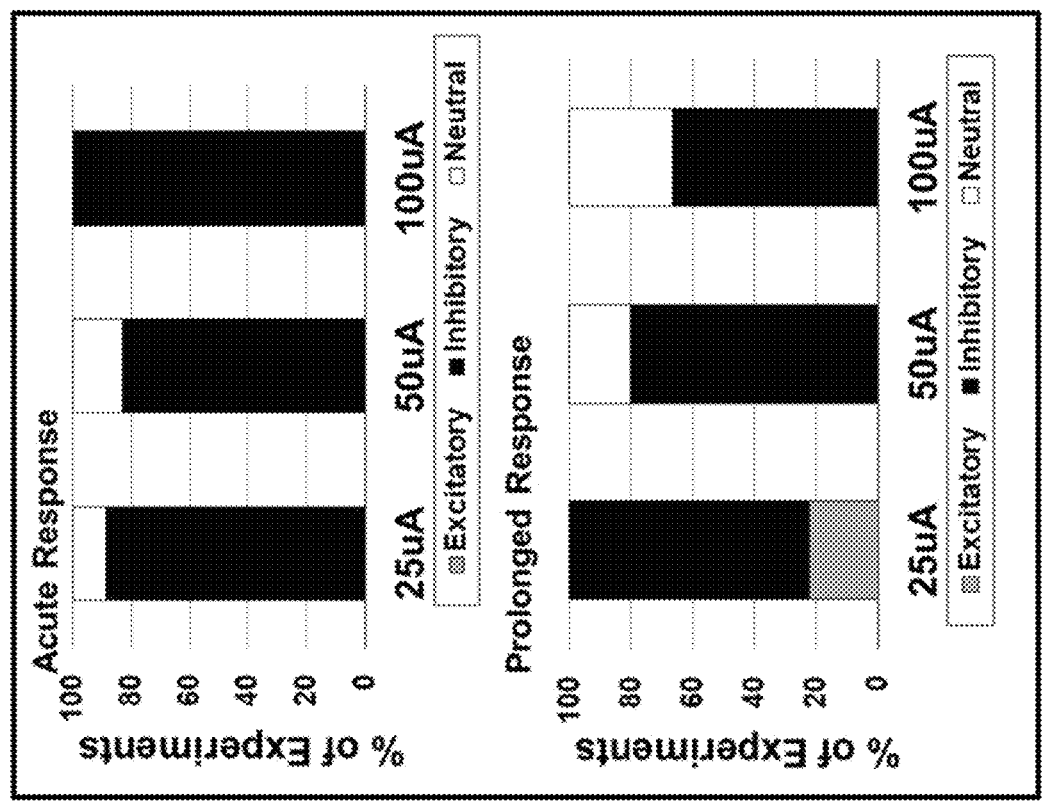
FIG. 40 shows summary data for the percentage of experiments that resulted in inhibitory, neutral, or excitatory bladder responses, across stimulation amplitudes of 25 µA, 50 µA and 100 µA all applied at 10 Hz.

FIG. 40 shows the incidence of inhibition evoked by SAFN stimulation, and shows that increasing the stimulation amplitude, while maintaining the frequency at 10 Hz, results in an increase in the number of rats that achieve acute bladder inhibition (top panel). Compared to the 90% response rate exhibited by SAFN at 25 µA, all rats respond to 10 Hz stimulation when the amplitude is increased to 100 µA (i.e., 100% response rate). This data suggests that, in addition to 20 Hz SAFN stimulation at 25 µA, higher amplitude SAFN stimulation at 10 Hz can also provide a reliable means of rapidly inhibiting the urinary bladder: higher stimulation amplitude can change the bladder response evoked by a selected stimulation frequency. Increasing the stimulation amplitude also affected the prolonged response evoked by SAFN stimulation at 10 Hz. As shown in the bottom panel, stimulation trials applied at larger stimulation amplitudes resulted in the loss of any post-stimulus excitation of bladder function. Lastly, we note a marginal increase in the bladder-inhibitory response rate between stimulation amplitudes of 25 µA and 50 µA: response rate increased from 77% to 80% (although this is likely noise).

A higher stimulation signal amplitude may be more likely to cause unwanted side effects such as pain, or adjacent nerve stimulation. However, the results suggest that the amplitude may be used as part of a stimulation protocol to modulate the amount of either excitation or inhibition of bladder activity that results from stimulation. For a given stimulation frequency, increasing the stimulation amplitude may cause the functional state of the urinary bladder to shift, for example, from one that is excitatory to one that is inhibitory.

The physiological evidence of an acute bladder-excitatory bladder response (or at least increased BCR) evoked, for example, by 2 Hz SAFN stimulation supports an embodiment of a neurostimulation system with a stimulation protocol for assistance in providing acute bladder emptying in patients diagnosed with UR or DU. A patient could select a stimulation program to initiate a "bladder voiding" protocol, either prior to (e.g., several minutes) or at the start of a void. Preferably, this acute therapy could be delivered by eTENS or a fully implanted nerve stimulation device.

Conversely, the evidence of an acute bladder-inhibitory bladder response evoked, for example, by 10 Hz SAFN stimulation (see FIG. 36a and FIG. 38) suggests an embodiment in which a neurostimulation system uses a stimulation protocol for immediate amelioration of OAB symptoms. This could benefit patients with sudden onset of strong urinary urgency that could result in an incontinence episode. eTENS is well-suited for PTN therapy and perhaps even better for SAFN stimulation, which has superficial branches, more superficial to the patient's skin.

Figure 41:
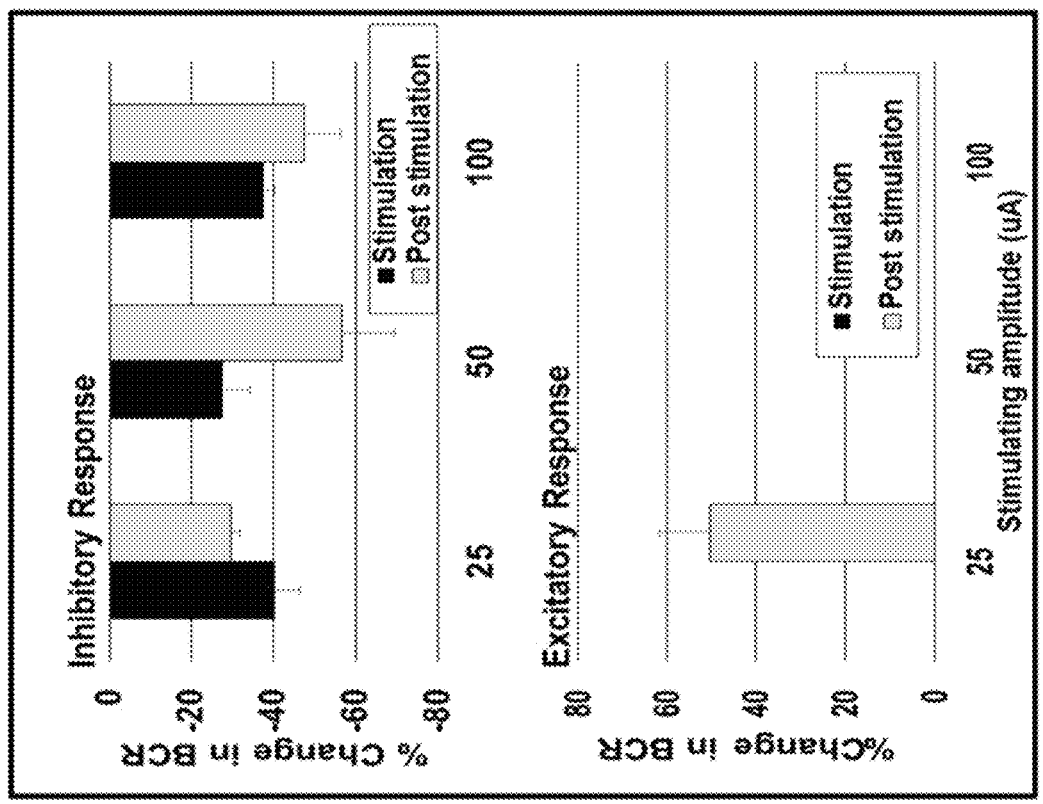
FIG. 41 is a summary of percentage changes in BCR for all SAFN stimulation trials at 10 Hz that were identified as inhibitory (top panel) and excitatory (bottom panel).

A further examination of the magnitude of changes in bladder function is presented in FIG. 41. The top panel shows the magnitude of acute bladder-inhibitory responses did not change much with increased stimulation amplitude. However, the prolonged bladder-inhibitory response showed a notable increase in the bladder-inhibitory response for the two higher amplitudes. The bottom panel of FIG. 41 reflect the findings in FIG. 40, where increased amplitude of SAFN stimulation abolishes the excitatory bladder response.

The data presented in FIG. 40 and FIG. 41, taken together, provide evidence that increasing the stimulation amplitude of SAFN stimulation (1) improves the response rate of the acute bladder-inhibitory reflex (100% at 100 µA), and (2) increases the magnitude the prolonged bladder-inhibitory reflex (87% increase between 25 µA and 50 µA). These results support that, in addition to the stimulation frequency as shown in FIG. 35 through FIG. 39, the pulse amplitude can also be adjusted for the stimulation protocol to achieve effective treatment of OAB. Selection or adjustment of stimulation signal amplitude can serve to change the effect of therapy from inhibitory to excitatory, and/or provide different amounts of bladder modulation, at least in the case of SAFN stimulation.

The results also suggest that, for SAFN stimulation, a medium (or high) amplitude signal may provide a better therapy than a low amplitude signal (e.g., at sensory threshold), as long as it can be well tolerated by patients. In one embodiment, the signal provided by a implanted stimulator is increased until the subject experiences an unwanted side effect, and then the signal is reduced a given percentage, such as to 80% of the signal that produced the unwanted sensation 9 (e.g. tingling or pain). In another embodiment the amplitude of the signal for SAFN stimulation is between 50 and 100 µA. Since the threshold may vary significantly from one patient to another it is likely best to set the amplitude individually for each patient. In an embodiment, a standard therapy will provide SAFN stimulation at 20 Hz using stimulation signals with amplitudes that the patient can tolerate (start at 25 uA). The patient response will be assessed by increasing in steps of, for example, 10 or 25 uA. If a patient cannot tolerate 20 Hz SAFN stimulation, or if this does not provide the desired inhibitory modulation of bladder activity, then a 10 Hz signal can be selected. If neither 20 Hz nor 10 Hz signals provide therapeutic benefit after several sessions, then the stimulation amplitude can be increased for the 10 Hz signal, or a different stimulation frequency can be selected, potentially between 2 Hz and 50 Hz. Further, alternating stimulation parameters, even during a single stimulation session, may be advantageous. For example, some patients may not be able to tolerate constant frequency and/or amplitude stimulation, and as a consequence time-varying stimulation patterns (variable frequency, amplitude, pulse width, etc) may be selected to improve overall therapeutic effectiveness and patient compliance.

If SAFN stimulation does not work, then an alternative therapy may be more successful, such as PTN, LPN or MPN stimulation provided by either an implantable stimulator or eTENS system. Accordingly, in a treatment method the site of stimulation may be adjusted to a different target nerve if stimulation of the first target nerve does not provide therapy. Additionally, in an embodiment both the first and second target nerve may be stimulated concurrently, or sequentially, by the stimulation protocol. If none of these options prove effective, then the clinician can suggest moving to a spinal target, and a test period using percutaneous spinal nerve stimulation with temporary leads (e.g., of L2-l4 nerve roots). If effective, the patient is surgically implanted with a lumbar nerve stimulation system that may, or may not also stimulate a sacral root such as S3.

Several clinical embodiments of the invention can serve to provide effective treatment of OAB and its symptoms. The therapy can be delivered by electrical nerve stimulation applied in the peripheral or central nervous systems (e.g. spinal) and can be achieved by a percutaneous needle electrode, conventional implantable pulse generator (IPG), a BION (active or passive model), eTENS, conventional TENS, magnetic stimulation, ultrasound stimulation or any other clinically viable method of neural activation. In one embodiment, the therapy can involve finite duration (e.g. 30-60 minutes) stimulation that is repeated on a pre-determined time schedule (e.g., daily, weekly, etc). Depending on the nerve stimulation technology used to activate targets, such as SAFN afferents, therapy can be provided in a clinical setting, or as an at-home system, or other manner. Based on the presented data of FIGS. 34-41, SAFN stimulation delivered at a frequency of 20 Hz, pulse duration of 200 μs, and stimulation amplitude at approximately 1× to 2× the sensory threshold of a subject (e.g., 25 μA), and below a sensation that causes discomfort, should provide improved suppression of OAB symptoms and preferable response rates among many patients. The options of modifying the stimulation frequency (between 2 Hz and 50 Hz), the stimulation amplitude, and even the site of stimulation, provides further tools for the clinician to program a "customized stimulation profile" for a stimulation protocol that will improve long-term compliance to, for example, SAFN therapy. Changes in the stimulation waveform (e.g., sinusoidal) and pulse width may also contribute to achieving effective therapy.

Some side effects, such as potential issues associated with paresthesia—typically encountered during sensory nerve stimulation—may be circumvented by using stimulation protocols with time-varying paradigms of stimulation in the case of the SAFN and other targets disclosed herein. This may include, for example, periodic increases and decreases in stimulation amplitude, pulse width, frequency, waveform, or any other relevant parameter. For example, rather than turning the stimulation signal off, it may be reduced by 30-50% in terms of duration or amplitude over a selected interval. These changes may occur over periods of milliseconds, seconds, minutes, or hours. Moreover, one or more of these parameters may be varied simultaneously or at different pre-determined times. These changes can be controlled by the stimulation protocol of a device 50.

In an embodiment, SAFN stimulation therapy (e.g., 30 minutes of nerve stimulation) may be provided at random times throughout the urinary cycle, or it may be prescribed by the clinician to be delivered at specific points within the cycle. For example, SAFN therapy for treating OAB may be most effective immediately prior to or following a void, the early phase of the bladder storage period (up to 50% of bladder capacity), the latter phase of the bladder storage period (between 50% and 100% of bladder capacity), or during the voiding period. The therapy can be provided at points in the cycle that are identified automatically by the therapy protocol of an implanted or external device, or by the patient. For example, a patient may use an external device 72 to indicate this to an implanted device 110 or may simply operate an external neurostimulator device to provide therapy.

Stimulation Protocol Assessment and Adjustment.

The stimulation parameters may be modified to improve the therapeutic effect, patient comfort, or both of a therapy such as SAFN therapy. The assessment of stimulation 628 depicted in FIG. 52 can occur for acute changes (approximately during stimulation) or can occur for prolonged "post stimulation" changes, which can persist over minutes, hours, or days after a stimulation trial is provided to the patient. The measured change that is assessed may be physiological such as bladder pressure (obtained by one or more sensors 634 as seen in FIG. 53*a*) or maximum bladder capacity, or may be assessed using patient symptoms. The assessment may utilize a stimulation protocol that provides at least two different types of stimulation protocols (e.g., to 2 different sites or using different stimulation signals) and the patients response can be assessed in order to adjust or select the subsequent stimulation 630 of FIG. 52.

Figure 52:
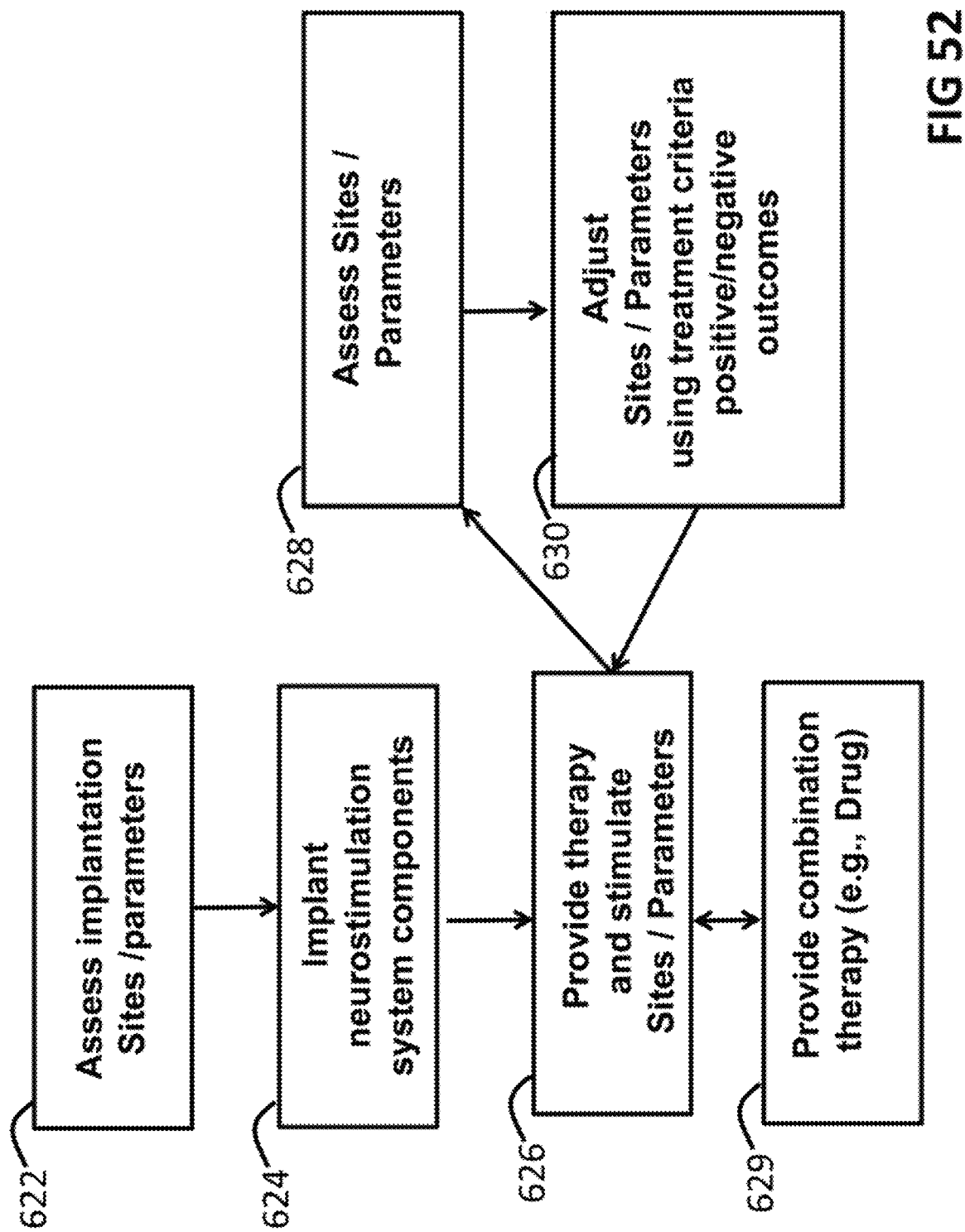
FIG. 52 shows the steps in a method of providing nerve stimulation.
Figure 53:
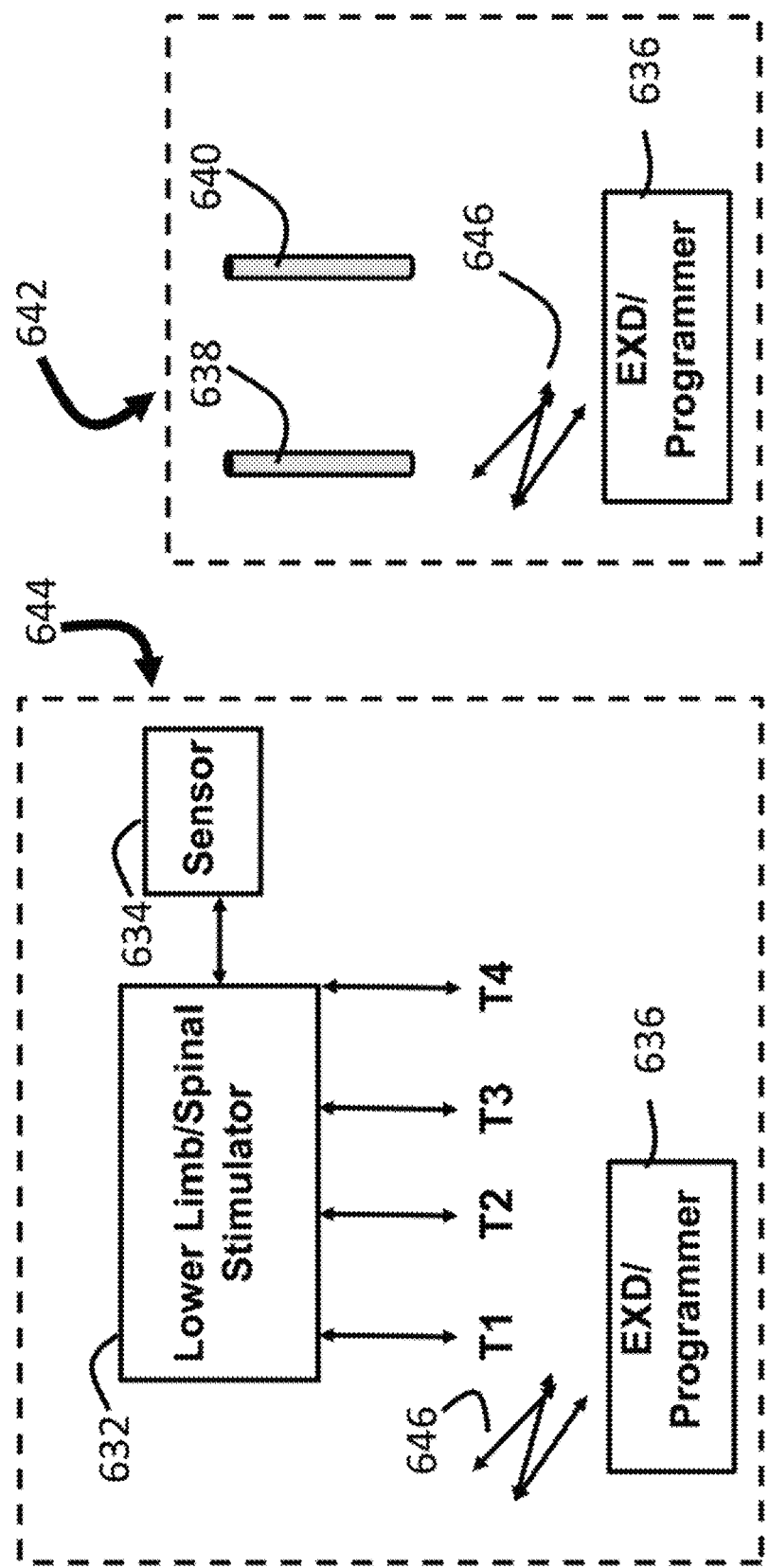
FIGS. 53a,b show neurostimulator systems having at least one neurostimulator that may be implanted in a location to provide stimulation to multiple spinal or lower limb targets.

Additionally, referring to FIG. 52, parameter values that guide the two different stimulation protocols can be implemented 626 and/or assessed 628 independently, one for acute treatment and one for a chronic (or prolonged post-stimulation) therapy regimen. The acute treatment may occur in addition to, or instead of, the therapy program implemented for chronic therapy. For example, periodic low amplitude MPN may be best for continuous treatment in a particular patient (chronic paradigm), but if there is an acute event (e.g., increased sense of bladder urgency), and the patient wishes rapid and supplemental therapy (e.g., to obtain better symptom relief), an acute stimulation protocol can be selected for addressing the immediate symptom(s).

In one embodiment, assessment can occur at an interval after implantation and a patient may be asked to drink an amount of water (e.g. 2-5 glasses) that serves as a stressor. The patient then waits until an urge to urinate occurs. An assessment period may provide at least 1 stimulation signal for at least 2 different targets and the subject can be asked both during stimulation and after (prolonged effect), to rate "subjective urge" both during and after the stimulation protocol. This protocol can be used to assess at least 2 stimulation sites/signals. In an embodiment of an assessment protocol, the stimulation frequency for a given target is increased from 2 Hz to 25 or 50 Hz, in 3 or 4 Hz steps. Each setting can last for a given duration (such as 1 minute) and the subject can provide verbal or other indication of urge. This can be repeated for a second candidate site. The most effective stimulation protocol(s) identified by these post-surgical tests can be used subsequently during therapy.

Selective Nerve Branch Stimulation.

The prior art has not previously shown any clinically significant differences between stimulation of the MPN, LPN, and PTN targets for treating lower urinary tract dysfunction, such as OAB. A plausible reason for attempting stimulating the LPN or MPN, rather than the PTN, may be that these targets could decrease levels of pain or discomfort of some subjects by either minimizing the total number of PTN fibers that contribute to these unwanted sensations or by avoiding to concomitant activation of non-targeted nerve fibers within the ankle region (e.g., sural nerve). Another reason is that electrical activation of PTN branches within the foot may be achieved with TENS and thus could be seen as easier to implement clinically than percutaneous PTN stimulation. However, the data presented herein suggest the clinical advantage that electrical stimulation of these different neural targets may lead to different levels of therapeutic efficacy in OAB patients: patients who are refractory to one stimulation site may respond very differently to another target nerve. Accordingly, an implantable neurostimulator may be improved by allowing selective activation of more than one of these neural targets (PTN, LPN, MPN and SAFN). An example is a patient where stimulation of the PTN trunk does not provide therapy benefit, while one of the PTN nerve branches does provide the desired therapy.

The novel results shown here support that electrical stimulation of the PTN, LPN, MPN, and SAFN can independently and uniquely provide (or at least differ in efficacy with respect to) control of bladder function/continence, and by association, other functional targets within the abdominal and/or pelvic viscera, e.g. bladder, urethral sphincter, intestines, the uterus (in females), rectum, and anal sphincter. A system that provides selective nerve stimulation to any one of these peripheral nerve targets, or to one or more of their corresponding spinal roots, can be used to achieve unique and effective therapeutic results. Further, therapy response may vary at a nerve target in a frequency-dependent and/or amplitude dependent manner. Additionally, providing distinct stimulation input(s) in order to differentially and independently modulate at least one of at least two of these nerve targets may itself achieve therapeutic outcomes, or even augment the therapeutic effectiveness of electrically stimulating a single neural target such as the PTN. Delivering electrical neuromodulation therapy by alternating the stimulation site over time may offer advantages such as decreasing the risk of interaction effects (e.g., as may occur when the net stimulation results in a decrease in bladder modulation effectiveness compared to that obtained when only one of the nerve targets is stimulated) and decreasing demands on a power source such as a battery when two sites are stimulated simultaneously. Alternating nerve targets may also serve to decrease the risk of adaptive, habituation, or compensatory processes related to long term nerve stimulation of a single target.

The data presented in, for example, in FIGS. 13, 14, 36, and 38, show that the therapeutic efficacy obtained by stimulating a first nerve target of either LPN, MPN, SAFN or PTN may not be effective, or may be less effective, than stimulating an alternative nerve target. Systems which are configured to stimulate a second target in the case that a first target does not meet a therapy criterion can provide improved benefit. In order to assess the candidate targets, a method can include implanting 30 at least one stimulator electrode which stimulates at least two of a plurality of nerve targets at least one of sequentially, concurrently, and independently. In an embodiment an assessment protocol 34 operate using an evaluation protocol, such as stimulating a first target at two or more frequencies or rates such as 5, 10, 15, 20, 25, and 30 Hz. The therapy may be assessed during stimulation or after an interval such as minutes, days, weeks, or months after each of at least two of these frequencies have been used to provide stimulation of a patient. Additionally, assessment 34 can then repeated for the second target. The results of stimulating the at least two targets can then be assessed for measures such as urgency and frequency of daily voiding. In an embodiment, when the frequencies of the signals have been selected (e.g., using the 2 protocols and sites that produced the best results for the best and second best target independently), a further step is accomplished in which each of the targets are stimulated alone and then both targets are stimulated in combination. The stimulation protocol can then provide nerve stimulation 626 that resulted in the greatest therapeutic response, either at one or both stimulation sites. Alternatively, if only one site produced therapy, then the second site may not be used. Assessment of therapeutic efficacy can be assessed for the different stimulation signals used in the protocols either during stimulation or after stimulation. When assessment occurs during stimulation the assessment may include, for example, measuring the subjective ratings of a subject or can be data sensed by a sensor. After stimulation, assessment may include data recorded in a bladder diary or online database.

In an embodiment, an implantable system for stimulation of at least one nerve branch of the PTN may occur without a stimulator implanted near target a site within the foot of a patient that is distal to the talus. Although the PTN branches become physically discrete within the foot distally, using this region even with an IPC may be uncomfortable, may be prone to component migration, and may increase the risk of damage and complications to the system components and surrounding tissue due to pressure and sheer. Additionally, tunneling lead wires from a neurostimulator located near the ankle to locations in the foot may be prone to problems such as lead dislodgement and fracture. Surgically accessing each PTN nerve branch (e.g. at or slightly below the level of the medial malleolus location) and providing selective branch stimulation within this single anatomical area may be more suitable than relying upon stimulation sites more distally within the foot. The PTN branches may be surgically accessed using a first nerve cuff to stimulate the LPN and a second nerve cuff to stimulate then MPN, or different contacts of a multi-contact nerve cuff, lead, or electrode array 662 may be used near the site where the PTN divides into these branches. Alternatively, an electrode lead configured with at least one electrically conductive "tooth" or wedge, can be conveniently used to stimulate at least one nerve branch of the PTN, when implanted, for example, by a neurosurgeon to avoid excessive damage of the nerve tissue. Multiple teeth can be used to selectively stimulate more than one PTN branch. For example, multiple teeth can be provided using devices such as the longitudinal intrafascicular electrode (LIFE). Alternatively, although more problematic (as stated above), one or more target nerve branches in the foot itself may also be used to provide selective PTN nerve branch stimulation with at least one implantable stimulator.

A main advantage of the invention, is to provide stimulation protocols which rely upon stimulating one of the PTN nerve branches, rather than the full PTN trunk, since the novel nerve branch data provided herein showed that for some patients, at least for a given frequency and amplitude (and set of 1 or more electrode contacts used to provide the stimulation to a target), selective nerve branch stimulation may produce more effective acute or prolonged modulation of bladder activity than full PTN trunk stimulation. The disclosed systems and methods may also be designed to realize stimulation protocols that are based upon a finding that, at least for some animals, a stimulation signal can cause either excitation or inhibition based upon at least one of: stimulation frequency, stimulation amplitude, and nerve target. Particular nerve branches, or associated spinal roots, may produce bladder excitation or inhibition dependent upon one or more stimulation parameters. Although the data disclosed herein was derived from electrical nerve stimulation at distal sites of the peripheral nervous system, the invention also supports novel stimulation paradigms for spinal targets which correspond to these peripheral pathways and which may produce results well aligned with those shown herein. Furthermore, just as LPN stimulation may not be effective in a patient, and a different target such as the MPN can provide better therapy when selectively stimulated, this may be true at spinal stimulation locations. For both peripheral, or spinal, or mixtures of the two, combination therapy of at least two targets may provide better therapy than a single site.

A system may provide independent stimulation to at least 2 nerve targets, although only one may be relied upon if, after implantation, only one is found to provide the benefit to the patient. In some instances, combination LPN and MPN stimulation may not provide therapy benefit, or may provide worse benefit, then when the same stimulation frequency is used to modulate both targets. In an embodiment, a method used by a stimulation protocol of an implanted neurostimulator has a first step of providing and assessing stimulation of a first target to derive successful stimulation parameters (e.g., frequency, amplitude) for producing intended bladder modulation. This step is then repeated for a second target candidate. The two targets may then be used together to provide improved therapy. However, therapy should also be assessed when combining targets using the successful stimulation signals, to ensure that the combined stimulation (e.g., provided simultaneously, periodically, or in an alternating manner, etc) provides improved therapeutic effects to either stimulation provided alone. Additionally, in the course of therapy, if sufficient therapeutic benefit is not sustained, then the second target can be added or removed (if already present) from the stimulation protocol.

Results presented herein suggest that the PTN and SAFN stimulation relate to at least partially different bladder modulation mechanisms/pathways. For example, significantly lower stimulation amplitudes are effective for modulating bladder activity using the SAFN compared to the PTN, and its branches suggesting a different bladder reflex mechanism. Differences found at peripheral target sites suggest that the corresponding spinal nerve roots may also modulate bladder activity through different central and peripheral reflex systems. Accordingly, L2, L3 and L4 (SAFN nerve roots) may provide different sensory inputs from the commonly used S3 for modulating bladder function. Further, this characteristic can extend to the full set of spinal roots including L5 to S4 (i.e., tibial nerve roots). It follows that stimulation of L2 and/or L3, and/or L4 instead of, or in combination with, S3, or other tibial nerve roots, may improve therapy in some patients with pelvic floor disorders such as overactive bladder by treating the disorder using different mechanisms. Such modulation may similarly be sensitive to stimulation signal characteristics—including at least the stimulation frequency and amplitude—that may provide for either inhibition or excitation of bladder activity. It is likely that the SAFN produces bladder modulatory effects primarily via L3 and L4 nerve roots, and to a lesser extent via the surrounding L2 and L5 roots. Electrical activation of more than one spinal nerve root may be required to produce therapeutic efficacy that is similar to that produced by the peripheral SAFN stimulation in the lower leg, which activates multiple spinal targets. In an embodiment, a neurostimulator is configured with a stimulation protocol that provides a first stimulation signal to a first electrode stimulator to stimulate at least one of an L3 or L4 nerve spinal root target and a second stimulation signal to a second electrode to stimulate an S3 spinal root nerve target.

The ability of stimulation signals with different amplitude and frequency combinations to cause either bladder excitation or inhibition at the same stimulation site may extend to other spinal nerve root stimulation sites than those disclosed above, such targets selected between T1-S4. The SAFN, stimulated peripherally in the lower leg, has thus far been shown to be the most effective site of stimulation for modulating bladder activity, suggesting the L3-L4 roots may be more sensitive as well. The LPN data at 2 Hz and 50 Hz show the strongest excitation acute and prolonged response. The PTN stimulation also shows this reflex, but this seems to be mediated primarily by the LPN: selective stimulation of LPN may be more effective in producing excitation.

An embodiment of the stimulation protocol may be based upon LPN stimulation results that may correspond to a spinal nerve set 3 (including S1,S2 roots), and MPN stimulation results that may correspond to spinal nerve set 4 (including L4,L5 roots, see Atlas of Human Anatomy, Frank Netter). These two sets of spinal nerve roots may be used in a stimulation protocol that is configured to stimulate at least a first nerve target selected from set 3 and a second nerve target selected from set 4 in order to take advantage of the differential responses shown in the data presented herein for LPN and MPN stimulation. For example, S1 and S2 may be more useful in providing bladder excitation than other targets, especially with stimulation frequencies in the 2 and 50 Hz range, since this was seen for LPN.

Since LPN was found to be effective in the rat data results presented herein, indicates that the sural nerve (and its cutaneous nerve branches with corresponding L5, S1, S2 spinal nerves) may also be an effective peripheral target since both the LPN and sural nerve terminate in the S1, S2 spinal roots. Likewise, the sciatic nerve, femoral nerve, and lateral cutaneous femoral nerve branches may also be appropriate due to the origin of their spinal roots. It is a novel feature of the invention to selectively stimulate individual nerve branches, since selective activation of peripheral nerve branches, especially those of the lower limb, such as the LPN and MPN have shown to produce different/better results than stimulation of the whole nerve trunk. Further, since two or more branches may produce different results, stimulation protocols and related assessment should incorporate this finding into stimulation protocols that treat separate nerve branches as different target candidates.

In an embodiment an assessment procedure is provided before the start of therapeutic stimulation of the patient. In the assessment procedure, a subject is stimulated using at least 2 temporary stimulation leads. The leads are configured to stimulate at least 2 nerve targets selected to be from L2 to S5, where a first is implanted to stimulate a site in L2-L4, and the second to stimulate at a site at L5-s5. Both during and after stimulation is provided, sensed data and/or subjective evaluation by the patient, may be obtained from the patient in order to assess the acute and/or prolonged effect on bladder function and related symptoms. During treatment one or more targets and stimulation signals which provided for improved therapy results during the assessment procedure are selected for subsequent therapy provided by a treatment protocol.

In an embodiment, a system and method for treating OAB comprises drug therapy such as transurethral injection of Botox into the bladder wall 629, intrathecal injection or oral consumption. The drug may be provided or adjusted in order to enable a broader range of nerve stimulation parameters to provide effective bladder modulation and also decrease unwanted side-effects elicited by nerve stimulation. For example, providing a drug may allow therapy benefit to be obtained at a lower level of stimulation. Adjustments to drug may involve, for example, oral dosage, volume per injection, drug concentration, and number of locations of injections. Additionally, the provision of electrical stimulation can decrease the amount of drug needed and the associated side-effects of the drug therapy used to treat overactive bladder. The combination of electrical and drug therapy may result in a synergistic therapeutic outcome that requires either reduced drug use, or reduced amplitude of electrical energy during stimulation, or both.

Multi-Modal Stimulation.

Nerve stimulation can rely upon stimulation signals of various modalities. Examples of ultrasound transducers which can be used to deliver ultrasound to stimulate tissue are disclosed in U.S. Patent Application Publications 20150025422 and 20140094720 (both entitled "Methods and Devices for Modulating Cellular Activity Using Ultrasound") as well as 20110213200 ("Orgasmatron via deep-brain neuromodulation"). The prior art does not use an implanted passive element to absorb, reflect, or focus the stimulation energy in any manner. There is no provision of an IPC designed to be resonant with the supplied energy. U.S. Patent Application Publications 20140316499 and 20130096656 (both entitled "Neurostimulator") and 20100130867 ("Ultrasound frequency resonant dipole for medical use") disclose materials with beneficial properties and configurations that may be used to convert sound to electrical stimulation. These patent publications are incorporated herein by reference in their entirety for all purposes. The use of absorbing or reflecting sound in order to focus modulation energy within local tissue, such as to produce peripheral nerve stimulation in the treatment of OAB according to the principles of the current invention is not disclosed by the aforementioned prior art. The IPC may be selected to be made from a material including polyvinylidene fluoride, ceramic, crystal metal quartz. The IPC can have a biocompatible coating that is effectively transparent to ultrasound. When two IPCs are activated separately, the first and second materials should have resonant frequencies (and other relevant sound characteristics related to absorbing or reflecting sound) sufficiently dissimilar that when the first and second IPCs are exposed to a signal having a frequency similar to the resonant frequency of the first IPC, the second IPC does not create a significant vibration. Although the prior art suggests frequencies of ultrasound that are suitable to stimulate tissue, other frequencies of sound or vibration, which are sufficiently lower may also be useful in this application. The size, shape, and density of the IPC can be adjusted so that the IPC is maximally activated by the incoming energy.

Additional Stimulator Embodiments.

Figure 42:
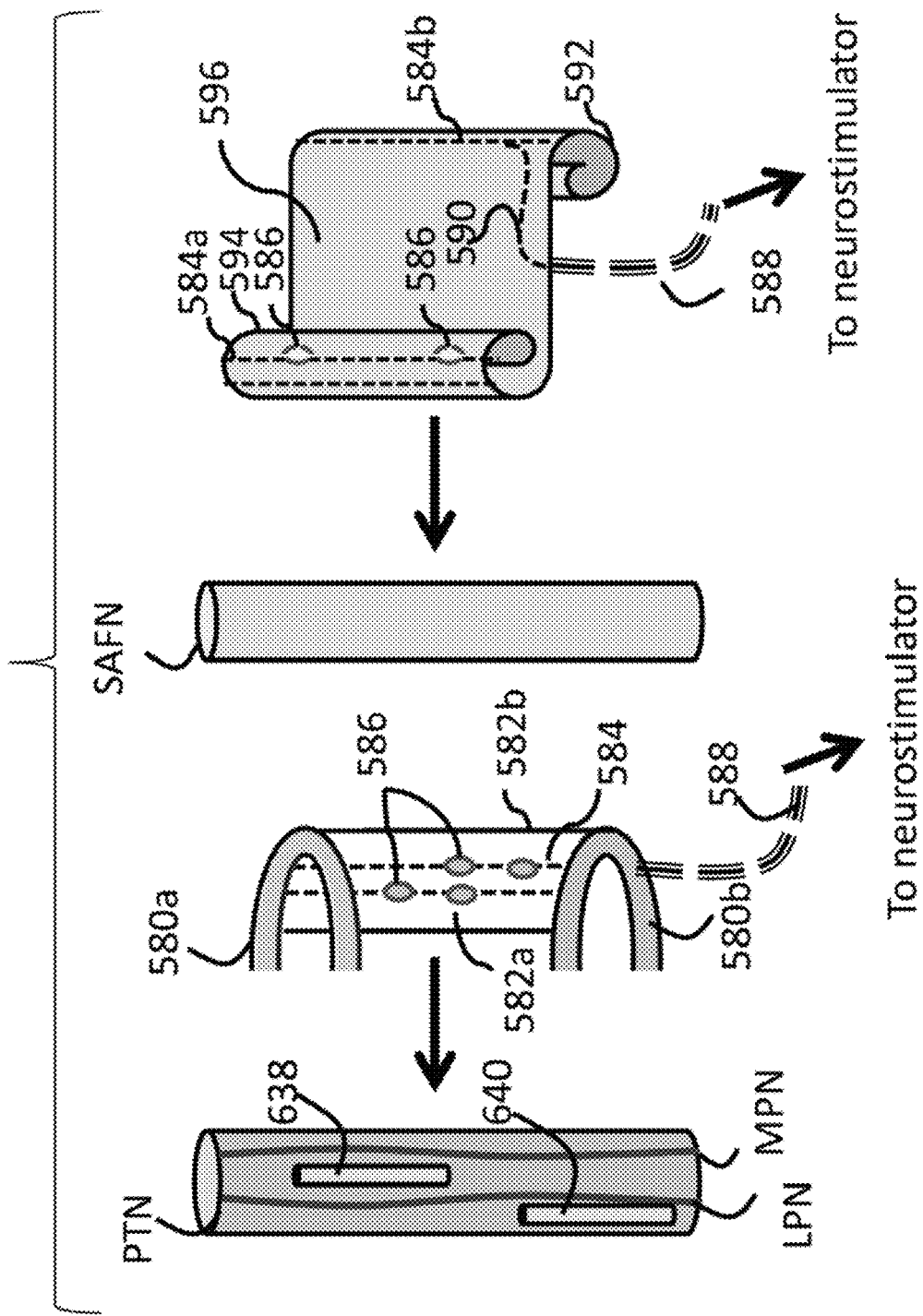
FIG. 42 is a schematic view of small "microneurostimulator" devices and nerve cuff embodiments configured for stimulating target nerves.

The methods and systems disclosed here may utilize a number of alternative embodiments to provide selective nerve stimulation. Because the nerve targets in the lower leg may be very near each other various embodiments may provide advantages in providing selective stimulation according to the principles of the disclosed invention. In FIG. 42 to FIG. 51, the relative size, position, and shape of the nerve and the system components are not meant to be limiting and are presented for illustration purposes only. FIG. 42 shows several system components which can be used to implement various strategies for providing selective nerve stimulation. In an embodiment stimulator includes a flexible annular, or semi-annular (i.e. concave) nerve cuff comprising a top side 580a and a bottom side 580b with a non-conductive wall there between, having an inner wall surface 582a and an outer wall surface 582b. When multiple electrode contacts 586 are disposed on the inner wall 582a, such may be positioned near a target nerve or nerves fascicles within a nerve trunk, for example, MPN and LPN during implantation (which may or may not be visible at the level near the medial malleolus). The conductive pathways 584 may be insulated and can supply electrical power to the contacts 586. Alternatively, if the contacts 586 are not provided then the conductive pathways may not be insulated (or may be partially insulated) in order to serve as electrode contacts themselves. Each conductive pathway 584 may contain multiple conductive conduits and can independently operate more than the set of two contacts 586 shown. Although physical proximity of an electrode contact 586 to a target nerve may be straightforward, and placement during implantation allows target nerve branches to be stimulated directly by contacts, in another embodiment the stimulation protocol activates different patterns of the electrical contacts 586 in order to steer the electrical field to a target a selected nerve or a nerve branch within the nerve trunk (e.g., to target LPN within the PTN). Although current steering (spatial biasing of the electrical field) using an electrode array is well known, the benefit of stimulating a nerve selected branch rather than the entire PTN was not known prior to the data presented here. U.S. Pat. No. 8,509,920 entitled "Electrode arrangements for medical lead" discloses a system that may allow for this feature and is incorporated by reference herein. The electrical signals can be transmitted to the electrical contacts 586 and pathways 584 by means of a multi-stranded cable 588 that communicates stimulation signals from a neurostimulator. Alternatively, microcircuitry may be provided at the junction of the bottom side 580b and the stranded cable 588 to allow for multiplexing and signal routing. A signal router and paths between the stranded cable 588 and the conductive pathways 584 are not shown in FIG. 42 for purposes of clarity. Additionally, the nerve cuff may be designed to be more fully closed during implantation but is shown in the current form for illustration. In an embodiment, only one or two electrode contacts are used and each of these may be realized to reside within a large area of the cuff, such as extending the entire length, the entire width, or along a large part of entire inner surface of the nerve cuff.

In an embodiment, at least some electrical contacts 586 and pathways 584 are positioned on the outside wall 582b of the nerve cuff. In the example of FIG. 42, therefore, the inner wall electrical contact stimulators will serve to stimulate at first nerve target such as the PTN, LPN, or MPN, and the outer wall stimulators can stimulate at second nerve target such as the SAFN. Since the inner and outer walls 582a, 582b are non-conductive, when the contacts are positioned away from the edges then the stimulation of a target #1 should be well insulated and should deter modulation of a second target #2. FIG. 42 is not drawn to scale and the arrow pointing to the left indicates that the nerve cuff can be positioned close to, and even wrapped around, the PTN nerve during implantation by a surgeon. In some anatomical regions the SAFN is much further from the PTN, and so a more appropriate embodiment would, for example, illustrate the nerve fiber on the left to be the LPN and the nerve fiber on the right to be the MPN, which may have been dissected away from the remainder of the PTN nerve trunk. The cuff may also prove useful for selective LPN/MPN stimulation when implanted near a region where the PTN bifurcates into the LPN and MPN branches.

FIG. 42 also shows a microneurostimulator device 638 such as a battery powered, wirelessly powered (e.g., RF/magnetic/microwave) driven device which may be similar to that produced by, for example, Stimwave. The device 628, may utilize RF energy for obtaining power wirelessly from an external device 636, as shown in FIG. 53a, configured for providing wireless power and data signals 646. Although the neurostimulators 638,640 shown here do not have electrodes shown on their housing, it is understood that these, as well as those shown in other figures, may have one or more electrode contacts disposed on their housing and that these may extend radially around their exterior or may be realized as a electrode grid array on their surface that approximates the configuration found on a multi-polar paddle electrode and further the device 638 can communicate with electrode leads to provide stimulation. In an embodiment the device 638, or at least a portion of the device, can be injected into a nerve trunk such as the PTN during implantation, or injected into tissue proximate the PTN. The device 638 may have electrode contacts at its top and bottom surface which can provide stimulation or the contacts may reside along the length of the device 638, although these are not shown in every figure. When a single device is used, a pair of contacts may reside upon a particular portion the surface of the device 638 in order to stimulate a nerve target disposed spatially (e.g., to the left) of the implanted device while the other contacts reside on the opposite surface to stimulate a different nerve target (e.g., to the right) relative to the position of the device. Similar to the IPC designs, device 638 may be provided with tines, or anchors, order to affix the device in position as well as having other attachment means such as at least one ring along its body that allows a suture to be treaded through so that the device may then be sutured into place. In an embodiment where more than one device 638 is provided with the first device may be implanted to stimulate a first target such as the MPN and a second device 640 implanted to stimulate a second target such as the LPN. When two or more neurostimulators 638, 640 are provided, these can obtain power and be controlled from the same external device EXD 636 which is configured to provide a combination stimulation protocol by operating the two or more implanted devices in order to realize a distributed neurostimulation system 642.

U.S. Pat. No. 8,509,920 entitled "Electrode arrangements for medical lead", incorporated herein by reference in its entirety for all purposes, discloses an electrode lead which has multiple contacts arranged longitudinally along its inner surface. In embodiments related to the current invention, one or more electrodes may be employed to selectively apply an electrical signal to a particular set of nerves, or nerve fibers within a fascicle of the nerve.

An alternative nerve cuff design is shown on the right side of FIG. 42 and includes a first cuff enclosure 592 and a second cuff enclosure 594 which have independently operable electrical contacts 586 and pathways 584a,b (additional contacts and pathways are not shown for clarity purposes). A routing pathway 590 communicates signals between the multi-stranded stimulator electrode 588 (connected to the neurostimulator) and the conductive pathways 584a,b so that stimulation signals 588 reach their intended nerve target.

Figure 43:
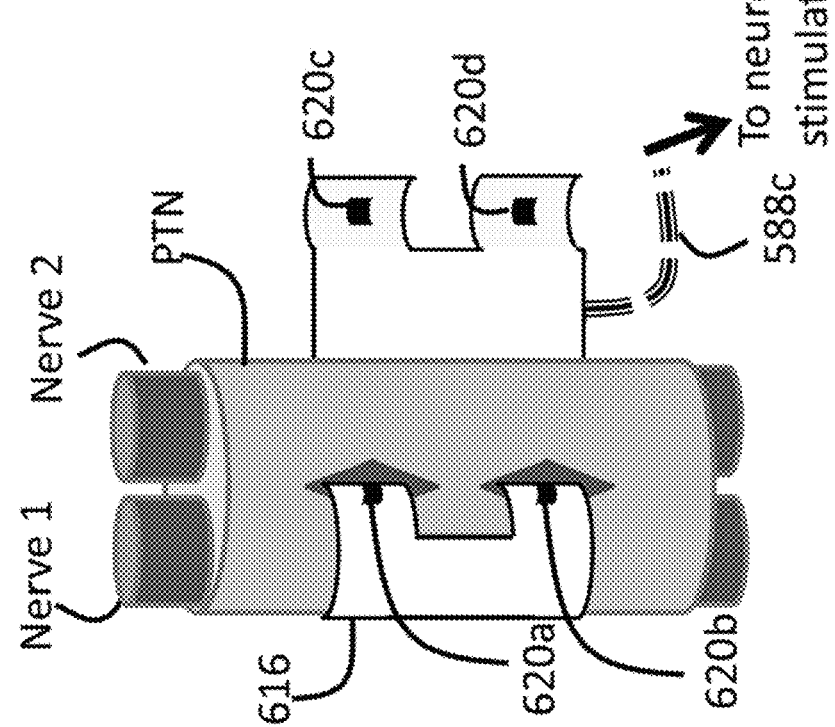
FIG. 43 is a schematic view of an alternative embodiment of a nerve cuff, where the electrode contacts are located to provide selective stimulation of nerve targets.

FIG. 43 shows an alternative embodiment of an implantable nerve cuff, in which electrode contacts 620a,b may be located to stimulate a first nerve target 1, and 620c,d stimulate a second nerve target 2, using stimulation signals supplied by the stimulator conduit 588c. The electrode contacts may reside only on the inside or outside of the cuff, depending upon how the cuff is implanted by a surgeon. The nerve cuff itself may be made of conductive material (and may be coated partially or fully with non-conductive material).

Figure 44:
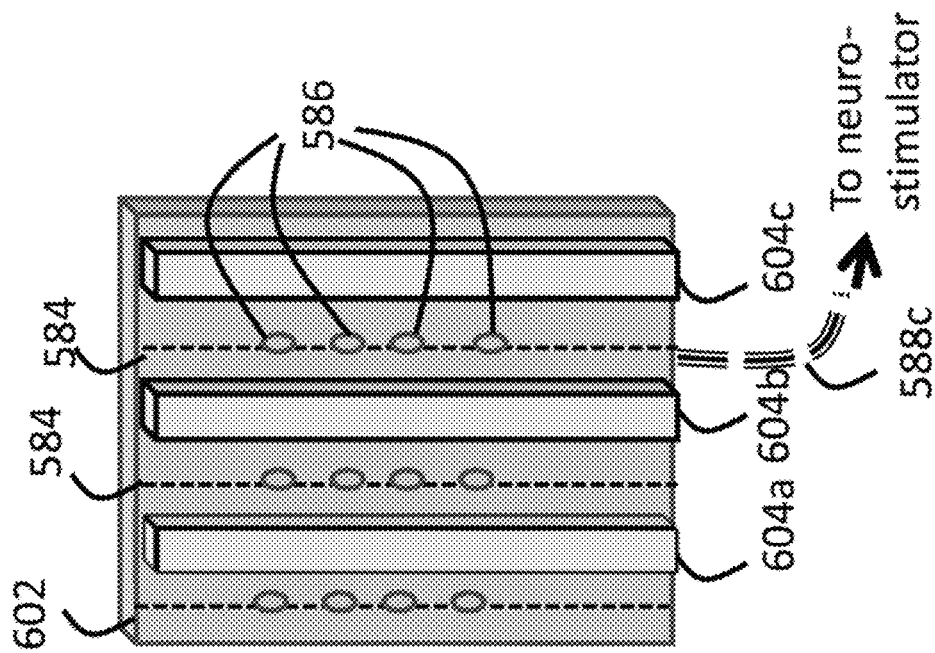
FIG. 44 is a schematic view of embodiments of an electrode array having canals for physically separating, and selectively stimulating, nerve fascicle targets.

In an alternative embodiment shown in FIG. 44, a nerve cuff electrode design is shown which may have two or three non-conductive, separation walls 604a, 604b, 604c which reside on non-conductive back-plate 602, which may be rigid, or made partially of a flexible material such as silicon. Each of two or more nerves are placed within the nerve cuff so that each reside within one of the canals that are separated by the walls 604. In an embodiment, a second (full or partial) back-plate is provided opposite to the first back-plate 602 during implantation. In this manner, the walls can define enclosed pathways. The channels do not have to be parallel and can be unequally spaced to conform to selected nerve targets.

Figure 45:
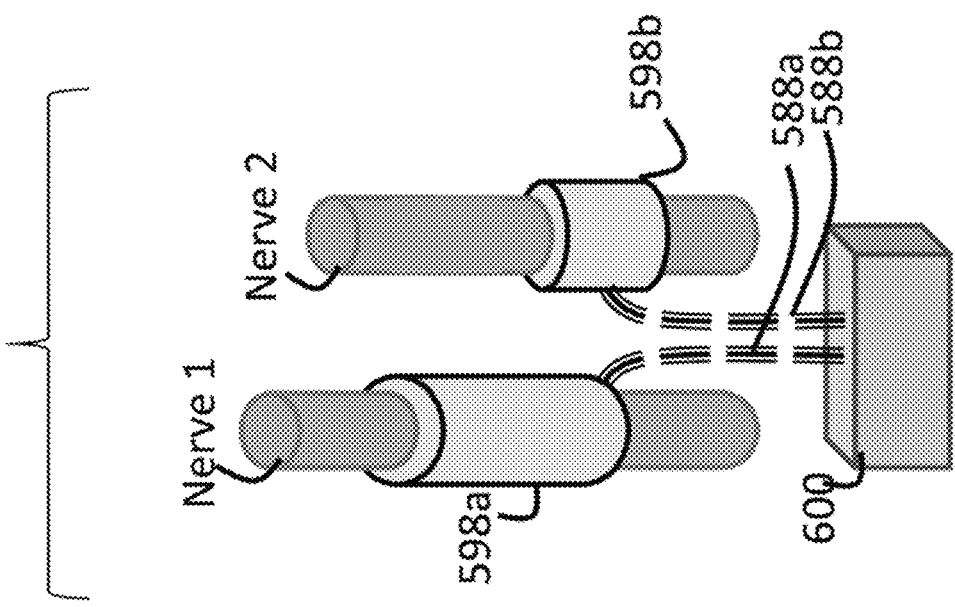
FIG. 45 is a schematic view of an alternative embodiment of a nerve stimulation system.

In an alternative embodiment shown in FIG. 45, an implantable neurostimulator 600 can send signals to modulate two nerve targets, for example, the LPN and MPN (in this case labeled Nerve 1 and Nerve 2) in an independent manner, by sending unique signals through multi-stranded pathways 588a, 588b to electrode contacts within the nerve cuffs 598a, 598b. In an embodiment in which the nerve cuffs 598a,598b are simply realized using conductive material, these may serve as the stimulators themselves and no contacts are provided. Nerve cuffs 598a,598b may be serve as IPCs that are paired to work with an external stimulator rather than working with an implantable device 600. In either case the partial or full cuffs can be formed or fabricated of a material that biases them in the closed position so that the inner space has a radius that can accommodate the nerve target. In an embodiment, the cuffs may also be made of a thin flexible conductive material that allows the cuff to be gently wrapped around the nerve. The IPC can have at least one surface that is electrically conductive so that an eTENS can be provided. In an embodiment an elastic or deformable cable can be wrapped around the cuff in order to bias it against the nerve and deter migration. The IPCs may be realized using two different lengths and may be implanted further away than shown, in order to increase the ease and accuracy of providing selective nerve branch stimulation. Additionally, is understood that in figures shows a neurostimulator using a nerve cuff, this could be realized using a lead-type single or multi-contact electrode array such as is often used to provide stimulation of the brain, spinal cord, or peripheral targets. For example, electrodes can be realized as one or two column paddle type leads or passive tip leads with steroid-elution coatings to improve post-surgical recovery. In embodiments nerve cuffs can be configured with adaptors to attach to conduits provide by a neurostimulator in the case where an implantable pulse generator may subsequently use the cuff after eTENS to provide stimulation.

Figure 46:
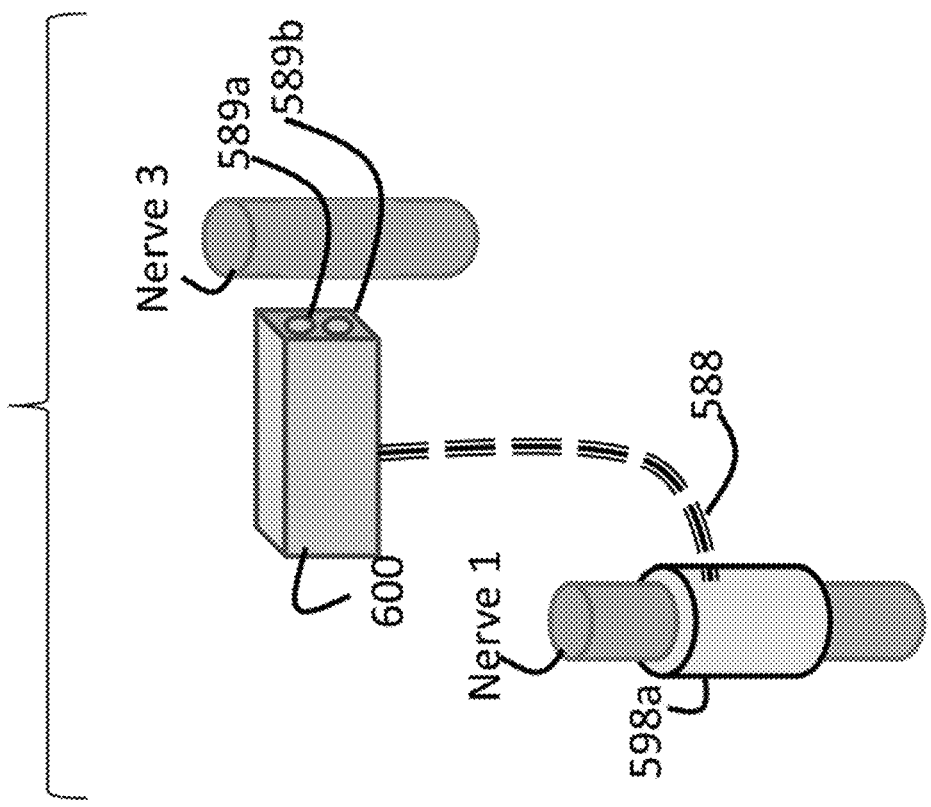
FIG. 46 is a schematic view of an alternative embodiment of a nerve stimulation system.

In an alternative embodiment shown in FIG. 46, an implantable neurostimulator 600 can provide stimulation signals to modulate, for example, the PTN and SAFN (in this case nerve 1 and nerve 2) to realize a selective nerve stimulation protocol. This can be achieved by positioning the neurostimulator 600 at a location below the knee and near a location where the SAFN stimulation has been found to be effective. Electrode contact 589a, can provide stimulation to the SAFN (Nerve 2) using a conductive region of the casing of the neurostimulator 600, or a stimulation grid array which is designed to be the cathode electrode, and contact 598a can serve as the anode or vice versa. Alternatively, contacts 589a and 589b may both be provided on the housing, or using a grid array, to enable a more focal field of bipolar stimulation to be provided. Accordingly, in one embodiment the neurostimulator 600 can provide stimulation signals through the multi-stranded pathway 588, to electrode contacts within the nerve cuff 598a which may be located near the ankle and configured to stimulate Nerve 1, while the neurostimulator is located higher in the leg and the neurostimulator housing, or contacts on the housing, provide stimulation of at least one branch of the SAFN.

In an alternative embodiment, the stimulator cuff 598a may be realized as a transverse intra fascicular multichannel electrode (TIME) which can be inserted transversally for a peripheral nerve, such as the PTN, to selectively activate subsets of axons in different fascicles, such as those of the MPN and LPN. Other embodiments may use longitudinal intra fascicular electrodes (LIFE), multichannel electrodes, or multipolar cuff electrodes can also be used (Badia et al. Comparative analysis of transverse intrafascicular multichannel, longitudinal intrafascicular and multipolar cuff electrodes for the selective stimulation of nerve fascicles. J Neural Eng. 2011 8(3):036023). In an embodiment the cuff is wrapped fully or partially around a vascular bundle and at last one electrode contact stimulator is configured to extend from a surface of the cuff and project into or near a nerve target in order to stimulate that target. This may be surgically easier to achieve with less risk of producing nerve damage when providing, for example, selective nerve stimulation of a nerve branch. Note that it may not be known which nerve target of a nerve fascicle an electrode contact is stimulating during the provision of therapy. For example, if there are 4 contacts and contact #3 successfully produces therapy, then it may not be known whether this occurs via the MPN, LPN, both, or otherwise. The stimulation protocol or assessment procedure may simply be configured so that a contact, or a combination of contacts, is used to provide stimulation. The results disclosed herein serve to support the use of a system which may use stimulation protocols and stimulators to stimulate different nerve branches selectively. Accordingly, an embodiment is supported which uses a particular electrode contact of a set of contacts, or a particular set of contacts from a larger set (e.g. to provide field steering). Prior to the results presented herein the PTN and its branches were treated as equivalent targets which would lead to similar results due to stimulation.

In an embodiment, a system for treating a patient with an overactive bladder condition is provided including a neurostimulator having a processor configured for operating a stimulation protocol to provide at least one stimulation signal to at least one stimulator in order to provide stimulation selectively to at least a first nerve target. The at least one stimulator is adapted to be implanted within the patient and configured to selectively stimulate at least a first nerve target that is a portion of the tibial nerve trunk at a location substantially between a knee and a heel of the patient. The stimulator may have at least a single electrode contact that is physically located next to a portion of the posterior tibial nerve that has been assessed as being a suitable target (during an assessment procedure). Alternatively, multiple contacts may be used. Use of combinations of stimulation signal characteristics (e.g., frequency, amplitude, polarity) and sets of 2 or more electrodes which have been found to produce therapeutic results can be set as values in a stimulation protocol which subsequently provides therapy to the patient. In this embodiment the stimulation system operates upon a strategy that recognizes that different branches of the posterior tibial nerve may produce different therapeutic effects, without requiring a particular electrode contact to be conceptually, or otherwise, mapped to a particular nerve target. Successful stimulation parameters can be assessed by trial and error, and then subsequently used. Nevertheless, when available, using anatomical landmarks, or imaging data, to align electrode contacts with particular nerve branch targets may improve performance of the system and decrease the time needed to derive successful stimulation protocols.

Figure 47:
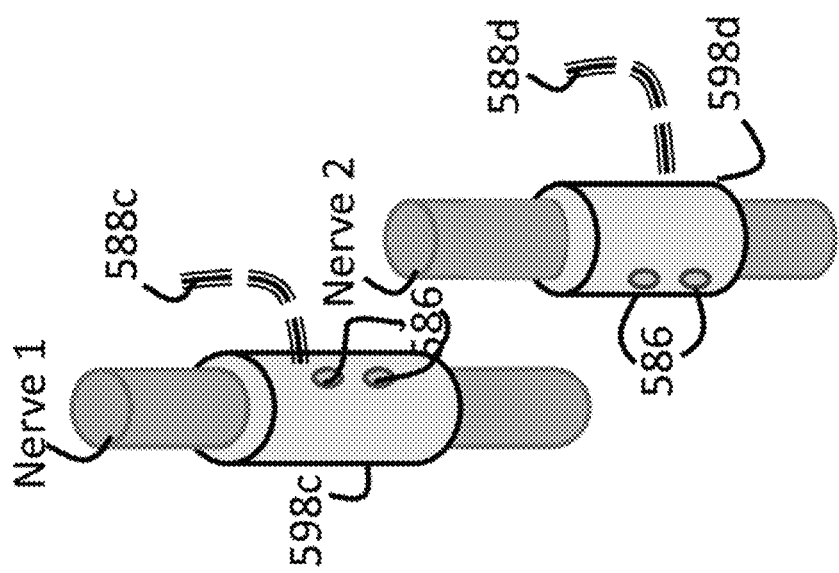
FIG. 47 is a schematic drawing of a peripheral electrode which is a nerve cuff designed to selectively activate one or more branches of a compound nerve trunk such as the posterior tibial nerve.

In an alternative embodiment shown in FIG. 47, nerve cuffs 598c, 598d are shown in which the cuff itself is made of non-conductive material, or may have a metallic core and be insulated with a non-metallic material. In this example, the electrode contacts 586 are configured to stimulate a nerve that is external to the nerve cuff. Alternatively or additionally, contacts may be located on the inside wall of the nerve cuff in order to stimulate the nerve within the cuff. The inner and outer electrode contacts 586 may be independently operable to provide several different stimulation signals. Although the nerve cuffs 598c, 598d are shown as fully closed cylinders, this is to approximate their closed position and these can be uncoiled by opening up the cuff against its biased, closed, position as is well known in the art. Target Nerves 1 and 2 may be located near each other, or far away, such as the LPN branches for the left and right side of the body and may be driven by two different neurostimulators.

Figure 48:
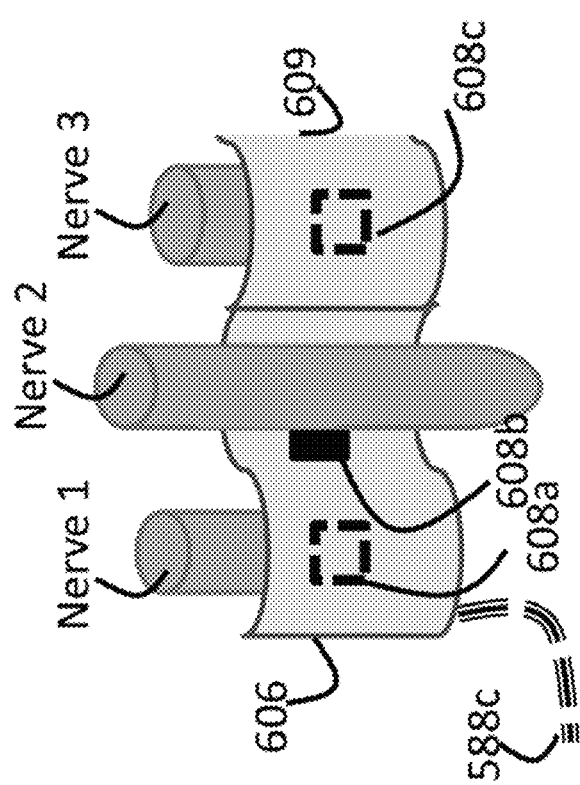
FIG. 48 is a schematic view of further embodiments of an electrode which is a nerve cuff.

In an alternative embodiment shown in FIG. 48, a nerve cuff 606 is shown and can be made of either a non-conductive and flexible substrate such as silicone or a coated metal foil. The cuff 606 has at least-two electrode contacts 608a, 608b, and 608c, which, in this example, are configured to stimulate three nerves or nerve fascicles. For example, contacts 608a and 608c are disposed on a first side of the cuff 606 that faces into the page as indicated by their dashed-lines, while 608b is on the second side, side facing out of the page. As in the other designs, a multistranded cable 588c can provide stimulation signals to the stimulator contacts and additional contacts may also be provided to enable bipolar stimulation protocols. The right edge 609 of the cuff may be extended in order to provide sufficient material to wrap the cuff around all three nerves at least 1, 2 or 3 times in order to secure the cuff more firmly in place. The cuff can also be made of a biocompatible material that is similar to cloth in texture and allows the nerves to be gentle wrapped. Suture holes may also be provided into order to secure the wrapping and to secure the cuff to appropriate adjacent anchor points. In an embodiment, each of the electrode contacts can instead be realized by externally powered neurostimulators that reside in a non-conductive flexible material which may be wrapped around the nerve.

Figure 49:
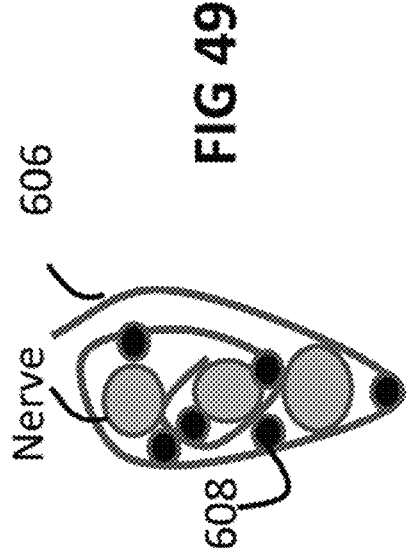
FIG. 49 is a schematic view of further embodiments of a nerve cuff.

In an embodiment shown in FIG. 49, which is a top view, a nerve cuff 606 is shown, with contacts 608 residing on the first (inner) surface of the cuff which has been concentrically wrapped around three nerves or nerve branches. Elements related to providing the electrical stimulation to the contacts have been omitted from the figure for ease of viewing. Alternatively, a helical lead array, containing 3 loops which may individually engage the PTN, LPN, and MPN is an embodiment that may work well to provide selective nerve stimulation.

The system may use one or more stimulator electrodes to stimulate a nerve branch such as least one of the LPN and MPN and SAFN in several manners using the cuff designs disclosed in FIG. 42 to FIG. 47. In one embodiment, at least one nerve branch, such as the LPN and MPN is surgically accessed by separating portions of the target nerve branches from the full posterior tibial nerve trunk or by accessing the nerves adjacent to bifurcation. For example, a nerve cuff is attached to a section of the target nerve branch with electrode contacts configured to approximately selectively stimulate the nerve branch, using a portion of the posterior tibial nerve trunk (e.g. near the ankle) that has been surgically accessed. In this example, as depicted in FIG. 484, one nerve cuff 598a can be applied to, or near, a section of the LPN (Nerve 1, in this example) and another 598b can be used to stimulate a section of the MPN (Nerve 2, in this example). When the nerve cuff functions as a passive IPC that is not used with an implanted neurostimulator device 600, then 598a,b can simply be realized as conductive sleeves that are paired to work with at least one external stimulator. When two sections of two nerve branches are targeted near the human ankle by dissecting the PTN nerve trunk then during implantation the LPN and MPN can be identified visually. Further, by stimulating the separated nerve section and ensuring that the associated sensed EMG activity (or visually seen muscle movement) is recorded at the respective muscle group (e.g., big toe for MPN, or 3 smallest toes for LPN) can confirm the correct placement of selection made visually. In this manner, the PTN, MPN, and LPN can all be stimulated from a single region.

In another embodiment, one or more nerve cuffs 598 (e.g., 598c and 598d in FIG. 47) can also be used to facilitate selective activation of nerve branches using percutaneous stimulation whereby the percutaneous needle is positioned within the patient in order to make electrical contact with at least one nerve cuff that has been implanted to enable selective modulation of the LPN, MPN, saphenous nerve, or other target and facilitate the consistent provision of selective nerve branch stimulation. To clarify, percutaneous stimulation, without an IPC such as a nerve cuff, may have difficulty in providing selective nerve branch stimulation to a patient when using a single entry point near the ankle since the nerves may be hard to find without surgery. One or more IPCs may be configured on or near nerve targets and configured to receive the needle. A patient or doctor can feel when the tip of the needle touches the implantable IPC. In another embodiment one or more stimulators are simply positioned adjacent to each target nerve or nerve branch, without any dissection of the nerve trunk, in order to provide stimulation, such as by and implanted device to an intended target.

The results of FIG. 41 indicate that size of current that is used to stimulate the saphenous nerve can be less (e.g. 16% to 50%) of the amplitude that is used to stimulate other nerve targets such as the LPN or MPN. In an embodiment, a range of approximately 0.025-0.10 mA may be used instead of approximately 0.12-0.18 mA range in a rat. If this lower threshold is also found in humans then this may offer the advantages of decreased amount of energy (e.g., voltage/current) and thus less drain on a battery that powers a neurostimulator, the ability to use a smaller battery, providing a longer cycle between recharging, and less risk of side effects such as pain, due to unintentional stimulation of lower non-target lower limb muscles. Alternatively, higher amplitude stimulation may be used. When selective stimulation is directed at a nerve branch, the aim is to stimulate that nerve branch and not unintended adjacent targets. In some embodiments disclosed in this specification, selective stimulation of the tibial nerve trunk indicates the intentional stimulation of the full trunk rather than the individual branches.

As an alternative to adjusting the stimulation parameters (e.g., amplitude, pulse width, and frequency), selective electrical activation of one or more subsets of SAFN fibers may provide an effective means of achieving effect treatment of bladder dysfunction. As an example, FIG. 50a shows a system for achieving this at the level of the lower leg, below the level of the knee. In humans, the SAFN exhibits multiple divisions that result in a plurality of distal branches innervating different cutaneous areas of the lower leg, ankle, and foot. At the level of the medial gastrocnemius muscle, a multi-contact electrode grid array 610, having at least two contacts, on at least a top or bottom surface of the electrode, can be implanted subcutaneously between the muscle and skin layers and can be powered by the stimulation module 54 (depicted in FIGS. 18a and 18b) of the implanted neurostimulator 632. This array 610 can be powered by various types of energy sources (e.g., battery powered stimulation module or wireless powered stimulation module) that are connected via a multi-strand lead-wire 611 when the grid is not formed onto the housing of a neurostimulator. The neurostimulator 632 can be programmed to provide at least one stimulation signal to one or more rows or contacts on the grid array to provide a spatially focused or distributed stimulation signal such that therapeutic SAFN stimulation obtained. For example, the number and spacing of the active electrical contacts can be titrated to match the preference or response profile of the patient. The patient may adjust the contacts that are used in manual manner based upon a subjective experience such as tingling, or this can be done using sensed data or otherwise. This type of approach may be particularly effective if electrical activation of one or more specific SAFN branch(es) causes severe painful sensations, that for example may be related to injury to the corresponding or surrounding region of the lower leg (e.g., allodynia).

FIG. 50a also shows another embodiment of a multipolar electrode of the invention that can be implemented at or near the level of the medial malleolus. This anatomical location provides access to both the SAFN and PTN. In this case, a linear (lead-type) electrode array 614 can be implanted subcutaneously such that one or more of the electrode contacts are located in close proximity to one or more SAFN branch and also the PTN to provide stimulation of at least one of these targets. The stimulator 632 (such as that shown in FIG. 53a), which is connected via a lead wire 611, can be programmed to deliver electrical pulses to one or more of these neural targets such that effective treatment of bladder symptoms is achieved. In two neurostimulators 638, 640 are also shown stimulating two branches associated with the SAFN that may be at the level of the knee or below.

Figure 50D:
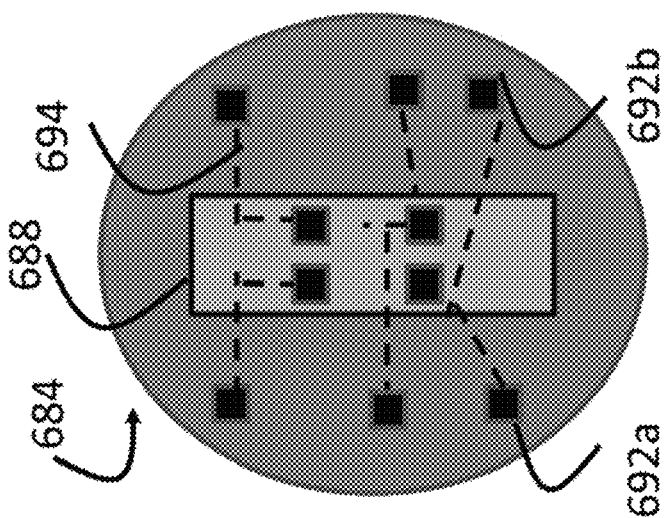
FIGS. 50b-d are schematic diagrams of an implantable neurostimulator and a stimulation system which uses an electrode array grid accessory.
Figure 50C:
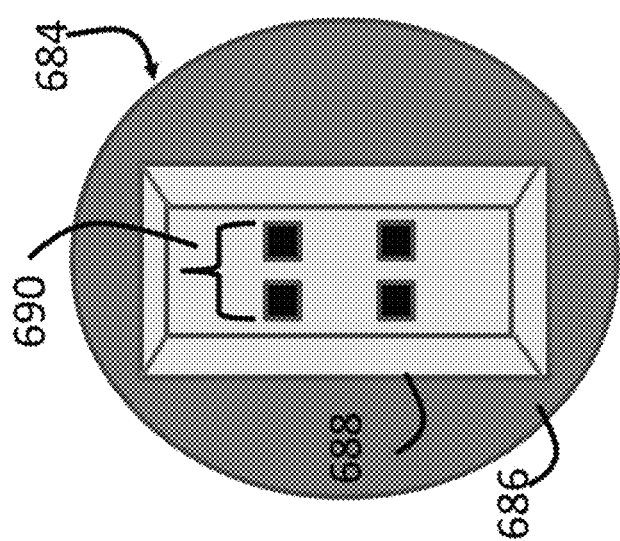
Figure 50B:
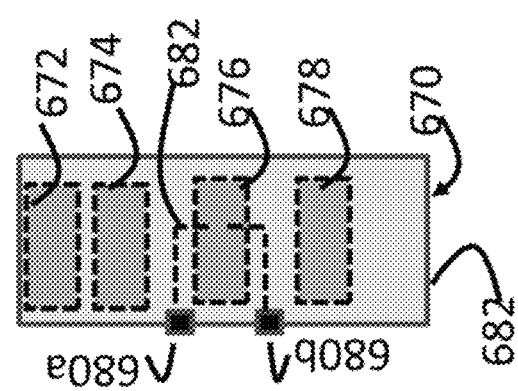

Further alternative embodiments of systems and methods are shown in FIG. 50b-e. FIG. 50b shows an implantable neurostimulator 670, with modules including a control module 672 having a processor and circuitry for controlling the other modules, a power module 674 including battery and/or antennae and/or induction coil as well as other circuitry for wireless power harvesting, regulation, and conversion, an AD/DA module 676 which can include safety circuitry for ensuring that stimulation is provided in a safe manner and configured for implementing stimulation and sensing operations under control of a therapy protocol as directed by the control module 672, and a communication module 678 configured to allow communication with other devices of a neurostimulation system such as an external device (not shown). At least two stimulators 680a, 680b are provided on the housing 682 of the neurostimulator. The at least two stimulators can be realized in various manners, such as within a stimulation grid array containing 2 rows each of 2 electrode contacts, or two ring electrodes that extend partially or fully around the housing of the neurostimulator 670.

In an embodiment of the invention, a neurostimulator may not be shaped or sized in order to provide stimulation to one or more nerve branches that may be distributed in space over a region that is larger than the stimulator. In order to address this problem, the neurostimulator can be operated in collaboration with components that can extend the stimulation field across a larger area. FIG. 50c shows an electrode grid array accessory 684 which can be realized to include at least: a support structure 686, which may be realized, for example, as a silicon disk with or without internal or external skeleton components to assist with maintaining shape; a receiving compartment 688 for receiving the neurostimulator 670, and electrode receiver contacts 690 which are configured to connect with stimulators provided on the neurostimulator. Additional elements may be included such as covers to provide a sealed connection between the neurostimulator and the accessory and suture holes to maintain the position of the accessory, etc. Further, as is shown in FIG. 50d, various elements of the accessory can assist in stimulation being provided to adjacent tissue. FIG. 50d shows dashed lines representing various signal routing pathways 694 that connect each of the electrode receiver contacts 690 to electrode contacts such as 692a, 692b. The signal routing pathways 694 and associated stimulators 692a,692b can operate in a fixed manner or a portion of the AD/DA module 676 of the neurostimulation system can be disposed within the accessory 684 and under control of the neurostimulator 670 or external patient device 72. One or more of the electrode contacts 692a,692b can be located on a first surface (facing outward from the page) of the accessory, on a second surface that is opposite to the first surface, or both.

Figure 50E:
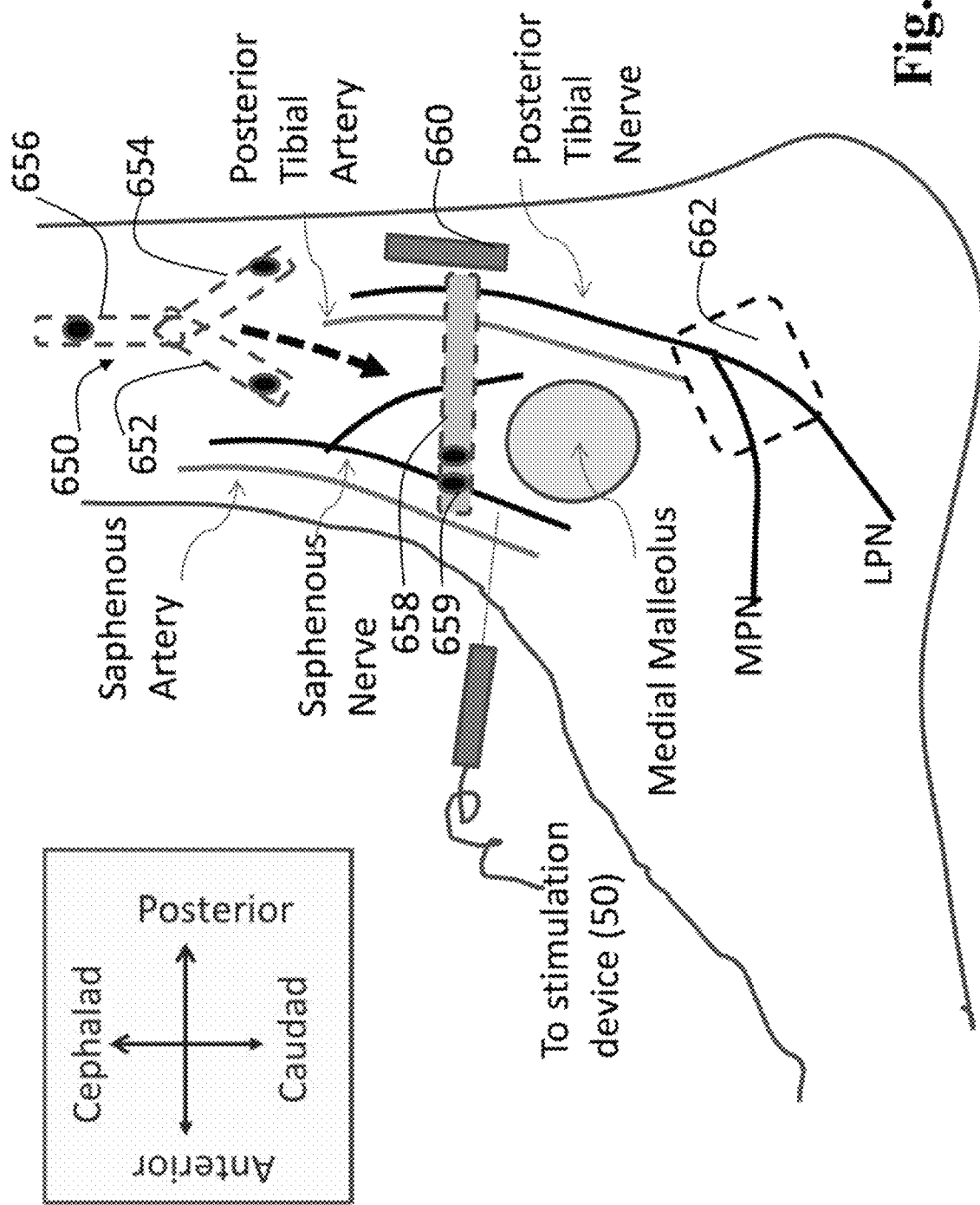
FIG. 50e is a schematic diagram of various types of neurostimulators, stimulators, and stimulation locations near and in a foot.

FIG. 50e, shows an embodiment an implanted neurostimulator 650 for stimulating both the SAFN and the PTN is shown having a first stimulator 652 having at least one electrode configured to be implanted relatively anterior (e.g., anterior to the medial malleolus) for stimulation of the SAFN and a second stimulator 654 having at least one electrode that is configured to be implanted relatively posterior (e.g., posterior to the medial malleolus) for stimulation of the PTN. A third electrode may be positioned on a third stimulator 656 located part way between the first and second stimulator in order to serve as an anode electrode while the electrodes on the first and/or second, stimulator serve as cathode (or vice versa). Alternatively, rather than a single electrode contact the first and second stimulator 652,654 may each be configured with two or more electrode contacts in order to provide two localized fields, for stimulating the PTN and SAFN in a bipolar fashion, respectively. In an embodiment, a pair of bipolar electrodes can be used to generate localized areas of neural activation (e.g., inter-electrode distance of each bi-pole between 3 and 5 mm and a stimulation amplitude up to 10 mA) and thereby independently stimulate each neural target. The three stimulators 652,654,656 are configured in an upside-down "Y" configuration, but other configurations are also possible to allow for stimulation of both the PTN and SAFN. For example, in an embodiment, a neurostimulator or stimulator connected 658 to a microneurostimulator 660 can be realized as a multi-contact paddle electrode that is implanted on the medial aspect of the lower leg (in an anterior-to-posterior orientation), such that it spans across a region cephalad to the medial malleolus of a patient and a first set of contacts 659 are located anteriorly to stimulate the SAFN, and second set of contacts are configured posteriorly to stimulate the PTN. Similar to neurostimulator 650, the neurostimulator 660 can be shaped to allow for stimulation of both PTN and SAFN and the electrode contacts can reside on the housing.

Additionally, a neurostimulator with a grid electrode array 662 may be positioned to stimulate both the SAFN at an anterior location and the SAFN at a posterior location, and the electrode contacts that are activated during therapy can be selected or adjusted after implantation. Such a neurostimulator with a grid array 662 is shown in the figure for stimulating the LPN and/or MPN at a location below the medial malleolus. When a grid array stimulator similar to that of FIG. 50c-d is used, the position of the electrode contacts can be formed into the support structure at locations selected due to imaging or other data related to the patient.

Although the nerve stimulation systems can be provided to stimulate the SAFN and PTN branches at relatively anterior and posterior locations, respectively, nerve stimulation system configurations can utilize electrodes located only in locations posterior to the tibia/medial malleolus. For example, a neurostimulator 660 with ring electrodes circumferentially disposed on its housing, can be positioned posterior to the medial malleolus and configured to stimulate both the PTN and also the SAFN fibers that either innervate the skin superficial to the PTN or continue subcutaneously to innervate skin areas caudad (or distal) to the stimulating electrode location. In an embodiment, a neurostimulator 660 is positioned approximately 1.5 to 2.5 cm below the skin to target the electrical activation of the PTN, but the amplitude is increased to a level sufficient enough to simultaneously stimulate the SAFN branches or fibers that are located superficial to the PTN. In an alternative embodiment, a neurostimulator is positioned 0.5 to 1.5 cm below the skin to stimulate the SAFN branches or fibers that terminate within or pass under the skin, but the amplitude is increased to a level sufficient enough to simultaneously stimulate the underlying PTN. In order to allow the electric field to stimulate both neural targets, an implanted stimulator (for example, paddle type electrode) should have electrodes configured on both the side facing the skin to stimulate SAFN fibers and the opposite side facing the PTN. Additionally, a neurostimulator with circumferential ring electrodes can be used to achieve co-activation of SAFN and PTN fibers. In an embodiment designed to create a field capable of simultaneously stimulating both the PTN and the SAFN branches/fibers, the inter-electrode spacing between active electrode contacts disposed on the surface of the neurostimulator 660, should be at least 5 mm, but preferably greater than 10 mm to create a larger stimulation field.

In an embodiment where a single set of electrodes, comprised of two or more electrode contacts, are used to stimulate both the PTN and the SAFN branches/fibers from the same stimulation signal field, a method may include applying electrical pulses to one or more electrode contacts of the implanted device to activate both the tibial and SAFN cutaneous terminal fibers at least 50% of the time from the same field relative to the activity which occurs in the absence of the stimulation. Alternatively, at least 2 different electrodes may be implanted and configured to simultaneously, or selectively, produce two fields that are oriented for selectively modulating the PTN and cutaneous SAFN fibers, respectively.

It may be that using a single set of electrode contacts to stimulate both the PTN and adjacent SAFN fibers can produce unwanted side effects such as subject discomfort. This is because the amplitude needed to stimulate both the PTN and the SAFN from the same electrodes will also increase the risk of stimulation other sensory nerves that can cause the subject discomfort or pain. In an embodiment, a neurostimulator is used to provide a first field to stimulate the PTN using inward facing electrodes disposed on an inward facing surface of the stimulator and a second field to stimulate the PTN using outward facing electrodes disposed on the outward facing surface of the stimulator. The stimulator may be realized within a non-conductive substrate (e.g., silicone) such as that shown in FIG. 50d with electrodes disposed on a first surface and second surface, to direct and bias the first and second fields towards their respective nerve targets.

It is likely that a neurostimulator such as a microneurostimulator (e.g. BION) intended to stimulate the PTN in isolation would be implanted close to the PTN in order to maximize the intended therapeutic effects of the stimulation while minimizing any potential side-effects caused by stimulation spillover. While this may improve stimulation of the PTN it may decrease the ability of the neurostimulator to further augment the therapeutic outcome by also activating SAFN branches/fibers located in proximity of the stimulating electrode. Accordingly, a method may include positioning a neurostimulator at least 1 cm superficial from the PTN in order to improve the likelihood of stimulating both PTN and SAFN nerves. An alternative method for stimulating both the PTN and SAFN may include positioning at least a first stimulator of an implantable device adjacent to or near the SAFN or PTN of a patient and then angling the neurostimulator to also provide stimulation of the other nerve target rather than positioning and aligning the stimulator to only stimulate one of the two nerves. In an embodiment one end of a neurostimulator, or an electrode/contact of the stimulator is implanted at most approximately 1.5 cm from the PTN and the other end of the neurostimulator is positioned at most approximately 1.5 cm from the SAFN, or its cutaneous nerve terminals. For example, a neurostimulator having electrodes on its surface, can be implanted so that one end of the stimulator is closer to the PTN than the SAFN and the other end is closer to the SAFN than the PTN. The stimulation amplitude can then be set to cause stimulation of both the SAFN and PTN. An embodiment includes positioning one or more electrodes of an implantable device adjacent to or near a SAFN or PTN branch of a patient and stimulating with an amplitude that causes activation of both nerves to increase by least 50% over which occurs in the absence of stimulation.

An embodiment of a percutaneous treatment system is also shown that uses percutaneous needle electrode 657 to provide SAFN stimulation to a patient. After the needle 657 is inserted, for example, at a position cephalad and anterior to the medial malleolus, a device 50 can be used to provide a stimulation protocol similar to that used for PTN stimulation, with a current of about 0.5-9 mA (increased until a patient feels a cutaneous sensation) presented at 10 or 20 Hz to provide stimulation during a treatment session lasting about 30 minutes. A conductive pad with at least one conductive portion can serve as a return electrode and or ground is placed over the medial aspect of the calcaneus and also connected to the device 50. Treatment may have both an induction interval, with weekly or bi-weekly stimulation sessions, followed by a maintenance interval of less frequent treatment. The stimulator may allow the user to also select or configure additional protocols. For example, a user can independently modify the frequency, amplitude, and time using a graphical control and "+", "−" buttons to change the values. Additionally, the user can choose from, or create, additional protocols. A protocol parameter can be called "ramp mode", which when selected causes a selected stimulation parameter such as stimulation amplitude to vary over a range such as +/−2 uA during the session instead of maintaining a constant value. One protocol can be called "10/20", which stimulates for 50% of the time at 10 Hz and the other 50% at 20 Hz.

Figure 54:
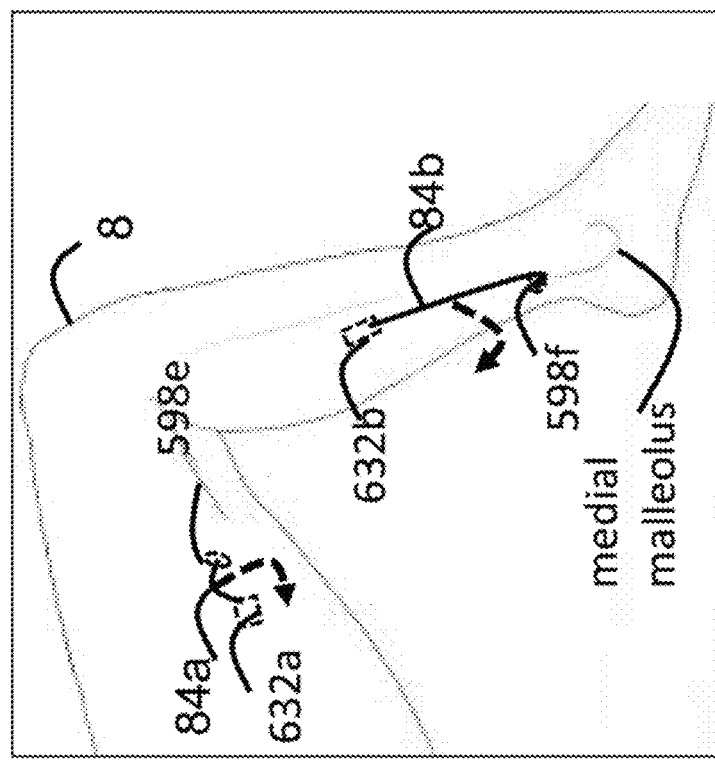
FIG. 54 shows alternative embodiments of neurostimulation systems implemented on the medial side of a leg.

In an embodiment shown in FIG. 54, an implanted neurostimulator device 632b can provide stimulation signals to an IPC nerve cuff or lead-type multi-contact electrode array 598f, configured to stimulate a target in the medial aspect of the ankle region such as the PTN or SAFN using a stimulator conduit 84b. The nerve cuff 598f may be configured with two or more independently operable electrodes to provide localized bipolar stimulation of a target nerve, or may only include a single electrode and the return path is provided by a stimulator on the neurostimulator device 632b. In the latter case, the cuff 598f can be implanted and configured to activate electrically the PTN or SAFN near the medial malleolus, while the stimulator provided on the neurostimulator device 632b can serve to stimulate the SAFN in the leg, such as the SAFN nerve or it branches which terminate in the skin. In one embodiment, the neurostimulator is implanted and operated to cause the nerve cuff to stimulate the PTN using a monopolar electrode and the return path is between the neurostimulator and the nerve cuff. The stimulation amplitude is then increased until the subject senses a tingling in their leg and then more, less, or an equal amount of stimulation is provided during subsequent therapy. Additionally, at least one electrode used to provide stimulation near the neurostimulator device can be made larger to increase the chance of stimulating cutaneous branches of the SAFN.

Additional System Embodiments

Figure 51:
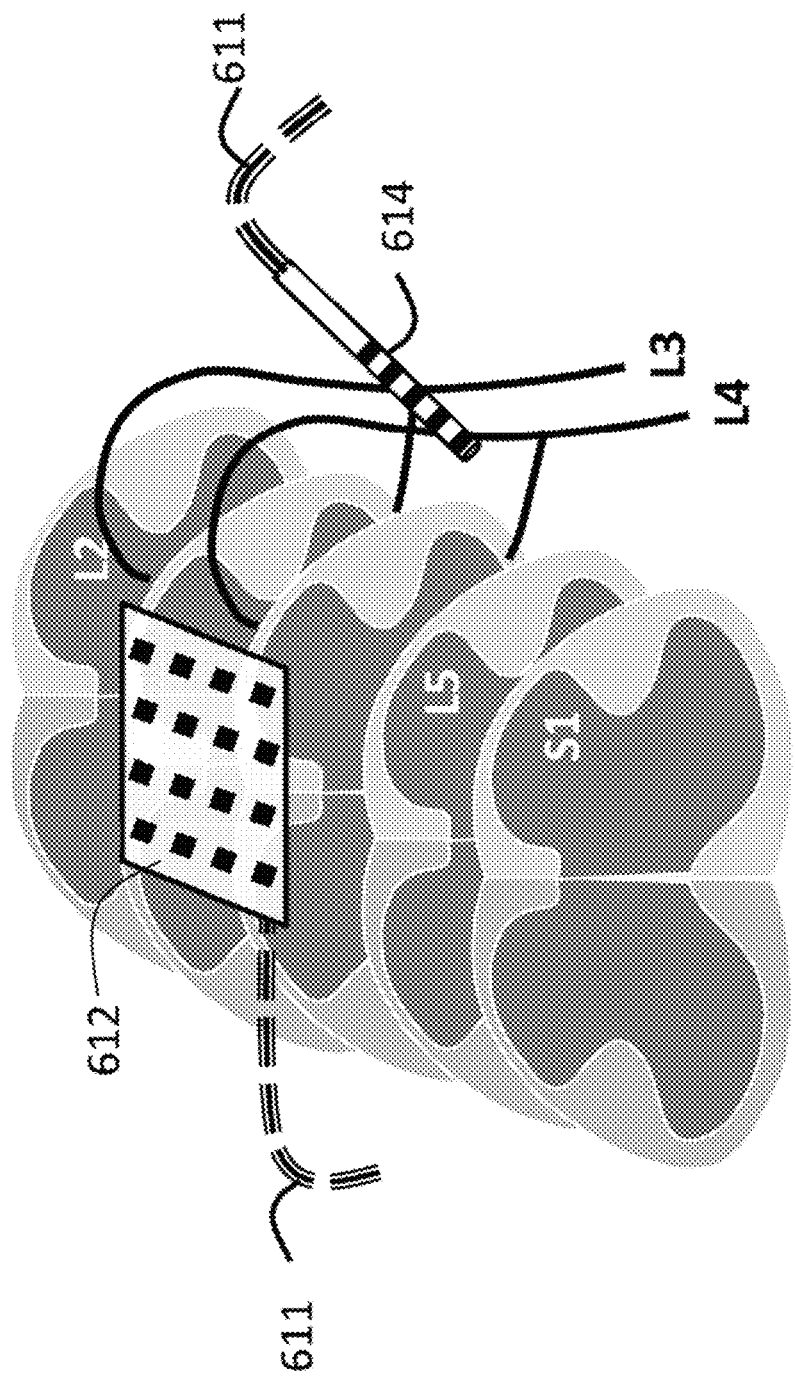
FIG. 51 is a schematic drawing of multi-contact array electrodes that are implanted to selectively activate one or more targets of the lumbar spinal cord and/or lumbar spinal nerve roots.

In an embodiment, electrical activation of SAFN afferents is achieved by delivering stimulation at the level of the spinal cord. As shown in FIG. 51, a multi-contact grid electrode array 612 having at least 2 contacts can be implanted near the dorsal surface of the lumbar spinal cord such that one or more electrode contacts are able to selectively activate nervous tissue with electrical pulses. A single electrode array 612 may be constructed large enough to provide electrical pulses at targets along the entire L2-L4 region or it may be small enough to be implanted through, or adjacent to, respective foramen and to stimulate a specific region (e.g., L4). A single array or multiple arrays may be used to capture complementary subsets of nerve roots located at target anatomical locations (e.g., L2 and L4 stimulation). The array 612 may be implanted external to or underneath the dura to provide more selective electrical nerve stimulation.

An embodiment includes a method of electrically activating spinal nerve roots within the region of the lumbar spinal cord using a lead-type multi-contact electrode array 614. Mechanical stability may be improved using a tined array design. In FIG. 51 the lead-type array 614 is positioned (e.g. rostro-caudally) such that one or more spinal nerve roots (e.g. L3 and L4) is selectively activated. The clinician may program a neurostimulator to stimulate two or more nerve roots synchronously, alternatingly, out-of-phase, or can select stimulation of only one nerve root. Alternatively, the lead-type array 614 is positioned (e.g., anterior-posterior direction) such that only one spinal nerve root (e.g., L4) is targeted, but the multiple stimulation sites provide for selecting one or more channels (e.g., monopolar, bipolar, or tripolar) for treatment of bladder symptoms. In an embodiment, the lead array 614 or stimulators 638 may stimulate a spinal target by implantation adjacent to the associated foramen and may reside in the epidural space. The lead can be spiral and reside around a nerve root, upon lumbar vertebra or about the sacrum.

FIG. 52 shows method for providing nerve stimulation including the steps of assessing implantation sites and parameters 622, implanting a neurostimulation system components 624, including at least one stimulator, and providing therapy 626. In an embodiment, steps including assessing sites and parameters 628, and adjusting at least one of the sites and parameters 630 may be done in order to provide stimulation that has therapeutic benefit. A stimulation assessment protocol comprises a patient being stimulated before, during or after one or more "assessment interval". Stimulation signals which meet treatment a criterion provide improved therapy are selected and stored to define the signals and sites of therapy protocols subsequently used during treatment.

In an embodiment, a method of treating OAB includes combination therapy. The provision and operation of a neurostimulator having a processor configured for operating a stimulation protocol that provides at least one stimulation signal to at least one stimulator for providing selective stimulation of at least one nerve target; and, the at least one stimulator is configured to selectively stimulate at least a first nerve branch nerve target of the SAFN or one PTN branch at a location approximately between the knee and the heel; and, the at least one stimulator provides at least one electrical stimulation parameter assessed to be effective to at least a first nerve branch. The provision of a drug therapy 629 can also occur. A target such as the PTN, MPN, LPN, SAFN at peripheral site or associated spinal root. The drug therapy 629 can involve oral ingestion of a drug such as an anti-cholinergics, or transurethral or intrathecal injection of a drug such as botox into the bladder wall (e.g., as may occur intra-vesicle). The drug therapy may enable the nerve stimulation to be more effective in bladder inhibition and patient tolerance to stimulation. The drug therapy may involve titrating the dosage of a drug such as botox (e.g. volume per injection, drug concentration, number of locations within the bladder) to enable a broader range of peripheral nerve stimulation parameters to be used to provide effective bladder inhibition. The electrical stimulation may enable less dosage or frequency of drug therapy needed to sustain treatment of OAB. The electrical stimulation may enable the drug therapy to occur with smaller volume or lower concentration of intra-vesically injected botox, such as to minimize the incidence of urinary retention (i.e., need for urethral catheterization).

FIG. 53a shows a neurostimulator system 644, having a neurostimulator 632, and sensor 634, and which is configured to communicate with an external programmer EXD 636 using wireless signals 646. In one embodiment the EXD 636, can provide both communication and power wireless signals 646 in order to provide power. The neurostimulator 632 can be configured with multiple conduits to provide stimulation to at least one target nerve (T1-T4). An EXD patient programmer 636 or neurostimulator 632 can operate a processor to provide therapy program that using, in part, a historical patient record algorithm defined in the protocols and parameters module 66. The algorithm can operate to obtain, assess, and store a historical patient record in, for example, memory 60. The historical record stored in memory 60 can include, for example, 1) all parameters, adjustments, and times related to stimulation, 2) a record of the system alerting a patient by, for example, sending a communication signal to the EXD 636, or triggered by time intervals expiring, time of day, or sensed data meeting one or more treatment criteria, 3) patient input data, including input by the patient into the EXD 636 that caused stimulation to be delayed 4) patient diary information such as subjective information input by a patient using the EXD 636 as may occur spontaneously, according to a schedule, and/or in response to questions posed to the patient by the EXD (or realized by a smartphone application operating on the patient's cellphone), about voiding, subjective scores related to voiding urgency, pain, sensitivity, etc.

In an embodiment, a system for treating incontinence can comprise: a sensor 634 which is part of a sensing module 55 which is adapted to generate a signal responsive to a state of a patient related to bladder or bowel activity; at least one stimulator 114 having an electrode, the stimulator adapted to modulate a pelvic floor activity of the patient by stimulation of at least one spinal target such as L2, L3 L4; and a control module 52 of a neurostimulator device 632, which is adapted to receive the signal from the sensing module, to analyze the signal so as to detect an event related to bladder or bowel activity, and, responsive to detection of the event, operate to make an adjustment in the stimulation protocol of the protocols and parameters module 66 to cause a change in the nerve modulation provided to the at least one electrode. The adjustment to the stimulation protocol can be starting or increasing the strength of modulation when an event is detected. The control module 52 can be adapted to apply a first waveform to the stimulator responsive to determining that the detected event is related to an incontinence event that is imminent, and wherein the control module is adapted to apply a second waveform, different from the first waveform, responsive to determining that the event is not imminent. The detected event may be related to an incontinence event that is eminent and is detected when sensed activity is above a threshold set for the patient. In an embodiment, the first waveform is related to deterring the acute response of the bladder to stimulation and the second waveform is related to the deterring the prolonged response of the bladder to stimulation. The sensor can be implanted and configured for measuring muscle activity related to fecal or urinary voiding. Instead of, or in addition to, bladder modulation, the stimulation may also be oriented towards modulation of other tissue, for example, it may promote anal sphincter muscle contraction.

When a sensor is not used, a method of treating a patient may simply comprise: with a processor of the control module 52, controlling a stimulation generator of a neurostimulator 632 to deliver electrical stimulation to one or more tissue sites proximate to one or more spinal nerves from L2 to S4 of a patient, in a frequency dependent manner, to generate an inhibition or excitation bladder activity related to voiding, as per a therapy protocol. The stimulation protocol implemented by the system 644 is configured so electrical stimulation delivered at one of the one or more tissue site to be a stimulation signal having a frequency that has been shown in a patient to lead to decreased bladder contraction as part of a bladder relaxation therapy protocol provided by the processor in order to decrease voiding activity. The stimulation protocol defined in protocol module 66 is configured so electrical stimulation delivered at one of the one or more tissue site comprises a stimulation signal having a frequency that has been shown in a patient to lead to increased bladder contraction as part of a bladder excitation therapy protocol in order to increase voiding activity.

FIG. 53b shows a system having a neurostimulator device 638 such as a wirelessly powered device which may harvest wireless power to stimulate at least a first nerve target. An external device 636 is configured for providing wireless power and data signals 646 to the device 638 to realize a stimulation protocol. A second neurostimulator device 640 may also be provided to stimulate a second target. When two or more microneurostimulator devices 638, 640 are provided, these can obtain power and be independently controlled from the same external device EXD 636. The EXD 636 has a processor which is configured to operate the EXD to provide a stimulation protocol by operating the two or more implanted devices that work as a distributed neurostimulation system 642. When multiple devices 638, 640 provide at least one stimulation protocol then these can cooperate, for example, to provide stimulation of multiple SAFN branches.

FIG. 54 shows a first neurostimulator system 644 in the leg of a patient 8, with a neurostimulator device 632a which provides stimulation signals to a IPC nerve cuff 598e using a stimulator conduit 84a. A second neurostimulator system 644 is also shown in the lower leg of a patient 8, with a neurostimulator device 632b which provides stimulation signals to an IPC nerve cuff 598f configured to stimulate a target in the medial malleolus such as the PTN or SAFN using a stimulator conduit 84b. US Pat App No. 20080234782, to Haugland, incorporated by reference herein discloses various systems and methods that can be used when implementing stimulation protocols and systems of the present invention in the leg of a patient.

In an embodiment, a system to modulate bladder activity for treating a patient having a bladder dysfunction or disorder includes a processor for operating a signal generator of a stimulation module according to a stimulation protocol to provide a first stimulation signal and neurostimulator configured to provide the stimulation signal to a stimulator adapted to be positioned below the knee of the patient and adjacent to a portion of a SAFN of the patient for stimulating the SAFN, whereby bladder activity is modulated. The stimulation protocol defines a stimulation signal to have a frequency selected to provide an inhibitory effect of bladder activity such as within the approximate range of 10 Hz to 20 Hz a frequency selected to be substantially in at least one of a 2 Hz range and 50 Hz range to provide an excitatory effect on bladder activity. The stimulation signal can be selected to have a predetermined combination of frequency and amplitude determined to increase or decrease bladder activity of the patient during a previous assessment interval or has been shown in a previous sample of patients to increase or decrease bladder activity. The stimulator is adapted to be positioned adjacent to a portion of the SAFN of the patient for providing stimulation at a location that is cephalad to the medial malleolus and anterior to the medial malleolus within the approximate range of 1 to 3 cm or cephalad to the medial malleolus and posterior to the saphenous vein at a displaced distance within the approximate range of 1-2 cm, and at a subcutaneous depth within the approximate range of 0.5 cm and 1.5 cm or at a location adjacent to the anterior side or posterior side of the medial malleolus, adjacent to the posterior side of the medial malleolus. Alternatively, a stimulator is positioned on a housing of the neurostimulator implanted at a position proximate to a medial malleolus of the patient and adjacent to a portion of the SAFN of the patient. The position is also adjacent to a portion of the PTN with the neurostimulator being configured to provide stimulation using at least two electrode contacts on the stimulator configured with an inter-contact distance of at least 5 mm. Further, the stimulation signal can have an amplitude sufficient to provide concurrent stimulation of the PTN and at least one branch of the SAFN that is located superficial to the PTN. Additionally, in an embodiment, the system having a processor for operating a signal generator of a stimulation module according to a stimulation protocol can be configured to provide at least a second stimulation signal from a second stimulator adapted to be positioned below a knee of the patient and adjacent to a portion of a posterior tibial nerve of the patient and configured to provide stimulation of the posterior tibial nerve in order to modulate bladder activity. The stimulation module can use a stimulation protocol configured to provide the first stimulation signal and second stimulation signal substantially simultaneously or at differing times to deter interaction effects between the first and second stimulation signals. The first stimulation signal and second stimulation signal can occur at the same or different frequencies, and may be unique in stimulation parameters. In an embodiment, the first stimulator is an electrode implanted at a location that is approximately 3 cm to 5 cm cephalad and 1 cm to 2 cm anterior to a medial malleolus of the patient and the second electrode is implanted at a location that is approximately 3 cm to 5 cm cephalad and approximately 1 cm to 3 cm posterior to the medial malleolus. The system may have one stimulator that is adapted to be positioned adjacent to a portion of the saphenous nerve of the patient for providing cutaneous stimulation at a location that is on the medial side of a leg of the patient and within the approximate range of 3 cm to 10 cm below a knee of the patient. Further, the stimulator may be adapted to be positioned adjacent to a portion of the saphenous nerve of the patient for providing cutaneous stimulation at a location that is on the medial side of the leg within the approximate range of 3-10 cm below a knee of the patient and the stimulation signal is provided to at least one branch of the saphenous nerve at approximately an amplitude that produces a cutaneous sensation in the lower part of a leg of the patient.

In an embodiment, a stimulation target nerve can be selected at a location below a pelvis region of the patient, such as near the femoral nerve of the patient substantially above the knee for targeting and stimulating the SAFN of the patient. Providing stimulation of the saphenous nerve can entail providing a low amplitude stimulus within the range of 25 uA-75 uA for stimulating the SAFN since it has been shown to modulate bladder activity with as little as 25 uA. Alternatively, the system can provide stimulation substantially at the level of the spinal cord to stimulate at least spinal roots that are associated with the SAFN. Stimulation therapy can be provided according to a first protocol to cause an acute change to bladder activity approximately during the stimulation interval or second protocol designed to cause a prolonged change to bladder activity lasting after the end of a stimulation interval, or both, where the acute stimulation occurs as needed. For example, the system, when implanted, can include a sensor and a sensing module as well as a control module configured to process sensed data, detect events in the sensed data, and adjust stimulation provided by the stimulation module to provide stimulation related to acute bladder modulation based upon the detection of at least one event in the sensed data related to for example, bladder activity and bladder volume. Alternatively, the stimulation protocol can simply adjust a stimulation characteristic if a first stimulation protocol does not provide sufficient modulation of bladder activity. Adjusting stimulation can include adjusting a frequency of modulation or implementing a stimulation signal that varies over time, such as a chirp. The modulation of bladder activity is provided in order to provide therapy to the patient in response to an unwanted symptom and the results of providing therapy can be to relieve symptoms which in embodiments can be considered as resulting from modulation of bladder activity.

In an embodiment, a method for treating overactive bladder includes establishing a neurostimulator having a processor configured to provide a stimulation protocol that provides stimulation at a stimulator to modulate the SAFN and also at a second stimulator to stimulate the PTN, or the LPN/MPN branches at a location substantially between a knee and a heel of the patient. The method further includes applying an stimulation signal using parameters found to be effective to at least a one of the nerve targets and also providing a drug therapy to the patient.

In an embodiment, a system for treating a patient with an OAB condition includes a neurostimulator having a processor configured to provide a stimulation protocol that independently provides a stimulation signal to a stimulator for providing selective stimulation to a first nerve target and the stimulator is adapted to be implanted within the patient and configured to selectively stimulate a first nerve target that is a PTN, LPN, or MPN at a location substantially between a knee and a heel of the patient. the system is further configured with a stimulator implanted to stimulate an additional target of the SAFN, to provide a combination of concomitant electrical activation of the SAFN and at least one of the PTN, LPN, and MPN. The stimulator can have a first electrode contact and a second electrode contact which are supplied using a nerve cuff having a non-conductive inner annular wall, and a first electrode contact configured to stimulate the first target nerve branch and an outer annular wall that is non-conductive and a first electrode contact that is positioned to stimulate a second target.

In an embodiment, a system is configured to provide therapy to a patient suffering from an overactive bladder disorder comprising a first stimulator implanted in the patient and configured to selectively provide stimulation to at least a first nerve target and a second nerve target. The first nerve target is selected from the group of nerve targets: PTN, LPN, MPN, and SAFN, and the second nerve target selected to be a different target within the group of targets than that selected for the first nerve target. Additionally, at least one neurostimulator is configured for providing a stimulation protocol which is configured with at least a first stimulation signal to be applied to the first nerve target and a second signal to be applied to the second nerve target, wherein the stimulation protocol defines a first parameter value for the first signal and a second parameter value for the second signal and the first and second parameter values are selected to include at least one parameter value from the group of (1) stimulation frequency for determining the frequency of the two stimulation signals and (2) stimulation amplitude for determining at least one of the current or voltage of the two stimulation signals. The first and second stimulation signals are selected to be signals that have been assessed to provide desired modulation of bladder activity in the patient or in a sample population. In an embodiment, the second stimulation signal is applied by the stimulation protocol to the SAFN and the current or voltage of the stimulation signal is approximately 30%-60% less than the value used for the first stimulation signal. the first signal and second stimulation signals can be to be signals that have been assessed as having therapeutic efficacy in the patient when presented in combination to each of two target nerves.

In an embodiment, a system is configured to treat pelvic floor dysfunction or provide relief of symptoms in a patient comprising a neurostimulator having a stimulator configured to stimulate a first nerve target with a first stimulation signal and a second nerve target with a second stimulation signal, wherein the first stimulation signal is selected to be therapeutic at the first stimulation target and the second stimulation signal is selected to be therapeutic at the second stimulation target, and the first and second stimulation targets are selected to be at least two of the set including: PTN, LPN, MPN, and SAFN.

In an embodiment, a system is configured to treat a bladder disorder and comprises an implanted neurostimulator having a stimulation protocol which is configured to apply a first signal a first nerve target, the signal having been previously assessed as producing inhibition of bladder activity and additionally apply a second signal to a second target to produce excitation of bladder activity. The first stimulator can be implanted in a patient and configured to selectively stimulate at least a first nerve target selected from the group of: PTN, LPN, MPN, and SAFN. The first and second nerve targets can be the same nerve different targets. Additionally, the second stimulation signal is selected to be approximately above 35 Hz and below 100 Hz, for causing excitation of bladder activity.

In an embodiment, a system is configured to modulate voiding activity and/or related symptoms of a patient. The system can include a neurostimulator having a control module processor configured to control a stimulation module with a signal generator to provide a first therapy protocol that is configured to provide stimulation to a first stimulation site using a first stimulation signal having a first stimulation pattern that is selected to increase voiding activity and a second therapy protocol that is configured to provide stimulation to a stimulation site using a second stimulation signal having a second stimulation pattern that is selected to decrease voiding activity; and, a stimulator is configured to receive a stimulation signal from the neurostimulator and to stimulate a nerve target for at least one stimulation site. The at least one stimulation site for the first stimulation signal is a site selected for stimulating a nerve target selected from the set of nerves including: PTN, LPN, MPN, and SAFN.

In an embodiment, a system for treating overactive bladder comprises a neurostimulator, an external device which is a patient programmer, a processor for implementing a stimulation protocol which defines stimulation provided to a patient which is configured to stimulate a first candidate nerve target site with at least a first candidate stimulation signal applied to at least a first stimulator that receives the signal from the neurostimulator, adjust the protocol to adjust the at least one of the first candidate nerve target site or the first candidate stimulation signal, wherein the adjustment to the candidate nerve target site includes switching between at least two candidate nerve target sites selected from the group of: PTN, LPN, MPN and SAFN. Additionally the stimulation protocol is configured to stimulate at least two of the sites using at least the first stimulator. The stimulation protocol adjustment can contingently occurs during the provision of therapy. It can occur after stimulating the first candidate nerve target site with the first candidate stimulation signal and then determining if there is therapeutic benefit that meets a treatment criterion; and, if the criterion is met continuing to stimulate using the first candidate nerve target site and first candidate stimulation signal; and if the criterion is not met performing the step of adjusting the protocol and providing stimulation. Additionally, the adjustment of the protocol can contingently occur prior to, or intermittently during, the provision of therapy and includes: stimulating the first candidate nerve target site with the first candidate stimulation signal; collecting and storing or treatment data related to the efficacy of the stimulation in treating the disorder; adjusting the protocol to realize a treatment site and stimulation signal combination according to a protocol that is defined to realize a series of stimulation sites and stimulation signals; and, evaluating the treatment data to select at least one stimulation site and stimulation signal combination which provided improved therapy to the patient. The adjustment of the first candidate stimulation signal can include adjusting the frequency of the stimulation signal. Adjustment of the first candidate stimulation signal can also include switching between at least two of the frequencies selected from the group: 2 Hz, 5 Hz, 10 Hz, 15 Hz, 20 Hz, and 50 Hz, and further, if the two or more frequencies do not produce a therapeutic effect then assessing frequencies either above or below this range.

In an embodiment, a system is configured to treat a patient suffering from OAB comprising a stimulator implanted in a patient and configured to stimulate a first spinal nerve root target selected from the nerve group of: L2, L3 and L4. The stimulation can occur at between 5 and 50 Hz, and may preferably occur at 10 to 20 Hz when bladder inhibition is desired. The implanted neurostimulator has a stimulation protocol configured to apply a first stimulation signal to the first spinal nerve root target to modulate bladder activity and or relieve symptoms. The at least first spinal nerve root target can be selected to provide for both inhibition and excitation of bladder activity by using two different stimulation protocols. Alternatively, the spinal nerve root targets includes at least two spinal nerve root targets that are each selected to provide at least one of inhibition and excitation of bladder activity. Two different stimulation protocols can define stimulation signals with different frequencies and/or amplitudes for the one or two. The first stimulation signal can be selected to have a frequency which produces at least bladder activity inhibition or excitation in the patient. The system can include a second stimulator selected to stimulate a second nerve root target from a nerve group. The second stimulator can be selected to stimulate a second nerve root target from a nerve group of targets being L3 and L4. The second stimulator can be implanted in a patient and configured to stimulate a second spinal nerve target selected from the group of: L5, S1, S2, S3, and S4, which is preferably S3.

In an embodiment, a system is configured to treat a patient suffering from OAB and includes a first stimulator implanted in a patient and configured to stimulate at least a first spinal nerve root target selected from the group of: L2, L3, L4, and a second stimulator implanted in a patient and configured to stimulate at least a second spinal nerve root target selected from the group of: L5, S1, S2, S3, and S4. The implanted neurostimulator has a control module with a processor configured to implement a stimulation protocol which is configured to apply at least a first modulation signal to the first stimulator to modulate the first spinal nerve root target and a second modulation signal to the second stimulator to modulate the second spinal nerve root target. The modulation signals for modulating the first and second spinal nerve root targets can be independently set, and/or adjusted, by the stimulation protocol. The first modulation signal is selected to be a signal that has been assessed to produce therapeutic efficacy in the patient or which has been assessed to produce therapeutic efficacy in a sample population. Additionally, the first modulation signal and second modulation signal can be selected to be signals that have been assessed to produce therapeutic efficacy in the patient when presented in combination. Further, the first modulation signal and second modulation signal can be selected to be signals that have been assessed to produce therapeutic efficacy in the patient when presented together compared to the efficacy of the first modulation signal and the second modulation signal when presented alone. Additionally, the first modulation signal provided at the a first stimulator can be configured to stimulate at least a first spinal nerve root target selected from the group of: L2, L3, L4. The stimulation amplitude can be made sufficient to produce activation of somatic fibers used to achieve modulation effects.

EQUIVALENTS

The invention may be embodied in other specific forms without departing from the spirit or essential characteristics thereof. The foregoing embodiments are therefore to be considered in all respects illustrative rather than limiting on the invention described herein.

The various steps disclosed herein (such as, for non-limiting example, logic that performs a function or process) may be described as data and/or instructions embodied in various computer-readable media, in terms of their behavioral, and/or other characteristics. The logic and methods described herein may comprise, according to various embodiments of the invention, software, hardware, or a combination of software and hardware.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. When the word "or" is used in reference to a list of two or more items, that word covers all of the following interpretations of the word: any of the items in the list, all of the items in the list and any combination of the items in the list.

What is claimed is:

1. A method for treatment of a voiding disorder comprising:
configuring a first signal generator to generate a first stimulation signal effective in modulating the voiding disorder when the first stimulation signal is applied to a portion of a saphenous nerve of a person;
configuring a first stimulator to selectively stimulate the portion of the saphenous nerve of the person; and
providing the first stimulation signal to the first stimulator, whereby the portion of the saphenous nerve of the person is selectively activated and the voiding disorder of the person is modulated.

2. The method of claim 1, wherein the first signal generator is configured to generate the first stimulation signal based on satisfaction of a treatment criterion for the person or a patient population suffering from the voiding disorder.

3. The method of claim 1, further comprising:
configuring a second stimulator to stimulate at least one of a tibial nerve (TN), posterior tibial nerve (PTN), a lateral plantar nerve (LPN), or a medial plantar nerve (MPN); and
providing a second stimulation signal to the second stimulator, whereby the at least one of the TN, PTN, LPN, or MPN is activated.

4. The method of claim 1, further comprising:
activating, using a second stimulator, at least one of a TN, PTN, LPN, or MPN.

5. The method of claim 1, wherein:
the first stimulation signal and the first stimulator are configured to selectively activate the portion of the saphenous nerve of the person without activating an ipsilateral lower limb muscle of the person.

6. The method of claim 5, wherein:
the ipsilateral lower limb muscle of the person is a foot muscle of the person.

7. The method of claim 1, wherein configuring the first stimulator to selectively stimulate the portion of the saphenous nerve of the person comprises:
configuring the first stimulator to spatially focus an electrical field produced by the first stimulator to selectively activate the portion of the saphenous nerve of the person.

8. The method of claim 1, wherein configuring the first stimulator to selectively stimulate the portion of the saphenous nerve of the person comprises:
positioning contacts of the first stimulator along a stimulation axis based on a longitudinal axis of the portion of the saphenous nerve of the person.

9. The method of claim 1, wherein configuring the first stimulator to selectively stimulate the portion of the saphenous nerve of the person comprises:
positioning the first stimulator to extend an electric field substantially parallel to a longitudinal axis of the portion of the saphenous nerve of the person.

10. The method of claim 1, wherein the first stimulator comprises a nerve cuff, a conductive rod, a paddle electrode, an implanted electrode, or a multipolar lead-type electrode.

11. The method of claim 1, wherein the first stimulator comprises a plurality of independently operable stimulator contacts.

12. The method of claim 11, wherein the first stimulator comprises a grid array.

13. The method of claim 1, wherein the first stimulator comprises a percutaneous needle electrode or a transcutaneous electrical nerve stimulation electrode.

14. The method of claim 1, wherein the first stimulator comprises a magnetic stimulator.

15. The method of claim 1, wherein the first stimulator comprises a transcutaneous electrical nerve stimulation electrode configured to operate with an implanted passive component having a conductive portion.

16. The method of claim 1, wherein the voiding disorder comprises overactive bladder disorder, stress incontinence, or fecal incontinence.

17. The method of claim 1, wherein the voiding disorder comprises urinary retention or constipation.

18. The method of claim 1, wherein the voiding disorder comprises sexual dysfunction.

19. The method of claim 1, wherein the first stimulator is configured to selectively stimulate the portion of the saphenous nerve of the person at a location adjacent to a posterior side of a medial malleolus of the person.

20. The method of claim 1, wherein the first stimulator is configured to selectively stimulate the portion of the saphenous nerve of the person at a location cephalad to a medial malleolus and anterior to the medial malleolus within a range of about 1 to about 3 cm.

21. The method of claim 1, wherein the first stimulator is configured to selectively stimulate the portion of the saphenous nerve of the person at a location cephalad to a medial malleolus of the person and posterior to a saphenous vein of the person at a displaced distance within a range of about 1 cm to about 2 cm, and at a subcutaneous depth within a range of about 0.5 cm to about 1.5 cm.

22. The method of claim 1, wherein the first stimulator is configured to selectively stimulate the portion of the saphenous nerve of the person at a location having a subcutaneous depth within an approximate range of 0.5 cm to 1.5 cm.

23. The method of claim 1, wherein the first stimulator is configured to selectively stimulate the portion of the saphenous nerve of the person at a location that is selected from a group consisting of:
   laterally adjacent to the portion of a saphenous vein of the person;
   a position selected to provide stimulation of an anterior branch of a distal portion of the saphenous nerve; and
   approximately at a posterior edge of a greater saphenous vein.

24. The method of claim 1, wherein the first stimulator is configured to selectively stimulate at least one main saphenous nerve branch including an infrapatellar branch or a saphenous nerve branch which courses superficially down an anteromedial lower leg.

25. The method of claim 1, wherein the first stimulator is configured to selectively stimulate the portion of the saphenous nerve of the person at a location adjacent to a division of a distal portion of the saphenous nerve into anterior and posterior branches.

26. The method of claim 1, wherein the first stimulator is configured to selectively stimulate the portion of the saphenous nerve of the person at a location that is about 3 finger widths below a medial condyle of a tibia.

27. The method of claim 1, wherein the first stimulator is configured to selectively stimulate the person at a location that is selected based on imaging data.

28. The method of claim 1, wherein the first stimulator is configured to selectively stimulate the person at a location that is selected based on data related to fluoroscopy, x-ray, MRI, and/or ultrasound sonography.

29. The method of claim 1, wherein the first stimulator is configured to selectively stimulate the portion of the saphenous nerve of the person at a location confirmed by a report of the person of tingling or paresthesia.

30. The method of claim 1, wherein the first stimulator is configured to selectively stimulate the portion of the saphenous nerve of the person at a location confirmed by a detection of modulation of heart rate or blood pressure.

31. The method of claim 1, wherein the first stimulator is configured to selectively stimulate the portion of the saphenous nerve of the person at a location confirmed by evocation of a bladder response.

32. The method of claim 1, wherein the first stimulator is configured to selectively stimulate the portion of the saphenous nerve of the person at a location confirmed by an assessment procedure in which correct activation of the saphenous nerve is assessed by a percutaneous electrode stimulating one or more candidate sites.

33. The method of claim 1, wherein the first stimulator is configured to selectively stimulate the portion of the saphenous nerve of the person at a location confirmed by an assessment that includes evaluation of acute responses while the first stimulation signal is being applied.

34. The method of claim 1, wherein the first stimulator is configured to selectively stimulate the portion of the saphenous nerve without activating the tibial nerve or branches thereof.

35. The method of claim 1, wherein the first stimulator is configured to selectively stimulate the portion of the saphenous nerve of the person at a location confirmed by an assessment that includes evaluation of post-stimulation responses which occurs subsequent to applying the first stimulation signal.

36. A treatment system comprising:
   a processor for operating a signal generator according to a stimulation protocol to provide at least one stimulation signal, the processor configured to store at least one of a plurality of parameters selected from a group of frequency values, amplitude values, frequency value ranges, amplitude value ranges, and combinations thereof, effective in modulating a voiding disorder when the at least one stimulation signal is applied to a portion of a saphenous nerve of a person for targeting said saphenous nerve; and,
   a first neurostimulator coupled to the processor and the signal generator, the first neurostimulator configured to provide the at least one transcutaneous electrical stimulation signal in accordance with the stimulation protocol using at least one stimulator, the at least one stimulator adapted to be positioned external to a body of said person at or below a knee of the person and to selectively stimulate the portion of the saphenous nerve of the person, whereby the portion of the saphenous nerve is selectively activated and the voiding dysfunction of the person is modulated.

37. The system of claim 36, wherein the at least one stimulator comprises a plurality of independently operable stimulator contacts.

38. The system of claim 36, wherein the at least one stimulator is configured to selectively stimulate the portion of the saphenous nerve without activating the tibial nerve or branches thereof.

39. The system of claim 36, wherein the stimulation signal has a frequency of between 1 and 50 Hz.

* * * * *